United States Patent
Ruvkun et al.

(10) Patent No.: US 6,225,120 B1
(45) Date of Patent: May 1, 2001

(54) THERAPEUTIC AND DIAGNOSTIC TOOLS FOR IMPAIRED GLUCOSE TOLERANCE CONDITIONS

(75) Inventors: Gary Ruvkun, Newton; Koutarou Kimura, Boston; Garth Patterson, Charlestown; Scott Ogg, Newton; Suzanne Paradis, Somerville; Heidi Tissenbaum, Belmont, all of MA (US); Jason Morris, New York, NY (US); Allison Koweek, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 08/857,076

(22) Filed: May 15, 1997

(51) Int. Cl.$^7$ .............................. C12N 5/00; C12N 15/00; A01K 67/00

(52) U.S. Cl. ...................... 435/375; 435/320.1; 435/325; 800/3

(58) Field of Search ...................... 800/3, 18, 8; 424/9.1; 514/2; 435/455, 465, 320.1, 325, 375

(56) References Cited

U.S. PATENT DOCUMENTS 5,196,333  3/1993  Chalfie et al. ................... 435/240.1

OTHER PUBLICATIONS

Murakami et al, Genetics 143:1207–1218 1996.*
Strojek RM and Wagner TE Genetic Engineering: Principles and Methods 10:221–246, 1988.*
Larsan et al, Genetics 139:1567–1583, 1995.*
Kuo et al, PNAS, 92:6911–6914, 1995.*
Lonnqvist et al Nat. Med. 1(9):950–953, 1995.*
Galili et al., "Fusion of a fork head domain gene to PAX3 in the Solid Tumour Alveolar Rhabdomyosarcoma," Nat. Genet. 5:230–235 (1993).
Kimura et al., "daf–2, an Insulin Receptor–Like Gene That Regulates Longevity and Diapause in Caenorhabditis elegans," Science 277:942–946 (1997).
Lin et al., "daf–16: An HNF–3/Forkhead Family Member That Can Function to Double the Life–Span of Caenorhabditis elegans," Science 278:1319–1322 (1997).
McCombie et al., "Caenorhabditis elegans Expressed Sequence Tags Identify Gene Families and Potential Disease Gene Homologues," Nature Genetics 1:124–131 (1992).
Murakami et al., "A Genetic Pathway Conferring Life Extension and Resistance to UV Stress in Caenorhabditis elegans," Genetics 143:1207–1218 (1996).
Waterston et al., "A Survey of Expressed Genes in Caenorhabditis elegans," Nature Genetics 1:114–123 (1992).
Zwaal et al., "Target–Selected Gene Inactivation in Caenorhabditis elegans by Using a Frozen Transposon Insertion Mutant Bank," Proc. Natl. Acad. Sci. USA 90:7431–7435 (1993).

Gil et al., "Regulation of the Insulin–Like Developmental Pathway of Caenorhabditis elegans by a Homolog of the PTEN Tumor Suppressor Gene," Proc. Natl. Acad. Sci. USA 96:2925–2930 (1999).
Arpagaus, Vertebrate insulin induces diapause termination in Pieris brassicae pupae, Roux's Arch. Dev. Biol., 196:527–530 (1987).
Baker et al., A novel mesoderm inducer, Madr2, functions in the activin signal transduction pathway, Genes and Development, 10:1880–1889 (1996).
Bargmann et al., Control of Larval Development by Chemosensory Neurons in Caenorhabditis elegans, Science, 251:1243–1246 (1991).
Brown–Borg et al., Dwarf mice and the ageing process, Nature, 384:33 (1996).
Brüning et al., Development of a Novel Polygenic Model of NIDDM in Mice Heterozygous for IR and IRS–1 Null Alleles, Cell, 88:561–572 (1997).
Coleman, Obesity Genes: Beneficial Effects in Heterozygous Mice, Science, 203:663–665 (1979).
Dorman et al., The age–1 and daf–2 Genes Function in a Common Pathway to Control the Lifespan of Caenorhabditis elegans, Genetics, 141:1399–1406 (1995).
Ebina et al., The Human Insulin Receptor cDNA: The Structural Basis for Hormone–Activated Transmembrane Signalling, Cell, 40:747–758 (1985).
Estevez et al., The daf–4 gene encodes a bone morphogenetic protein receptor controlling C. elegans dauer larva development, Nature, 365:644–649 (1993).
Ewbank et al., Structural and Functional Conservation of the Caenorhabditis elegans Timing Gene clk–1, Science, 275:980–983 (1997).
Fernandez et al., The Drosophila insulin receptor homolog: a gene essential for embryonic development encodes two receptor isoforms with different signaling potential, EMBO J., 14:3373–3384 (1995).
Georgi et al., daf–1, a C. elegans Gene Controlling Dauer Larva Development, Encodes a Novel Receptor Protein Kinase, Cell, 61:635–645 (1990).
Golden et al., The Caenorhabditis elegans Dauer Larva: Developmental Effects of Pheromone, Food, and Temperature, Developmental Biology, 102:368–378 (1984).
Golden et al., A pheromone–induced developmental switch in Caenorhabditis elegans: Temperature–sensitive mutants reveal a wild–type temperature–dependent process, Proc. Natl. Proc. Acad. Sci. U.S.A., 81:819–823 (1984).
Gottlieb et al., daf–2, daf–16 and daf–23: Genetically Interacting Genes Controlling Dauer Formation in Caenorhabditis elegans, Genetics, 137:107–120 (1994).

(List continued on next page.)

Primary Examiner—Deborah J. R. Clark
Assistant Examiner—Sumesh Kaushal
(74) Attorney, Agent, or Firm—Clark & Elbing LLP

(57) ABSTRACT

Disclosed herein are novel genes and methods for the screening of therapeutics useful for treating impaired glucose tolerance conditions, as well as diagnostics and therapeutic compositions for identifying or treating such conditions.

6 Claims, 45 Drawing Sheets

OTHER PUBLICATIONS

Graff et al., Xenopus Mad Proteins Transduce Distinct Subsets of Signals for the TGFβ Superfamily, *Cell*, 85:479–487 (1996).

Green et al., Responses of Embryonic Xenopus Cells to Activin and FGF Are Separated by Multiple Dose Thresholds and Correspond to Distinct Axes of the Mesoderm, *Cell*, 71:731–739 (1992).

Hahn et al., DPC4, A Candidate Tumor Suppressor Gene at Human Chromosome 18q21.1, *Science*, 271:350–353 (1996).

Hemmings, Akt Signaling: Linking Membrane Events to Life and Death Decisions, *Science*, 275:628–630 (1997).

Hetru et al., Isolation and structural characterization of an insulin–related molecule, a predominant neuropeptide from *Locusta migratoria, Eur. J. Biochem.*, 201:495–499 (1991).

Hoodless et al., MADR1, a MAD–Related Protein That Functions in BMP2 Signaling Pathways, *Cell*, 85:489–500 (1996).

Hotamisligil et al., Adipose Expression of Tumor Necrosis Factor–α: Direct Role in Obesity–Linked Insulin Resistance, *Science*, 259:87–91 (1993).

Hubbard et al., Crystal structure of the tyrosine kinase domain of the human insulin receptor, *Nature*, 372:746–754 (1994).

Jonas et al., Regulation by insulin of a unique neuronal $Ca^{2+}$ pool and of neuropeptide secretion, *Nature*, 385:343–346 (1997).

Kahn et al., Genetics of Non–Insulin–Dependent (Type–II) Diabetes Mellitus, *Annu. Rev. Med.*, 47:509–531 (1996).

Kawakami et al., Molecular Cloning of the *Bombyx mori* Prothoracicotropic Hormone, *Science*, 247:1333–1335 (1990).

Kenyon et al., A *C. elegans* mutant that lives twice as long as wild type, *Nature*, 366:461–464 (1993).

Kim et al., Detection of mutations in the insulin receptor gene in patients with insulin resistance by analysis of single–stranded conformational polymorphisms, *Diabetologia*, 35:261–266 (1992).

Kimble, Alterations in Cell Lineage following Laser Ablation of Cells in the Somatic Gonad of *Caenorhabditis elegans, Developmental Biology*, 87:286–300 (1981).

Klass, A Method for the Isolation of Longevity Mutants in the Nematode *Caenorhabditis elegans* and Initial Results, *Mechanisms of Ageing and Dev.*, 22:279–286 (1983).

Krause, Transcription and Translation, Chapter 20, *Methods Cell Biol.*, Academic Press, San Diego, CA, 48:483–512 (1995).

Lagna et al., Partnership between DPC4 and SMAD proteins in TGF–β signalling pathways, *Nature*, 383:832–836 (1996).

Larsen et al., Genes that Regulate Both Development and Longevity in *Caenorhabditis elegans, Genetics*, 139:1567–1583 (1995).

Liu et al., A human Mad protein acting as a BMP–regulated transcriptional activator, *Nature*, 381:620–623 (1996).

Lonnqvist et al., Overexpression of the obese (ob) gene in adipose tissue of human obese subjects, *Nat. Med.* 1:950–953 (1995).

Macias–Silva et al., MADR2 Is a Substrate of the TGFβ Receptor and Its Phosphorylation Is Required for Nuclear Accumulation and Signaling, *Cell*, 87:1215–1224 (1996).

Malone et al., A Screen for Nonconditional Dauer–Constitutive Mutations in *Caenorhabditis elegans, Genetics*, 136:879–886, (1994).

Mathews et al., Regulation of insulin–like growth factor I gene expression by growth hormone, *Proc. Natl. Acad. Sci. U.S.A.*, 83:9343–9347 (1986).

Mello et al., Efficient gene transfer in *C. elegans*: extrachromosomal maintenance and integration of transforming sequences, *EMBO J.*, 10:3959–3970 (1991).

Morris et al., A phosphatidylinositol–3–OH kinase family member regulating longevity and diapause in *Caenorhabditis elegans, Nature*, 382:536–539 (1996).

Nagasawa et al., Amino–Terminal Amino Acid Sequence of the Silkworm Prothoracicotropic Hormone: Homology with Insulin, *Science*, 266:1344–1345 (1984).

Ogg et al., The Fork head transcription factor DAF–16 transduces insulin–like metabolic and longevity signals in *C. elegans, Nature*, 389:994–999 (1997).

O'Riordan et al., Intermediary Metabolism in the Dauer Larva of the Nematode *Caenorhabditis elegans*–II. The Glyoxylate Cycle and Fatty–Acid Oxidation, *Comp. Biochem. & Physiol.*, 95B:125–130 (1990).

O'Riordan et al., Intermediary Metabolism in the Dauer Larva of the Nematode *Caenorhabditis elegans*–I. Glycolysis, Gluconeogenesis, Oxidative Phosphorylation and the Tricarboxylic Acid Cycle, *Comp. Biochem. & Physiol.*, 92B:233–238 (1989).

Popham et al., Aspects of the fine structure of the dauer larva of the nematode *Caenorhabditis elegans, Can. J. Zool.*, 57:794–800 (1979).

Reinhardt et al., Selective Coexpression of Insulin Receptor–related Receptor (IRR) and TRK in NGF–Sensitive Neurons, *J. Neurosci.*, 14:4674–4683 (1994).

Ren et al., Control of *C. elegans* Larval Development by Neuronal Expression of a TGF–β Homolog, *Science*, 274:1389–1391 (1996).

Riddle et al., Interacting genes in nematode dauer larva formation, *Nature*, 290:668–671 (1981).

Riddle, D. et al., Genetic and Environmental Regulation of Dauer Larva Develompent, *C. elegans* II, pp. 739–768 (1997).

Roovers et al., Characterization of a putative molluscan insulin–related peptide receptor, *Gene*, 162:181–188 (1995).

Savage et al., *Caenorhabditis elegans* genes sma–2, sma–3, and sma–4 define a conserved family of transforming growth factor β pathway components, *PNAS*, 93:790–794 (1996).

Schackwitz et al., Chemosensory Neurons Function in Parallel to Mediate a Pheromone Response in *C. elegans, Neuron*, 17:719–728 (1996).

Shier et al., Primary Structure of a Putative Receptor for a Ligand of the Insulin Family, *J. Biol. Chem.*, 264:14605–14608 (1989).

Songyang et al., SH2 Domains Recognize Specific Phosphopeptide Sequences, *Cell*, 72:767–778 (1993).

Swanson et al., Critical Periods in the Development of the *Caenorhabditis elegans* Dauer Larva, *Developmental Biology*, 84:27–40 (1981).

Taylor, Lilly Lecture: Molecular Mechanisms of Insulin Resistance, *Diabetes*, 41:1473–1490 (1992).

Thomas et al., Evidence for Parallel Processing of Sensory Information Controlling Dauer Formation in *Caenorhabditis elegans, Genetics*, 134:1105–1117 (1993).

Ullrich et al., Human insulin receptor and its relationship to the tyrosine kinase family of oncogenes, *Nature*, 313:756–761 (1985).

Ullrich et al., Insulin–like growth factor I receptor primary structure: comparison with insulin receptor suggests structural determinants that define functional specificity, *EMBO J.*, 5:2503–2512 (1986).

Vowels et al., Genetic Analysis of Chemosensory Control of Dauer Formation in *Caenorhabditis elegans, Genetics*, 130:105–123 (1992).

Wadsworth et al., Developmental Regulation of Energy Metabolism in *Caenorhabditis elegans, Develop. Biol.*, 132:167–173 (1989).

White et al., The Insulin Signaling System, *J. Biol. Chem.*, 269:1–4 (1994).

Wrana et al., MAD–related proteins in TGF–$\beta$ signalling, *Trends Genet.*, 12:493–496 (1996).

Yoshimasa et al., Effects of Amino Acid Replacements within the Tetrabasic Cleavage Site on the Processing of the Human Insulin Receptor Precursor Expressed in Chinese Hamster Ovary Cells, *J. Biol. Chem.*, 265:17230–17237 (1990).

Zhang et al., Receptor–associated Mad homologues synergize as effectors of the TGF–$\beta$ response, *Nature*, 383:168–172 (1996).

\* cited by examiner

```
   1 MTSLMLLLLLFAFVQPCASIVEKRCGPIDIRNRPWDIKPQWSKLGDPNEKDLAGQRMVNCT
  61 VVEGSLTISFVLKHKTKAQEEMHRSLQPRYSQDEFITFPHLREITGTLLVFETEGLVDLR
 121 KIFPNLRVIGGRSLIQHYALIIYRNPDLEIGLDKLSVIRNGGVRIIDNRKLCYTKTIDWK
 181 HLITSSINDVVVDNAAEYAVTETGLMCPRGACEEDKGESKCHYLEEKNQEQGVERVQSCW
 241 SNTTCQKSCAYDRLLPTKEIGPGCDANGDRCHDQCVGGCERVNDATACHACKNVYHKGKC
 301 IEKCDAHLYLLLQRRCVTREQCLQLNPVLSNKTVPIKATAGLCSDKCPDGYQINPDDHRE
 361 CRKCVGKCEIVQEINHVIDTFPKAQAIRLCNIIDGNLTIEIRGKQDSGMASELKDIFANI
 421 HTITGYLLVRQSSPFISLNMFRNLRRIEAKSLFRNLYAITVFENPNLKKLFDSTTDLTLD
 481 RGTVSIANNKMLCFKYIKQLMSKLNIPLDPIDQSEGTNGEKAICEDMAINVSITAVNADS
 541 VFFSWPSFNITDIDQRKFLGYELFFKEVPRIDENMTIEEDRSACVDSWQSVFKQYYETSN
 601 GEPTPDIFMDIGPRERIRPNTLYAYYVATQMVLHAGAKNGVSKIGFVRTSYYTPDPPTLA
 661 LAQVDSDAIHITWEAPLQPNGDLTHYTIMWRENEVSPYEEAEKFCTDASTPANRQRTKDP
 721 KETIVADKPVDIPSSRTVAPTLLTMMGHEDQQKTCAATPGCCSCSAIEESSEQNKKKRPD
 781 PMSAIESSAFENKLLDEVLMPRDTMRVRRSIEDANRVSEELEKAENLGKAPKTLGGKKPL
 841 IHISKKKPSSSSTTSTPAPTIASMYALTRKPTTVPGTRIRLYEIYEPLPGSWAINVSALA
 901 LDNSYVIRNLKHYTLYAISLSACQNMTVPGASCSISHRAGALKRTKHITDIDKVLNETIE
 961 WRFMNNSQQVNVTWDPPTEVNGGIFGYVVKLKSKVDGSIVMTRCVGAKRGYSTRNQGVLF
1021 QNLADGRYFVSVTATSVHGAGPEAESSDPIVVMTPGFFTVEIILGMLLVFLILMSIAGCI
1081 IYYYIQVRYGKKVKALSDFMQLNPEYCVDNKYNADDWELRQDDVVLGQQCGEGSFGKVYL
1141 GTGNNVVSLMGDRFGPCAIKINVDDPASTENLNYLMEANIMKNFKTNFIVQLYGVISTVQ
1201 PAMVVMEMMDLGNLRDYLRSKREDEVFNETDCNFFDIIPRDKFHEWAAQICDGMAYLESL
1261 KFCHRDLAARNCMINRDETVKIGDFGMARDLFYHDYYKPSGKRMMPVRWMSPESLKDGKF
1321 DSKSDVWSFGVVLYEMVTLGAQPYIGLSNDEVLNYIGMARKVIKKPECCENYWYKVMKMC
1381 WRYSPRDRPTFLQLVHLIAAEASPEFRDLSFVLTDNQMILDDSEALDLDDIDDTDMNDQV
1441 VEVAPDVENVEVQSDSERRNTDSIPLKQFKTIPPINATTSHSTISIDETPMKAKQREGSL
1501 DEEYALMNHSGGPSDAEVRTYAGDGDYVERDVRENDVPTRRNTGASTSSYTGGGPYCLTN
1561 RGGSNERGAGFGEAVRLTDVGSGHLNDDDYVEKEISSMDTRRSTGASSSSYGVPQTNWS
1621 GNRGATYYTSKAQQAATAAAAAAALQQQQNGGRGDRLTQLPGTGHLQSTRGGQDGDYIE
1681 TEPKNYRNNGSPSRNGNSRDIFNGRSAFGENEHLIEDNEHHPLV
```

Fig. 2A

```
   1  ggtttaatta cccaagtttg agctccaaga gcacacatct gatcgtcgga
  51  ttctactgta ctccccgaaa aaccaacaaa aaacacaagt ttttgaacac
 101  ttgtaaatgc agacagaacg atgacgagaa tgaatattgt cagatgtcgg
 151  agacgacaca aaatttggaa aaatttggaa gaagagaatc tcggcccgag
 201  ctgctcgtcg acgacttcaa caaccgctgc caccgaagct ctcggaacaa
 251  ccactgagga tatgaggctt aagcagcagc gaagctcgtc gcgtgccacg
 301  gagcacgata ttgtcgacgg caatcaccac gacgacgagc acatcacaat
 351  gagacggctt cgacttgtca aaaattcgcg gacgcggcgt agaacgacgc
 401  ccgattcaag tatggactgc tatgaggaaa acccgccatc acaaaaactt
 451  caataaatta ttcttggatt tctaaaaagt catcaatgac gtcattaatg
 501  cttttactgc tattcgcttt tgtacagccg tgtgcctcaa tagtcgaaaa
 551  acgatgcggc ccaatcgata ttcgaaatag gccgtgggat attaagccgc
 601  aatggtcgaa acttggtgat ccgaacgaaa aagatttggc tggtcagaga
 651  atggtcaact gcacagtggt ggaaggttcg ctgacaatct catttgtact
 701  gaaacacaag acaaaagcac aagaagaaat gcatcgaagt ctacagccaa
 751  gatattccca agacgaattt atcactttc cgcatctacg tgaaattact
 801  ggaactctgc tcgttttga gactgaagga ttagtggatt tgcgtaaaat
 851  tttcccaaat cttcgtgtaa ttggaggccg ttcgctgatt caacactatg
 901  cgctgataat ttatcgaaat ccggatttgg agatcggtct tgacaagctt
 951  tccgtaattc gaaatggtgg tgtacggata atcgataatc gaaaactgtg
1001  ctacacgaaa acgattgatt ggaaacattt gatcacttct tccatcaacg
1051  atgttgtcgt tgataatgct gccgagtacg ctgtcactga gactggattg
1101  atgtgcccac gtggagcttg cgaagaggat aaaggcgaat caaagtgtca
1151  ttatttggag gaaaagaatc aggaacaagg tgtcgaaaga gttcagagtt
1201  gttggtcgaa caccacttgc caaaagtctt gtgcttatga tcgtcttctt
1251  ccaacgaaag aaatcggacc gggatgtgat gcgaacggcg atcgatgtca
1301  cgatcaatgc gtgggcggtt gtgagcgtgt gaatgatgcc acagcatgcc
1351  acgcgtgcaa gaatgtctat cacaagggaa agtgtatcga aagtgtgat
1401  gctcacctgt accttctcct tcaacgtcgt tgtgtgaccc gtgagcagtg
1451  tctgcagctg aatccggtgc tctcgaacaa aacagtgcct atcaaggcga
1501  cggcaggcct ttgctcggat aaatgtcccg atggttatca aatcaacccg
1551  gatgatcatc gagaatgccg aaaatgcgtt ggcaagtgtg agattgtgtg
1601  cgagatcaat cacgtcattg atacgtttcc gaaggcacag gcgatcaggc
1651  tatgcaatat tattgacgga aatctgacga tcgagattcg cggaaaacag
1701  gattcgggaa tggcgtccga gttgaaggat atatttgcga acattcacac
1751  gatcaccggc tacctgttgg tacgtcaatc gtcaccgttt atctcgttga
1801  acatgttccg gaatttacga cgtattgagg caaagtcact gttcagaaat
1851  ctatatgcta tcacagtttt tgaaaatccg aatttaaaaa agctattcga
1901  ttcaacgacg gatttgacgc ttgatcgtgg aactgtgtca attgccaata
1951  acaagatgtt atgcttcaag tatatcaagc agctaatgtc aaagttaaat
2001  ataccactcg atccgataga tcaatcagaa gggacaaatg gtgagaaggn
2051  aatctgtgag gatatggcaa tcaacgtgag catcacagcg gtcaacgcgg
2101  actcggtctt ctttagttgg ccctcattca acattaccga tatagatcag
2151  cgaaagtttc tcggctacga gctcttcttc aaagaagtcc cacgaatcga
2201  tgagaacatg acgatcgaag aggatcgaag tgcgtgtgtc gattcgtggc
2251  agagtgtctt caaacagtac tacgagacgt cgaacggtga accgaccccg
2301  gacatttta tggatattgg accgcgcgag cgaattcggc gaatacgct
2351  ctacgcgtac tatgtggcga cgcagatggt gttgcatgcc ggtgcgaaga
2401  acggtgtatc gaagattggt tttgtgagga cgagctacta tacgcctgat
2451  cctccgacgt tggcactagc gcaagtcgat tcggacgcta ttcatattac
2501  gtgggaagcg ccgctccaac cgaacggaga cctcacgcat tacacaatta
2551  tgtggcgtga gaatgaagtg agcccgtacg aggaagccga aaagttttgt
2601  acagatgcaa gcaccccgc aaatcgacaa cgcacgaaag atccgaaaga
2651  gacgattgta gccgataagc cagtcgatat tccgtcatca cgtaccgtag
2701  ctccgacact tttgactatg atgggtcacg aagatcagca gaaaacgtgc
```

```
2751  gctgcaacgc ccggttgttg ttcgtgttcg gctatcgaag aatcatcgga
2801  acagaacaag aagaagcgac cggatccgat gtcggcgatc gaatcatctg
2851  catttgagaa taagctgttg gatgaggttt taatgccgag agacacgatg
2901  cgagtgagac gatcaattga agacgcgaat cgagtcagtg aagagttgga
2951  aaaagctgaa aatttgggaa aagctccaaa aactctcggt ggaaagaagc
3001  cgctgatcca tatttcgaag aagaagccgt cgagcagcag caccacatcc
3051  acaccggctc caacgatcgc atcaatgtat gccttaacaa ggaaaccgac
3101  tacggtgccg ggaacaagga ttcggctcta cgagatctac gaacctttac
3151  ccggaagctg ggcgattaat gtatcagctc tggcattgga taatagttat
3201  gtgatacgaa atttgaagca ttacacactt tatgcgattt ctctatccgc
3251  gtgccaaaac atgacagtac ccggagcatc ttgctcaata tcccatcgtg
3301  cgggagcatt gaaacgaaca aaacacatca cagacattga taaagtgttg
3351  aatgaaacaa ttgaatggag atttatgaat aatagtcaac aagtcaacgt
3401  gacgtgggat ccaccgactg aagtgaatgg tggaatattc ggttatgttg
3451  taaagcttaa gtcaaaagtc gatggatcaa ttgttatgac gagatgtgtc
3501  ggtgcgaaga gaggatattc aacacggaat cagggtgtcc tattccagaa
3551  tttggccgat ggacgttatt ttgtctcagt aacggcgacc tctgtacacg
3601  gcgctggacc ggaagccgaa tcctccgacc caatcgtcgt catgacgcca
3651  ggcttcttca ctgtggaaat cattctcggc atgcttctcg tcttttttgat
3701  tttaatgtca attgccggtt gtataatcta ctactacatt caagtacgct
3751  acggcaaaaa agtgaaagct ctatctgact ttatgcaatt gaatcccgaa
3801  tattgtgtgg acaataagta caatgcagac gattgggagc tacggcagga
3851  tgatgttgtg ctcggacaac agtgtggaga gggatcattc ggaaaagtgt
3901  acctaggaac tggaaataat gttgtttctc tgatgggtga tcgtttcgga
3951  ccgtgtgcta ttaagattaa tgtagatgat ccagcgtcga ctgagaatct
4001  caactatctc atggaagcta atattatgaa gaactttaag actaacttta
4051  tcgtccaact gtacggagtt atctctactg tacaaccagc gatggttgtg
4101  atggaaatga tggatcttgg aaatctccgt gactatctcc gatcgaaacg
4151  cgaagacgaa gtgttcaatg agacggactg caactttttc gacataatcc
4201  cgagggataa attccatgag tgggccgcac agatttgtga tggtatggcg
4251  tacctggagt cgctcaagtt ttgccatcga gatctcgccg cacgtaattg
4301  catgataaat cgggatgaga ctgtcaagat tggagatttc ggaatggctc
4351  gtgatctatt ctatcatgac tattataagc catcgggcaa gcgtatgatg
4401  cctgttcgat ggatgtcacc cgagtcgttg aaagacggaa agtttgactc
4451  gaaatctgat gtttggagct tcggagttgt tctctatgaa atggttacac
4501  tcggtgctca gccatatatt ggtttgagta atgatgaggt gttgaattat
4551  attggaatgg cccggaaggt tatcaagaag cccgaatgtt gtgaaaacta
4601  ttggtataag gtgatgaaaa tgtgctggag atactcacct cgggatcgtc
4651  cgacgttcct ccagctcgtt catcttctag cagctgaagc ttcaccagaa
4701  ttccgagatt tatcatttgt cctaaccgat aatcaaatga tccttgacga
4751  ttcagaagca ctggatcttg atgatattga tgatactgat atgaatgatc
4801  aggttgtcga ggtggcaccg gatgttgaga acgtcgaggt tcagagtgat
4851  tcggaacgtc ggaatacgga ttcaataccg ttgaaacagt ttaagacgat
4901  ccctccgatc aatgcgacga cgagtcattc gacaatatcg attgatgaga
4951  caccgatgaa agcgaagcag cgagaaggat cgctggatga ggagtacgca
5001  ttgatgaatc atagtggagg tccgagtgat gcggaagttc ggacgtatgc
5051  tggtgatgga gattatgtgg agagagatgt tcgagagaat gatgtgccaa
5101  cgcgacgaaa tactggtgca tcaacatcaa gttacacagg tggtggtcca
5151  tattgcctaa caaatcgtgg tggttcaaat gaacgaggag ccggtttcgg
5201  tgaagcagta cgattaactg atggtgttgg aagtggacat taaatgatg
5251  atgattatgt tgaaaaagag atatcatcca tggatacgcg ccggagcacg
5301  ggcgcctcga gctcttccta cggtgttcca cagacgaatt ggagtggaaa
5351  tcgtggtgcc acgtattata cgagtaaagc tcaacaggca gcaactgcag
5401  cagcagcagc agcagcagct ctccaacagc aacaaaatgg tggtcgaggc
5451  gatcgattaa ctcaactacc cggaactgga catttacaat cgacacgtgg
5501  tggacaagat ggagattata ttgaaactga accgaaaaat tatagaaata
```

```
5551  atggatctcc atcgcgaaac ggcaacagcc gtgacatttt caacggacgt
5601  tcggctttcg gtgaaaatga gcatctaatc gaggataatg agcatcatcc
5651  acttgtctga aaccccaaa aaatcccgcc tcttaaatta taaattatct
5701  cccacattat catatctcta cacgaatatc ggattttttt tcagattttt
5751  tctgaaaaat tctgaataat tttacccat ttttcaaatc tctgtatttt
5801  tttttgttat tacccc
```

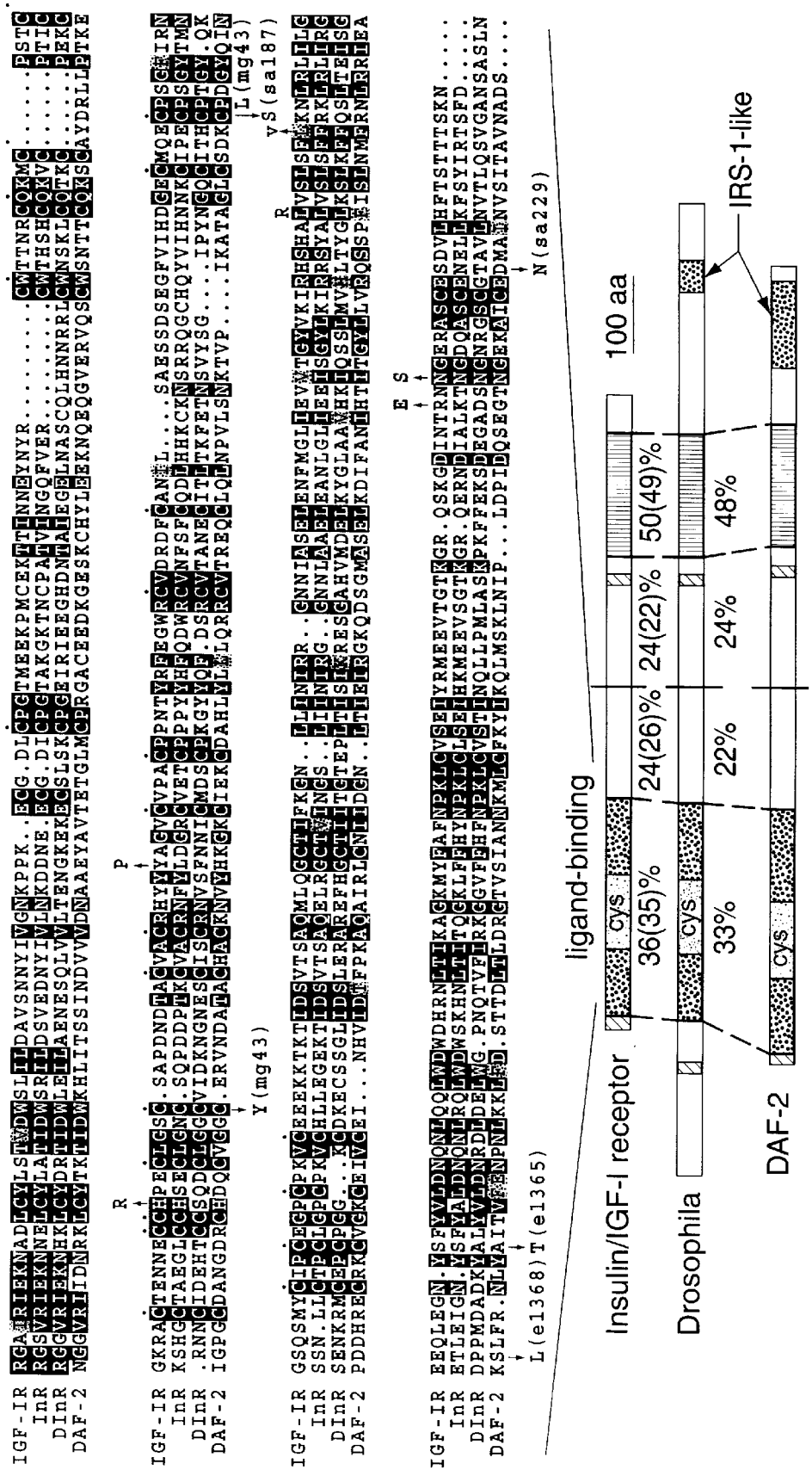
Fig. 2C (sheet 1 of 2)

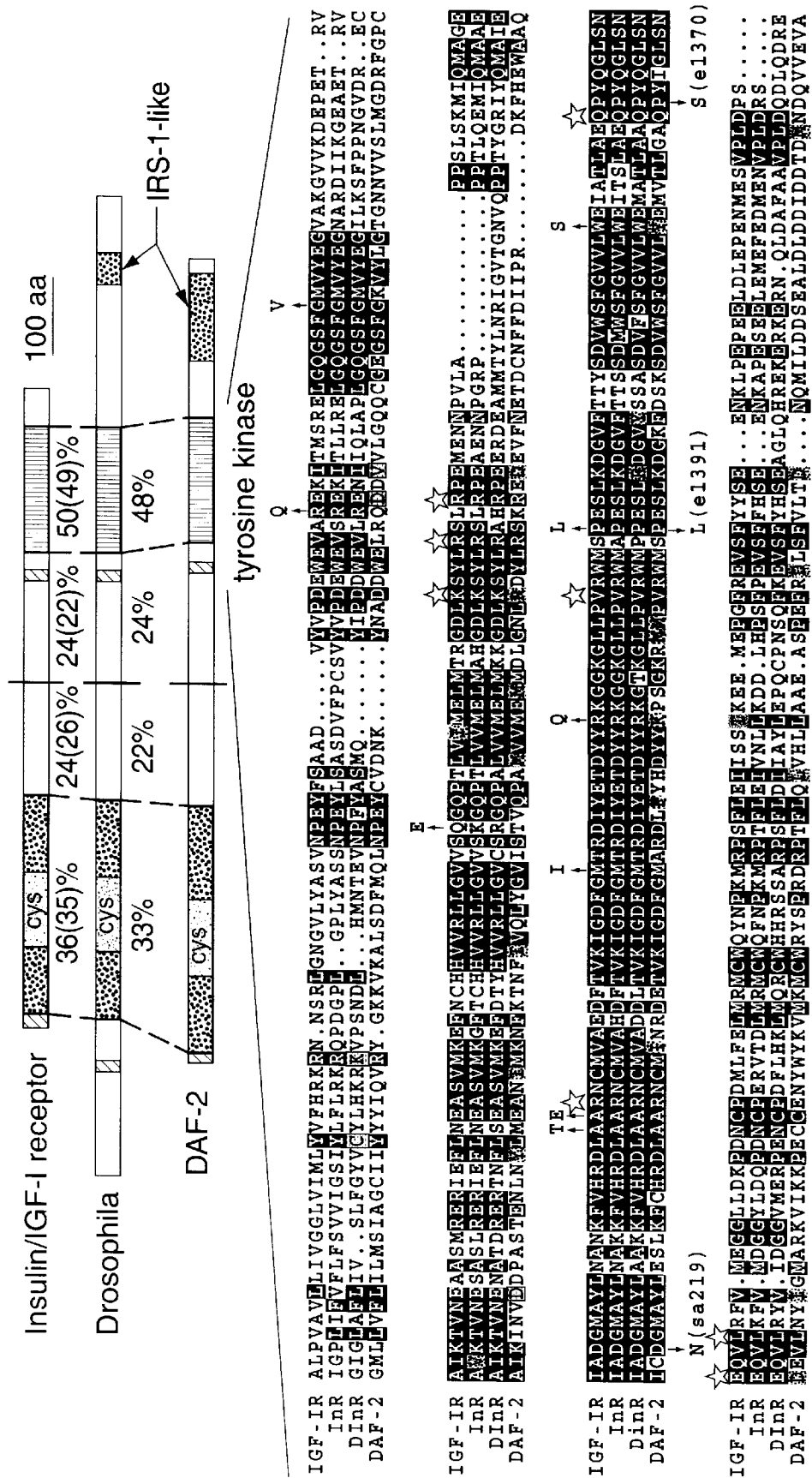
Fig. 2C (sheet 2 of 2)

Domain I

```
DAF-3   .NIDREFDQKACESLVKKLKDKKNDLQNLIDVVLSKGTKYTGCITIPRTLDG
         | ||||||||| || | ||      |    | ||  ||||||
DPC4    GGESETFAKRAIESLVKKLKEKKDELDSLITAITTNGAHPSKCVTIQRTLDG
            mg125 P->L
        RLQVHGRKGFPHVVYGKLWRFNEMTKNETRHVDHCKHAFEMKSDMVCVNPYH
        |||| |||||||| |   ||||   |||  || || | ||||||||
        RLQVAGRKGFPHVIYARLWRWPDLHKNELKHVKYCQYAFDLKCDSVCVNPYH
```

Domain II

```
DAF-3   IVYYEKNLQIGE..KKCSRGNFHVDGGFI..CSENRYSLGLEPNPIREPVAFKV
        |||    | ||    |      |         |    | ||  | |
DPC4    IAYFEMDVQVGETFKVPSSCPIVTVDGYVDPSGGDRFCLGQLSNVHRTEAIERA
            mg132  G->E
        RKAIVDGIRFSYKKDGSVWLQNRMKYPVFVTSGYLDEQSGGLKKDKVHKVYGCA
        |  |    |    | ||      ||| |    |||       ||| | |
        RLHIGKGVQLECKGEGDVWVRCLSDHAVFVQSYYLDREAGRAPGDAVHKIYPSA

SIKTFGFNVSKQIIRDALLSKQMA....TMYLQGKLTPMNYIYEKKTQEELRRE
        ||| |                  ||     |         |          |
        YIKVFDLRQCHRQMQQQAATAQAAAAAQAAAVAGNIPGPGSVGGIAPAISLSAA

ATRTTDSLAKYCCVRVSFCKGFGEAYPERPSIHDCPVWIELKINIAYDFMD
         |   |   |  |  || || ||||     |     ||| |    |  |
        AGIGVDDLRRLCILRMSFVKGWGPDYP.RQSIKETPCWIEIHLHRALQLLD
```

Fig. 5C

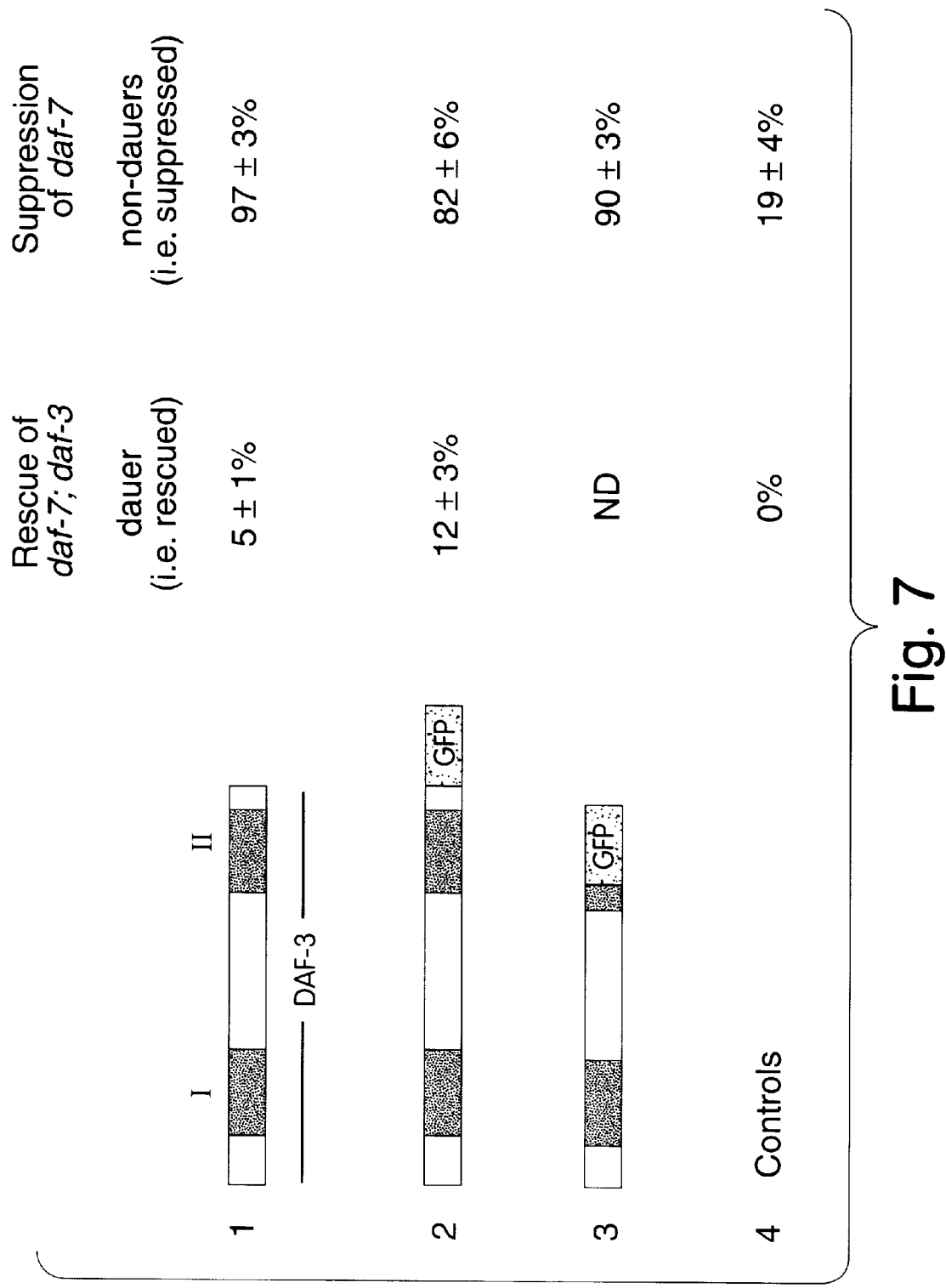

```
   1  atgaagctaa tagcaacttc tcttctagtt cccgacgagc acacaccgat
  51  gatgtcacca gtgaatacaa ctacaaagat tctacaacgg agtggtatta
 101  aaatggaaat cccgccatat ttggatccag acagtcagga tgatgacccg
 151  gaagatggtg tcaactaccc ggatccagat ttatttgaca caaaaaacac
 201  aaatatgacc gagtacgatt ggatgtgtt gaagcttgga aaaccagcag
 251  tagatgaagc acggaaaaag atcgaagttc ccgacgctag tgcgccgcca
 301  aacaaaattg tagaatattt gatgtattat agaacgttaa agaaagtga
 351  actcatacaa ctgaatgcgt atcggacaaa acgaaatcga ttatcgttga
 401  acttggtcaa aaacaatatt gatcgagagt tcgaccaaaa agcttgcgag
 451  tccctggtga aaaaattgaa ggataagaag aatgatctcc agaacctgat
 501  tgatgtggtt ctttcaaaag gtacaaaata taccggttgc attacaattc
 551  caaggacact tgatggccgg ttacaggtcc acggaagaaa aggtttccct
 601  cacgtagtct atggcaaact gtggaggttt aatgaaatga caaaaaacga
 651  aacgcgtcat gtggaccact gcaagcacgc atttgaaatg aaaagtgaca
 701  tggtatgcgt gaatccctat cactacgaaa ttgtcattgg aactatgatt
 751  gttgggcaga gggatcatga caatcgagat atgccgccgc cacatcaacg
 801  ctaccacact ccaggtcggc aggatccagt tgacgatatg agtagattta
 851  taccaccagc ttccattcgt ccgcctccga tgaacatgca cacaaggcct
 901  cagcctatgc ctcaacaatt gccttcagtt ggcgcaacgt ttgcccatcc
 951  tctcccacat caggcgccac ataacccagg ggtttcacat ccgtactcca
1001  ttgctccaca gacccattac ccgttgaaca tgaacccaat tccgcaaatg
1051  ccgcaaatgc cacaaatgcc accacctctc catcagggat atggaatgaa
1101  tgggccgagt tgctcttcag aaaacaacaa tccattccac caaaatcacc
1151  attataatga tattagccat ccaaatcact attcctacga ctgtggtccg
1201  aacttgtacg ggtttccaac tccttatccg gattttcacc atcctttcaa
1251  tcagcaacca caccagccgc acaactatc acaaaaccat acgtcccaac
1301  aaggcagtca tcaaccaggg caccaaggtc aggtaccgaa tgatccacca
1351  atttcaagac cagtgttaca accatcaaca gtcaccttgg acgtgttccg
1401  tcggtactgt agacagacat ttggaaatcg atttttgaa ggagaaagtg
1451  aacaatccgg cgcaataatt cggtctagta acaaattcat tgaagaattt
1501  gattcgccga tttgtggtgt gacagttgtt cgaccgcgga tgacagacgg
1551  tgaggttttg gagaacatca tgccggaaga tgcaccatat catgacattt
1601  gcaagttcat tttgaggctc acatcagaaa gtgtaacttt ctcaggagag
1651  gggccagaag ttagtgattt gaacgaaaaa tggggaacaa ttgtgtacta
1701  tgagaaaaat ttgcaaattg gcgagaaaaa atgttcgaga ggaaatttcc
1751  acgtggatgg cggattcatt tgctctgaga atcgttacag tctcggactt
1801  gagccaaatc caattagaga accagtggcg tttaaagttc gtaaagcaat
1851  agtggatgga attcgctttt cctacaaaaa agacgggagt gtttggcttc
1901  aaaaccgcat gaagtacccg gtatttgtca cttctgggta tctcgacgag
1951  caatcaggag gcctaaagaa ggataaagtg cacaaagttt acggatgtgc
2001  gtctatcaaa acgtttggct tcaacgtttc caaacaaatc atcagagacg
2051  cgcttctttc caagcaaatg gcaacaatgt acttgcaagg aaaattgact
```

```
2101  ccgatgaatt atatctacga gaagaagact caggaagagc tgcgaaggga
2151  agcaacacgc accactgatt cattggccaa gtactgttgt gtccgtgtct
2201  cgttctgcaa aggatttgga gaagcatacc cagaacgccc gtcaattcat
2251  gattgtccag tttggattga gttgaaaatc aacattgcct acgatttcat
2301  ggattcaatc tgccagtaca taaccaactg cttcgagccg ctaggaatgg
2351  aagattttgc aaaattggga atcaacgtca gtgatgacta aatgataact
2401  tttttcactc accctactag atactgattt agtcttattc caaatcatcc
2451  aacgatatca aacttttttcc tttgaacttt gcatactatg ttatcacaag
2501  ttccaagcag tttcaataca aacataggat atgttaacaa cttttgataa
2551  gaatcaagtt accaactgtt cattgtgagc tttgagctgt atagaaggac
2601  aatgtatccc atacctcaat ctttaatagt catcagtcac tggtcccgca
2651  ccaattttt  cgattcgcat atgtcatata ttgcaccgtg gccctttta
2701  ttgtaacttt taatatattt tcttcccaac ttgtgaatat gattgatgaa
2751  ccaccatttt gagtaataaa tgtattttt  gtgg
```

```
   1  gtaatcaaat  tgtaaaggaa  aaatattaat  agtcagagta  cacataaatg
  51  ggtgatcatc  ataatttaac  gggccttccc  ggtacctcca  tcccgccaca
 101  gttcaactat  tctcagcccg  gtaccagcac  cggaggcccg  ctttatggtg
 151  gaaaaccttc  tcatggattg  gaagatattc  ctgatgtaga  ggaatatgag
 201  aggaacctgc  tcggggctgg  agcaggtttt  aatctgctca  atgtaggaaa
 251  tatggctaat  gttcccgacg  agcacacacc  gatgatgtca  ccagtgaata
 301  caactacaaa  gattctacaa  cggagtggta  ttaaaatgga  aatcccgcca
 351  tatttggatc  cagacagtca  ggatgatgac  ccggaagatg  gtgtcaacta
 401  cccggatcca  gatttatttg  acacaaaaaa  cacaaatatg  accgagtacg
 451  atttggatgt  gttgaagctt  ggaaaaccag  cagtagatga  agcacggaaa
 501  aagatcgaag  ttcccgacgc  tagtgcgccg  ccaaacaaaa  ttgtagaata
 551  tttgatgtat  tatagaacgt  taaaagaaag  tgaactcata  caactgaatg
 601  cgtatcggac  aaaacgaaat  cgattatcgt  tgaacttggt  caaaaacaat
 651  attgatcgag  agttcgacca  aaaagcttgc  gagtccctgg  tgaaaaaatt
 701  gaaggataag  aagaatgatc  tccagaacct  gattgatgtg  gttctttcaa
 751  aaggtacaaa  atataccggt  tgcattacaa  ttccaaggac  acttgatggc
 801  cggttacagg  tccacggaag  aaaaggtttc  cctcacgtag  tctatggcaa
 851  actgtggagg  tttaatgaaa  tgacaaaaaa  cgaaacgcgt  catgtggacc
 901  actgcaagca  cgcatttgaa  atgaaaagtg  acatggtatg  cgtgaatccc
 951  tatcactacg  aaattgtcat  tggaactatg  attgttgggc  agagggatca
1001  tgacaatcga  gatatgccgc  cgccacatca  acgctaccac  actccaggtc
1051  ggcaggatcc  agttgacgat  atgagtagat  ttataccacc  agcttccatt
1101  cgtccgcctc  cgatgaacat  gcacacaagg  cctcagccta  tgcctcaaca
1151  attgccttca  gttggcgcaa  cgtttgccca  tcctctccca  catcaggcgc
1201  cacataaccc  aggggtttca  catccgtact  ccattgctcc  acagacccat
1251  tacccgttga  acatgaaccc  aattccgcaa  atgccgcaaa  tgccacaaat
1301  gccaccacct  ctccatcagg  gatatggaat  gaatgggccg  agttgctctt
1351  cagaaaacaa  caatccattc  caccaaaatc  accattataa  tgatattagc
1401  catccaaatc  actattccta  cgactgtggt  ccgaacttgt  acgggtttcc
1451  aactccttat  ccggattttc  accatccttt  caatcagcaa  ccacaccagc
1501  cgccacaact  atcacaaaac  catacgtccc  aacaaggcag  tcatcaacca
1551  gggcaccaag  gtcaggtacc  gaatgatcca  ccaatttcaa  gaccagtgtt
1601  acaaccatca  acagtcacct  tggacgtgtt  ccgtcggtac  tgtagacaga
1651  catttggaaa  tcgattttt   gaaggagaaa  gtgaacaatc  cggcgcaata
1701  attcggtcta  gtaacaaatt  cattgaagaa  tttgattcgc  cgatttgtgg
1751  tgtgacagtt  gttcgaccgc  ggatgacaga  cggtgaggtt  ttggagaaca
1801  tcatgccgga  agatgcacca  tatcatgaca  tttgcaagtt  catttttgagg
1851  ctcacatcag  aaagtgtaac  tttctcagga  gagggccag   aagttagtga
1901  tttgaacgaa  aaatggggaa  caattgtgta  ctatgagaaa  aatttgcaaa
1951  ttggcgagaa  aaaatgttcg  agaggaaatt  tccacgtgga  tggcggattc
2001  atttgctctg  agaatcgtta  cagtctcgga  cttgagccaa  atccaattag
2051  agaaccagtg  gcgtttaaag  ttcgtaaagc  aatagtggat  ggaattcgct
```

```
2101  tttcctacaa aaaagacggg agtgtttggc ttcaaaaccg catgaagtac
2151  ccggtatttg tcacttctgg gtatctcgac gagcaatcag gaggcctaaa
2201  gaaggataaa gtgcacaaag tttacggatg tgcgtctatc aaaacgtttg
2251  gcttcaacgt ttccaaacaa atcatcagag acgcgcttct ttccaagcaa
2301  atggcaacaa tgtacttgca aggaaaattg actccgatga attatatcta
2351  cgagaagaag actcaggaag agctgcgaag ggaagcaaca cgcaccactg
2401  attcattggc caagtactgt tgtgtccgtg tctcgttctg caaaggattt
2451  ggagaagcat acccagaacg cccgtcaatt catgattgtc cagtttggat
2501  tgagttgaaa atcaacattg cctacgattt catggattca atctgccagt
2551  acataaccaa ctgcttcgag ccgctaggaa tggaagattt tgcaaaattg
2601  ggaatcaacg tcagtgatga ctaaatgata acttttttca ctcaccctac
2651  tagatactga tttagtctta ttccaaatca tccaacgata tcaaactttt
2701  tcctttgaac tttgcatact atgttatcac aagttccaag cagtttcaat
2751  acaaacatag gatatgttaa caacttttga taagaatcaa gttaccaact
2801  gttcattgtg agctttgagc tgtatagaag gacaatgtat cccatacctc
2851  aatctttaat agtcatcagt cactggtccc gcaccaattt tttcgattcg
2901  catatgtcat atattgcacc gtggcccttt ttattgtaac ttttaatata
2951  tttcttccc aacttgtgaa tatgattgat gaaccaccat tttgagtaat
3001  aaatgtattt tttgtgg
```

```
   1  gtaatcaaat tgtaaaggaa aaatattaat agtcagagta cacataaatg
  51  ggtgatcatc ataatttaac gggccttccc ggtacctcca tcccgccaca
 101  gttcaactat tctcagcccg gtaccagcac cggaggcccg ctttatggtg
 151  gaaaaccttc tcatggattg gaagatattc ctgatgtaga ggaatatgag
 201  aggaacctgc tcggggctgg agcaggtttt aatctgctca atgtaggaaa
 251  tatggctaat gaatttaaac caataatcac attggacacg aaaccacctc
 301  gtgatgccaa caagtcattg gcattcaatg gcgggttgaa gctaatcact
 351  ccgaaaactg aagttcccga cgagcacaca ccgatgatgt caccagtgaa
 401  tacaactaca aagattctac aacggagtgg tattaaaatg gaaatcccgc
 451  catatttgga tccagacagt caggatgatg acccggaaga tggtgtcaac
 501  tacccggatc cagatttatt tgacacaaaa aacacaaata tgaccgagta
 551  cgatttggat gtgttgaagc ttggaaaacc agcagtagat gaagcacgga
 601  aaaagatcga agttcccgac gctagtgcgc cgccaaacaa aattgtagaa
 651  tatttgatgt attatagaac gttaaaagaa agtgaactca tacaactgaa
 701  tgcgtatcgg acaaaacgaa atcgattatc gttgaacttg gtcaaaaaca
 751  atattgatcg agagttcgac caaaaagctt gcgagtccct ggtgaaaaaa
 801  ttgaaggata agaagaatga tctccagaac ctgattgatg tggttctttc
 851  aaaaggtaca aaatataccg gttgcattac aattccaagg acacttgatg
 901  gccggttaca ggtccacgga agaaaaggtt tccctcacgt agtctatggc
 951  aaactgtgga ggtttaatga aatgacaaaa aacgaaacgc gtcatgtgga
1001  ccactgcaag cacgcatttg aaatgaaaag tgacatggta tgcgtgaatc
1051  cctatcacta cgaaattgtc attggaacta tgattgttgg gcagagggat
1101  catgacaatc gagatatgcc gccgccacat caacgctacc acactccagg
1151  tcggcaggat ccagttgacg atatgagtag atttatacca ccagcttcca
1201  ttcgtccgcc tccgatgaac atgcacacaa ggcctcagcc tatgcctcaa
1251  caattgcctt cagttggcgc aacgtttgcc catcctctcc cacatcaggc
1301  gccacataac ccaggggttt cacatccgta ctccattgct ccacagaccc
1351  attcccgtt gaacatgaac ccaattccgc aaatgccgca aatgccacaa
1401  atgccaccac ctctccatca gggatatgga atgaatgggc cgagttgctc
1451  ttcagaaaac aacaatccat tccaccaaaa tcaccattat aatgatatta
1501  gccatccaaa tcactattcc tacgactgtg gtccgaactt gtacgggttt
1551  ccaactcctt atccggattt tcaccatcct ttcaatcagc aaccacacca
1601  gccgccacaa ctatcacaaa accatacgtc ccaacaaggc agtcatcaac
1651  cagggcacca aggtcaggta ccgaatgatc caccaatttc aagaccagtg
1701  ttacaaccat caacagtcac cttggacgtg ttccgtcggt actgtagaca
1751  gacatttgga aatcgatttt ttgaaggaga aagtgaacaa tccggcgcaa
1801  taattcggtc tagtaacaaa ttcattgaag aatttgattc gccgatttgt
1851  ggtgtgacag ttgttcgacc gcggatgaca gacggtgagg ttttggagaa
1901  catcatgccg gaagatgcac catatcatga catttgcaag ttcattttga
1951  ggctcacatc agaaagtgta actttctcag gagaggggcc agaagttagt
2001  gatttgaacg aaaaatgggg aacaattgtg tactatgaga aaaatttgca
2051  aattggcgag aaaaaatgtt cgagaggaaa tttccacgtg gatggcggat
```

```
2101  tcatttgctc tgagaatcgt tacagtctcg gacttgagcc aaatccaatt
2151  agagaaccag tggcgtttaa agttcgtaaa gcaatagtgg atggaattcg
2201  cttttcctac aaaaaagacg ggagtgtttg gcttcaaaac cgcatgaagt
2251  acccggtatt tgtcacttct gggtatctcg acgagcaatc aggaggccta
2301  aagaaggata aagtgcacaa agtttacgga tgtgcgtcta tcaaaacgtt
2351  tggcttcaac gtttccaaac aaatcatcag agacgcgctt ctttccaagc
2401  aaatggcaac aatgtacttg caaggaaaat tgactccgat gaattatatc
2451  tacgagaaga agactcagga agagctgcga agggaagcaa cacgcaccac
2501  tgattcattg gccaagtact gttgtgtccg tgtctcgttc tgcaaaggat
2551  ttggagaagc atacccagaa cgcccgtcaa ttcatgattg tccagtttgg
2601  attgagttga aaatcaacat tgcctacgat ttcatggatt caatctgcca
2651  gtacataacc aactgcttcg agccgctagg aatggaagat tttgcaaaat
2701  tgggaatcaa cgtcagtgat gactaaatga taactttttt cactcaccct
2751  actagatact gatttagtct tattccaaat catccaacga tatcaaactt
2801  tttcctttga actttgcata ctatgttatc acaagttcca agcagtttca
2851  atacaaacat aggatatgtt aacaactttt gataagaatc aagttaccaa
2901  ctgttcattg tgagctttga gctgtataga aggacaatgt atcccatacc
2951  tcaatcttta atagtcatca gtcactggtc ccgcaccaat tttttcgatt
3001  cgcatatgtc atatattgca ccgtggccct ttttattgta acttttaata
3051  tattttcttc ccaacttgtg aatatgattg atgaaccacc attttgagta
3101  ataaatgtat tttttgtgg
```

```
  1  MKLIATSLLV PDEHTPMMSP VNTTTKILQR SGIKMEIPPY LDPDSQDDDP
 51  EDGVNYPDPD LFDTKNTNMT EYDLDVLKLG KPAVDEARKK IEVPDASAPP
101  NKIVEYLMYY RTLKESELIQ LNAYRTKRNR LSLNLVKNNI DREFDQKACE
151  SLVKKLKDKK NDLQNLIDVV LSKGTKYTGC ITIPRTLDGR LQVHGRKGFP
201  HVVYGKLWRF NEMTKNETRH VDHCKHAFEM KSDMVCVNPY HYEIVIGTMI
251  VGQRDHDNRD MPPPHQRYHT PGRQDPVDDM SRFIPPASIR PPPMNMHTRP
301  QPMPQQLPSV GATFAHPLPH QAPHNPGVSH PYSIAPQTHY PLNMNPIPQM
351  PQMPQMPPPL HQGYGMNGPS CSSENNNPFH QNHHYNDISH PNHYSYDCGP
401  NLYGFPTPYP DFHHPFNQQP HQPPQLSQNH TSQQGSHQPG HQGQVPNDPP
451  ISRPVLQPST VTLDVFRRYC RQTFGNRFFE GESEQSGAII RSSNKFIEEF
501  DSPICGVTVV RPRMTDGEVL ENIMPEDAPY HDICKFILRL TSESVTFSGE
551  GPEVSDLNEK WGTIVYYEKN LQIGEKKCSR GNFHVDGGFI CSENRYSLGL
601  EPNPIREPVA FKVRKAIVDG IRFSYKKDGS VWLQNRMKYP VFVTSGYLDE
651  QSGGLKKDKV HKVYGCASIK TFGFNVSKQI IRDALLSKQM ATMYLQGKLT
701  PMNYIYEKKT QEELRREATR TTDSLAKYCC VRVSFCKGFG EAYPERPSIH
751  DCPVWIELKI NIAYDFMDSI CQYITNCFEP LGMEDFAKLG INVSDD
```

Fig. 12A

```
  1 MGDHHNLTGL PGTSIPPQFN YSQPGTSTGG PLYGGKPSHG LEDIPDVEEY
 51 ERNLLGAGAG FNLLNVGNMA NVPDEHTPMM SPVNTTTKIL QRSGIKMEIP
101 PYLDPDSQDD DPEDGVNYPD PDLFDTKNTN MTEYDLDVLK LGKPAVDEAR
151 KKIEVPDASA PPNKIVEYLM YYRTLKESEL IQLNAYRTKR NRLSLNLVKN
201 NIDREFDQKA CESLVKKLKD KKNDLQNLID VVLSKGTKYT GCITIPRTLD
251 GRLQVHGRKG FPHVVYGKLW RFNEMTKNET RHVDHCKHAF EMKSDMVCVN
301 PYHYEIVIGT MIVGQRDHDN RDMPPPHQRY HTPGRQDPVD DMSRFIPPAS
351 IRPPPMNMHT RPQPMPQQLP SVGATFAHPL PHQAPHNPGV SHPYSIAPQT
401 HYPLNMNPIP QMPQMPQMPP PLHQGYGMNG PSCSSENNNP FHQNHHYNDI
451 SHPNHYSYDC GPNLYGFPTP YPDFHHPFNQ QPHQPPQLSQ NHTSQQGSHQ
501 PGHQGQVPND PPISRPVLQP STVTLDVFRR YCRQTFGNRF FEGESEQSGA
551 IIRSSNKFIE EFDSPICGVT VVRPRMTDGE VLENIMPEDA PYHDICKFIL
601 RLTSESVTFS GEGPEVSDLN EKWGTIVYYE KNLQIGEKKC SRGNFHVDGG
651 FICSENRYSL GLEPNPIREP VAFKVRKAIV DGIRFSYKKD GSVWLQNRMK
701 YPVFVTSGYL DEQSGGLKKD KVHKVYGCAS IKTFGFNVSK QIIRDALLSK
751 QMATMYLQGK LTPMNYIYEK KTQEELRREA TRTTDSLAKY CCVRVSFCKG
801 FGEAYPERPS IHDCPVWIEL KINIAYDFMD SICQYITNCF EPLGMEDFAK
851 LGINVSDD
```

Fig. 12B

```
  1 MGDHHNLTGL PGTSIPPQFN YSQPGTSTGG PLYGGKPSHG LEDIPDVEEY
 51 ERNLLGAGAG FNLLNVGNMA NEFKPIITLD TKPPRDANKS LAFNGGLKLI
101 TPKTEVPDEH TPMMSPVNTT TKILQRSGIK MEIPPYLDPD SQDDDPEDGV
151 NYPDPDLFDT KNTNMTEYDL DVLKLGKPAV DEARKKIEVP DASAPPNKIV
201 EYLMYYRTLK ESELIQLNAY RTKRNRLSLN LVKNNIDREF DQKACESLVK
251 KLKDKKNDLQ NLIDVVLSKG TKYTGCITIP RTLDGRLQVH GRKGFPHVVY
301 GKLWRFNEMT KNETRHVDHC KHAFEMKSDM VCVNPYHYEI VIGTMIVGQR
351 DHDNRDMPPP HQRYHTPGRQ DPVDDMSRFI PPASIRPPPM NMHTRPQPMP
401 QQLPSVGATF AHPLPHQAPH NPGVSHPYSI APQTHYPLNM NPIPQMPQMP
451 QMPPPLHQGY GMNGPSCSSE NNNPFHQNHH YNDISHPNHY SYDCGPNLYG
501 FPTPYPDFHH PFNQQPHQPP QLSQNHTSQQ GSHQPGHQGQ VPNDPPISRP
551 VLQPSTVTLD VFRRYCRQTF GNRFFEGESE QSGAIIRSSN KFIEEFDSPI
601 CGVTVVRPRM TDGEVLENIM PEDAPYHDIC KFILRLTSES VTFSGEGPEV
651 SDLNEKWGTI VYYEKNLQIG EKKCSRGNFH VDGGFICSEN RYSLGLEPNP
701 IREPVAFKVR KAIVDGIRFS YKKDGSVWLQ NRMKYPVFVT SGYLDEQSGG
751 LKKDKVHKVY GCASIKTFGF NVSKQIIRDA LLSKQMATMY LQGKLTPMNY
801 IYEKKTQEEL RREATRTTDS LAKYCCVRVS FCKGFGEAYP ERPSIHDCPV
851 WIELKINIAY DFMDSICQYI TNCFEPLGME DFAKLGINVS DD
```

Fig. 12C tgatctttcaagccgaagcaatcaagacctcaaagccaatcaactctactcacttttcttcagaaccttaacttttgtg
tcactttccccaaaaaccgttcaagctgctgccttcactctcatccctcctcttactccttctttctcgtccgctacta
ctgtatcttctggacatctacctgtatacacaccagtggccagtcatctgccattacaatttcatcaattgacacttctt
caacaacaaccgccgtcctcattcactcccgattcttcctcatcctcaacatcgtcgtctttggctgaaattcccgaaga
cgttatgatggagatgctggtagatcagggaactgatgcatcgtcatccgcctccacgtccacctcatctgtttcgagat
tcggagcggacacgttcatgaatacaccggatgatgtgatgatgaatgatgatatggaaccgattcctcgtgatcggtgc
aatacgtggccaatgcgtaggccgcaactcgaaccaccactcaactcgagtcccattattcatgaacaaattcctgaaga
agatgctgacctatacgggagcaatgagcaatgtggacagctcggcggagcatcttcaaacgggtcgacagcaatgcttc
atactccagatggaagcaattctcatcagacatcgtttcttcggagtttcagaatgtccgaatcgccagacgataccgta
tcgggaaaaaagacaacgaccagacggaacgcttggggaaatatgtcatatgctgaacttatcactacagccattatggc
tagtccagagaaacggttaactcttgcacaagtttacgaatggatggtccagaatgttccatacttcagggataagggag
attcgaacagttcagctggatggaagaactcgatccgtcacaatctgtctcttcattctcgtttcatgcgaattcagaat
gaaggagccggaaagagctcgtggtgggttattaatccagatgcaaagccaggaatgaatccacggcgtacacgtgaacg
atccaatactattgagacgactacaaaggctcaactcgaaaaatctcgccgcggagccaagaagaggataaaggagagag
cattgatgggctcccttcactcgacacttaatggaaattcgattgccggatcgattcaaacgatttctcacgatttgtat
gatgatgatcaatgcaaggagcatttgataacgttccatcatctttccgtccccgaactcaatcgaacctctcgattcct
ggatcgtcgtctcgtgtttctccagctattggaagtgatatctatgatgatctagaattcccatcatgggttggcgaatc
ggttccagcaattccaagtgatattgttgatagaactgatcaaatgcgtatcgatgcaactactcatagttggtggagtt
cagattaagcaggagtcgaagccgattaagacggaaccaattgctccaccaccatcataccacgagttgaacagtgtccg
tggatcgtgtgctcagaatccacttcttcgaaatccaattgtgccaagcactaacttcaagccaatgccactaccgggtg
cctatggaaactatcaaaatggtggaataactccaatcaattggctatcaacatccaactcatctccactgcctggaatt
caatcgtgtggaattgtagctgcacagcatactgtcgcttcttcatcggctcttccaattgatttggaaaatctgacact
tcccgatcagccactgatggatactatggatgttgatgcattgatcagacatgagctgagtcaagctggagggcagcata
ttcattttgatttgtaaattctcttcattttgtttccctggtgttgttcgaaagagagatagcaaagcagcgaggagtg
aggtaagcagcaataaaaattttggatttttttttggttttccagaaataatcgattttctggaaaatttcaaaaaaaa
atcggaattttagttaattatttgatgagaaaaaaaaattagaaaacataaggaaaaatgaaaagcgttttttttttttc
gaaaatttagaattctcctacatttccaataagggccttagaactgcaaacaaacaaaaattggaattttcgaatcaaa
aagttcccgaataaaagtagttcgaatattaaaaagcatttaatttcctcttaaaaaaattgaataatagccgaaattt
gcagattttttttctgaaaatcgaaaaaccaaaatttttgattttttaaattttttttttacttccagatagtaaaat
cattagcactgaaaattatttgaaaaaaaaacttcaaatacaaattttgttttcgaaaaaaaaaatttaaatatatatttt
cagaaatcttccgtcttcatcttttcaaatccctacctacacacactcaacgatcatcacagccagaccatcaatattct
tccaaatttgacgtcgttaatttttttcagttttttcaaaaactctattttctattttctgtcgtttgttcccctttc
tctcgtctaattccaacacattcatcccagtgacgtcgtgtaataataatataaaatacctcttctctcttttcttcccct
aatgcgaaatatcgaaaaaccgttgattattacctctttttttcttgtttttttttttctctctctctcccgtcatccag
gttcttcactctttaaatgctacctctatcccatctttttcgctgtaaatttgtttcgcaatcaaaactgctaaaacaca
ttccccaatctgtctttttaattgaattttcaaaaaatttgatttcttgatttctcttgtaattcttaattttcctc
tttttttccccctggtagcaaatgtctagcgattctctttcttttttgtttaactttcacatctggccgattcgaatc
ctccgtatacacacacacatagtaatctacctccaaaattttactgaaagatgtgatcccctctctgtctccctctacaa
aacattatttgtctgtttgtgtatattgccaccacgtcgatttttaaattaaaaccatcgttttttcttcttttctacttt
tttctcgaaaaatttaacaacacacaaaaaaatccttcaaaaaatctcagttttaaatggtgtggcaatatatcggatcc
ccctctacaccagaacagtcttgcaatttcagagaatgattttcagattttcatatcacaggcccccttttttttgcttg
tttttttctctacctctctttcttttcattctatttctctctcttgttttctctctgttatcctgtacatttccttcca
attctttctggctatttctgattttcgagttcatattctctacgtctcactttctctcgcgccacgccccctttttcgtc
tccctccgcccccaaatatatttgcgactgtatgatgatgatgatgatttaataaaaat

Fig. 13A

```
ttacacgtggccaatgcaacaatacatctatcaggaatcgtcagcaaccattccccatcaccatttaaatcaacacaaca
atccgtatcatccaatgcatcctcatcatcaattacctcatatgcaacaacttcctcaacctctattgaatcttaacatg
acgacgttaacatcttctggcagttccgtggccagttccattggaggcggagctcaatgctctccgtgcgcgtcgggctc
ctcgaccgctgcaacaaattcctctcaacagcagcagaccgttggtcaaatgcttgctgcatcggtgccttgttcttcat
ctggcatgacacttggaatgtcacttaatctgtcacaaggcggtggtccaatgccggcaaaaaagaagcgttgtcgtaag
aagccaaccgatcaattggcacagaagaaaccgaatccatggggtgaggaatcctattcggatatcattgccaaagcatt
ggaatcggcgccagacggaaggcttaaactcaatgagatttatcaatggttctctgataatattccctactttggagaac
gatctagtcccgaggaggccgccggatggaagaactcgatccgtcacaatctgtctcttcattctcgtttcatgcgaatt
cagaatgaaggagccggaaagagctcgtggtgggttattaatccagatgcaaagccaggaatgaatccacggcgtacacg
tgaacgatccaatactattgagacgactacaaaggctcaactcgaaaaatctcgccgcggagccaagaagaggataaagg
agagagcattgatgggctcccttcactcgacacttaatggaaattcgattgccggatcgattcaaacgatttctcacgat
ttgtatgatgatgattcaatgcaaggagcatttgataacgttccatcatctttccgtccccgaactcaatcgaacctctc
gattcctggatcgtcgtctcgtgtttctccagctattggaagtgatatctatgatgatctagaattcccatcatgggttg
gcgaatcggttccagcaattccaagtgatattgttgatagaactgatcaaatgcgtatcgatgcaactactcatattggt
ggagttcagattaagcaggagtcgaagccgattaagacggaaccaattgctccaccaccatcataccacgagttgaacag
tgtccgtggatcgtgtgctcagaatccacttcttcgaaatccaattgtgccaagcactaacttcaagccaatgccactac
cgggtgcctatggaaactatcaaaatggtggaataactccaatcaattggctatcaacatccaactcatctccactgcct
ggaattcaatcgtgtggaattgtagctgcacagcatactgtcgcttcttcatcggctcttccaattgatttggaaaatct
gacacttcccgatcagccactgatggatactatggatgttgatgcattgatcagacatgagctgagtcaagctggagggc
agcatattcattttgatttgtaaattctcttcattttgtttcccctggtgttgttcgaaagagagatagcaaagcagcga
ggagtgagaaatcttccgtcttcatcttttcaaatccctacctacacacactcaacgatcatcacagccagaccatcaat
attcttccaaattttgacgtcgttaattttttttcagttttttcaaaaactctattttctattttctgtcgtttgttccc
ctttctctcgtctaattccaacacattcatcccagtgacgtcgtgtaataataatataaaatacctcttctctcttttctt
cccctaatgcgaaatatcgaaaaaccgttgattattacctcttttttcttgtttttttttttctctctctctcccgtca
tccaggttcttcactcttaaatgctacctctatcccatctttttcgctgtaaatttgtttcgcaatcaaaactgctaaa
acacattccccaatctgtcttttttaattgaatttttcaaaaaatttgatttcttgatttctcttgtaattctttaattt
tcctcttttttttttccccctggtagcaaatgtctagcgattctctttctttttttgtttaactttcacatctggccgattc
gaatcctccgtatacacacacacatagtaatcctacctccaaaattttactgaaagatgtgatcccctctctgtctccctc
tacaaaacattatttgtctgtttgtgtatattgccaccacgtcgatttaaattaaaaccatcgttttttcttcttttct
acttttttctcgaaaaatttaacaacacacaaaaaaatccttcaaaaaatctcagttttaaatggtgtggcaatatatcg
gatccccctctacaccagaacagtcttgcaatttcagagaatgattttcagatttttcatatcacaggccccctttttt
gcttgttttttctctacctctctttcttttcattctatttctctctcttgttttctctctgttatcctgtacattttcc
ttccaattctttctggctatttctgattttcgagttcatattctctacgtctcactttctctcgcgccacgcccccttt
tcgtctccctccgcccccaaatatatttgcgactgtatgatgatgatgatgatttaataaaaat
```

Fig. 13B

MMEMLVDQGTDASSSASTSTSSVSRFGADTFMNTPDDVMMNDDMEPIPRDR
CNTWPMRRPQLEPPLNSSPIIHEQIPEEDADLYGSNEQCGQLGGASSNGST
AMLHTPDGSNSHQTSFPSDFRMSESPDDTVSGKKTTTRRNAWGNMSYAELI
TTAIMASPEKRLTLAQVYEWMVQNVPYFRDKGDSNSSAG<u>WKNSIR</u>HNLSLH
SRFMRIQNEGAGKSSWWVINPDAKPGMNPRRTRERSNTIETTTKAQLEKSR
RGAKKRIKERALMGSLHSTLNGNSIAGSIQTISHDLYDDDSMQGAFDNVPS
SFRPRTQSNLSIPGSSSRVSPAIGSDIYDDLEFPSWVGESVPAIPSDIVDR
TDQMRIDATTHIGGVQIKQESKPIKTEPIAPPPSYHELNSVRGSCAQNPLL
RNPIVPSTNFKPMPLPGAYGNYQNGGITPINWLSTSNSSPLPGIQSCGIVA
AQHTVASSSALPIDLENLTLPDQPLMDTMDVDALIRHELSQAGGQHIHFDL

Fig. 14A

MQQYIYQESSATIPHHHLNQHNNPYHPMHPHHQLPHMQQLPQPLLNLNMTT
LTSSGSSVASSIGGGAQCSPCASGSSTAATNSSQQQQTVGQMLAASVPCSS
SGMTLGMSLNLSQGGGPMPAKKKRCRKKPTDQLAQKKPNPWGEESYSDIIA
KALESAPDGRLKLNEIYQWFSDNIPYFGERSSPEEAAG<u>WKNSIR</u>HNLSLHS
RFMRIQNEGAGKSSWWVINPDAKPGMNPRRTRERSNTIETTTKAQLEKSRR
GAKKRIKERALMGSLHSTLNGNSIAGSIQTISHDLYDDDSMQGAFDNVPSS
FRPRTQSNLSIPGSSSRVSPAIGSDIYDDLEFPSWVGESVPAIPSDIVDRT
DQMRIDATTHIGGVQIKQESKPIKTEPIAPPPSYHELNSVRGSCAQNPLLR
NPIVPSTNFKPMPLPGAYGNYQNGGITPINWLSTSNSSPLPGIQSCGIVAA
QHTVASSSALPIDLENLTLPDQPLMDTMDVDALIRHELSQAGGQHIHFDL

Fig. 14B

```
   1 cggaagccat ggagctcgag atctgattgc tggacacgga cggaactccg acgtatctcg
  61 cagatgcatg ttaacatttt acatccacaa ctgcaaacga tggtcgagca gtggcaaatg
 121 cgagaacgcc catcgctgga gaccgagaat ggcaaaggat cgctgctcct ggaaaatgaa
 181 ggtgtcgcag atatcatcac tatgtgtcca ttcggagaag ttattagtgt agtatttccg
 241 tggtttcttg caaatgtgcg aacatcgcta gaaatcaagc tatcagattt caaacatcaa
 301 cttttcgaat tgattgctcc gatgaagtgg ggaacatatt ccgtaaagcc acaggattat
 361 gtgttcagac agttgaataa tttcggcgaa attgaagtta tatttaacga cgatcaaccc
 421 ctgtcgaaat tagagctcca cggcactttc ccaatgcttt ttctctacca acctgatgga
 481 ataaacaggg ataaagaatt aatgagtgat ataagtcatt gtctaggata ctcactggat
 541 aaactggaag agagcctcga tgaggaactc cgtcaatttc gtgcttctct ctgggctcgt
 601 acgaagaaaa cgtgcttgac acgtggactt gagggtacca gtcactacgc gttccccgaa
 661 gaacagtact tgtgtgttgg tgaatcgtgc ccgaaagatt tggaatcaaa agtcaaggct
 721 gccaagctga gttatcagat gttttggaga aaacgtaaag cggaaatcaa tggagtttgc
 781 gagaaaatga tgaagattca aattgaattc aatccgaacg aaactccgaa atctctgctt
 841 cacacgtttc tctacgaaat gcgaaaattg gatgtatacg ataccgatga tcctgcagat
 901 gaaggatggt ttcttcaatt ggctggacgt accacgtttg ttacaaatcc agatgtcaaa
 961 cttacgtctt atgatggtgt ccgttcggaa ctggaaagct atcgatgccc tggattcgtt
1021 gttcgccgac aatcactagt cctcaaagac tattgtcgcc caaaaccact ctacgaacca
1081 cattatgtga gagcacacga acgaaaactt gctctagacg tgctcagcgt gtctatagat
1141 agcacaccaa aacagagcaa gaacagtgac atggttatga ctgattttcg tccgacagct
1201 tcactcaaac aagtttcact ttgggacctt gacgcgaatc ttatgatacg gcctgtaat
1261 atttctggat tcgatttccc ggccgacgtg gatatgtacg ttcgaatcga attcagtgta
1321 tatgtgggga cactgacgct ggcatcaaaa tctacaacaa aagtgaatgc tcaatttgca
1381 aaatggaata aggaaatgta cacttttgat ctatacatga aggatatgcc accatctgca
1441 gtactcagca ttcgtgtttt gtacggaaaa gtgaaattaa aaagtgaaga attcgaagtt
1501 ggttgggtaa atatgtccct aaccgattgg agagatgaac tacgacaagg acaattttta
1561 ttccatctgt gggctcctga accgactgcc aatcgtagta ggatcggaga aaatggagca
1621 aggataggca ccaacgcagc ggttacaatt gaaatctcaa gttatggtgg tagagttcga
1681 atgccgagtc aaggacaata cacatatctc gtcaagcacc gaagtacttg gacggaaact
1741 ttgaatatta tgggtgatga ctatgagtcg tgtatcagag atccaggata taagaagctt
1801 cagatgcttg tcaagaagca tgaatctgga attgtattag aggaagatga acaacgtcat
1861 gtctggatgt ggaggagata cattcaaaag caggagcctg atttgctcat tgtgctctcc
1921 gaactcgcat ttgtgtggac tgatcgtgag aacttttccg agctctatgt gatgcttgaa
1981 aaatggaaac cgccgagtgt ggcagccgcg ttgactttgc ttggaaaacg ttgcacggat
2041 cgtgtgattc gaaagtttgc agtggagaag ttgaatgagc agctgagccc ggtcacattc
2101 catctttca tattgcctct catacaggcg ttgaagtacg aaccgcgtgc tcaatcggaa
2161 gttggaatga tgctcttgac tagagctctc tgcgattatc gaattggaca tcgactttc
2221 tggctgctcc gtgcagagat tgctcgtttg agagattgtg atctgaaaag tgaagaatat
2281 cgccgtatct cacttctgat ggaagcttac ctccgtggaa atgaagagca catcaagatc
2341 atcacccgac aagttgacat ggttgatgag ctcacacgaa tcagcactct tgtcaaagga
2401 atgccaaaag atgttgctac gatgaaactg cgtgacgagc ttcgatcgat tagtcataaa
2461 atggaaaata tggattctcc actggatcct gtgtacaaac tgggtgaaat gataatcgac
2521 aaagccatcg tcctaggaag tgcaaaacgt ccgttaatgc ttcactggaa gaacaaaaat
2581 ccaaagagtg acctgcacct tccgttctgt gcaatgatct tcaagaatgg agacgatctt
2641 cgccaggaca tgcttgttct tcaagttctc gaagttatgg ataacatctg gaaggctgca
```

```
2701 aacattgatt gctgtttgaa cccgtacgca gttcttccaa tgggagaaat gattggaatt
2761 attgaagttg tgcctaattg taaaacaata ttcgagattc aagttggaac aggattcatg
2821 aatacagcag ttcggagtat tgatccttcg tttatgaata agtggattcg gaaacaatgc
2881 ggaattgaag atgaaaagaa gaaaagcaaa aaggactcta cgaaaaatcc catcgaaaag
2941 aagattgata atactcaagc catgaagaaa tattttgaaa gtgtcgatcg attcctatac
3001 tcgtgtgttg gatattcagt tgccacgtac ataatgggaa tcaaggatcg tcacagtgat
3061 aatctgatgc tcactgaaga tggaaaatat gtccacattg atttcggtca cattttggga
3121 cacggaaaga ccaaacttgg gatccagcga gatcgtcaac cgtttattct aaccgaacac
3181 tttatgacag tgattcgatc gggtaaatct gtggatggaa attcgcatga gctacaaaaa
3241 ttcaaaacgt tatgcgtcga agcctacgaa gtaatgtgga ataatcgaga tttgttcgtt
3301 tccttgttca ccttgatgct cggaatggag ttgcctgagc tgtcgacgaa agcggatttg
3361 gatcatttga agaaaaccct cttctgcaat ggagaaagca agaagaagc gagaaagttt
3421 ttcgctggaa tctacgaaga agccttcaat ggatcatggt ctaccaaaac gaattggctc
3481 ttccacgcag tcaaacacta ctga
```

```
   1 RKPWSSRSDC WTRTELRRIS QMHVNILHPQ LQTMVEQWQM RERPSLETEN GKGSLLLENE
  61 GVADIITMCP FGEVISVVFP WFLANVRTSL EIKLSDFKHQ LFELIAPMKW GTYSVKPQDY
 121 VFRQLNNFGE IEVIFNDDQP LSKLELHGTF PMLFLYQPDG INRDKELMSD ISHCLGYSLD
 181 KLEESLDEEL RQFRASLWAR TKKTCLTRGL EGTSHYAFPE EQYLCVGESC PKDLESKVKA
 241 AKLSYQMFWR KRKAEINGVC EKMMKIQIEF NPNETPKSLL HTFLYEMRKL DVYDTDDPAD
 301 EGWFLQLAGR TTFVTNPDVK LTSYDGVRSE LESYRCPGFV VRRQSLVLKD YCRPKPLYEP
 361 HYVRAHERKL ALDVLSVSID STPKQSKNSD MVMTDFRPTA SLKQVSLWDL DANLMIRPVN
 421 ISGFDFPADV DMYVRIEFSV YVGTLTLASK STTKVNAQFA KWNKEMYTFD LYMKDMPPSA
 481 VLSIRVLYGK VKLKSEEFEV GWVNMSLTDW RDELRQGQFL FHLWAPEPTA NRSRIGENGA
 541 RIGTNAAVTI EISSYGGRVR MPSQGQYTYL VKHRSTWTET LNIMGDDYES CIRDPGYKKL
 601 QMLVKKHESG IVLEEDEQRH VWMWRRYIQK QEPDLLIVLS ELAFVWTDRE NFSELYVMLE
 661 KWKPPSVAAA LTLLGKRCTD RVIRKFAVEK LNEQLSPVTF HLFILPLIQA LKYEPRAQSE
 721 VGMMLLTRAL CDYRIGHRLF WLLRAEIARL RDCDLKSEEY RRISLLMEAY LRGNEEHIKI
 781 ITRQVDMVDE LTRISTLVKG MPKDVATMKL RDELRSISHK MENMDSPLDP VYKLGEMIID
 841 KAIVLGSAKR PLMLHWKNKN PKSDLHLPFC AMIFKNGDDL RQDMLVLQVL EVMDNIWKAA
 901 NIDCCLNPYA VLPMGEMIGI IEVVPNCKTI FEIQVGTGFM NTAVRSIDPS FMNKWIRKQC
 961 GIEDEKKKSK KDSTKNPIEK KIDNTQAMKK YFESVDRFLY SCVGYSVATY IMGIKDRHSD
1021 NLMLTEDGKY VHIDFGHILG HGKTKLGIQR DRQPFILTEH FMTVIRSGKS VDGNSHELQK
1081 FKTLCVEAYE VMWNNRDLFV SLFTLMLGME LPELSTKADL DHLKKTLFCN GESKEEARKF
1141 FAGIYEEAFN GSWSTKTNWL FHAVKHY
```

Comparison of the human AKT protein sequence to the cosmid sequence
C12D8, located in the genetic interval where sup(mg144) maps. Numbering in the AKT
protein sequence by amino acid residues, and in the cosmid sequence by nucleotide
position.

```
Score = 450 (207.4 bits), Expect = 5.2e-165, Sum P(7) = 5.2e-165
Identities = 79/121 (65%), Positives = 97/121 (80%), Frame = +1

Query:    319 EVLEDNDYGRAVDWWGLGVVMYEMMCGRLPFYNQDHEKLFELILMEEIRFPRTLGPEAKS 378
              +VL+D+DYGR VDWWG+GVVMYEMMCGRLPFY++DH KLFELI+ ++RFP  L EA++
Sbjct:  33685 QVLDDHDYGRCVDWWGVGVVMYEMMCGRLPFYSKDHNKLFELIMAGDLRFPSKLSQEART 33864

Query:    379 LLSGLLKKDPTQRLGGGSEDAKEIMQHRFFANIVWQDVYEKKLSPPFKPQVTSETDTRYFD 439
              LL+GLL KDPTQRLGGG EDA EI +  FF  + W+  Y K++ PP+KP V SETDT YFD
Sbjct:  33865 LLTGLLVKDPTQRLGGGPEDALEICRADFFRTVDWEATYRKEIEPPYKPNVQSETDTSYFD 34047

Score = 256 (118.0 bits), Expect = 5.2e-165, Sum P(7) = 5.2e-165
Identities = 48/66 (72%), Positives = 59/66 (89%), Frame = +1

Query:    146 TMNEFEYLKLLGKGTFGKVILVKEKATGRYYAMKILKKEVIVAKDEVAHTLTENRVLQNS 205
              TM +F++LK+LGKGTFGKVIL KEK T + YA+KILKK+VI+A++EVAHTLTENRVLQ
Sbjct:  32314 TMEDFDFLKVLGKGTFGKVILCKEKRTQKLYAIKILKKDVIIAREEVAHTLTENRVLQRC 32493

Query:    206 RHPFLT 211
              +HPFLT
Sbjct:  32494 KHPFLT 32511

Score = 190 (87.6 bits), Expect = 5.2e-165, Sum P(7) = 5.2e-165
Identities = 36/45 (80%), Positives = 37/45 (82%), Frame = +2

Query:    276 KLENLMLDKDGHIKITDFGLCKEGIKDGATMKTFCGTPEYLAPEV 320
              KLENL+LDKDGHIKI DFGLCKE I G    TFCGTPEYLAPEV
Sbjct:  33509 KLENLLLDKDGHIKIADFGLCKEEISFGDKTSTFCGTPEYLAPEV 33643

Score = 188 (86.7 bits), Expect = 5.2e-165, Sum P(7) = 5.2e-165
Identities = 37/57 (64%), Positives = 42/57 (73%), Frame = +3

Query:    209 FLTALKYSFQTHDRLCFVMEYANGGELFFHLSRERVFSEDRARFYGAEIVSALDYLH 265
              +   LKYSFQ   LCFVM++ANGGELF H+ +   FSE RARFYGAEIV AL YLH
Sbjct:  32667 YFQELKYSFQEQHYLCFVMQFANGGELFTHVRKCGTFSEPRARFYGAEIVLALGYLH 32837

Score = 166 (76.5 bits), Expect = 5.2e-165, Sum P(7) = 5.2e-165
Identities = 29/59 (49%), Positives = 42/59 (71%), Frame = +1

Query:     53 NNFSVAQCQLMKTERPRPNTFIIRCLQWTTVIERTFHVETPEEREEWATAIQTVADGLK 111
              + F++  Q M E+PRPN F++RCLQWTTVIERTF+ E+ E R+ W AI++++   K
Sbjct:  31846 STFAIFYFQTMLFEKPRPNMFMVRCLQWTTVIERTFYAESAEVRQRWIHAIESISKKYK 32022

Score = 134 (61.8 bits), Expect = 5.2e-167, Sum P(8) = 5.2e-167
Identities = 24/33 (72%), Positives = 30/33 (90%), Frame = +3

Query:    210 LTALKYSFQTHDRLCFVMEYANGGELFFHLSRE 242
              L  LKYSFQT+DRLCFVME+A GG+L++HL+RE
Sbjct:  33156 LQELKYSFQTNDRLCFVMEFAIGGDLYYHLNRE 33254
```

Fig. 25

THERAPEUTIC AND DIAGNOSTIC TOOLS FOR IMPAIRED GLUCOSE TOLERANCE CONDITIONS

STATEMENT AS TO FEDERALLY SPONSORED RESEARCH

This invention was made in part with Government funding, and the Government therefore has certain rights in the invention.

BACKGROUND OF THE INVENTION

This invention relates to compositions and methods useful for delaying or ameliorating human diseases associated with glucose intolerance.

Diabetes is a major disease affecting over 16 million individuals in the United States alone at an annual cost of over 92 billion dollars.

Type I diabetes or insulin-dependent diabetes (IDDD) is an autoimmune disease. In the IDDM patient, the immune system attacks and destroys the insulin-producing beta cells in the pancreas. The central role of insulin in human metabolism is to aid in the transport of glucose into muscle cells and fat cells. The body's inability to produce insulin results in hyperglycemia, ketoacidosis, thirst, and weight loss. In addition, diabetics often suffer from chronic atherosclerosis and kidney and eyesight failure. A patient with IDDM requires daily injections of insulin to survive.

The most common form of diabetes is non-insulin dependent diabetes (NIDDM) or Type II diabetes. Type II diabetes is a heterogenous group of disorders in which hyperglycemia results from both impaired insulin secretory response to glucose and decreased insulin effectiveness (i.e., insulin resistance). Older people who are overweight are at particular risk for Type II diabetes. Genetic studies have suggested that, Type II diabetes is found in families and that the disease may be due to multiple genetic defects. In addition, the link between obesity and Type II diabetes is strong. Approximately 80 percent of Type II diabetics are obese. Weight loss and exercise can be effective to keep blood glucose levels normal, reducing the long-term complications of the disease.

At present there are few reliable methods for presymptomatic diagnosis of a genetic predisposition for diabetes or obesity. The search for genetic markers linked to diabetes and obesity has proven difficult, and this is especially true for Type II diabetes.

Treatments for diabetes emphasize control of blood glucose through blood glucose monitoring. The majority of patients take oral medications and/or insulin injections for appropriate control. Treatment of diabetes is generally chronic and lifelong, and treatments are generally not satisfactory over the long run. In addition, insulin treatment may become increasingly ineffective as the disease progresses. While insulin has been known for decades, and within the past decade, the receptors for insulin and aspects of its signaling pathway have been identified, the transcriptional output from these signaling pathways have not been characterized. In addition, the molecular basis of the obesity-induced insulin resistance is unknown.

SUMMARY OF THE INVENTION

We have discovered that the C. elegans metabolic regulatory genes daf-2 and age-1 encode homologues of the mammalian insulin receptor/PI 3-kinase signaling pathway proteins, respectively. We have also discovered that the DAF-16 forkhead protein represents the major transcriptional output of this insulin signaling pathway. For example, we have discovered that it is the dysregulation of the DAF-16 transcription factor in the absence of insulin signaling that leads to metabolic defects; inactivation of DAF-16 reverses the metabolic defects caused by lack of insulin signaling in C. elegans. Finally, we have found that the C. elegans daf-7, daf-1, daf-4, daf-8, daf-14, and daf-3 genes encode neuroendocrine/target tissue TGF-β type signal transduction molecules that genetically interact with the insulin signaling pathway. Similarly, we have shown that the metabolic defects caused by lack of neuroendocrine TGF-β signals can be reversed by inactivation of the DAF-3 transcription factor.

Together, this evidence indicates that the DAF-16, DAF-3, DAF-8, and DAF-14 transcriptional outputs of these converging signaling pathways regulate metabolism. In addition, these discoveries also indicate that insulin and TGF-β-like signals are integrated in humans to regulate metabolism, and that the homologues of other DAF proteins are likely to be defective or down regulated in human diabetic pedigrees as well as obesity induced diabetes. These results therefore indicate that the C. elegans daf genes are excellent candidate genes and proteins for human disease associated with glucose intolerance, e.g., diabetes, obesity, and atherosclerosis. Our findings indicate that the human homologues of these daf genes and proteins mediate insulin signaling in normal people and may be defective or misregulated in diabetics. Moreover, our findings indicate that there are at least two classes of type II diabetics: those with defects in the TGF-β signaling genes, and those with defects in insulin signaling genes. Below we describe exemplary sequence and functional characteristics of the human homologues of the daf genes.

The discovery of converging DAF-7 and DAF-2 insulin-like signaling indicates that many cases of obesity-induced and genetically-induced diabetes (and obesity) may be treated by administration of a human DAF-7 polypeptide.

The discovery that defects in the TGF-β signaling pathway can be suppressed by decreases in DAF-3 pathway activity and that defects in the insulin pathway can be suppressed by decreases in DAF-16 activity highlight the utility of transcriptional regulatory DAF proteins in drug development; in particular, drugs that inhibit the activity of these proteins are useful for reversing the effects of obesity-induced or genetically-induced defects in DAF-7 TGF-β type or insulin signaling.

In one aspect, the invention features a substantially pure preparation of a DAF-2 polypeptide, which can be derived from an animal (for example, a mammal, such as a human, or an invertebrate, such as C. elegans). In preferred embodiments, the DAF-2 polypeptide has insulin receptor (InR) activity, insulin receptor related activity, insulin-like growth factor receptor (IGF-1) receptor activity, or a combination of these activities.

The invention also features isolated DNA encoding a DAF-2 polypeptide. This isolated DNA can have a nucleotide sequence that includes, for example, the nucleotide sequence of the daf-2 gene shown in FIG. 2B. This isolated DNA can also, in preferred embodiments, complement a daf-2 mutation in C. elegans, an InR mutation in a mouse, or an IGF-1 receptor mutation in a mouse.

The isolated DNA encoding a DAF-2 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-2, age-1, daf-16, daf-1, daf-4, daf-3, and akt promoters. The isolated DNA encoding a DAF-2 polypeptide, or a vector including this DNA, can be contained in a cell, such as a bacterial, mammalian, or nematode cell.

Also included in the invention is a method of producing a recombinant DAF-2 polypeptide, and a DAF-2 polypeptide produced by this method. This method involves (a) providing a cell transformed with isolated DNA that (i) encodes a DAF-2 polypeptide, and (ii) is positioned for expression in the cell, under conditions for expressing the isolated DNA, and (b) isolating the recombinant DAF-2 polypeptide.

A substantially pure antibody, such as a monoclonal or polyclonal antibody, that specifically recognizes and binds a DAF-2 polypeptide is also included in the invention.

The invention also features a method of detecting a gene, or a portion of a gene, that is found in a human cell and has sequence identity to the daf-2 sequence of FIG. 2B. In this method, isolated DNA encoding a DAF-2 polypeptide, a portion of such DNA greater than about 12 residues in length, or a degenerate oligonucleotide corresponding to SEQ ID NOS: 33, 34, 79, 80, 81, 82, 83, or 84, is contacted with a preparation of DNA from the human cell under hybridization conditions that provide detection of DNA sequences having about 70% or greater nucleic acid sequence identity to the daf-2 sequence of FIG. 2B. This method can also include a step of testing the gene, or portion thereof, for the ability to functionally complement a *C. elegans* daf-2 mutant.

Another method included in the invention is a method of isolating a gene, or a portion of a gene, that is found in a human cell and has at least 90% nucleic acid sequence identity to a sequence encoding SEQ ID NOS: 33, 34, 79, 80, 81, 82, 83, or 84. This method involves (a) amplifying by PCR the human gene, or portion thereof, using oligonucleotide primers that (i) are each greater than about 12 residues in length, and (ii) each have regions of complementarity to opposite DNA strands in a region of the nucleotide sequence of FIG. 2B, and (b) isolating the human gene, or portion thereof. This method can also include a step of testing the gene, or portion thereof, for the ability to functionally complement a *C. elegans* daf-2 mutant.

In another aspect, the invention features a substantially pure preparation of a DAF-3 polypeptide, which can be derived from an animal (for example, a mammal, such as a human, or an invertebrate, such as *C. elegans*). In a preferred embodiment, the polypeptide is a SMAD protein. In other preferred embodiments, the polypeptide is capable of binding and interacting with a nematode DAF-1, DAF-4, DAF-8, DAF-14, or DAF-16 polypeptide.

The invention also features isolated DNA encoding a DAF-3 polypeptide. This isolated DNA can have a sequence that includes, for example, the nucleotide sequence of a daf-3 gene shown in FIGS. 11A, 11B, or 11C. This isolated DNA can also, in preferred embodiments, complement a daf-3 mutation in *C. elegans* or complement a daf-3 knockout mouse.

The isolated DNA encoding a DAF-3 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-3, daf-4, daf-16, daf-2, age-1, and akt promoters. The isolated DNA encoding a DAF-3 polypeptide, or a vector including this DNA, can be contained in a cell, such as a bacterial, mammalian, or nematode cell.

Also included in the invention is a method of producing a recombinant DAF-3 polypeptide, and a DAF-3 polypeptide produced by this method. This method involves (a) providing a cell transformed with isolated DNA that (i) encodes a DAF-3 polypeptide, and (ii) is positioned for expression in the cell, under conditions for expressing the isolated DNA, and (b) isolating the recombinant DAF-3 polypeptide.

A substantially pure antibody, such as a monoclonal or polyclonal antibody, that specifically recognizes and binds a DAF-3 polypeptide is also included in the invention.

The invention also features a method of detecting a gene, or a portion of a gene, that is found in a human cell and has sequence identity to any of the daf-3 sequences of FIGS. 11A, 11B, or 11C. In this method, isolated DNA encoding a DAF-3 polypeptide, a portion of such DNA that is greater than about 12 residues in length, or a degenerate oligonucleotide corresponding to SEQ ID NOS: 35, 36, or 85, is contacted with a preparation of DNA from the human cell under hybridization conditions that provide detection of DNA sequences having about 70% or greater nucleic acid sequence identity to any of the daf-3 sequences of FIGS. 11A, 11B, or 11C. This method can also include a step of testing the gene, or portion thereof, for the ability to functionally complement a *C. elegans* daf-3 mutant.

Another method included in the invention is a method of isolating a gene, or a portion thereof, that is found in a human cell and has at least 90% nucleic acid sequence identity to a sequence encoding SEQ ID NOS: 35, 36, or 85. This method includes (a) amplifying by PCR the human gene, or portion thereof, using oligonucleotide primers that (i) are each greater than about 12 residues in length, and (ii) each have regions of complementarity to opposite DNA strands in a region of any of the nucleotide sequences of FIGS. 11A, 11B, or 11C, and (b) isolating the human gene, or portion thereof. This method can also include a step of testing the gene, or portion thereof, for the ability to functionally complement a *C. elegans* daf-3 mutant.

In yet another aspect, the invention features a substantially pure preparation of DAF-16 polypeptide, which can be derived from an animal (for example, a mammal, such as a human, or an invertebrate, such as *C. elegans*). In a preferred embodiment, the polypeptide is a forkhead transcription factor that binds DNA. In other preferred embodiments, the polypeptide is capable of interacting with a polypeptide selected from the group consisting of DAF-3, DAF-8, and DAF-14.

The invention also features isolated DNA encoding a DAF-16 polypeptide. This isolated DNA can have a sequence that includes, for example, the sequence of the daf-16 gene shown in FIGS. 13A or 13B. This isolated DNA can also, in preferred embodiments, complement a daf-16 mutation in *C. elegans*, or complement an FKHR or AFX mutation in a mouse.

The isolated DNA encoding a DAF-16 polypeptide can be included in a vector, such as a vector that is capable of directing the expression of the protein encoded by the DNA in a vector-containing cell. The isolated DNA in the vector can be operatively linked to a promoter, for example, a promoter selected from the group consisting of daf-2, age-1, daf-16, daf-3, daf-4, and akt promoters. The isolated DNA encoding a DAF-16 polypeptide, or a vector containing this DNA, can be contained in a cell, such as a bacterial, mammalian, or nematode cell.

Also included in the invention is a method for producing a recombinant DAF-16 polypeptide, and a DAF-16 polypeptide produced by this method. This method involves (a) providing a cell transformed with purified DNA that (i) encodes a DAF-16 polypeptide, and (ii) is positioned for expression in the cell, under conditions for expressing the isolated DNA, and (b) isolating the recombinant DAF-16 polypeptide.

A substantially pure antibody, such as a monoclonal or polyclonal antibody, that specifically recognizes and binds a DAF-16 polypeptide is also included in the invention.

The invention also features a method of detecting a gene, or a portion of a gene, that is found in a human cell and has sequence identity to the daf-16 sequence of FIGS. 13A or 13B. In this method, isolated DNA encoding a DAF-16 polypeptide, a portion of such DNA that is greater than about 12 residues in length, or a degenerate oligonucleotide corresponding to SEQ ID NO: 54, 55, 56, or 57, is contacted with a preparation of DNA from the human cell under hybridization conditions that provide detection of DNA sequences having about 70% or greater nucleic acid sequence identity to the daf-16 sequence of FIGS. 13A or 13B. This method can also include a step of testing the gene, or portion of the gene, for the ability to functionally complement a *C. elegans* daf-16 mutant.

Another method included in the invention is a method of isolating a gene, or a portion of a gene, that is found in a human cell and has at least 90% nucleic acid sequence identity to a sequence encoding SEQ ID NO: 54, 55, 56, or 57. This method involves (a) amplifying by PCR the human gene, or portion thereof, using oligonucleotide primers that (i) are each greater than about 12 residues in length, and (ii) each have regions of complementarity to opposite DNA strands in a region of the nucleotide sequence of FIGS. 13A or 13B, and (b) isolating the human gene, or portion thereof. This method can also include a step of testing the gene, or portion thereof, for the ability to functionally complement a *C. elegans* daf-16 mutant.

In another aspect, the invention features a method of determining whether a human gene is involved in an impaired glucose tolerance condition (for example, a condition involving atherosclerosis) or obesity. This method involves (a) providing a nematode having a mutation in a daf or age gene, and (b) expressing in the nematode the human gene, which is operatively linked to a nematode gene promoter. Complementation of the daf or age mutation in the nematode is indicative of a human gene that is involved in an impaired glucose tolerance condition or obesity. In preferred embodiments, the nematode gene promoter is selected from the group consisting of daf-1, daf-3, daf-4, daf-2, age-1, and akt gene promoters. In other preferred embodiments, the daf mutation is selected from the group consisting of daf-2, daf-3, daf-1, daf-4, daf-7, daf-8, daf-11, daf-12, daf-14, and daf-16 mutations. In yet another preferred embodiment, the mutation can also be found in the age-1 gene.

In further aspects, the invention features methods for diagnosing an impaired glucose tolerance condition (for example, Type II diabetes or a condition involving atherosclerosis), or a propensity for such a condition, in a patient. One such method includes analyzing the DNA of the patient to determine whether the DNA contains a mutation in a daf gene. Identification of such a mutation indicates that the patient has an impaired glucose tolerance condition or a propensity for such a condition. The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers, and analyzing the amplified gene, or a fragment thereof, for the presence of the mutation. In preferred embodiments, the daf gene analyzed in this method is, for example, a daf-1, daf-2, daf-3, daf-4, daf-7, daf-8, daf-11, daf-12, daf-14, or daf-16 coding sequence, or the daf gene is FKHR or AFX.

Another method for diagnosing an impaired glucose tolerance condition, such as Type II diabetes, or a propensity for such a condition, in a patient, includes analyzing the DNA of the patient to determine whether the DNA contains a mutation in an age gene. Identification of such a mutation indicates that the patient has an impaired glucose tolerance condition or a propensity for such a condition. The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers and analyzing the amplified gene, or fragment thereof, for the presence of the mutation. In a preferred embodiment, the age gene is an age-1 coding sequence.

Yet another method for diagnosing an impaired glucose tolerance condition, such as Type II diabetes or a condition that involves atherosclerosis, or a propensity for such a condition, in a patient, includes analyzing the DNA of the patient to determine whether the DNA contains a mutation in an akt gene. Identification of such a mutation indicates that the patient has an impaired glucose tolerance condition (for example, Type II diabetes) or a propensity for such a condition (for example, a pre-diabetic condition). The analysis in this method can be carried out, for example, by nucleotide sequencing or RFLP analysis. The analysis can also include amplifying (for example, by PCR or reverse transcriptase PCR) the gene (for example, a human gene), or a fragment thereof, using primers and analyzing the amplified gene, or fragment thereof, for the presence of the mutation.

The invention also includes kits for use in the diagnosis of an impaired glucose tolerance condition, or a propensity for such a condition, in a patient. One such kit includes a PCR primer complementary to a daf nucleic acid sequence and instructions for diagnosing an impaired glucose tolerance condition or a propensity for such a condition. Another kit includes a PCR primer complementary to an age nucleic acid sequence and instructions for diagnosing an impaired glucose tolerance condition or a propensity for such a condition. Yet another kit includes a PCR primer complementary to an akt nucleic acid sequence and instructions for diagnosing an impaired glucose tolerance condition or a propensity for such a condition.

In another aspect, the invention features methods for ameliorating or delaying the onset of an impaired glucose tolerance condition (for example, Type II diabetes) in a patient. In one such method a therapeutically effective amount of a DAF polypeptide (for example, the human or nematode DAF-7 polypeptide) is administered to the patient. In another method, which can be used, for example, in the case of a condition involving atherosclerosis, a therapeutically effective amount of a compound that is capable of inhibiting the activity of a DAF-16 or DAF-3 polypeptide is administered to the patient. In yet another method, a therapeutically effective amount of a compound that activates a DAF-1, DAF-4, DAF-8, DAF-11, or DAF-14 polypeptide is administered to the patient.

Another aspect of the invention provides methods for ameliorating or preventing obesity (for example, obesity associated with Type II diabetes) in a patient. One such method involves administering to the patient a therapeutically effective amount of a DAF polypeptide, such as a human or nematode DAF-7 polypeptide. Another such method involves administering to the patient a therapeutically effective amount of a compound that is capable of inhibiting the activity of a DAF-16 or DAF-3 polypeptide.

Yet another aspect of the invention features a transgenic, non-human animal, such as a mouse or a nematode, whose germ cells and somatic cells contain a transgene coding for a mutant DAF polypeptide, for example, a mutant DAF polypeptide that is derived from a human. In preferred embodiments, the mutant DAF polypeptide is a DAF-1, DAF-2, DAF-3, DAF-4, DAF-7, DAF-8, DAF-11, DAF-12, DAF-14, or DAF-16 polypeptide. In another preferred embodiment, the transgene includes a knockout mutation.

In a related aspect, the invention features a transgenic, non-human animal, such as a mouse or a nematode, whose germ cells and somatic cells contain a transgene coding for a mutant AGE polypeptide, for example, a mutant AGE polypeptide derived from a human. In a preferred embodiment, the mutant AGE polypeptide is an AGE-1 polypeptide. In another preferred embodiment, the transgene includes a knockout mutation.

In yet another aspect, the invention features a transgenic, non-human animal, such as a mouse or a nematode, whose germ cells and somatic cells contain a transgene coding for a mutant AKT polypeptide, for example, a mutant AKT polypeptide derived from a human. In a preferred embodiment, the transgene includes a knockout mutation.

In related aspects, the invention features cells (for example, cells isolated from a mammal, such as mouse, human, or nematode cells) isolated from the transgenic animals described above.

The invention also includes methods for producing transgenic, non-human animals. For example, the invention includes a method for producing a transgenic, non-human animal that lacks an endogenous daf gene and is capable of expressing a human DAF polypeptide. This method involves (a) providing a transgenic, non-human animal whose germ cells and somatic cells contain a mutation in a daf gene, and (b) introducing a transgene that (i) encodes a human DAF polypeptide, and (ii) is capable of expressing the human polypeptide, into an embryonal cell of the non-human animal.

Another method included in the invention can be used for producing a transgenic, non-human animal that lacks an endogenous age gene and is capable of expressing a human AGE polypeptide. This method involves (a) providing a transgenic, non-human animal whose germ cells and somatic cells contain a mutation in an age gene, and (b) introducing a transgene that (i) encodes a human AGE polypeptide, and (ii) is capable of expressing the human polypeptide, into an embryonal cell of the non-human animal.

Similarly, the invention includes a method for producing a transgenic, non-human animal that lacks an endogenous akt gene and is capable of expressing of expressing a human AKT polypeptide. This method involves (a) providing a transgenic, non-human animal whose germ cells and somatic cells contain a mutation in an akt gene, and (b) introducing a transgene that (i) encodes a human AKT polypeptide, and (ii) is capable of expressing the human polypeptide, into an embryonal cell of the non-human animal.

Another aspect of the invention features a method of screening for a compound that increases the activity of a DAF polypeptide. This method includes (a) exposing a non-human transgenic animal whose germ cells and somatic cells contain a transgene coding for a mutant DAF polypeptide to a candidate compound, and (b) determining the activity of the DAF polypeptide in the transgenic animal. An increase in DAF polypeptide activity, as compared to untreated controls, is indicative of a compound that is capable of increasing DAF polypeptide activity. In preferred embodiments, the compound can be used to treat an impaired glucose tolerance condition or obesity.

In a related aspect, the invention features a method of screening for a compound that decreases the activity of a DAF polypeptide. This method includes (a) exposing a non-human transgenic animal whose germ cells and somatic cells contain a transgene coding for a mutant DAF polypeptide to a candidate compound, and (b) determining the activity of the DAF polypeptide in the transgenic animal. A decrease in DAF polypeptide activity, as compared to untreated controls, is indicative of a compound that is capable of decreasing DAF polypeptide activity. In preferred embodiments, the compound can be used to treat an impaired glucose tolerance condition, obesity, or atherosclerosis. In other preferred embodiments, the compound decreases the activity of DAF-3 or DAF-16.

In another aspect, the invention features a method of screening for a compound that increases the activity of an AGE polypeptide. This method includes (a) exposing a non-human transgenic animal whose germ cells and somatic cells contain a transgene coding for a mutant AGE polypeptide to a candidate compound, and (b) determining the activity of the AGE polypeptide in the transgenic animal. An increase in AGE polypeptide activity, as compared to untreated controls, is indicative of a compound that is capable of increasing AGE polypeptide activity. In preferred embodiments, the compound can be used to treat an impaired glucose tolerance condition, obesity, or atherosclerosis.

In a related aspect, the invention features a method of screening for a compound that decreases the activity of a AGE polypeptide. This method includes (a) exposing a non-human, transgenic animal whose germ cells and somatic cells contain a transgene coding for a mutant AGE polypeptide to a candidate compound, and (b) determining the activity of the AGE polypeptide in the transgenic animal. A decrease in AGE polypeptide activity, as compared to untreated controls, is indicative of a compound that is capable of decreasing AGE polypeptide activity. In preferred embodiments, the compound can be used to treat an impaired glucose tolerance condition, obesity, or atherosclerosis. In another preferred embodiment, the AGE polypeptide is AGE-1.

In another aspect, the invention features a method of screening for a compound that increases the activity of an AKT polypeptide. This method includes (a) exposing a transgenic, non-human animal whose germ cells and somatic cells contain a transgene coding for a mutant AKT polypeptide to a candidate compound, and (b) determining the activity of the AKT polypeptide in the transgenic animal. An increase in AKT polypeptide activity, as compared to untreated controls, is indicative of a compound that is capable of increasing AKT polypeptide activity. In preferred embodiments, the compound can be used to treat an impaired glucose tolerance condition, obesity, or atherosclerosis.

In a related aspect, the invention features a method of screening for a compound that decreases the activity of a AKT polypeptide. This method includes (a) exposing a transgenic, non-human animal whose germ cells and somatic cells contain a transgene coding for a mutant AKT polypeptide to a candidate compound, and (b) determining the activity of the AKT polypeptide in the transgenic animal. A decrease in AKT polypeptide activity, as compared to untreated controls, is indicative of a compound that is capable of decreasing AKT polypeptide activity. In preferred embodiments, the compound can be used to treat an impaired glucose tolerance condition or obesity.

Also included in the invention is a method of screening for a compound that is capable of ameliorating or delaying an impaired glucose tolerance condition. This method involves (a) exposing a transgenic, non-human animal whose germ cells and somatic cells contain a transgene coding for a mutant DAF, AGE, or AKT polypeptide to a candidate compound, and (b) monitoring the blood glucose level of the animal. A compound that promotes maintenance of a physiologically acceptable level of blood glucose in the animal, as compared to untreated controls, is indicative of a compound that is capable of ameliorating or delaying an impaired glucose tolerance condition. In a preferred embodiment, the compound can be used to treat Type II diabetes.

Another method of screening for a compound that is capable of ameliorating or delaying obesity is also included in the invention. This method involves (a) exposing a transgenic, non-human animal whose germ cells and somatic cells contain a transgene coding for a mutant DAF, AGE, or AKT polypeptide to a candidate compound, and (b) monitoring the adipose tissue of the animal. A compound that promotes maintenance of a physiologically acceptable level of adipose tissue in the animal, as compared to untreated controls, is indicative of a compound that is capable of ameliorating or delaying obesity.

A related method of the invention can be used for screening for a compound that is capable of ameliorating or delaying atherosclerosis. This method involves (a) exposing a transgenic, non-human animal whose germ cells and somatic cells contain a transgene coding for a mutant DAF, AGE, or AKT polypeptide to a candidate compound, and (b) monitoring the adipose tissue of the animal. A compound that promotes maintenance of a physiologically acceptable level of adipose tissue in the animal, as compared to untreated controls, is indicative of a compound that is capable of ameliorating or delaying atherosclerosis.

In another aspect, the invention includes a method for identifying a modulatory compound that is capable of decreasing the expression of a daf gene. This method involves (a) providing a cell expressing the daf gene, and (b) contacting the cell with a candidate compound. A decrease in daf expression following contact with the candidate compound identifies a modulatory compound. In preferred embodiments, the compound can be used to treat an impaired glucose tolerance condition or obesity. In other preferred embodiments, the compound is capable of decreasing the expression of DAF-3 or DAF-16. This method can be carried out in an animal, such as a nematode.

In a related aspect, the invention includes a method for the identification of a modulatory compound that is capable of increasing the expression of a daf gene. This method involves (a) providing a cell expressing the daf gene, and (b) contacting the cell with a candidate compound. An increase in daf expression following contact with the candidate compound identifies a modulatory compound. In preferred embodiments, the compound can be used to treat an impaired glucose tolerance condition or obesity. In other preferred embodiments, the compound is capable of increasing expression of DAF-1, DAF-2, DAF-4, DAF-7, DAF-8, DAF-11, or DAF-14. This method can be carried out in an animal, such as a nematode.

In another aspect, the invention includes a method for the identification of a modulatory compound that is capable of increasing the expression of an age-1 gene. This method involves (a) providing a cell expressing the age-1 gene, and (b) contacting the cell with a candidate compound. An increase in age-1 expression following contact with the candidate compound identifies a modulatory compound. In preferred embodiments, the compound is capable of treating an impaired glucose tolerance condition or obesity. This method can be carried out in an animal, such as a nematode.

In another aspect, the invention provides a method for identification of a compound that is capable of ameliorating or delaying an impaired glucose tolerance condition. This method involves (a) providing a dauer larvae including a mutation in a daf gene, and (b) contacting the dauer larvae with a compound. Release from the dauer larval state is an indication that the compound is capable of ameliorating or delaying an impaired glucose tolerance condition. In a preferred embodiment, the dauer larvae carries a daf-2 mutation. In another preferred embodiment, the dauer larvae is from C. elegans. In yet another embodiment, the impaired glucose tolerance condition involves obesity or atherosclerosis.

In a related aspect, the invention provides a method for identification of a compound that is capable of ameliorating or delaying an impaired glucose tolerance condition. This method involves (a) providing a dauer larvae including a mutation in an age-1 gene, and (b) contacting the dauer larvae with a compound. Release from the dauer larval state is an indication that the compound is capable of ameliorating or delaying an impaired glucose tolerance condition. In a preferred embodiment, the dauer larvae carries an age-1 mutation. In another preferred embodiment, the dauer larvae is from C. elegans. In yet another preferred embodiment, the impaired glucose tolerance condition involves obesity or atherosclerosis.

In another related aspect, the invention provides a method for the identification of a compound that is capable of ameliorating or delaying an impaired glucose tolerance condition. This method involves (a) providing a dauer larvae including a mutation in an akt gene, and (b) contacting the dauer larvae with a compound. Release from the dauer larval state is an indication that the compound is capable of ameliorating or delaying an impaired glucose tolerance condition. In a preferred embodiment, the dauer larvae is from C. elegans. In another preferred embodiment, the impaired glucose tolerance condition involves obesity or atherosclerosis.

In another aspect, the invention provides a method for the identification of a compound for ameliorating or delaying an impaired glucose tolerance condition. This method involves (a) combining PIP3 and an AKT polypeptide in the presence and absence of a compound under conditions that allow PIP3:AKT complex formation, (b) identifying a compound that is capable of decreasing the formation of the PIP3:AKT complex, and (c) determining whether the compound identified in step (b) is capable of increasing AKT activity. An increase in AKT kinase activity is taken as an indication of a compound useful for ameliorating or delaying an impaired glucose tolerance condition.

In yet another aspect, the invention provides a method for the identification of a compound for ameliorating or delaying an impaired glucose tolerance condition. This method involves (a) providing a daf-7, daf-3 mutant nematode, (b) expressing in the cells of the nematode a mammalian DAF-3 polypeptide, whereby the nematode forms a dauer larva, and (c) contacting the dauer larva with a compound. A release from the dauer larval state is an indication that the compound is capable of ameliorating or delaying the glucose intolerance condition.

In a final aspect, the invention features a method for the identification of a compound for ameliorating or delaying an impaired glucose tolerance condition. This method involves (a) providing a daf-2, daf-16 mutant nematode, (b) expressing in the cells of the nematode a mammalian DAF-16 polypeptide, whereby the nematode forms a dauer larva, and (c) contacting the dauer larva with a compound. A release from the dauer larval state is an indication that the compound is capable of ameliorating or delaying the glucose intolerance condition.

As used herein, by a "DAF" polypeptide is meant a polypeptide that functionally complements a *C. elegans* daf mutation and/or that has at least 60%, preferably 75%, and more preferably 90% amino acid sequence identity to a 100 amino acid region (and preferably a conserved domain) of a *C. elegans* DAF polypeptide. Complementation may be assayed in an organism (for example, in a nematode) or in a cell culture system. Complementation may be partial or complete, but must provide a detectable increase in function (as described herein). DAF polypeptides are encoded by "DAF" genes or nucleic acid sequences.

By an "AGE" polypeptide is meant a polypeptide that functionally complements a *C. elegans* age mutation and/or that has at least 60%, preferably 75%, and more preferably 90% amino acid sequence identity to a 100 amino acid region (and preferably a conserved domain) of a *C. elegans* AGE polypeptide. Complementation may be assayed in an organism (for example, in a nematode) or in a cell culture system. Complementation may be partial or complete, but must provide a detectable increase in a known AGE function. AGE polypeptides are encoded by "AGE" genes or nucleic acid sequences.

As used herein, by an "AKT" polypeptide is meant a polypeptide that functionally complements a *C. elegans* akt mutation and/or that possess at least 64% amino acid sequence identity to SEQ ID NO: 60, at least 71% amino acid sequence identity to SEQ ID NO: 61, at least 79% amino acid sequence identity to SEQ ID NO: 62, at least 63% amino acid sequence identity to SEQ ID NO: 63, at least 48% amino acid sequence identity to SEQ ID NO: 64, at least 70% amino acid sequence identity to SEQ ID NO: 65, at least 64% amino acid sequence identity to SEQ ID NO: 66, at least 67% amino acid sequence identity to SEQ ID NO: 67, or a combination thereof. Complementation may be assayed in an organism (for example, in a nematode) or in a cell culture system. Complementation may be partial or complete, but must provide a detectable increase in a known AKT function. AKT polypeptides are encoded by "AKT" genes or nucleic acid sequences.

By a "DAF-2 polypeptide" is meant a polypeptide that complements (as defined above) a *C. elegans* daf-2 mutation and/or that possesses at least 61% amino acid sequence identity to SEQ ID NO: 33, at least 31% amino acid sequence identity to SEQ ID NO: 34, at least 43% amino acid sequence identity to SEQ ID NO: 79, at least 35% amino acid sequence identity to SEQ ID NO: 80, at least 35% amino acid sequence identity to SEQ ID NO: 81, at least 48% amino acid sequence identity to SEQ ID NO: 82, at least 43% amino acid sequence identity to SEQ ID NO: 83, at least 40% amino acid sequence identity to SEQ ID NO: 84, or a combination thereof. Preferably, a DAF-2 polypeptide includes an aspartic acid, a proline, a proline, a serine, an alanine, an aspartic acid, a cysteine, or a proline at amino acid positions corresponding to *C. elegans* DAF-2 amino acids 1252, 1312, 1343, 347, 451, 458, 526, 279, and 348 respectively, or a combination thereof.

By a "DAF-3 polypeptide" is meant a polypeptide that complements (as defined above) a *C. elegans* daf-3 mutation and/or that possesses at least 60% amino acid sequence identity to SEQ ID NO: 35, at least 38% amino acid sequence identity to SEQ ID NO: 36, at least 47% amino acid sequence identity to SEQ ID NO: 85, or a combination thereof Preferably, a DAF-3 polypeptide includes a proline or a glycine at amino acid positions corresponding to *C. elegans* daf-3 amino acids at positions 200 (proline) and/or 620 (glycine) in FIG. 12A, respectively, or a combination thereof. For example, the polypeptide may include a proline in the motif GRKGFPHV or a glycine in the motif RXX-IXXG (where X is any amino acid).

By a "DAF-16 polypeptide" is meant a polypeptide that complements (as defined above) a *C. elegans* daf-16 mutation and/or that possesses at least 71% amino acid sequence identity to SEQ ID NO: 54, at least 35% amino acid sequence identity to SEQ ID NO: 55, at least 65% amino acid sequence identity to SEQ ID NO: 56, at least 53% amino acid sequence identity to SEQ ID NO: 57, or a combination thereof. In addition, a DAF-16 polypeptide preferably includes a serine residue in the conserved motif WKNSIRH (SEQ ID NO: 59).

By a "DAF-7 polypeptide" is meant a polypeptide that complements (as defined above) a *C. elegans* daf-7 mutation and/or that possesses at least 29% amino acid sequence identity to SEQ ID NO: 26, at least 66% amino acid sequence identity to SEQ ID NO: 27, at least 45% amino acid sequence identity to SEQ ID NO: 28, at least 33% amino acid sequence identity to SEQ ID NO: 29, at least 56% amino acid sequence identity to SEQ ID NO: 30, at least 75% sequence identity to SEQ ID No: 51, or a combination thereof. Preferably, a DAF-7 polypeptide includes a proline or a glycine at amino acid positions corresponding to *C. elegans* daf-7 amino acids 271 and 280, respectively, or a combination thereof.

By a "DAF-8 polypeptide" is meant a polypeptide that complements (as defined above) a *C. elegans* daf-8 mutation and/or that possesses at least 46% amino acid sequence identity to SEQ ID NO: 23, at least 45% amino acid sequence identity to SEQ ID NO: 24, at least 36% amino acid sequence identity to SEQ ID NO: 25, or a combination thereof.

By an "AGE-1 polypeptide" is meant a polypeptide that complements (as defined above) a *C. elegans* age-1 mutation (previously known as a daf-23 mutation) and/or that possesses at least 40% amino acid sequence identity to SEQ ID NO: 17, at least 45% amino acid sequence identity to SEQ ID NO: 18, at least 30% amino acid sequence identity to SEQ ID NO: 19, at least 24% amino acid sequence identity to SEQ ID NO: 38, or a combination thereof. Preferably, an AGE-1 polypeptide includes an alanine at amino acid positions corresponding to *C. elegans* age-1 amino acids 845.

By a "DAF-1 polypeptide" is meant a polypeptide that complements (as defined above) a *C. elegans* daf-1 mutation and/or that possesses at least 45% amino acid sequence identity to SEQ ID NO: 13, at least 35% amino acid sequence identity to SEQ ID NO: 14, at least 65% amino acid sequence identity to SEQ ID NO: 15, at least 25% amino acid sequence identity to SEQ ID NO: 16, or a combination thereof. Preferably, a DAF-1 polypeptide includes a proline at the amino acid position corresponding to C elegans DAF-1 amino acid 546.

By a "DAF-4 polypeptide" is meant a polypeptide that complements (as defined above) a *C. elegans* daf-4 mutation and/or that possesses at least 45% amino acid sequence identity to SEQ ID NO: 20, at least 40% amino acid sequence identity to SEQ ID NO: 21, at least 44% amino acid sequence identity to SEQ ID NO: 22, or a combination thereof.

By a "DAF-11 polypeptide" is meant a polypeptide that complements (as defined above) a *C. elegans* daf-11 mutation and/or that possesses at least 40% amino acid sequence identity to SEQ ID NO: 75, at least 43% amino acid sequence identity to SEQ ID NO: 76, at least 36% amino acid sequence identity to SEQ ID NO: 77, at least 65% amino acid sequence identity to SEQ ID NO: 78, or a combination thereof.

By a "DAF-12 polypeptide" is meant a polypeptide that complements (as defined above) a *C. elegans* daf-12 mutation and/or that possesses at least 42% amino acid sequence identity to SEQ ID NO: 72, at least 58% amino acid sequence identity to SEQ ID NO: 73, at least 34% amino acid sequence identity to SEQ ID NO: 74, or a combination thereof.

By a "DAF-14 polypeptide" is meant a polypeptide that complements (as defined above) a *C. elegans* daf-14 mutation and/or that possesses at least 48% amino acid sequence identity to SEQ ID NO: 68, at least 37% amino acid sequence identity to SEQ ID NO: 69, at least 48% amino acid sequence identity to SEQ ID NO: 70, at least 37% amino acid sequence identity to SEQ ID NO: 71, or a combination thereof.

By "insulin receptor activity" is meant any activity exhibited by an insulin receptor and measured by either (i) activation of insulin receptor substrate-1 (IRS-1) phosphorylation and recruitment of PI-3 kinase, (ii) activation of glucose transporter (Glut 4) fusion with a cellular membrane and concomitant glucose uptake, or (iii) activation of glycogen and/or fat synthesis and concomitant inhibition of gluconeogenesis or lipolysis or both.

By "insulin receptor related activity" is meant any activity not directly attributable to the insulin receptor but that is measured by an activation of IRS-1 phosphorylation and recruitment of PI3-kinase.

By "IGF-1 receptor activity" is meant any activity exhibited by an insulin-like growth factor-1 receptor and measured by (i) activation of IRS-1 phosphorylation and recruitment of PI-3 kinase, (ii) activation of cell division in NIH3T3 cells (e.g., as described in Gronborg et al., J. Biol. Chem. 268: 23435–23440, 1993), or (iii) activation of bone growth in, for example, the mouse model.

By "SMAD protein" is meant a protein that is capable of coupling to TGF-β type ser/thr receptors. Smad proteins typically contain a smad conserved motif as described by Derynk et al. (*Cell* 87: 173, 1996). Exemplary smad proteins include, without limitation, DAF-3, MADR-2, MAD, DPC-4, and Sma-2.

By "AKT activity" is meant any activity exhibited by an AKT polypeptide and measured by phosphatidylinositol-regulated increases in serine phosphorylation of GSK-3 or activation of non-dauer growth in *C. elegans* akt mutants.

By "impaired glucose tolerance condition" is meant any condition in which blood sugar levels are inappropriately elevated or lack normal metabolic regulation. Examples of such conditions include, without limitation, Type I diabetes, Type II diabetes, and gestational diabetes, and may be associated with obesity and atherosclerosis.

By "protein" or "polypeptide" is meant any chain of amino acids, regardless of length or post-translational modification (e.g., glycosylation or phosphorylation).

By "substantially pure" is meant a preparation which is at least 60% by weight (dry weight) the compound of interest, e.g., any of the polypeptides of the invention such as the DAF-2, DAF-3, or DAF-16 polypeptides or DAF-2, DAF-3, or DAF-16-specific antibodies. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "isolated DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By a "substantially identical" polypeptide sequence is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein).

Preferably, such a sequence is at least 75%, more preferably 85%, and most preferably 95% identical at the amino acid level to the sequence used for comparison.

Homology is typically measured using sequence analysis software (e.g., Sequence Analysis Software Package of the Genetics Computer Group, University of Wisconsin Biotechnology Center, 1710 University Avenue, Madison, Wis. 53705 or BLAST software available from the National Library of Medicine). Examples of useful software include the programs, Pileup and PrettyBox. Such software matches similar sequences by assigning degrees of homology to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 75%, more preferably 85%, and most preferably 95% identical at the amino acid level to the sequence of comparison. If nucleic acid sequences are compared a "substantially identical" nucleic acid sequence is one which is at least 85%, more preferably 90%, and most preferably 95% identical to the sequence of comparison. The length of nucleic acid sequence comparison will generally be at least 50 nucleotides, preferably at least 60 nucleotides, more preferably at least 75 nucleotides, and most preferably 110 nucleotides. Again, homology is typically measured using sequence analysis software (e.g., Sequence Analysis Software Package of the Genetics Computer Group, University of Wisconsin Biotechnology Center, 1710 University Avenue, Madison, Wis. 53705).

By "positioned for expression" is meant that the DNA molecule is positioned adjacent to a DNA sequence which directs transcription and translation of the sequence (i.e., facilitates the production of any of the polypeptides disclosed herein including, but not limited to, DAF-2, DAF-3, and DAF-16 and any human homolog thereof).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds a polypeptide of the invention (e.g., DAF-2, DAF-3, and DAF-16) but which does not substantially recognize and bind other molecules in a sample (e.g., a biological sample) which naturally includes a polypeptide of the invention. An antibody which "specifically binds" such a polypeptide is sufficient to detect protein product in such a biological sample using one or more of the standard immunological techniques available to those in the art (for example, Western blotting or immunoprecipitation).

By "immunological methods" is meant any assay involving antibody-based detection techniques including, without limitation, Western blotting, immunoprecipitation, and direct and competitive ELISA and RIA techniques.

By "means for detecting" is meant any one or a series of components that sufficiently indicate a detection event of interest. Such means involve at least one label that may be assayed or observed, including, without limitation, radioactive, fluorescent, and chemiluminescent labels.

By "hybridization techniques" is meant any detection assay involving specific interactions (based on complementarity) between nucleic acid strands, including DNA-DNA, RNA-RNA, and DNA-RNA interactions. Such hybridization techniques may, if desired, include a PCR amplification step.

By a "modulatory compound", as used herein, is meant any compound capable of either decreasing DAF-3 and DAF-16 expression (i.e., at the level of transcription, translation, or post-translation) or decreasing DAF-3 and DAF-16 protein levels or activity. Also included are compounds capable of either increasing DAF-1, DAF-2, DAF-4, DAF-8, DAF-7, DAF-11, DAF-14, AGE-1, and AKT expression (i.e., at the level of transcription, translation, or post-translation) or increasing DAF-1, DAF-2, DAF-4, DAF-8, DAF-7, DAF-11, DAF-14, AGE-1, and AKT protein levels or their corresponding activities.

By "complementation" is meant an improvement of a genetic defect or mutation. In one example, complementation of a genetic defect in a daf, age, or akt gene can be carried out by providing the wild-type daf, age, or akt genes, respectively. Complementation is generally accomplished by expressing the wild-type version of the protein in a host cell or animal bearing a mutant or inactive version of the gene.

Other features and advantages of the invention will be apparent from the following detailed description thereof, and from the claims.

DETAILED DESCRIPTION

The drawings will first be described.

DRAWINGS

FIG. 1 shows the genetic and physical map of C. elegans daf-2. The top panel shows the genetic map of daf-2. daf-2 maps on the left arm of chromosome III 11.4 map units to the right of dpy-1 and 1.6 map units to the left of ben-1 (ACeDB). The middle panel shows the physical map of daf-2. daf-2 maps between mgP34 and mgP44 in a region not covered by cosmid clones but covered by YAC Y53G8. Cosmids from the approximate daf-2 genetic location detect RFLPs between C. elegans strains Bristol N2 and Bergerac RC301. mgP31 on cosmid T21A6 is a HindIII RFLP: 5.3 kb in Bristol, 4.5 kb in RC301. mgP33 on cosmid T02B2 is a HindIII RFLP: 9 kb in Bristol, 8 kb in RC301. mgP34 on cosmid R10F2 is an EcoRI RFLP: 4.1 and 2.8 kb in Bristol, 3.6 kb in RC301. mgP44 on cosmid R07G11 is a complex EcoRI RFLP: 2.9 kb, 2.4 kb, 1.9 kb and 1.7 kb in Bristol; 3.6 kb, 2.5 kb and 1.6 kb in RC301. mgP35 on cosmid T10D5 is a StyI RFLP: 5.4 kb in Bristol, 5.8 kb in RC301. mgP32 on cosmid C42B8 is a StyI RFLP: 2.8 kb in Bristol; 2.9 kb in RC301. mgP48 detected with daf-2 probe (nt 1277–2126 and 3747–4650) is a HindIII RFLP: 4.3 kb and 71 kb in Bristol and 4.1 kb and 6.2 kb in RC301. Thirty-one out of thirty-three Dpy-non-Daf recombinants carry the RC301 allele of mgP34 whereas all thirty-three recombinants in this interval carry the RC301 allele of mgP44, mapping daf-2 0.69 map units to the right of mgP34 and to the left of mgP44. Fourteen out of twenty-four Ben-non-Daf recombinants carry the RC301 mgP44 allele whereas all of these recombinants carry the RC301 allele of mgP34, mapping daf-2 0.66 map units to the left of mgP44.

Y53G8 YAC DNA was isolated from CHEF gels as described in Ausubel et al. (Current Protocols in Molecular Biology, John Wiley & Sons, New York, N.Y., 1990), labeled, and shown to hybridize to multiple restriction fragments from cosmids bearing mgP34 and mgP44. A probe from the insulin receptor homolog on Y53G8 detects the mgP48 RFLP between N2 and RC301. All thirty-three Dpy-non-Daf and all twenty-four Ben-non-Daf recombinants described above carry the RC301 allele of mgP48, indicating that daf-2 could not be separated from this insulin receptor gene by these fifty-seven recombination events in a thirteen map unit interval.

The bottom panel shows the structure of daf-2 cDNA. The daf-2 cDNA was amplified from a cDNA library constructed according to standard methods by PCR using internal primers derived from the genomic shotgun sequences, vector sequence primers (for 3' end) and an SL1 transspliced leader PCR primer (M. Krause, In: Methods Cell Biol., vol. 48, pp. 483–512, H. F. Epstein and D. C. Shakes, eds., Academic Press, San Diego, Calif., 1995). To isolate a cDNA, pooled plasmid DNA from 106 clones of a 107 clone complexity cDNA library was used as a PCR template. To obtain a daf-2 cDNA 3' end, daf-2 internal primer CGCTACG-GCAAAAAAGTGAA (SEQ ID NO: 1) in the kinase domain and a cloning vector primer CGATGATGAA-GATACCCC (SEQ ID NO: 2) were used in a nested PCR reaction with adjacent internal primers. For the cDNA fragment from the ligand-binding domain to the kinase domain, PCR was carried out with TGATGCGAACGGC-GATCGAT (SEQ ID NO: 3) and ACGCTGGATCATCTA-CATTA (SEQ ID NO: 4) primers. For the daf-2 5' end, SL1 primer GGTTTAATTACCCAAGTTTGAG (SEQ ID NO: 5) and one internal daf-2 primer GCTCACGGGTCACA-CAACGA (SEQ ID NO: 6) were used in a nested PCR reaction with adjacent internal primers. Using PCR to amplify genomic DNA from a set of 20 daf-2 mutants, we searched for daf-2 mutations in a 0.8 kb region of the ligand binding domain and in a 0.9 kb region of the kinase domain. For sequencing the ligand-binding domain PCR primers TGATGCGAACGGCGATCGAT (SEQ ID NO: 7) and TGAGGGCCAACTAAAGAAGAC (SEQ ID NO: 8) were used. In the kinase domain primers CGCTACG-GCAAAAAAGTGAA (SEQ ID NO: 9) and GACGATC-CCGAGGTGAGTAT (SEQ ID NO: 10) were used. The presence of an SL1 spliced leader sequence indicates a full length daf-2 cDNA. The predicted ORF is shown as a box; 5' and 3' UTRs are shown as thick bars. The predicted DAF-2 initiator methionine at base 486 is preceded by an in frame stop codon 63 bases upstream. The predicted DAF-2 stop codon is found at base 5658. No consensus polyadenylation signal was found in the cDNA nor in genomic shotgun sequence #00678, which extends 302 bp further downstream. The initial insulin receptor homolog shotgun sequences are shown as thin bars above the box.

Introns were detected by a combination of in silico genomic and cDNA sequence comparison, and by comparison of PCR products derived from cDNA and genomic DNA templates. The open triangles over a vertical bar indicate positions of the detected exon/intron boundaries. All the intron donor sites have GT consensus and the acceptor sites have AG consensus (Krause, 1995 supra). The triangles without a vertical bar indicate the approximate intron locations determined by comparison of PCR products using genomic DNA or cDNA as a template. Intron lengths were estimated by comparison of the PCR product size using cDNA or genomic DNA templates. Genomic regions corresponding to some of the introns could not be PCR amplified suggesting that these introns are long. The minimum daf-2 gene size based on this analysis is 33 kb.

FIG. 2A shows the predicted C. elegans DAF-2 amino acid sequence. The predicted cysteine-rich region (amino acids 207–372) and tyrosine kinase domain (amino acids 1124–1398) are boxed. The signal peptide (amino acids 1–20), proteolysis site (amino acids 806–809), transmembrane domain (amino acids 1062–1085), and PTB binding motif in the juxtamembrane region (NPEY, amino acids 1103–1106) are underlined. Three DAF-2 tyrosine residues, Y1293, Y1296 and Y1297, in the region corresponding to the insulin receptor kinase Y1158 to Y1163 activation loop are likely to be autophosphorylated, based on the predicted similarity between the DAF-2 and insulin receptor phosphorylation targets (FIG. 2B). Another likely target for DAF-2 autophosphorylation is the Y1106 NPEY motif located in the region corresponding to the insulin receptor juxtamembrane region NPEY motif (at Y972), that has been shown to mediate IRS-1 binding via its PTB domain to the insulin receptor (White and Kahn, J. Biol. Chem. 269: 1–4, 1994). While DAF-2 bears one YXXM motif implicated in coupling to PI 3-kinase, mammalian IRS-1 and Drosophila insulin receptor (Fernandez et al., EMBO J. 14: 3373–3384, 1995) bear multiple YXXM motifs. Although no p85-like adaptor subunit has yet been detected in the C. elegans database, the AGE-1 homology to mammalian p110 suggests the existence of a homologous or analogous adaptor (Morris et al., Nature 382: 536–539, 1996). In the DAF-2 C-terminal domain, two other tyrosine residues may be autophosphorylated and bound to particular SH2-containing proteins: Y1678 binding to a PLC-g or SHP-2 homolog, and Y1686, perhaps binding to SEM-5 (FIG. 2A) (Songyang et al., Cell 72: 767–778, 1993). While mutations in, for example, ras and MAP kinase have not been identified in screens for dauer constitutive or dauer defective mutations, these general signaling pathway proteins may couple to DAF-2 as they couple to insulin signaling in vertebrates (White and Kahn, J. Biol. Chem. 269: 1–4, 1994). The predicted phosphotyrosine residues in juxtamembrane region and the kinase domain activation loop are circled. In the extended C-terminal region, predicted phosphotyrosine residues are also circled and SH2-binding sites are underlined (see below).

FIG. 2B shows the cDNA encoding the C. elegans DAF-2.

FIG. 2C shows the amino acid comparison of C. elegans DAF-2 to the human insulin receptor and human IGF-I receptor (shown in parenthesis), and to the Drosophila insulin receptor homolog, with daf-2 and human insulin receptor mutations highlighted. Six daf-2 mutations map in the ligand-binding domain: sa187 (C347S, TGT to AGT), e1368 (S451L, TCA to TTA), e1365 (A458T, GCT to ACT), sa229 (D526N, GAT to AAT), and two mutations in mg43 (C279Y, TGT to TAT and P348L, CCC to CTC). Three daf-2 mutations substitute conserved amino acid residues in the insulin receptor kinase domain: sa219 (D1252N, GAT to AAT), e1391 (P1312L, CCC to CTC), and e1370 (P1343S, CCA to TCA). Darkened residues indicate amino acid identity. Hatched residues indicate amino acid similarity. The percentages under the domains represents the percentage of identity observed between DAF-2 and each receptor. The corresponding BLAST probabilities of DAF-2 random match to each protein is: $6.4 \times 10^{-157}$ (human insulin receptor), $2.7 \times 10^{-156}$ (human IGF-I receptor), $2.1 \times 10^{-153}$ (molluscan InR homolog), $8.3 \times 10^{-153}$ (mosquito InR homlogoue), $1.6 \times 10^{-138}$ (human insulin receptor-related receptor), $1.7 \times 10^{-122}$ (Drosophila InR homolog ), $2.0 \times 10^{-108}$ (Hydra InR homolog). DAF-2 is more distant from the next most closely related kinase families: $8.9 \times 10^{-58}$ (v-ros) and $3.0 \times 10^{-51}$ (trkC neurotrophin receptor).

Conserved cysteine residues in the ligand-binding domain (top) are marked with dots. In the kinase domain, active site residues that mediate insulin receptor kinase specificity are marked with stars. All of these residues are homologous in DAF-2. The mutations found in human patients are indicated at the top of the row, and daf-2 allele substitutions are indicated below with allele names. The sequence alignments were done with GCG programs, Pileup and Prettybox, and the identities were calculated with the GCG program, Gap.

FIG. 3 is a photograph showing the metabolic control by C. elegans daf-2 and daf-7. The top panel shows low levels of fat accumulation in a wild type L3 animal grown at 25° C. that has been stained with Sudan black. Non-starved animals were fixed in 1% paraformaldehyde in PBS, frozen at −70° C., and freeze-thawed three times. Fixed animals were washed three times in PBS, and then incubated overnight in 1X Sudan black according to standard methods. The next panel shows higher levels of fat accumulation in daf-2(e1370) grown at the non-permissive temperature of 25° C. These animals accumulate fat in both intestinal and hypodermal cells. daf-2(e1370) animals grown at 15° C., the permissive temperature, accumulate low levels of fat, like wild type (data not shown). The next panel shows high fat levels in the intestine and hypodermis of daf-7(e1372) animals grown at 25° C. The bottom panel shows high levels of fat in daf-2(e1370) animals grown at the permissive temperature until the L4 stage and then shifted to the non-permissive temperature. This shows that daf-2 regulates metabolism without entry into the dauer stage.

FIG. 4 is a schematic diagram showing a model of insulin signaling in the C. elegans dauer formation pathway. In the absence of dauer pheromone, an insulin-like ligand activates DAF-2, and DAF-7 TGF-β-like signal activates the DAF-1 and DAF-4 receptors. Activated DAF-2 autophosphorylates particular tyrosine residues and recruits signaling molecules, including the PI 3-kinase homolog (a heterodimer of an as yet unidentified p85 homolog and the PI 3-kinase catalytic subunit AGE-1). The AGE-1 PI 3-kinase produces PIP3 second messenger. This second messenger may regulate glucose transport (White and Kahn, 1994 supra), metabolic kinase cascades that include AKT and GSK-3 (Hemmings, Science 226:1344–1345, 1984; Jonas et al., Nature, 385:343–346, 1997), and transcription and translation of metabolic genes (White and Kahn, 1994, supra). DAF-16 acts downstream of DAF-2 and AGE-1 in this pathway and is negatively regulated by them (Vowels and Thomas, Genetics, 130:105–123, 1992; Gottlieb and Ruvkun, Genetics, 137:107–110, 1994). While both the DAF-7/TGF-β and DAF-2/insulin signaling pathways converge to control dauer formation, only the DAF-2 pathway controls reproductive phase longevity. This may be due to non-transcriptional outputs of DAF-2 suggested by precedents from insulin receptor signaling. DAF-7 signaling output is predicted to be only transcriptional as described herein.

FIG. 5A shows that C. elegans daf-3 was genetically mapped to a region on the X chromosome between aex-3 and unc-1. Cosmid and plasmid clones from the region were assayed for transformation rescue (Mello et al., EMBO J 10: 3959–3970,1991). Plasmid pRF4 (rol-6 transformation marker, 100 ng/ml), and cosmids (5–6 ng/ml) were injected into the gonad of daf-7 (e1372); daf-3 (e1376) animals. Transgenic animals were scored for dauer formation at 25° C.; a dauer (i.e., a return to the daf-7 phenotype) indicates rescue of daf-3; clones that rescue daf3 are boxed. B0217 rescues the daf-3 phenotype; eighteen of nineteen transgenic lines were rescued (~80% dauers). Examination of sequence provided by the C. elegans Sequencing Consortium revealed a Smad homologous gene on B0217. A 13 kb subclone of B0217 containing just the Smad also rescues daf-3 (see FIG. 3). No rescue was seen upon injection of other cosmids from the region, B0504 (7 lines tested, <1% rescue) and C05H10 (10 lines tested, <1% rescue). mgDf90 is a deletion that removes all of daf-3.

FIG. 5B shows the structure of the C. elegans daf-3 coding region. The top is the exon/intron structure of daf-3; coding exons are filled boxes, non-coding regions are open boxes, and lines are introns. daf-3 cDNAs were isolated according to standard methods. Four cDNAs were sequenced completely; their N-termini are indicated by vertical lines. These three cDNAs contain ~400 bp of 3' UTR, but no poly-A tail; a C. elegans consensus polyadenylation sequence is found 12 bp from the 3' end of the cDNAs. The longest of this cDNA appears full-length, as it contains a methionine codon and the genomic sequence contains no other methionine codon and no putative splice sites upstream before in-frame stop codons. To further characterize the 5' end of daf-3, PCR products from libraries or individual daf-3 cDNAs were sequenced. From DNA isolated from a cDNA library, we amplified a product with a primer to SL1 and to a region in conserved domain I (shown as primer 1). For the individual cDNAs, we amplified with a primer to the cDNA vector and primer 1. These PCR products were sequenced from primer 2 to the 5' end, and we found that there is alternative splicing at the 5' end of daf-3, upstream of the conserved domains. The two alternate splice forms are indicated, and the ends of individual cDNAs are indicated by vertical lines. Note that the second has the trans-spliced leader SL1 that is found at the 5' end of many C. elegans cDNAs; thus, this cDNA shows a bona fide 5' end of daf-3.

FIG. 5C shows the protein sequence alignment of C. elegans daf-3 and the closest homolog found to date, human DPC4, in the Smad conserved domains I and II. Dots indicate gaps introduced to maximize alignment. DAF-3 is 55% identical to DPC4 in domain I and 30% identical in domain II. daf-3(mg125) and daf-3(mg132) mutations are indicated by boldface and underline. The Smad mutational hotspot is underlined. In addition to mg125 and mg132, seven other daf-3 alleles were sequenced in the hotspot; none of them contains a mutation. Alleles sequenced were mg91, mg93, mg105, mg121, mg126, mg133 (isolated by A. Koweek and G. Patterson, unpublished) and sa205.

FIGS. 6A–6G is a panel of photographs showing C. elegans DAF-3 and DAF-4 expression. These photographs show GFP fluorescence, paired with DAPI fluorescence or Nomarski optics photographs, as marked. All DAF-3 photographs show animals with the second plasmid from FIG. 6A illustrates DAF-3/GFP head expression in an L1 animal. FIG. 6B illustrates DAF-3/GFP expression in the ventral nerve cord of an adult animal. L1 animals demonstrated similar expression patterns. FIG. 6C illustrates DAF-3/GFP expression in the intestine of an L1 animal. FIG. 6D illustrates DAF-3/GFP expression in the distal tip cell of an L4 animal. FIG. 6E illustrates DAF-3/GFP expression in an embryo with approximately 200 nuclei. FIG. 6F illustrates DAF-4/GFP expression in the head of an L1 animal. FIG. 6G illustrates DAF-4/GFP expression in the dorsal nerve cord and ventral nerve cord of an L4 animal.

FIG. 7 is a table that shows the rescuing ability and suppression of C. elegans daf-7 by daf-3 plasmids. The solid boxes represent the Smad conserved domains I and II of daf-3; the stippled boxes represent green fluorescent protein (GFP). For all experiments shown, daf-3 plasmids were injected at a concentration of 10 ng/ml, and the pRF4 injection marker was injected at a concentration of 90 ng/ml. To score dauer formation, transgenic adult animals were allowed to lay eggs on plates for several hours at room temperature and were then removed. The plates were scored after two days at 25° C. The rescue experiment shows the rescue of daf-7(m62); daf-3(e1376) by each of the fusion proteins. Failure to rescue results in rolling nondauers, while rescue of daf-3 results in rolling dauers (the daf-7 phenotype). The control is an array with the pRF4 transformation marker and a non-rescuing cosmid. For each construct, four or more lines were measured in two separate experiments. To measure suppression of daf-7, transgenic arrays were crossed into daf-7 (for plasmids 1 and 3), or produced by injecting directly into daf-7 (for plasmid 2). Transgenic (rolling) animals were scored for suppression of daf-7 (=nondauers) or failure to suppress daf-7 (=dauers). The controls are two array strains with the pRF4 marker and an unrelated GFP expressing transgene.

FIG. 8A is a photographs showing that DAF-3/GFP is associated with metaphase chromosomes. Fixed L1 animals were immunostained with anti-GFP antibody and anti-α-tublin antibody. DNA was visualized using DAPI staining.

FIG. 8B is a photograph showing that a truncated C. elegans daf-3/GFP protein is predominantly nuclear. Wild-type animals were injected with the truncated construct shown in FIG. 7 at a concentration of 10 ng/ml. The pRF4 transformation marker was injected at 100 ng/ml. The photograph shows a late L1 or early L2 animal, and daf-3 is predominantly nuclear. The clear spot in the center of some of the nuclei is the nucleolus, which has no daf-3/GFP. All cells in these animals have predominantly nuclear daf-3/GFP, including the ventral cord neurons, intestinal cells, and distal tip cell (all shown), as well as head and tail neurons and hypodermal cells.

FIGS. 9A and 9B show models for the role of the C. elegans daf-3/DAF-8/DAF-14 Smad proteins in dauer formation. FIG. 9A shows dauer reproductive growth induction. FIG. 9B shows reproductive dauer growth induction.

FIGS. 11A–11C show the cDNA sequences of the differentially spliced C. elegans daf-3 transcripts (SEQ ID NOS: 39, 52, and 53).

FIGS. 12A–12C show the amino acid sequences of the C. elegans DAF-3 polypeptide isoforms (SEQ ID NOS: 40–42).

FIGS. 13A and 13B show the cDNA sequence of the differentially spliced C. elegans daf-16 transcripts (SEQ ID NOS: 43 and 44).

FIGS. 14A and 14B show the amino acid sequences of the C. elegans DAF-16 polypeptide isoforms (SEQ ID NOS: 45 and 46).

FIG. 15 shows the cDNA sequence of the C. elegans age-1 gene (SEQ ID NO: 47).

FIG. 16 shows the amino acid sequence of the C. elegans AGE-1 polypeptide (SEQ ID NO: 48).

FIG. 21A is an illustration showing that human FKHR and AFX are the closest relatives to DAF-16. Note that the differentially spliced DAF-16 forkhead domain is less homologous.

FIG. 25 is an illustration showing the comparison of C. elegans AKT with mammalian AKT.

Figure 1:
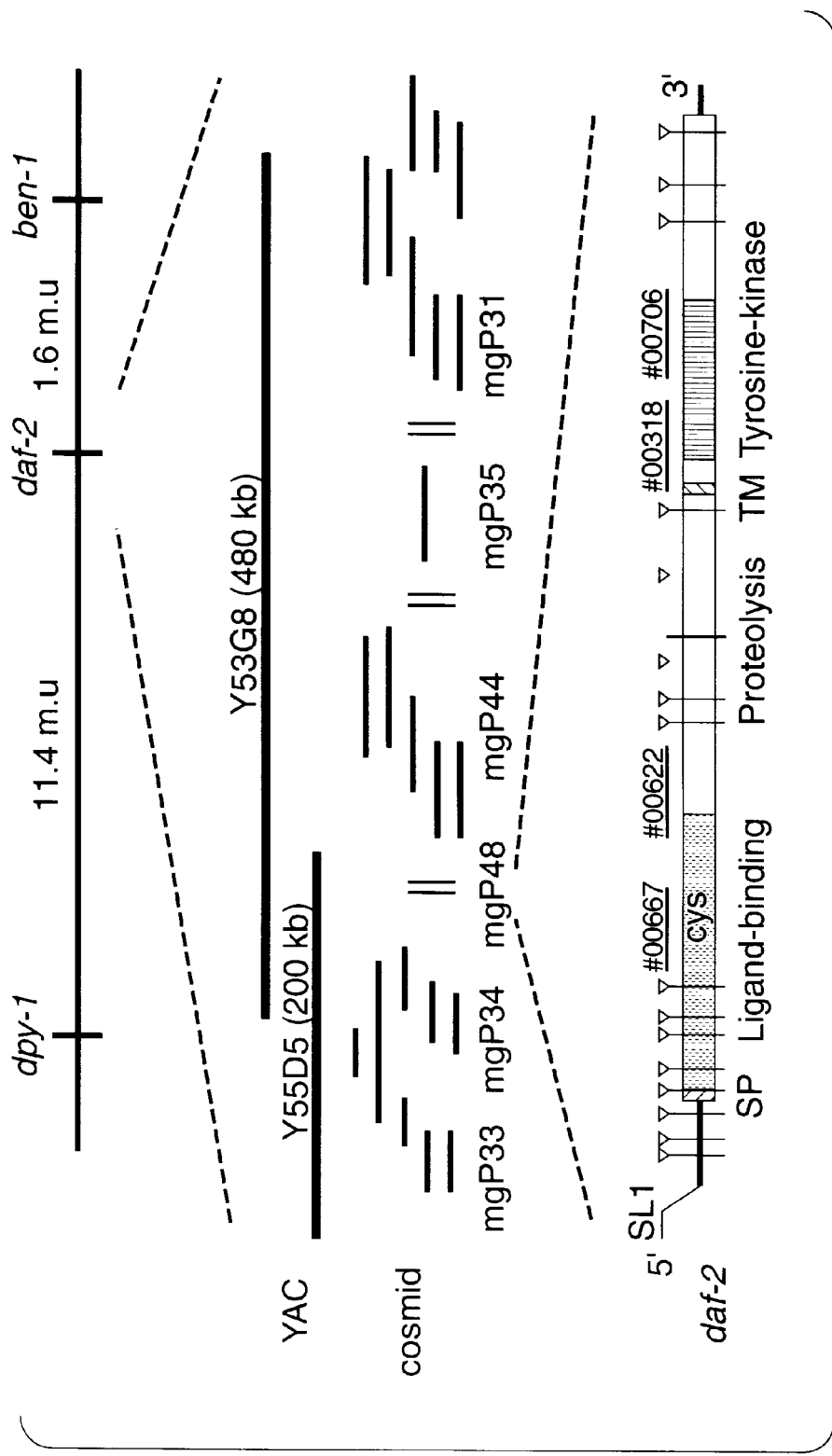

The DAF-2 Insulin Receptor Family Member Regulates Longevity and Diapause in C. elegans Arrest at the C. elegans dauer stage is normally triggered by a dauer-inducing pheromone detected by sensory neurons which signal via a complex pathway to target tissues that are remodeled and metabolically shifted such as the germ line, intestine, and ectoderm (Riddle, In: Caenorhabditis elegans II, D. Riddle, T. Blumenthal, B. Meyer, J. Priess, eds., Cold Spring Harbor Laboratory, Cold Spring Harbor, N.Y., 1997, pp. 739–768. Kenyon, op cit., pp. 791–813.). Genetic epistasis analysis of daf mutants that arrest at the dauer stage or enter the reproductive life cycle independent of pheromone regulation has revealed parallel genetic pathways that regulate distinct aspects of the dauer metamorphosis (Vowels and Thomas, Genetics 130: 105–123, 1992; Gottlieb and Ruvkun, Genetics 137: 107–120, 1994). The pathway that includes daf-2 is unique in that it controls both reproductive development and normal senescence: daf-2 mutant animals arrest development at the dauer larval stage and have dramatically increased longevity (Table I) (Riddle, In: Caenorhabditis elegans II, D. Riddle, T. Blumenthal, B. Meyer, J. Priess, eds., Cold Spring Harbor Laboratory, Cold Spring Harbor, N.Y., 1997, pp. 739–768; Kenyon, op cit. pp 791–813; Vowels and Thomas, Genetics 130: 105–123, 1992; Gottlieb and Ruvkun, Genetics 137: 107–120, 1994; Larsen et al., Genetics 139: 1567–1583, 1995; Kenyon et al., Nature 366: 461–464, 1993; Dorman et al., Genetics 141: 1399–1406, 1995).

Table I shows the percentage of dauer formation of daf-2 alleles and the associated mutations. Eggs from animals grown at 15° C. (day 0) were incubated at 15, 20, or 25° C. Numbers in parenthesis are animals counted. Numbers of wild-type animals and dauers were counted on day 3 (20° C. and 25° C.) or day 5 (15° C.). Most of the dauers marked with stars recovered by day 4 (sa229 at 25° C.) or by day 8 (sa229) and sa219 at 15° C., e1368 and sg219 at 20° C., and e1365 and e1368 at 25° C.). mg43 was studied as follows: dpy-1(el)daf-2(mg43); SDP3 animals were grown at 20° C. until the young adult stage. Eggs from five adults were laid at 15° C. or 20° C. and grown at the same temperatures. Numbers of Dpy-Daf animal and Dpy-non-Daf animals were counted on day 3 (20° C.) or day 5 (15° C.). Sg187 and sg229 were also studied by Malone and Thomas (Genetics 136:879–886, 1994).

Table I

| Region | Allele | mutation | Percentage of dauer formation of daf-2 alleles % dauer formation | | |
|---|---|---|---|---|---|
| | | | 15° C. | 20° C. | 25° C. |
| cys-rich | mg43 | C279Y& P348L | 100.0 (215) | 100.0(245) | n.d. |
| | sa187 | C347S | 0.4 (461) | 98.7(224) | 100(910) |
| ligand binding | e1368 | S451L | 0.0 (328) | 4.5*(418) | 99.7*(698) |
| | e1365 | A458T | 0.0 450 | 0.0(461) | 99.4*(814) |
| | sa229 | D526N | 3.4* (234) | n.d. | 22.1*(420) |
| | sa219 | D1252N | 10.0* (460) | 99.7*(396) | 100(514) |
| ki- | e1391 | P1312L | 3.3 | 100(323) | 100(322) |

Table I-continued

| Region | Allele | mutation | Percentage of dauer formation of daf-2 alleles % dauer formation | | |
|---|---|---|---|---|---|
| | | | 15° C. | 20° C. | 25° C. |
| nase | e1370 | P1343S | (332) 0.0 (520) | 0.0(188) | 100(635) |

Genetic mapping using both visible genetic markers and restriction fragment length polymorphism (RFLP) markers places daf-2 between mgP34 and mgP44 (FIG. 1). While cosmid coverage of this physical genetic region is not complete, YAC Y53G8 carries the genomic region that includes mgP34 and mgP44, which flank daf-2 (FIG. 1). As a step in the C. elegans genome sequencing effort, random M13 subclones derived from Y53G8 were sequenced by the Genome Sequencing Center.

Sequence Identities Show that DAF-2 is Likely to Bind to an Insulin-like Ligand and to Phoshorylate Tyrosine Residues The amino acid sequences and nucleotide sequences encoding DAF-2 are shown in FIGS. 2A and 2B, respectively. Using BLASTX to compare 570 translated Y53G8 M13 subclone sequences against the Genbank protein database, we found that four sequences are homologous to the mammalian insulin receptor family. An insulin receptor was a good daf-2 candidate gene because insulin regulates vertebrate growth and metabolism (White and Kahn, *J. Biol. Chem.* 269: 1–4, 1994), and because a phosphatidylinositol (PI) 3-kinase has been shown to act in both the insulin receptor and daf-2 pathways (White and Kahn, *J. Biol. Chem.* 269: 1–4, 1994; Morris et al., *Nature* 382: 536–539, 1996). The detection of multiple daf-2 mutations in the gene (see below), and the coincidence of the genetic location of this insulin receptor homolog with daf-2 (FIG. 2C) establish that this insulin receptor homolog corresponds to daf-2.

The daf-2 transcription unit and gene structure were determined using PCR primers derived from daf-2 genomic subclone sequences to amplify daf-2 genomic and cDNA regions. A probable full length daf-2 cDNA bears a 5172 base open reading frame, a 485 base 5' UTR and a 159 base 3' UTR (FIGS. 1, 2A). The predicted DAF-2 protein shows long regions of sequence identity to the insulin receptor family. Over the entire protein, DAF-2 is 35% identical to the human insulin receptor (Ebina et al., *Cell* 40: 747–58, 1985; Ullrich, et al., *Nature* 313: 756–61, 1985), 34% identical to the human IGF-I receptor (Ullrich, et al., *EMBO J.:* 5, 2503–12, 1986), and 33% identical to the human insulin receptor-related receptor (Shier and Watt, *J. Biol. Chem.* 264: 14605–8, 1989). DAF-2 is the only member of the insulin receptor family in the 90 Mb C. elegans genome sequence (about 90% complete) or in the 10 Mb C. elegans EST sequence database. Because it is equally distant from insulin, IGF-I, and insulin receptor-related receptors, DAF-2 is probably the homolog of the ancestor of these duplicated and diverged receptors, and thus may subserve any or all of the functions of these mammalian receptors (see below). Like these receptors, DAF-2 has a putative signal peptide, a cysteine-rich region in the putative ligand binding domain, a putative proteolysis site, a transmembrane domain, and a tyrosine kinase domain. In addition, DAF-2 has a C-terminal region that may serve a function similar to the mammalian insulin receptor substrate-1 (IRS-1) (FIG. 2; White and Kahn, *J. Biol. Chem.* 269: 1–4, 1994).

In the approximately 500 amino acid ligand-binding domain of the insulin receptor, DAF-2 is 36% identical to insulin receptor and 35% identical to the IGF-I receptor. Twenty-one of twenty-three phylogenetically conserved cysteine residues in this domain are conserved in DAF-2 (FIG. 2C). The DAF-2 cys-rich region is 34% identical to human insulin receptor and 28% identical to the IGF-I receptor. Six daf-2 mutations map in this domain (FIG. 2C, Table I). The mg43 and sa187 mutations substitute conserved residues in the cys-rich region (FIG. 2C). daf-2 (mg43) carries two mutations which substitute conserved residues, which may explain the strength of this allele (non-conditional, Table I). Other substitutions at non-conserved residues cause less severe phenotypes (Table I). Insulin resistant and diabetic patients with mutations in the ligand binding domain of the human insulin receptor gene have been identified (Taylor, *Diabetes* 41: 1473–1490, 1992) (see below). These mutations impair receptor transport to cell surface, or insulin binding affinity, or both. The DAF-2 mutations in this domain might similarly decrease receptor signaling to cause dauer arrest.

Insulin receptors are $\alpha 2,\beta 2$ tetramers proteolytically processed from a single precursor protein (White and Kahn, *J. Biol. Chem.* 269: 1–4, 1994). DAF-2 bears a probable protease recognition site at a position analogous to the insulin receptor processing site (RVRR 806–809) (Yoshimasa et al., *J. Biol. Chem.* 265: 17230–17237, 1990).

The 275 amino acid DAF-2 tyrosine kinase domain is 70% similar and 50% identical to the human insulin receptor kinase domain. Upon insulin binding, the intracellular tyrosine kinase domain of the insulin receptor phosphorylates particular tyrosine residues flanked by signature amino acid residues (upstream acidic and downstream hydrophobic amino acids (Songyang and Cantley, *Trends Biochem. Sci.* 20: 470–475, 1995)) in the intracellular domain as well as on IRS-1 (White and Kahn, *J. Biol. Chem.* 269: 1–4, 1994). Multiple DAF-2 tyrosine residues in these sequence contexts are likely autophosphorylation targets, including three tyrosines in a region similar to the insulin receptor activation loop and one in the juxtamembrane region as described above (FIG. 2C). Based on the crystal structure of the insulin receptor kinase domain bound to its activation loop, eight kinase domain residues mediate target site specificity (Hubbard et al., *Nature* 372: 746–754, 1994). In DAF-2 (but not in more distantly related receptor kinases), these residues are invariant (5/8) or replaced with similar amino acids (3/8: K to R, E to D) (FIG. 2C), suggesting that DAF-2 phosphorylates the same target tyrosine motifs as the insulin receptor kinase.

Three daf-2 missense mutations substitute conserved amino acid residues in the kinase domain (FIG. 2C, Table I). All three mutations cause moderate to strong dauer constitutive phenotype, but none are as strong as the non-conditional alleles, for example, mg43 (Table I). Human insulin receptor mutations in the kinase domain exhibit decreased kinase activity and cause severe insulin resistance and associated defects (FIG. 2C; Taylor, *Diabetes* 41: 1473–1490, 1992). Remarkably, a human diabetic insulin resistant patient bears the same amino acid substitution (P1178L) as daf-2(e1391) (Kim et al., *Diabetologia* 35:261–266, 1992). This patient was reported to be heterozygous for this substitution. daf-2(e1391) is not dominant whereas it is a highly penetrance recessive mutation (Table I).

To test for dominance of daf-2(e1391), using a genetically marked balancer chromosome, 105 dauers segregated from 485 daf-2/+ parents as expected for a recessive mutations.

The genotype of 76/77 of these animals was homozygous daf-2(e1391) whereas 1/77 of the dauers was daf-2 (e1391)/+, indicating a less than 1% dominance. It is possible that in contrast to C. elegans, the P1178L mutation in humans is dominant, or that the patient carries a second insulin receptor mutation in trans, or carries mutations in other genes (for example, other complex type II diabetes loci) that enhance the dominance of P1178L (Bruning et al., Cell 88: 561–572, 1997).

AGE-1 PI 3-kinase is a Major DAF-2 Signaling Output

Like the Drosophila insulin receptor homolog, DAF-2 has a long C-terminal extension that may function analogously to mammalian IRS-1 (Fernandez et al., EMBO J. 14: 3373–3384, 1995). In mammals, IRS-1 tyrosine residues are phosphorylated by the insulin receptor kinase, and these phosphotyrosines mediate binding to a variety of signaling proteins bearing SH2 domains (White and Kahn, J. Biol. Chem. 269: 1–4, 1994; Songyang et al., Cell 72: 767–778, 1993.). Many, but not all, of the DAF-2 C-terminal extension tyrosines bear flanking sequence motifs suggestive that they are autophosphorylated (FIG. 2A; Songyang and Cantley, Trends Biochem. Sci. 20: 470–475, 1995). Based on precedents from IRS-1 interactions with mammalian PI 3-kinases (White and Kahn, J. Biol. Chem. 269:1–4, 1994), a YXXM motif at DAF-2 Y1504 is likely to mediate interaction with the AGE-1 PI 3-kinase, which acts in the same genetic pathway as daf-2 (FIG. 4) (Morris et al., Nature 382: 536–539, 1996).

Three DAF-2 tyrosine residues, Y1293, Y1296 and Y1297, in the region corresponding to the insulin receptor kinase Y1158 to Y1163 activation loop are likely to be autophosphorylated, based on the predicted similarity between the DAF-2 and insulin receptor phosphorylation targets (FIG. 2C). Another likely target for DAF-2 autophosphorylation is the Y1106 NPEY motif located in the region corresponding to the insulin receptor juxtamembrane region NPEY motif (at Y972), that has been shown to mediate IRS-1 binding via its PTB domain to the insulin receptor (White and Kahn, J. Biol. Chem. 269: 1–4, 1994). While DAF-2 bears one YXXM motif implicated in coupling to PI 3-kinase, mammalian IRS-1 and Drosophila insulin receptor (Fernandez et al., EMBO J. 14: 3373–3384, 1995) bear multiple YXXM motifs. Although no p85-like adaptor subunit has yet been detected in the C. elegans database, the AGE-1 homology to mammalian p110 suggests the existence of a homologous or analogous adaptor (Morris et al., Nature 382: 536–539, 1996). In the DAF-2 C-terminal domain, two other tyrosine residues may be autophosphorylated and bound to particular SH2-containing proteins: Y1678 binding to a PLC-γ or SHP-2 homolog, and Y1686, perhaps binding to SEM-5 (FIG. 2A) (Songyang et al., Cell 72: 767–778, 1993). While mutations in, for example, ras and MAP kinase have not been identified in screens for dauer constitutive or dauer defective mutations, these general signaling pathway proteins may couple to DAF-2 as they couple to insulin signaling in vertebrates (White and Kahn, J. Biol. Chem. 269: 1–4, 1994).

The insulin receptor also couples to other signaling pathways (White and Kahn, J. Biol. Chem. 269: 1–4, 1994); analogous DAF-2 phosphotyrosine residues may mediate these interactions (as described above). Thus, we suggest that tyrosines in the DAF-2 cytoplasmic domain are autophosphorylated upon ligand binding, and recruit the AGE-1 PI-3 kinase homolog (as well as other molecules) to signal reproductive development and normal senescence.

Metabolic Control by daf-2 in Control of Diapause and Aging

Insulin and its receptor families play key roles in vertebrate (and by our evidence in invertebrates) metabolic and growth control (Kahn and Weir, eds., Joslin's Diabetes Mellitus, Lea & Febiger, 1994). Upon insulin release—by increasing blood glucose and autonomic inputs—insulin receptor engagement directs a shift in the activities of key metabolic enzymes, as well as changes in the transcription and translation of metabolic regulators in fat, liver, and muscle cells, all of which lead to assimilation of glucose into glycogen and fat (White and Kahn, J. Biol. Chem. 269: 1–4, 1994). IGF-I is released from the liver in response to pituitary growth hormone, and mediates many of the growth and development responses to that endocrine signal (Mathews et al., Proc Natl Acad Sci. U.S.A. 83: 9343–7, 1986). Interestingly, lifespan is dramatically increased in dwarf mice with defects in growth hormone signaling, and presumably decreased IGF-I signaling as well (Brown-Borg et al., Nature 384: 33, 1996). No function for the insulin receptor-related receptor has yet been established, though it is expressed in conjunction with NGF receptor (Reinhardt et al., J. Neurosci. 14: 4674–4683, 1994).

Figure 3:
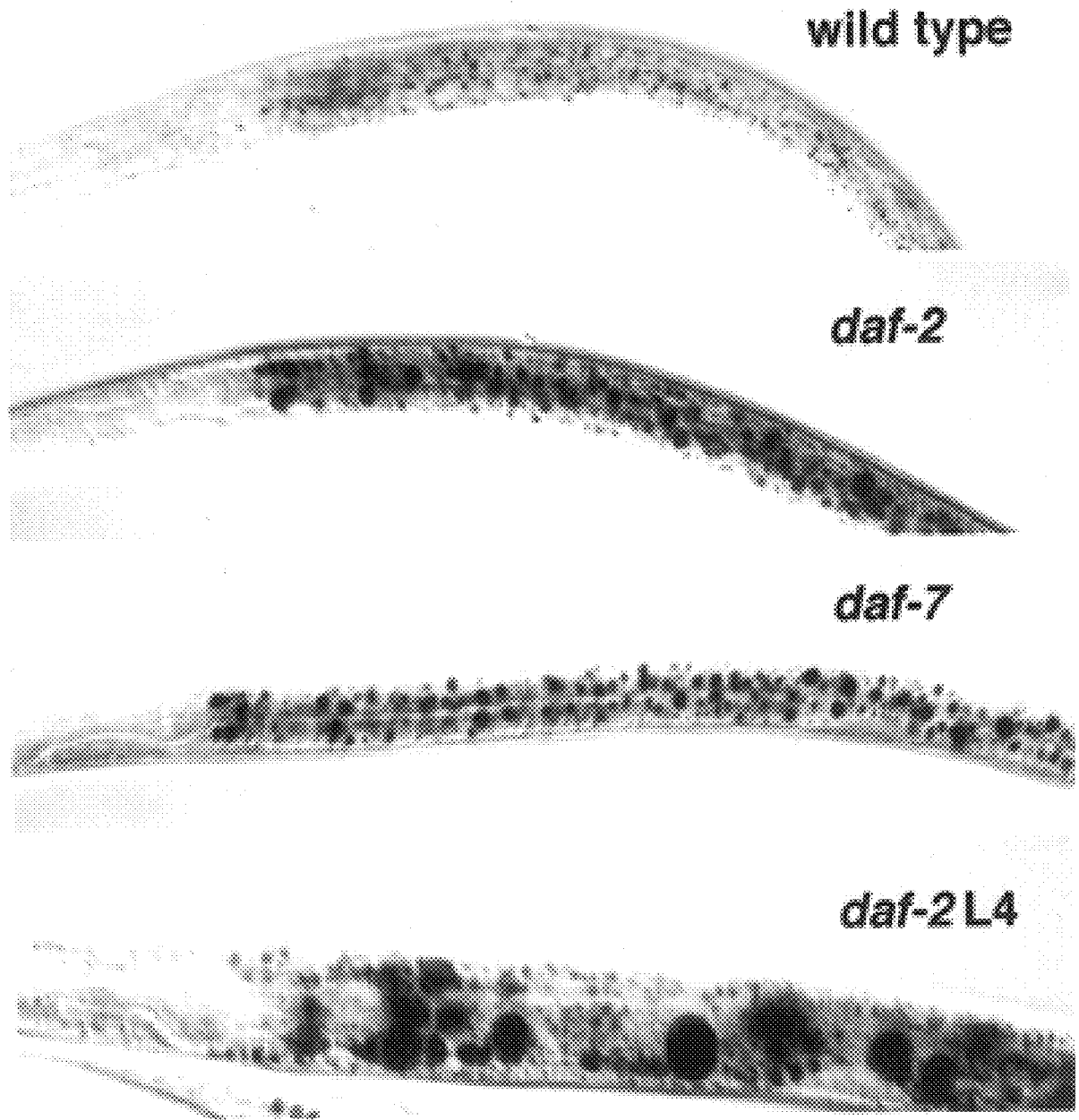

Diapause arrest in general and dauer arrest in particular are associated with major metabolic changes (Tauber et al., Seasonal Adaptation of Insects, Oxford University Press, New York, N.Y., 1986), consistent with a model that daf-2 acts in a metabolic regulatory pathway related to insulin signaling. In wild-type animals, DAF-2 signaling allows non-dauer reproductive growth, which is associated with utilization of food for growth in cell number and size, and small stores of fat (FIG. 3). In daf-2 mutant animals, metabolism is shifted to the production of fat (FIG. 3) and glycogen (data not shown) in intestinal and hypodermal cells. Even when a temperature-sensitive daf-2 mutant allele is shifted to the non-permissive temperature at the L4 or adult stage (after the critical period for daf-2 control of dauer formation), metabolism is shifted towards storage of fat (FIG. 3). Thus daf-2 also regulates metabolism during reproductive development. Similar metabolic shifts are seen in wild-type pheromone-induced dauers (data not shown), age-1 mutants (data not shown), and daf-7 mutants (FIG. 3). In support of this metabolic shift, in dauer larvae, enzymes that regulate glycolysis are down-regulated while those that regulate glycogen and fat synthesis are up-regulated, and there is ultrastructural evidence for increased lipid and glycogen (O'Riordan and Burnell, Comp. Biochem. & Physiol. 92B: 233–238, 1989; O'Riordan and Burnell, Comp. Biochem. & Physiol. 95B: 125–130, 1990; Popham and Webster, Can. J. Zool. 57: 794–800, 1978; Wadsworth and Riddle, Develop. Biol. 132: 167–173, 1989). The dauer metabolic shift is associated with arrest of germ line proliferation, and arrest of somatic cell division and enlargement (Riddle, In: Caenorhabditis elegans II, D. Riddle, T. Blumenthal, B. Meyer, J. Priess, eds., Cold Spring Harbor Laboratory, Cold Spring Harbor, N.Y., 1997, pp. 739–768; Kenyon, op cit., pp. 791–813).

There is precedent for insulin-like signaling in invertebrate metabolic and growth control: insulin-like growth factors have been detected in metabolism-regulating ganglia in molluscs (Roovers et al., Gene 162: 181–188, 1995) and regulate molting in locust (Hetru et al., Eur. J. Biochem 201: 495–499, 1991) and silkworm (Kawakami et al., Science 247: 1333–1335, 1990). Consistent with the daf-2 regulation of diapause, injection of insulin into diapausing Pieris brassicae (an insect) pupae induces recovery (Arpagaus, Roux's Arch. Dev. Biol. 196: 527–530, 1987).

Without being bound to a particular theory, we hypothesize that an insulin-like signal is up-regulated during reproductive development and stimulates DAF-2 receptor autophosphorylation and recruitment of the AGE-1 PI 3-kinase to produce the second messenger PIP3. AGE-1 is likely to be a major signaling output of DAF-2 because of the similarity of the age-1 and daf-2 mutant phenotypes and because of their similar placement in the epistasis pathway (Vowels and Thomas, *Genetics* 130: 105–123, 1992; Gottlieb and Ruvkun, *Genetics* 137: 107–120, 1994). Precedents from insulin receptor signaling suggest the following candidate targets for DAF-2/AGE-1/PIP3 regulation of metabolism: (1) membrane fusion of vesicles bearing glucose transporters (Kahn and Weir, eds., *Joslin's Diabetes Mellitus*, Lea & Febiger, 1994) (or more probably trehalose transporters (Tauber et al., *Seasonal Adaptation of Insects*, Oxford University Press, New York, N.Y., 1986)) to facilitate flux of this molecule for growth and reproductive metabolism; (2) PIP3 activates an AKT/GSK-3 kinase cascade (Hemmings, *Science* 275: 628–630, 1997) which may regulate the activities of glycogen and fat synthetic and lytic enzymes; (3) transcription and translation of metabolic genes such as PEPCK, GDH, fat synthetases, and lipases (White and Kahn, *J. Biol. Chem.* 269:1–4, 1994). Genetic epistasis analysis suggests that DAF-2/AGE-1 signaling negatively regulates daf-16 gene activity (Vowels and Thomas, *Genetics* 130: 105–123, 1992; Gottlieb and Ruvkun, *Genetics* 137: 107–120, 1994). DAF-16 could act at any point downstream of AGE-1 in this signaling pathway. Evidence is presented herein that DAF-16 represents the major transcriptional output to DAF-2/AGE-1 PIP3 signaling.

In addition to these metabolic changes, the DAF-2 signaling cascade also controls the reproductive maturation of the germ line as well as morphogenetic aspects of the pharynx and hypodermis (Riddle, In: *Caenorhabditis elegans* II, D. Riddle, T. Blumenthal, B. Meyer, J. Priess, eds., Cold Spring Harbor Laboratory, Cold Spring Harbor, N.Y., 1997, pp. 739–768; Kenyon, op cit., pp. 791–813). The DAF-2 receptor may act, for example, in the hypodermal and intestinal target tissues where we note a change in metabolism triggered by the dauer regulatory cascade (FIG. 3). It is also possible that DAF-2 regulates the metabolism and remodeling of tissues indirectly, for example, by controlling the production of other hormones (Nagasawa et al., *Science* 226: 1344–1345, 1984; Jonas, et al., *Nature* 385: 343–346, 1997). Expression and genetic mosaic analysis of daf-2 is essential to distinguish these models.

Even though DAF-2 and the mammalian insulin receptor both regulate metabolism, the metabolic defects associated with mutations in these receptors appear to be different. Complete loss of mammalian insulin receptor activity causes growth arrest at birth (Leprechaunism in humans), and a metabolic shift to runaway lipolysis and ketoacidosis (Kahn and Weir, eds., *Joslin's Diabetes Mellitus*, Lea & Febiger, 1994), rather than the fat accumulation we observe in daf-2 mutants (FIG. 3). This distinction between insulin receptor and daf-2 mutants may reflect distinct metabolic responses to this signaling, or a difference between complete loss and declines in insulin signaling. In humans, ketoacidosis is only induced during severe starvation or pathological states when insulin levels are very low (Kahn and Weir, eds., *Joslin's Diabetes Mellitus*, Lea & Febiger, 1994). Since none of the daf-2 mutations described herein are clear null mutations, it is possible that daf-2 dauer-constitutive alleles are more analogous to non-null human insulin receptor mutations. Most daf-2 alleles are temperature sensitive, including alleles isolated in genetic screens that would allow the recovery of non-temperature sensitive mutations (Vowels and Thomas, *Genetics* 130: 105–123, 1992; Gottlieb and Ruvkun, *Genetics* 137: 107–120, 1994). Substitutions of DAF-2 amino acid residues conserved across phylogeny cause more penetrant dauer arrest at all temperatures than substitutions of non-conserved residues. daf-2 mutants that arrest development at the dauer stage independent of growth temperature are likely to have the least gene activity (for example mg43). Several daf-2 alleles also cause 5% to 10% embryonic lethality (unpublished results), suggesting that daf-2 functions during embryonic development. None of the daf-2 mutations detected so far are nonsense, frameshift, or deletion alleles. It is possible that the daf-2 null phenotype is stronger than non-conditional dauer arrest, for example embryonic lethality. However, dauer constitutive daf-2 mutant alleles are isolated from EMS mutagenesis at a very high rate (about 1/300 chromosomes), suggesting that the existing alleles are not rare viable alleles. In fact, the 14 year old patient with the same insulin receptor mutation as daf-2(e1391) was morbidly obese (Kim et al., *Diabetologia* 35: 261–266, 1992), suggesting that metabolic effects of decreased insulin signaling may be similar to daf-2 mutants.

It may be significant to human diabetes that animals carrying mutations in daf-16 can grow reproductively even if they also carry daf-2 and age-1 mutations that disable insulin-like metabolic control signals (Vowels and Thomas, *Genetics* 130:105–123, 1992; Gottlieb and Ruvkun, *Genetics* 137:107–120, 1994). These data suggest that it is unregulated daf-16 gene activity that causes these metabolic shifts. The analogous metabolic defects associated with both type I and type II diabetes may be caused by similar unregulated activity of the human DAF-16 homolog. Below we disclose the molecular identity of daf-16. Inhibition of its activity is expected to ameliorate the metabolic dysregulation associated with insulin signaling defects.

DAF-16 Encodes a Forkhead Transcription Factor Homolog

Figure 27:
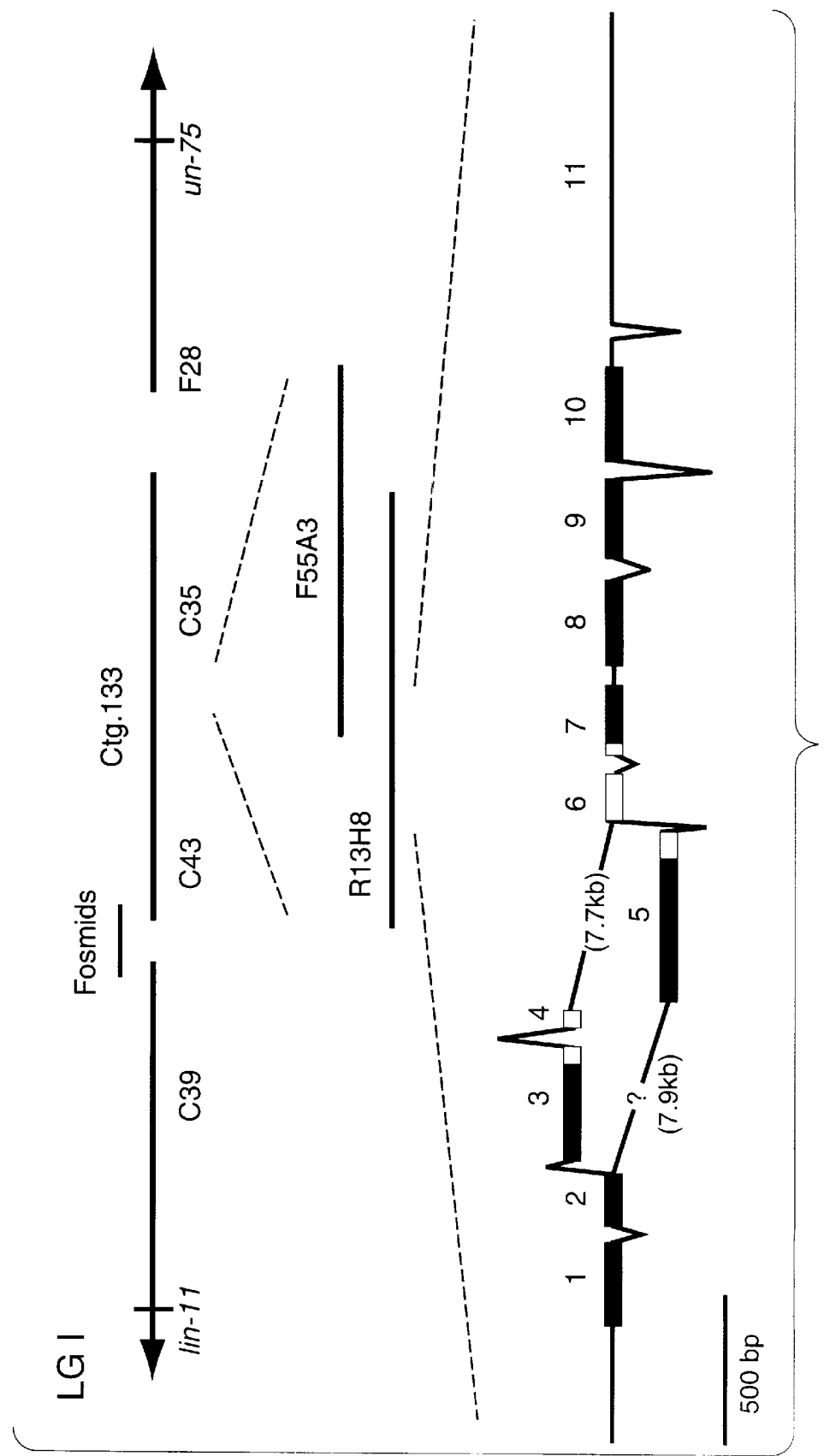
FIG. 27 is a schematic illustration showing the molecular map of daf-16.

Using a combination of genetic mapping and detection of multiple daf-16 mutations in a 5 kb region, we have determined the nucleic acid sequence of daf-16. daf-16 was mapped 1 map unit to the left of lin-11 and 3.3 map units right of unc-75 on Chromosome I. This region of the genome contained a gap that was not covered by cosmids nor YACs. We used a fosmid library (Genome Sciences, Inc.) to walk into the gap. Sequence analysis of the ends of four fosmids (H27K20, H01H03, H12I08, and H35K06) revealed that the previously unmapped contig 133 lies in the lin-11 unc-75 gap. Cosmids from the approximate daf-16 genetic location were used to detect RFLPs between *C. elegans* strains Bristol N2 and Bergerac RC301: mgP45 on cosmid C39H11, mgP46 on cosmid F28D9, mgP49 on cosmid C35E7, mgP50 is on cosmid C43H8. Zero out of 30-daf non-Unc recombinants carry the RC301 alleles of mgP45 and mgP50. Two out of 30 Daf non-Unc recombinants carry the RC301 allele of mgP49. 10 out of 30 Daf non-Unc recombinants carry the RC301 allele of mgP46. 1 out of 4 non-Lin Daf recombinants carry the N2 allele of mgP45. 4 out of 4 non-Lin Daf recombinants carry the N2 allele of mgP49. These data indicate that daf-16 lies between cosmids C43H8 and C35E7. The daf-16 gene was identified by identifying deletions (mgDf50) and point mutations (mg53 and mg54) within the forkhead gene on the cosmid R13H8 (FIG. 27). There are two major daf-16 transcripts whose sequences are shown in FIG. 13A and FIG. 13B (SEQ ID NOS: 43 and 44, respectively). The amino acid sequences coding for the DAF-16 isoforms are shown in FIGS. 14A–14C (SEQ ID NOS: 45–46).

We have detected three daf-16 mutations: (1) a large deletion of conserved regions in daf-16 (mg ΔF50) that proves that the daf-16 null phenotype is a suppression of daf-2 mutations; (2) a S to L substitution in exon 6 in daf-16 (mg 53) that alters a conserved WKNSIRH motif; and (3) a nonsense mutation in exon 3 in daf-16 (mg 54) that is predicted to truncate one of the daf-16 differentially spliced isoforms. Interestingly, this spliced isoform has a distinct forkhead DNA binding domain and is therefore expected to bind to distinct promoters or combinatorial partners. This mutant is a weak suppressor of daf-2, suggesting that both DAF-16 isoforms are necessary for metabolic control.

Figure 21A:
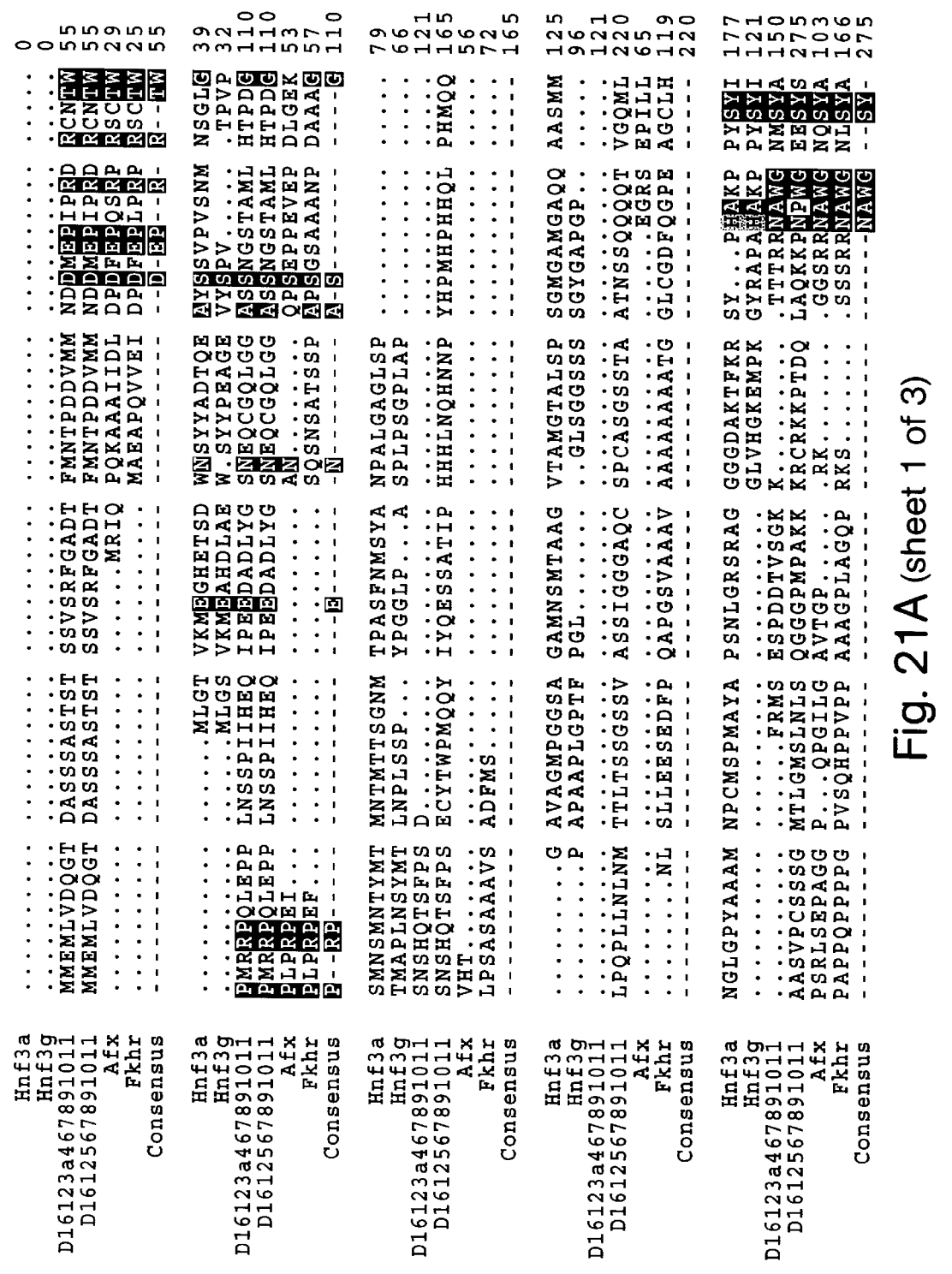
Figure 21A:
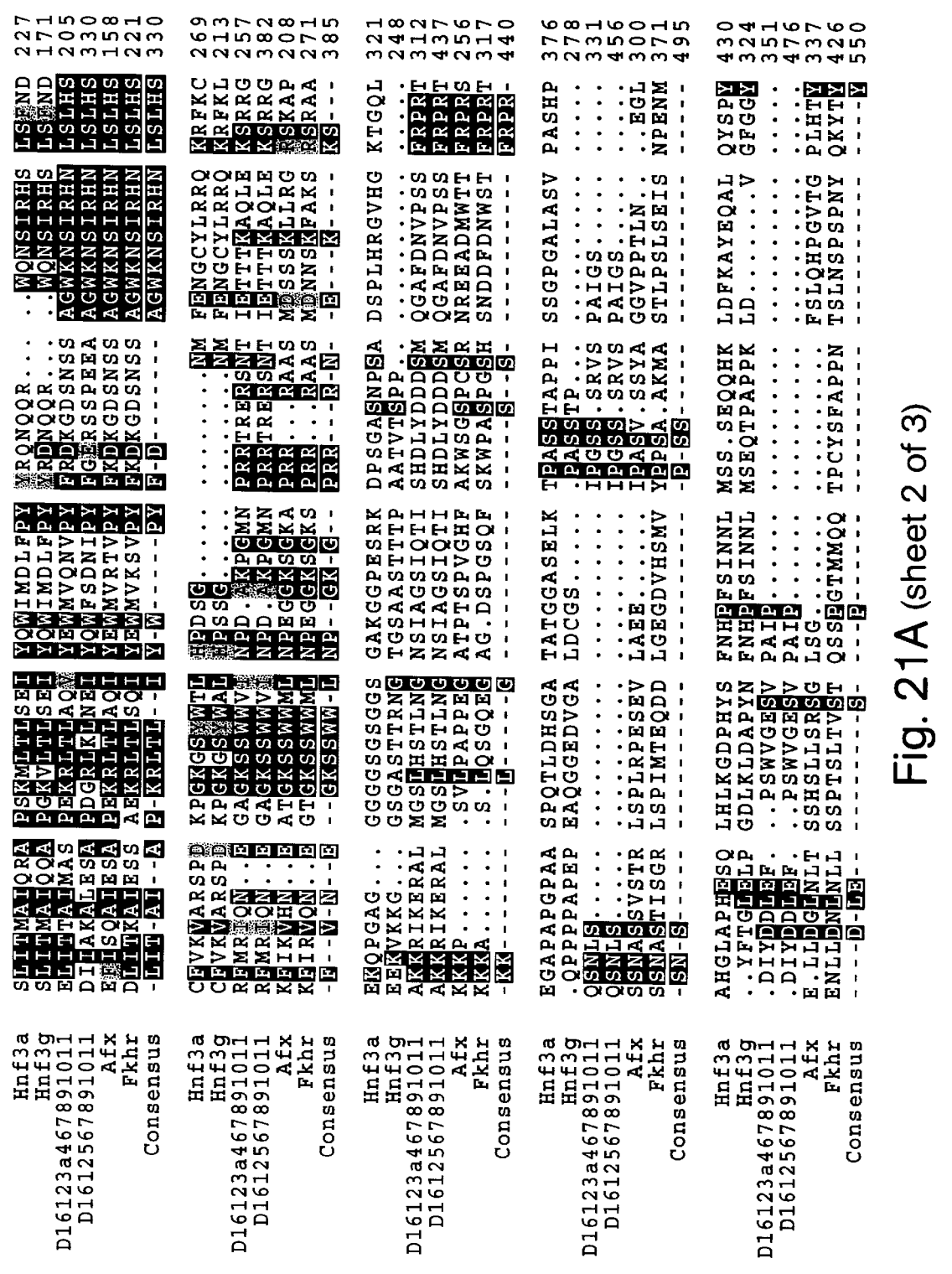
Figure 21A:
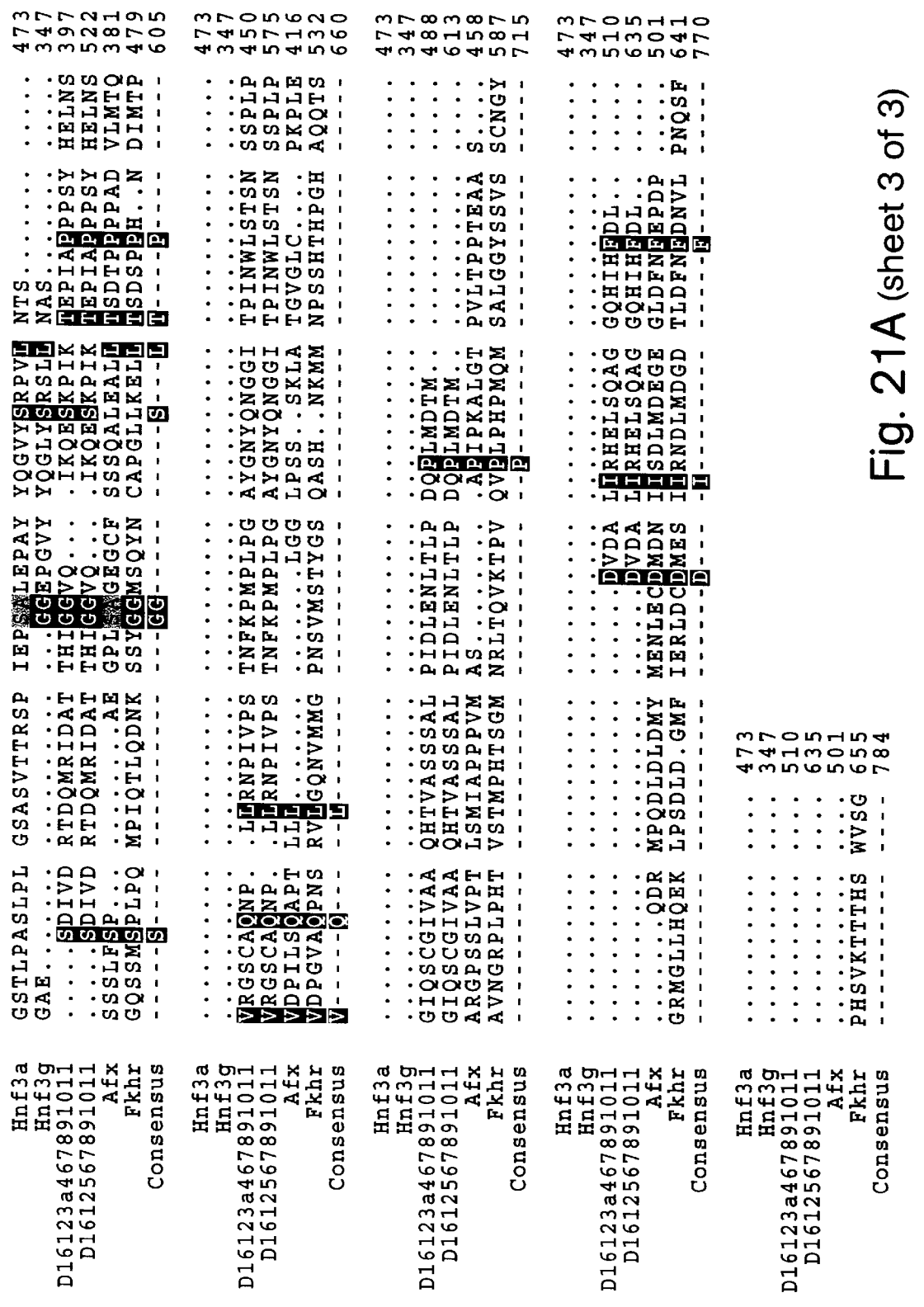
Figure 21B:
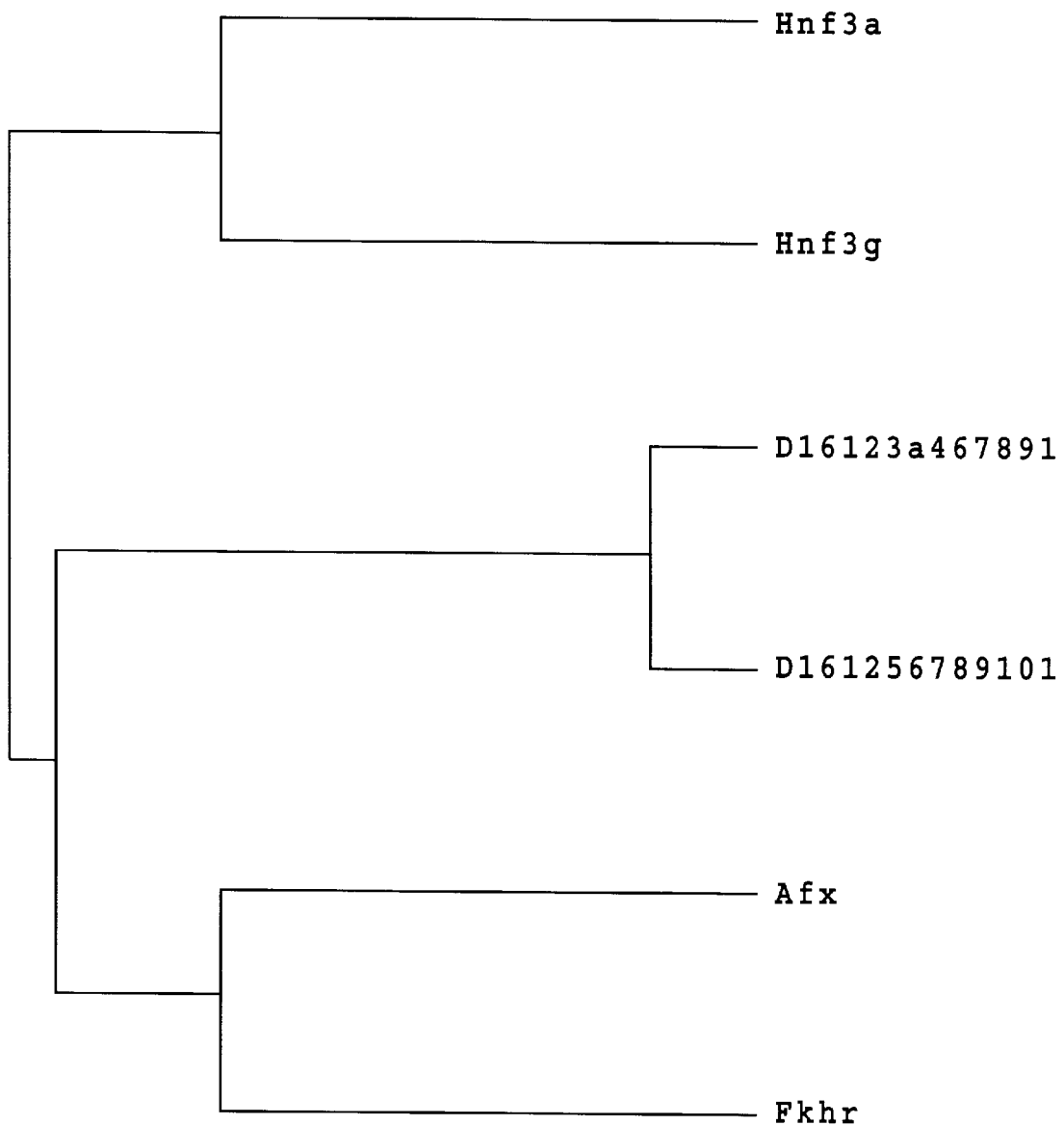
FIG. 21B is an illustration showing a forkhead family tree, illustrating that DAF-16 is much more closely related to FKHR and AFX than any other forkhead protein.

Sequence analysis has revealed that DAF-16 is a member of the forkhead (FH) transcription factor family (FIGS. 21A–21B). This strong amino acid homology indicates that DAF-16 is a transcription factor. Our genetic analysis indicates that DAF-16 activity is regulated by the DAF-2/AGE-1 insulin signaling pathway. Precedent from another receptor kinase signaling pathway endorses this model:

the C. elegans LIN-31 forkhead protein has been shown to be regulated by a tyrosine kinase signaling cascade from the LET-23 EGF receptor homolog (Kim, Genes Dev. 7: 933–947, 1993). Consistent with a model that DAF-16 acts downstream of insulin signaling, forkhead transcription factors have also been implicated in metabolic regulation: another FH family member is mammalian HNF-3, an endoderm-specific transcription factor that acts at the same metabolic control protein promoters as HNF-1 and HNF-4, both of which are mutant in maturity onset diabetes of the young (MODY) (Yamagata et al., Nature 384: 455–458, 1996; Yamagata et al., Nature 384:458–460, 1996).

The identification of DAF-16 as a forkhead transcription factor also explains much of the complex daf genetics of C. elegans. The convergence of DAF-7 TGF-β-like signaling and DAF-2 insulin-like signaling is also explained by our discovery that DAF-16 is a FH protein and DAF-3 is a Smad protein: Precedent for an interaction between Smad and forkhead proteins has been found in Xenopus. Response to the TGF-β superfamily relative activin in early frog development is mediated by an interaction between the distant relative of DAF-16 called FAST-1, and the Smad protein, Smad2 (Nature 383: 600–608, 1996). These proteins bind to an enhancer element that is very similar to the myosin II promoter to which DAF-3 binds (see below). Thus our molecular and genetic data indicate that the DAF Smad proteins and DAF-16 FH protein interact on metabolic control promoters.

Figure 22:
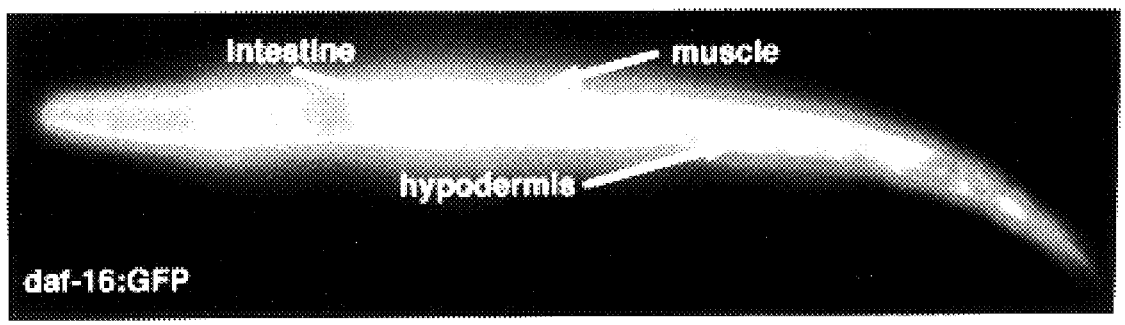
FIG. 22 is a photograph showing that daf-16 is expressed in target tissues, like daf-3. This supports the model that DAF-3 and DAF-16 are capable of interacting.

Interestingly, analogously to daf-16 bypass of the need for DAF-2 insulin receptor signaling in daf-16 mutant animals, lin-31 mutations suppress the need for LET-23 EGF signaling in C. elegans vulval development. These findings indicate that the DAF-2 receptor, a downstream signaling molecule (AGE-1), and a transcription factor target DAF-16 are involved in insulin-like signaling in C. elegans development. Without being bound by any particular theory, we hypothesize that C. elegans insulin signaling via DAF-2 and AGE-1 activate DAF-16 transcriptional activity, so that in a daf-2 or age-1 mutant, or in dauer pheromone, DAF-16 acts as a repressor protein causing a metabolic shift to fat metabolism. Our analysis of daf-16 expression shows that, like DAF-3, it is expressed in target tissues (FIG. 22). Our evidence indicates that Smad protein transcription factors (e.g., DAF 3, DAF8, DAF14) and DAF-16 act on a common set of promoters as combinatorial transcriptional regulators. Thus, it is at these metabolic genes that DAF-7 and TGF-β-like and DAF-2 insulin-like signals converge to control metabolism. In addition, our evidence indicates that in the presence of DAF-2 signaling (mimicking high insulin), DAF-16 acts as an activator of transcription, causing a shift in metabolism toward glucose utilization for cell growth. The molecular analysis described herein suggests that lack of daf-16 gene activity completely bypasses the need for insulin signaling in metabolic control by releasing metabolic control from DAF-16 repression. These data suggest that if a human DAF-16 homolog acts downstream of insulin signaling in humans, drugs could be developed that inhibit its activity to bypass the need for insulin signaling. Identification of a such a drug should provide a means for treating both Type I and Type II diabetes.

As shown in FIGS. 21A–21B, the human FKHR and AFX genes, identified as oncogene breakpoints but not as insulin signaling genes, are much more closely related to DAF-16 than the next closest relative in either Genbank or in the 94% complete C. elegans genome sequence. These data indicate that FKHR and AFX are excellent candidates for subserving the same function as C. elegans DAF-16: transduction of insulin signals and convergence with DAF-7-like Smad signals.

Evidence for the C. elegans AKT Kinase as the Probable Output of DAF-2/AGE-1 Signaling We screened genetically for mutations that bypass the need for age-1 signaling. This was done by mutagenizing a strain carrying an age-1(mg44) null mutation (this mutation was heterozygous to allow the strain to grow). After two generations, animals that could survive without age-1 gene activity were selected by their lack of arrest at the dauer stage. We identified daf-16 mutations, as expected. However, we also identified two new gain of function mutations, sup(mg142) and sup(mg144).

sup(mg144) suppresses three different age-1 alleles, indicating that this mutation bypasses the need for AGE-1 production of PIP3. For example, sup(mg144) suppresses the dauer arrest of age-1(mg44), (m333), (mg109) such that fertile adults are formed. sup(mg144) does not suppress the lack of insulin signaling in the daf-2 mutant: daf-2(e1370); sup(mg144) form dauers at 25 degrees. This suggests that not all of the DAF-2 signaling output is via AGE-1. However, in the absence of both DAF-2 and AGE-1 signaling, sup(mg144) weakly suppresses, allowing some fertile adults to bypass arrest at the dauer stage. daf-2 (e1370); sqt-1 age-1(mg44); sup(mg144 )form 8% fertile adults, 12% sterile adults, and 80% dauers at 25 degrees.

Interestingly, sup(mg144) is a dominant suppressor of age-1 mutations. sqt-1 age-1(mg44); sup(mg144)/+ form 100% fertile adults. The sup(mg144) parental genotype does not affect this outcome. This data indicates that sup(mg144) is a dominant activating or dominant inactivating mutation.

Figure 24:
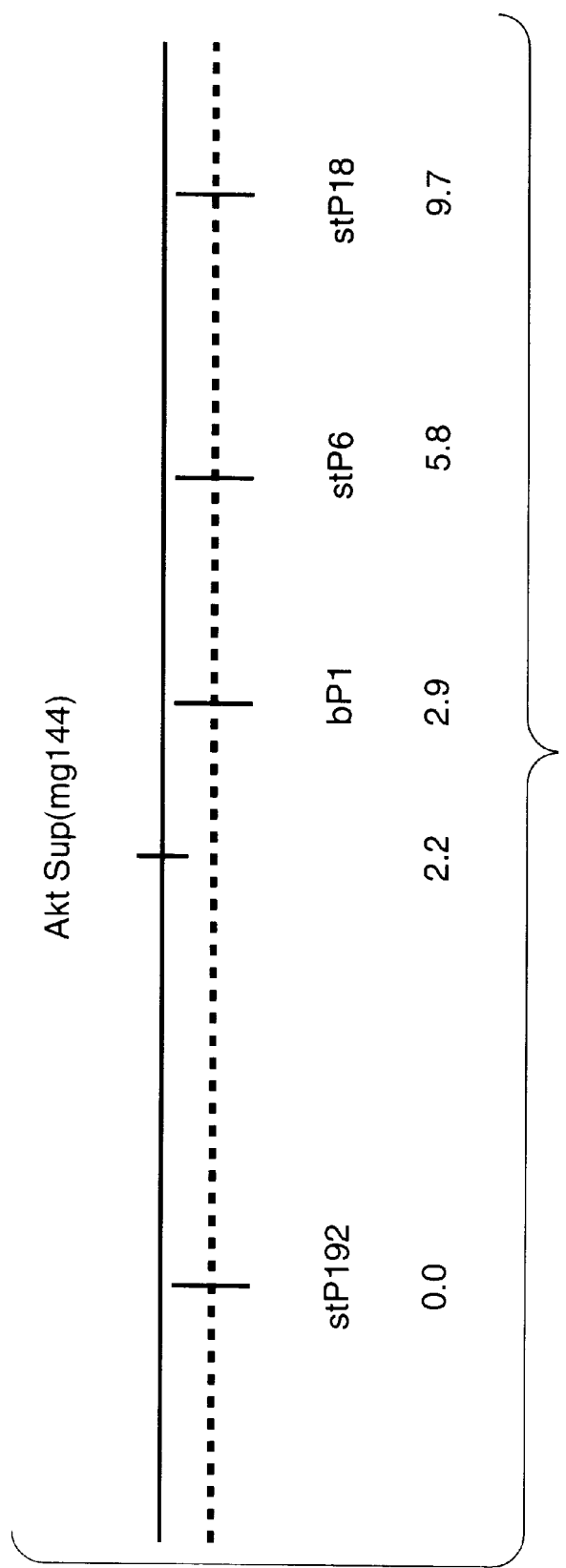
FIG. 24 is an illustration showing the genetic mapping of sup(mg144) to the AKT genetic region.

Genetic mapping indicates that sup(mg144) may identify an activating mutation in the C. elegans AKT homologue (FIG. 25). By placing sup(mg144) in trans to a multiply marked chromosome (using PCR based RFLPs), we found that sup(mg144) maps to a 2 map unit genetic interval that includes C. elegans AKT (FIG. 24).

2/39 sup(mg144 ) homozygous animals isolated from a sup(mg144)/polymorphic Bergerac chromosome parent recombined between sup(mg144)mg144 and stP6 (these animals also carried stP18). In this experiment mg144 was a het with RW7000 for three generations. So this places sup(mg144) approximately 2.2 mu to the left of stP6).

1/39 sup(mg144 ) homozygous animals isolated from a sup(mg144)/polymorphic Bergerac chromosome parent recombined between sup(mg144) and bP1. In this experiment mg144 was a het with RW7000 for two generations. So this number is approximately ⅟₈₀ or 1.2 mu from bP1.

Figure 26A:
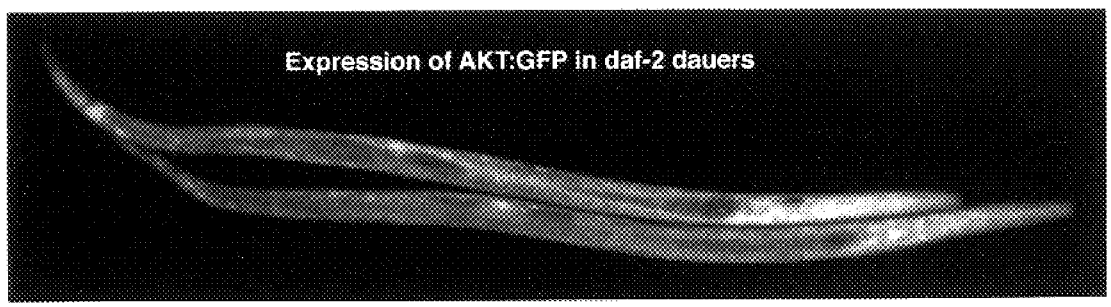
FIG. 26A is a photograph showing the expression of AKT:GFP in daf-2 dauers.
Figure 26B:
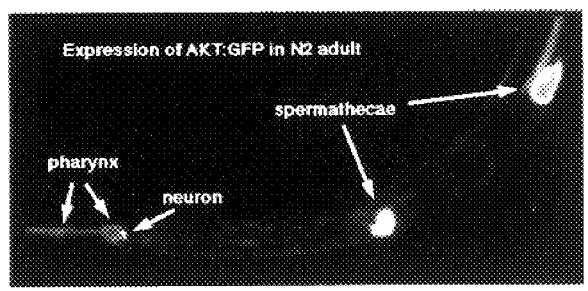
FIG. 26B is a photograph showing the expression of AKT:GFP in an N2 adult worm.

We generated a GFP fusion to AKT and showed that this gene is expressed at high levels in dauer larvae but at much lower levels and in fewer cells in wild type animals. (FIGS. 26A–26B) Thus AKT represents a dauer regulated gene that may respond to DAF-16 and DAF-3 transcriptional control. Multiple probable binding sites, related to the DAF-3 binding site in myoII have been identified.

Sup(mg142) Identifies Another Likely Output of age-1 Signaling mg142 suppresses three different age-1 alleles (age-1 (mg44), age-1(m333), and age-1(mg109) at 20 degrees. age-1(mg44); sup(mg142) form fertile adults at 15 and 20. At 25 degrees, they form 33% fertile adults and 67% sterile adults.

sqt-1 age-1(mg44); mg142/+ form 14% fertile adults and 86% sterile adults when the parent was homozygous for mg142. sqt-1 age-1(mg44); mg142/+ form 67% fertile adults and 33% sterile adults when the parent was heterozygous for mg142. daf-2(e1370); mg142 form sterile adults at 25 degrees; daf-2(e1370); sqt-1 age-1(mg44); mg142 form sterile adults and dauers at 25 degrees. Preliminary mapping places mg142 approximately 1.6 mu left of unc-1 on LGX

Diapause and Longevity

Weak daf-2 and age-1 mutants that do not arrest at the dauer stage nevertheless live much longer than wild-type (Larsen et al., *Genetics* 139: 1567–1583, 1995; Kenyon et al., *Nature* 366: 461–464, 1993; Dorman et al., *Genetics* 141: 1399–1406, 1995). This connection between longevity and diapause control may not be unique to *C. elegans*. Diapause arrest is an essential feature of many vertebrate and invertebrate life cycles, especially in regions with seasonal temperature and humidity extremes (Tauber et al., *Seasonal Adaptation of Insects*, Oxford University Press, New York, N.Y., 1986). Animals in diapause arrest slow their metabolism and their rates of aging, and can survive for periods for much longer than their reproductive lifespan (Tauber et al., supra, 1986).

Because insulin-like DAF-2/AGE-1 signaling mediates *C. elegans* diapause longevity control, the mammalian insulin signaling pathway may also control longevity homologously. In fact, the increase in longevity associated with decreased DAF-2 signaling is analogous to mammalian longevity increases associated with caloric restriction (Finch, *Longevity, Senescence and the Genome*, The University of Chicago Press, Chicago, 1990). It is possible that caloric restriction causes a decline in insulin signaling to induce a partial diapause state, like that induced in weak daf-2 and age-1 mutants. The induction of diapause-like states may affect post-reproductive longevity (Finch, supra), as in *C. elegans*. Alternatively, it is the changes in the mode and tempo of metabolism itself rather than diapause per se that causes increased longevity. Another long-lived *C. elegans* mutant, clk-1, may also regulate lifespan via such metabolic effects (Ewbank et al., *Science* 275: 980–983, 1997). This association of metabolic rate with longevity is also consistent with the correlation of free radical generation to aging (Finch, supra).

Synergistic Control of Metabolism and Diapause by Insulin and TGF-β Signaling Pathways In addition to DAF-2 signaling, the DAF-7 TGF-β neuroendocrine signal is also necessary for reproductive development of *C. elegans* (Ren et al., *Science* 274: 1389–1391, 1996; Schackwitz et al., *Neuron* 17: 719–728, 1996). The signals in these two pathways are not redundant: animals missing either daf-2 signaling or daf-7 signaling (FIG. 3) shift their metabolism and arrest at the dauer stage (Table II). In addition the phenotypes caused by mutations in either pathway are strongly synergistic, suggesting that the two pathways are integrated. Synchronised eggs were grown and counted as described above. daf-1(m40) and daf-2(e1370) form 100% dauer at 25° C. Numbers shown in Table II indicate percentage dauer formation and number of animals counted (in parenthesis). Data presented is the sum of three independent trials.

TABLE II

Synergy of daf-1 and daf-2

| | % dauer formation | |
|---|---|---|
| | 15° C. | 20° C. |
| daf-1 (m40) | 0.0 (532) | 1.9 (909) |
| daf-2 (e1370) | 0.0 (798) | 3.8 (503) |
| daf-1 (m40); daf-2 (e1370) | 19.4 (747) | 100 (718) |

This data indicates that DAF-7 TGF-β signals and DAF-2 ligand insulin-like signals are integrated. In support of this model, weak mutations in the daf-2 insulin signaling pathway and in the daf-7 TGF-β signaling pathway are highly synergistic (Table II). Genetic epistasis analysis indicates that the DAF-7 and DAF-2 pathways are parallel rather than sequential (Vowels and Thomas, *Genetics* 130: 105–123, 1992; Gottlieb and Ruvkun, *Genetics* 137: 107–120, 1994). That is, daf-16 mutations strongly suppress daf-2 mutations but not daf-7, daf-1, or daf-4 mutations, whereas daf-3 mutations strongly suppress daf-7, daf-1, and daf-4 mutations, but not daf-2 mutations. Analogous synergism between activin and FGF tyrosine kinase pathways in Xenopus mesoderm induction has been noted (Green et al., *Cell* 71: 731–739, 1992).

A dauer-inducing pheromone regulates the production of DAF-7 by the ASI sensory neuron (Ren et al., *Science* 274: 1389–1391, 1996; Schackwitz et al., *Neuron* 17: 719–728, 1996). Because animals carrying daf-7 nonsense or truncation mutations are responsive to pheromone (Golden and Riddle, *Proc. Natl. Acad. Sci. U.S.A.* 81: 819–823, 1984), we further suggest that the production of the insulin-like ligand for DAF-2 is also regulated by pheromone. It is not yet clear whether these DAF-7 and DAF-2 signals converge in target tissues or in other regulatory (i.e., hormonal) cells; however the expression of the DAF-7 receptor pathway genes in essentially all target tissues (infra) suggests that integration occurs there.

DAF-7 and Diabetes

Figure 17:
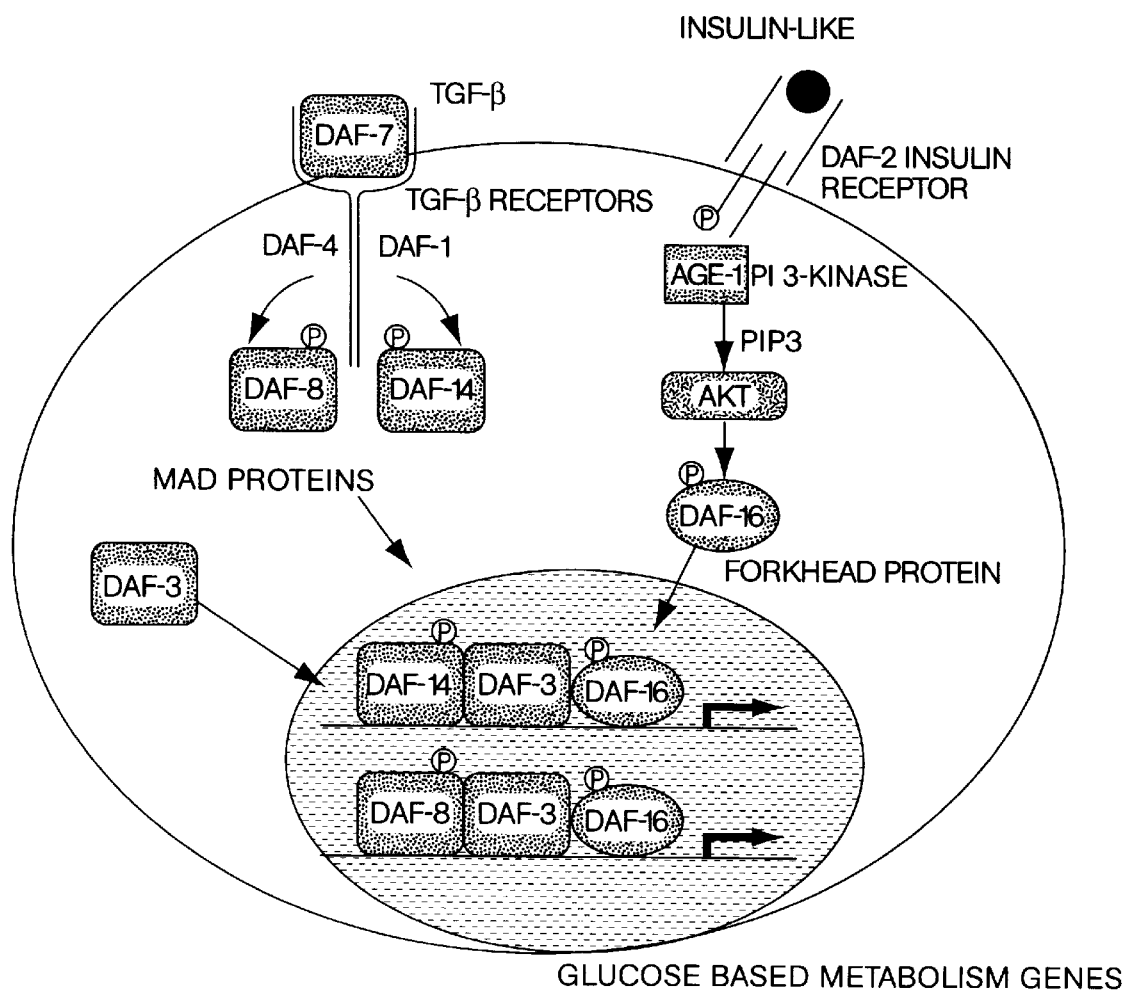
FIG. 17 is a schematic diagram illustrating that convergent TGF-β and insulin signaling activates glucose-based metabolic genes.
Figure 18:
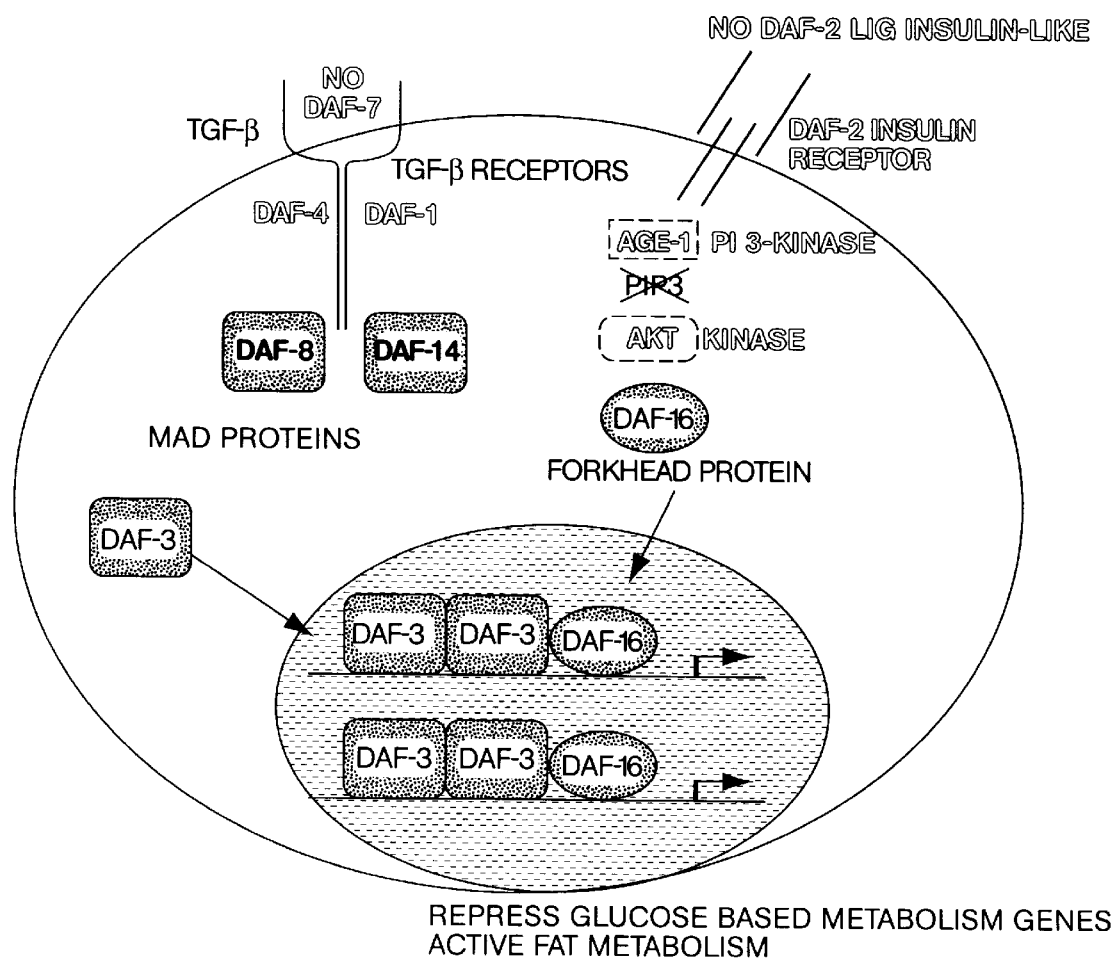
FIG. 18 is a schematic diagram illustrating a switch to fat-based metabolism in the absence of DAF-7 and DAF-2 signals (in pheromone).

Based on the data herein, we propose that in humans as in *C. elegans*, both a DAF-7-like neuroendocrine signal and insulin are necessary for metabolic control by insulin. According to this model, the failure of target tissues to respond to insulin signals in Type II diabetic patients could be due to defects either in the insulin or TGF-β-like control pathways. Pedigree analysis has shown a strong genetic component in Type II diabetes (Kahn et al., *Annu. Rev. Med.* 47: 509–531,1996). In addition, obesity is also a major risk factor in Type II diabetes (Kahn et al., *Annu. Rev. Med.* 47: 509–531,1996). Genetic or obesity-induced (Hotamisligil et al., *Science* 259: 87–91, 1993; Lonnqvist et al., *Nat Med* 1:

950–953, 1995) declines in a DAF-7-like signaling pathway could underlie the lack of response to insulin in Type II diabetes, just as in C. elegans daf-7 mutants cause metabolic defects very similar to daf-2 mutants. The discovery that the DAF-7 and DAF-2 pathways converge indicates that DAF-7 hormonal signals are defective in diabetic conditions (for example, Type II diabetes), and that administration of human DAF-7 is useful for ameliorating the glucose intolerance, ketoacidosis, and atherosclerosis associated with diabetes. This is shown schematically in FIGS. 17, 18, and 23.

Figure 4:
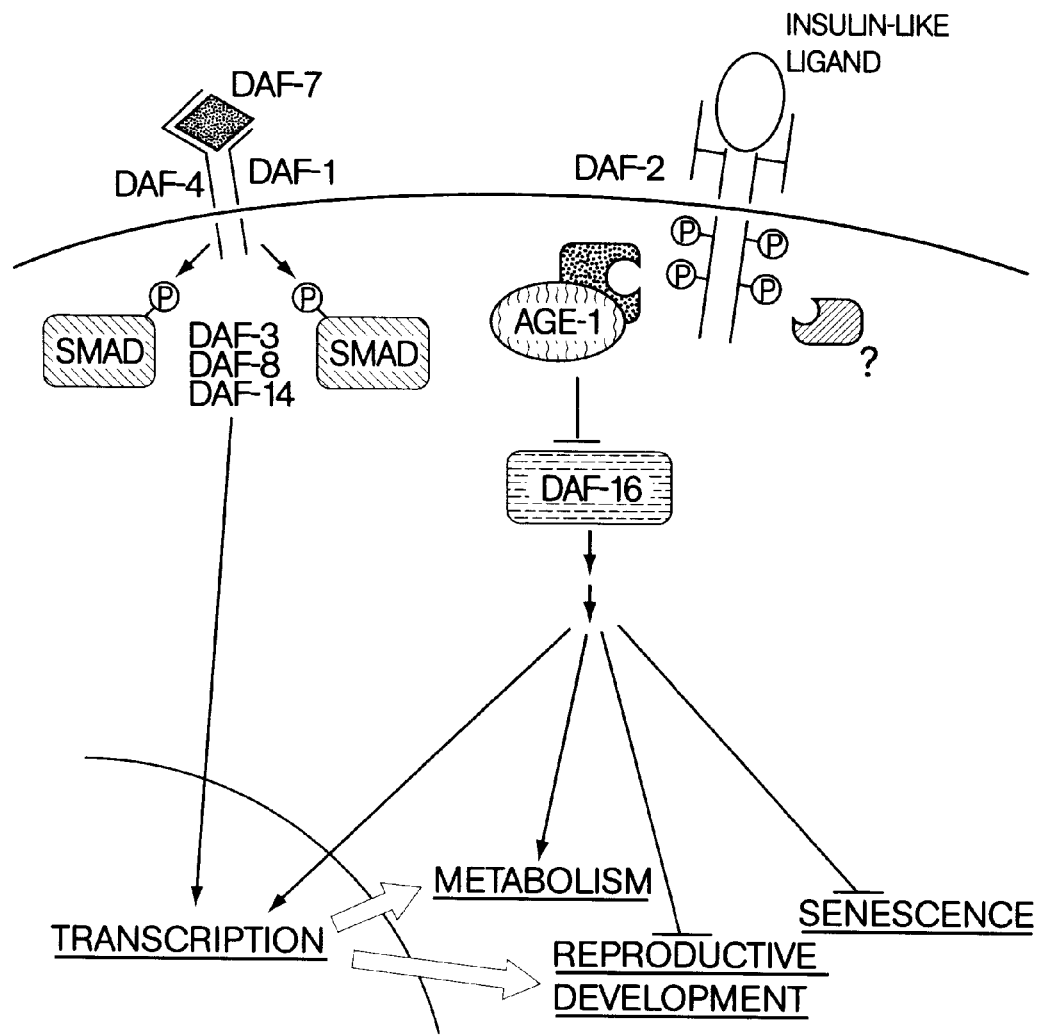

Whereas the DAF-7 TGF-β like and DAF-2 insulin-like signaling pathways converge to control diapause and metabolism, only the DAF-2/AGE-1 pathway has been implicated in reproductive adult stage longevity control in the absense of dauer formation (Larsen et al., *Genetics* 139: 1567–1583, 1995; Kenyon et al., *Nature* 366: 461–464, 1993; Dorman et al., *Genetics* 141: 1399–1406, 1995; and Morris et al., *Nature* 382: 536–539, 1996). Both pathways control the longevity increase associated with dauer arrest, since dauer larvae live much longer than reproductive C. elegans (Riddle, In: *Caenorhabditis elegans* II, D. Riddle, T. Blumenthal, B. Meyer, J. Priess, ed., Cold Spring Harbor Laboratory, Cold Spring Harbor, N.Y., 1997, pp. 739–768; Kenyon, op cit. pp., 791–813: Chayen and Bitensky, *Practical Histochemistry*, Chichester; New York: Wiley, 1991. The distinction between DAF-7 and DAF-2 regulation of longevity could also reflect a more profound regulation of metabolism by the DAF-2 pathway than the DAF-7 pathway (FIG. 4). For example, based on precedents from TGF-β signaling in other systems and analysis of this pathway in C. elegans, all of the known signaling output of the DAF-7 TGF-β pathway are via downstream Smad transcriptional regulation (infra). Insulin signaling, and by extension, DAF-2 signaling, is more ramified: outputs from this receptor regulate sugar transport, metabolic enzyme activities, translation of mRNAs encoding these and other enzymes, as well as transcription (White and Kahn, *J. Biol. Chem.* 269: 1–4, 1994). We suggest that it is the regulatory output distinct to the DAF-2 pathway that controls longevity. Alternatively, TGF-β and insulin-like signals may converge only during the L1 stage, when diapause is regulated, and that after this stage, only DAF-2 signaling is necessary for normal metabolic control.

The involvement of insulin and TGF-β signaling in C. elegans diapause control suggests that the homologous human pathways may similarly mediate response to famine. Just as environmental extremes can select for variation in the genetic pathways that regulate C. elegans dauer formation, famines and droughts in human history may have selected for analogous variants in the human homolog of the daf genes. In fact, heterozygous mice carrying either the db or ob recessive diabetes genes, survive fasting about 20% longer than wild type controls (Coleman, *Science* 203: 663–665, 1979). The high frequency of Type II diabetes in many human populations may be the legacy of such selections.

The DAF-3 Smad Protein Anatagonizes DAF-7 TGF-β Receptor Signaling in the C. elegans Dauer Regulatory Pathway In response to environmental signals C. elegans arrests development at the anatomically and metabolically distinctive third-larval dauer stage (Riddle In: *C. elegans* N, D. L. Riddle, T. Blumenthal, B. J. Meyer, J. R. Priess, eds., *Cold Spring Harbor Press*, 1997, pp. 739–768). Pheromone signal is transduced by chemosensory neurons (Bargmann and Horvitz, *Science* 251:1243, 1991) which couple to a TGF-β signaling pathway (Ren et al., *Science* 274:1389, 1996; Schackwitz et al., *Neuron* 17:719, 1989), as well as an insulin-related signaling pathway (as discussed, infra) to trigger changes in the development of the many tissues remodeled in dauer larvae (Riddle, supra). Mutations in daf-7 (a TGF-β homolog (Estevez et al., *Nature* 365:644, 1993)), daf-4 (a type II TGF-β receptor (Estevez et al., *Nature* 365:644, 1993)), daf-1 (a type I TGF-β receptor), daf-8, and daf-14 (Smad homolog) cause constitutive arrest at the dauer stage even in the absence of pheromone. These genes constitute a neuroendocrine signaling pathway that is active during non-dauer development: the DAF-7 TGF-β signal is produced by the sensory neuron ASI during non-dauer development, whereas daf-7 expression in this neuron is inhibited during dauer-inducing conditions (Ren, supra).

daf-7 and its receptors and Smad proteins are antagonists to daf-3. The dauer constitute phenotypes of mutations in the daf-7 signal transduction pathway genes (including putative null mutations) are fully suppressed by mutations in daf-3. These genetic data indicate that in the absence of daf-7 signaling, daf-3 acts to induce dauer arrest.

Figure 5A:
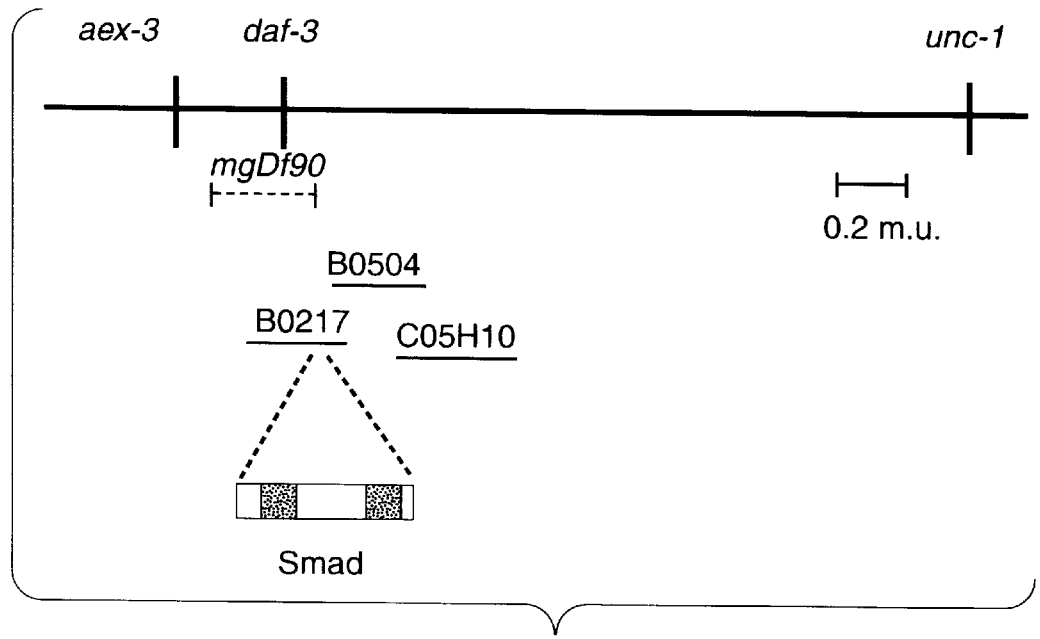
Figure 5B:
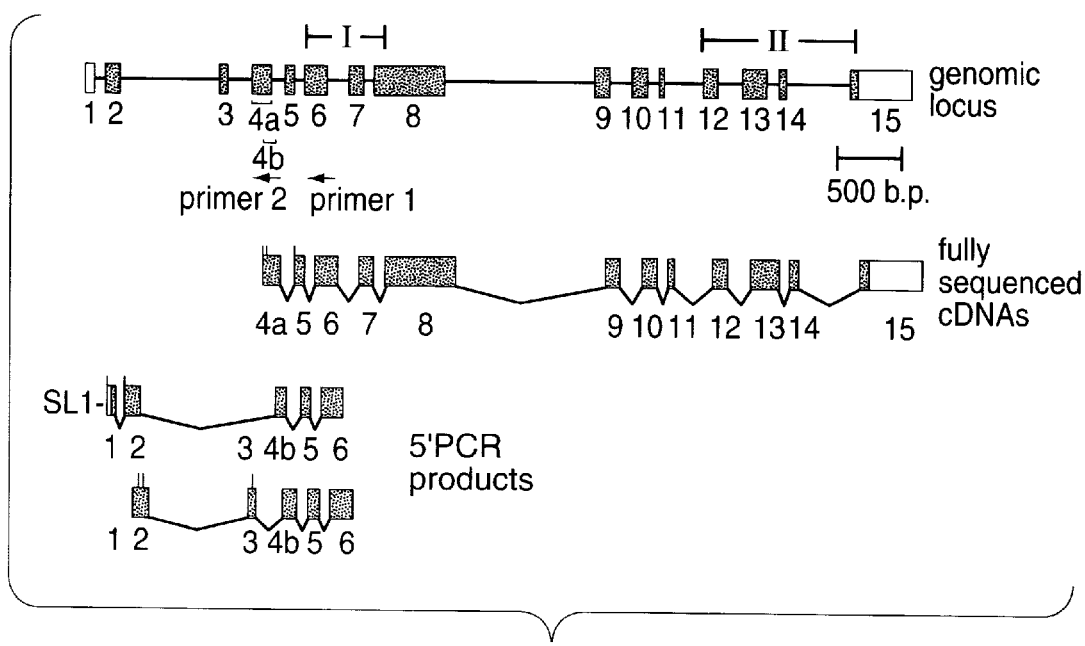

To discern the molecular basis of the DAF-3 function in this pathway, we determined the sequence and expression pattern of daf-3. Cosmids in the daf-3 genetic region were assayed for gene activity by transformation. Cosmid B0217 partially complemented a daf-3 mutation, while other cosmids from the region did not (FIG. 5A). A subclone of B0217 containing only the Smad homolog, but no other coding regions also rescued daf-3. Our detection of mutations in the Smad homolog (see below) confirmed its assignment to daf-3. Analysis of daf-3 cDNAs revealed that the gene was transcribed from fifteen exons and was alternatively spliced upstream of the region conserved in Smad proteins. (FIG. 5B) The biological activity of these alternatively spliced isoforms is unknown. The nucleotide (SEQ ID NO: 11) and amino acid sequences (SEQ ID NO: 12) of DAF-3 are shown in FIGS. 11 and 12, respectively.

Thus far, the C. elegans DAF-3 Smad protein is most closely related in sequence to DPC4, which is a putative cofactor for Smad1, Smad2, and Smad3 (Zhang et al., *Nature*, 383:168, 1996; Lagna et al., *Nature*, 383:832, 1996; Savage et al., *Proc. Natl. Acad. Sci.,* 93:790, 1996; Hahn et al., *Science*, 271:350 (1996). Smads have two conserved domains (Wrana et al., *Trends Genet.,* 12:493, 1996). DAF-3 has these two domains; compared to its closest known relative DPC-4, daf-3 has 55% amino acid identity in domain I and 30% in domain II (FIG. 5C). However, DPC-4 is not the mammalian DAF-3 homologue: C. elegans Sma-4, for example, is more closely related to DPC-4 than DAF-3.

We identified three mutations in daf-3, all of which were isolated as suppressors of daf-7(e1372). mgDf90 is a homozygous viable deletion of 15–90 kb that removes the entire Smad gene (FIG. 5A). mgDf90 was identified as a spontaneous mutation that suppressed daf-7 in the strain of GR1300 (daf-7 (e1372) III; mut-6(st 702) unc-22 (St192) IV). Thus, suppression of the daf-7 dauer constitutive phenotype of daf-3 is daf-3 null phenotype, demonstrating that wild-type DAF-3 acts antagonistically to signaling from the DAF-7 TGF-β pathway signaling. daf-3(mg125) and daf-3 (mg132) are missense mutations that alter conserved residues in domains 1 and 2 respectively (FIG. 5C). Most of the mutations detected in other Smads localize to a 45 amino acid segment of domain II (Wrana et al., *Trends in Genet.* 12:493, 1996). Clustering of mutations is observed even in DPC4, for which homozygous null mutations have been identified (Hahn et al., *Science* 271:350, 1996), so the clustering is unlikely to be due to selection for non-null mutations. This hotspot region was sequenced in nine daf-3 alleles, and no mutations were detected. This difference in mutation location may be a simple statistical anomaly, or may indicate functional differences between DAF-3 and other Smad proteins, consistent with the fact that DAF-3 is antagonized, rather than activated, by an upstream TGF-β molecule.

To determine where DAF-3 may function in control of dauer formation, we examined the expression pattern of a functional daf-3/Green Fluorescent Protein (GFP) fusion gene. This was accomplished by replacing a AvrII/SacI fragment from pGP8 with a PCR product in which several restriction sites were inserted after the last codon of daf-3 before the stop codon. A GFP/unc-54 3' end PCR product from pPD95.81 was cloned into the 3' restriction sites to produce pGP19. This DAF-3/GFP fusion partially rescues a daf-3 mutant (FIG. 7). GFP fluorescence therefore indicates the functional location of DAF-3. DAF-7 signaling from the ASI neuron begins during the L1 stage, and neuron ablations and dauer-formation assays in various environmental conditions indicate that the signal for dauer formation is also received during the first two larval stages (Ren et al., Science 274:1389, 1996, Schackwitz et al., Neuron 17:719, 1996; Bargmann and Horvitz, Science 251:1243, 1991; Golden and Riddle, Developmental Biology 102:368, 1984; Swanson and Riddle, Developmental Biology 84:27, 1981). Therefore, we most extensively examined L1 larvae.

Figure 6A:
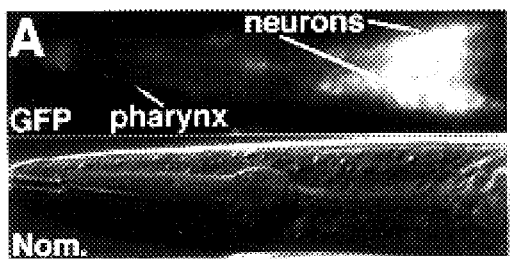
Figure 6B:
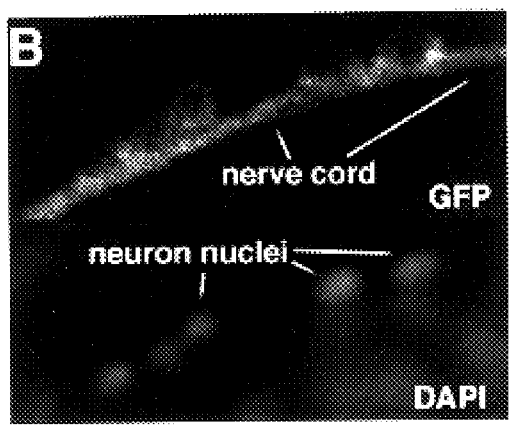
Figure 6C:
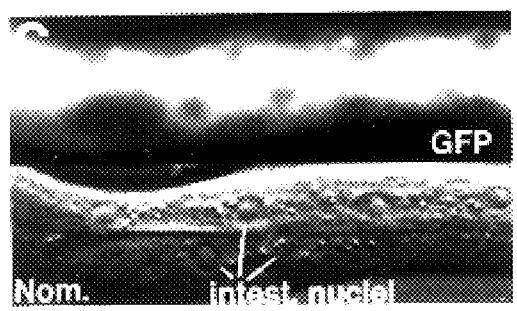
Figure 6D:
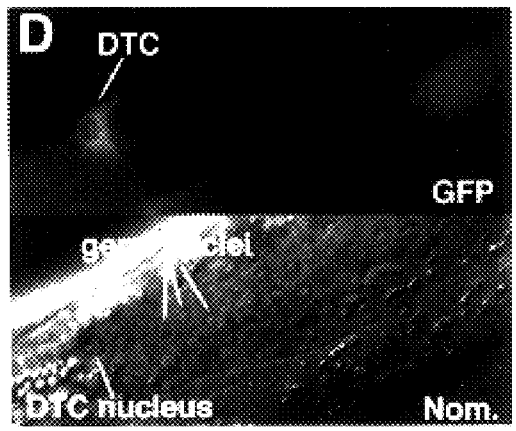
Figure 6E:
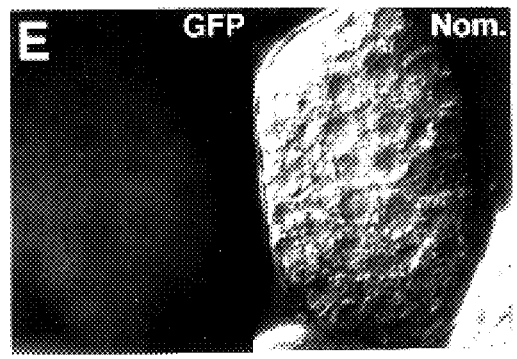
Figure 6F:
Figure 6G:

Almost every transgenic animal showed strong daf-3/GFP expression in head neurons (FIG. 6A), the ventral nerve cord (both cell bodies and processes, see FIG. 6B), the intestinal cells (FIG. 6C), especially the membrane adjacent to the intestinal lumen, the tail hypodermis, and tail neurons. For all GFP scoring, animals were grown at 25–26° C. For scoring of DAF-3/GFP in wild-type and in dauer constitutive mutant backgrounds, three or more lines were scored in each case. A large number of animals were surveyed to determine the expression pattern, and at least 30 animals were scored head-to-tail, and expression was tallied for each tissue. About half of the transgenic animals have weak expression in V blast cells, P blast cells, hyp7 hypodermal cells, and the pharynx. The weak expression impedes cell identification, but the main body of the pharynx is filled, implying expression in pharyngeal muscle (FIG. 6A). Expression is rarely detected in dorsal body wall muscle. The expression pattern in older larvae and adults is similar to that of L1 animals. In addition, DAF-3/GFP is expressed in the distal tip cells and in their precursors, Z1.a and Z4.p, throughout development (FIG. 6D, FIG. 8). DAF-3/GFP is also strongly expressed in unidentified vulval cells. In wild-type embryos of 200–400 cells, DAF-3/GFP is expressed uniformly thoughout the embryo (FIG. 6E). Under the conditions of the experiment, which promote reproductive growth, the subcellular localization of the DAF-3/GFP protein is mainly cytoplasmic (FIGS. 6B–E, and see below).

Because DAF-3 activity may be regulated by the DAF-1 and DAF-4 TGF-β receptors, we examined the expression of a DAF-4/GFP fusion in wild-type (FIGS. 6A–6G). This construct complements a daf-4 mutant. A 10 kb SalI fragment from cosmid CO5D2 contains 3 kb of sequence upstream of the daf-4 transcriptional start, and all of the daf-4 coding region except codons for the last fourteen residues of daf-4. This fragment was subcloned into the SalI site of the GFP plasmid TU#61 (Chalfie et al., Science 263: 802–805, 1994). This plasmid was injected into the daf-4 (m72) strain to test the fusion for DAF-4 activity. More than 95% of the transgenic animals were rescued for the dauer-constitutive and small phenotypes of daf-4(m72), indicating that the fusion has robust DAF-4 activity. The pattern of DAF-4/GFP expression is similar to that of daf-3/GFP, except that DAF-4/GFP is localized to membranes, consistent with its role as a receptor. DAF-4/GFP is expressed more strongly in the pharynx (FIGS. 6F–G), and more weakly in the ventral nerve cord cell bodies and the body hypodermis. Expression of DAF-4/GFP in wild-type animals is detected later than DAF-3/GFP. DAF-4/GFP is first detectable at late embryogenesis when the embryo resembles an L1 larva. The DAF4/GFP construct contains an older version of GFP than in DAF-3/GFP; in the older version, the chromophore takes longer to mature. To verify that the difference in embryonic expression of DAF4/GFP and DAF-3/GFP is not an artefact of the slower maturation time in the daf-4 strain, we used anti-GFP antibodies to assay GFP. These antibodies should recognize the two forms of GFP equally well. We found that the antibodies recapitulated the results with direct GFP fluorescence: DAF-3/GFP is expressed in early embryos; DAF-4/GFP is not. DAF-4/GFP is also not expressed in membrane surrounding the intestinal lumen, unlike DAF-3/GFP.

The combination of the DAF-3 and DAF-4 expression patterns suggests that these genes act in target tissues to transduce pheromone-regulated DAF-7 neuroendocrine signals. The early expression of DAF-3 in embryos is also consistent with a model that DAF-3 acts during embryonic development, for example, to mediate the development of neuronal pathways that emit neuroendocrine signals that antagonize DAF-7 TGF-β signaling during the L1 stage. However our data indicates that DAF-3 functions in transducing environmental signals during the L1 and L2 stages. This is supported by the following observations. (1) DAF-7 TGF-β signal from ASI neurons occurs during the L1 and L2 stages and is repressed by dauer-inducing environmental conditions. (2) Expression of the DAF-4 type II receptor begins in very late embryogenesis. (3) Expression patterns of DAF-3 and DAF-4 are coincident in most of the tissues remodeled during dauer morphogenesis. For example, the cuticle secreted by the hypodermis is modified, the pharynx is slimmed, and the lumen of the intestine is less convoluted. In addition, somatic gonad development is arrested in dauers, and the distal tip cell, in which DAF-3 is expressed, is an important regulator of that development (Kimble, Developmental Biology 87:286, 1981). In addition, the intestine and hypodermis of dauer larvae contain large fat stores indicative of a metabolic shift to fat storage. The expression of both the DAF-4 TGF-β family receptor kinase and the DAF-3 Smad protein in these target tissues is consistent with a model that the DAF-7 neuroendocrine signal from the ASI neuron is received directly by these tissues during non dauer development. In addition, the observation that DAF-4 and DAF-3 are expressed in many of the same cells is consistent with a model that DAF-4 signaling to downstream Smads (DAF-8 and DAF-14 are likely candidates) directly regulates DAF-3 gene activity. The TGF-β regulated nuclear localization and transcriptional activation of some Smad proteins suggests that DAF-3 might induce the dauer-specific changes by activating transcription in target tissues of genes required for dauer formation or repressing transcription of genes necessary for nondauer growth.

Smad1 and Smad2 relocalize to become predominantly nuclear when the upstream TGF-β signaling pathways are activated (Baker and Harland, Genes and Development 10: 1880, 1996; Hoodless et al., Cell 85:489, 1996; Liu et al., Nature 381:620, 1996; Macias-Silva et al., Cell 87:1215, 1996). In wild-type, DAF-3/GFP is primarily, although not exclusively, cytoplasmic. DAF-3/GFP subcellular distribution was examined in head neurons in the vicinity of ASI (the cell that produces the DAF-7 signal), as well as in intestinal cells. DAF-3/GFP was predominantly cytoplasmic in all animals. However, in all animals, dim GFP fluorescence was observed in the nucleus of some of the cells with bright fluoresence, and in approximately twenty-five percent of the animals, equivalent DAF-3/GFP levels in the nucleus and cytoplasm has observed in one or more cells.

Because DAF-3 is antagonized by the other members of the DAF-7 TGF-β pathway, we expect that DAF-3 is active (and perhaps localized to the nucleus) when these genes are inactive. We therefore observed the subcellular localization of the full-length DAF-3/GFP fusion protein in the head neurons, tail neurons, and intestine of dauer-constitutive mutant L1 worms, when DAF-3 gene activity is predicted to be highest. In DAF-1(m402), daf-4(m72), daf-7(m62), daf-8(sa233), and daf-14(m77) mutants, DAF-3/GFP was predominantly cytoplasmic, although, as in wild-type, cells were seen with some GFP in the nucleus. In three daf-4 (m72) mutant lines, DAF-3/GFP was localized to the nucleus more than in wild-type lines. When these strains were crossed to wild-type, the increased nuclear localization was seen in both the daf-4 and wild-type segregants. Thus the increased nuclear GFP was a property of the array, rather than of daf-4. Even in the neurons nearest to ASI, where the DAF-7 signal should be strongest, no change in DAF-3/GFP subcellular localization was detected. The DAF-3/GFP fusion protein is predominantly cytoplasmic in L1 and L2 stages of larvae induced to form dauers by environmental conditions or by mutations in the insulin receptor pathway gene daf-2, rather than by mutations in the DAF-7 signaling pathway mutants (data not shown). The tissue-specific expression pattern of DAF-3/GFP was unaltered in these mutant backgrounds (data not shown).

The finding that DAF-3/GFP subcellular localization is not strongly responsive to DAF-7 signaling defects or to dauer-inducing environmental conditions does not rule out a role for DAF-3 in the nucleus in dauer formation. Even though we detect no change in DAF-3/GFP subcellular localization, we do detect some DAF-3/GFP in nuclei, and a minor change in nuclear localization or a change in activity due to phosphorylation state may couple DAF-3 to DAF-7 signaling. In fact, the subcellular localization of Drosophila MAD protein is not detectably altered in wild-type when receptor signaling to MAD occurs; relocalization is seen only if the DPP ligand is drastically overexpressed. It is unlikely that a set of undiscovered TGF-β receptors regulates DAF-3. The C. elegans genome sequence is 90% complete, and there is only one candidate TGF-β receptor gene other than daft-1 and daf-4. If this receptor were a positive regulator of DAF-3, mutants would be expected to, like daf-3 mutants, suppress daf-7 mutants. This receptor acts in a signaling pathway distinct from DAF-3, and it is not a suppressor of daf-7.

Figure 8A:
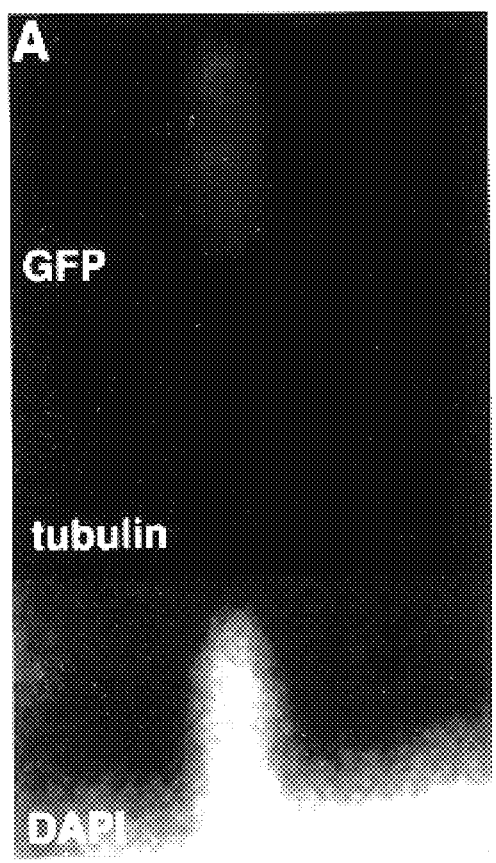
Figure 8B:
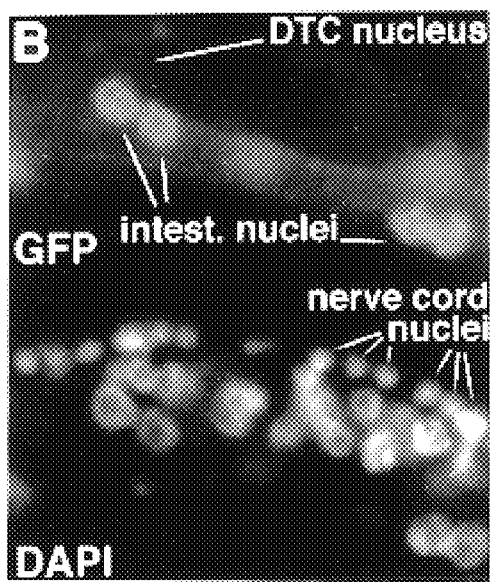

The implication from Smad homology that DAF-3 is active in the nucleus is supported by two additional observations. First, DAF-3/GFP is associated with chromosomes in intestinal cells during mitosis. These cells divide at the end of the L1 stage, and antibody staining with anti-GFP antibodies and anti-α-tubulin antibodies reveals that DAF-3/GFP is found associated with DNA between the spindles during mitosis (FIG. 8A). We see DAF-3 GFP co-localized with DAPI from prophase to late anaphase. DAF-3/GFP was associated with nuclei in prophase by the following criteria. The spindles were present on either side of the nucleus, but the nucleus has not completely broken down. In particular, an indistinct nucleolus was present. DAF-3/GFP continues to co-localize with DAPI until the chromosomes have separated to the normal distance by which nuclei are separated in the intestine, implying continued association until telophase. At this point in mitosis, DAF-3/GFP fades and becomes undectectable before the nuclei reform the nuclear envelope and nucleolus. Thus, DAF-3 can, indirectly or directly, bind DNA, consistent with the hypothesis that it is a transcriptional activator that acts in the nucleus. DAF-3 is not predicted from its mutant phenotype to have a role in mitosis. It is possible that the brighter GFP on mitotic chromosomes is due to increased access to DNA due to the breakdown of the nuclear envelope. The second indication of DAF-3 function in the nucleus is our examination of a truncated DAF-3/GFP fusion that is missing most of conserved domain II. The truncated construct pGP7 consists of 8 kb of daf-3 fused to GFP. An 8 kb EcoRl fragment from B0217 was cloned into the EcoRl site of pBluescript SK(−). A PvuI/SalI fragment of this subclone was ligated to a PvuI/SalI fragment from the GFP vector pPD95.81. The resulting plasmid contains ~2.5 kb of sequence upstream of the 5'-most exon of daf-3 and coding region through the first 58 amino acid residues of domain II. The remaining 175 amino acids of daf-3 and the 3' noncoding region are replaced with GFP and the unc-54 3' end. Three transgenic lines were isolated, and all had a similar phenotype. This fusion protein interferes with dauer induction; like a daf-3 loss-of-function mutant, it suppresses mutations in daf-7 (FIG. 7). This truncated protein is predominantly nuclear, suggesting that it represses dauer formation by acting in the nucleus (FIG. 8B). This result implies that wild-type DAF-3 also has a function in the nucleus. The full-length DAF-3/GFP construct also suppresses mutations in daf-7, as does a full-length DAF-3 construct without GFP (FIG. 7). This suppression indicates that overexpression of DAF-3 in the cytoplasm has dominant-negative activity, perhaps due to interference with DAF-3 interactions with receptors or cofactors such as other Smads.

Figure 9A:
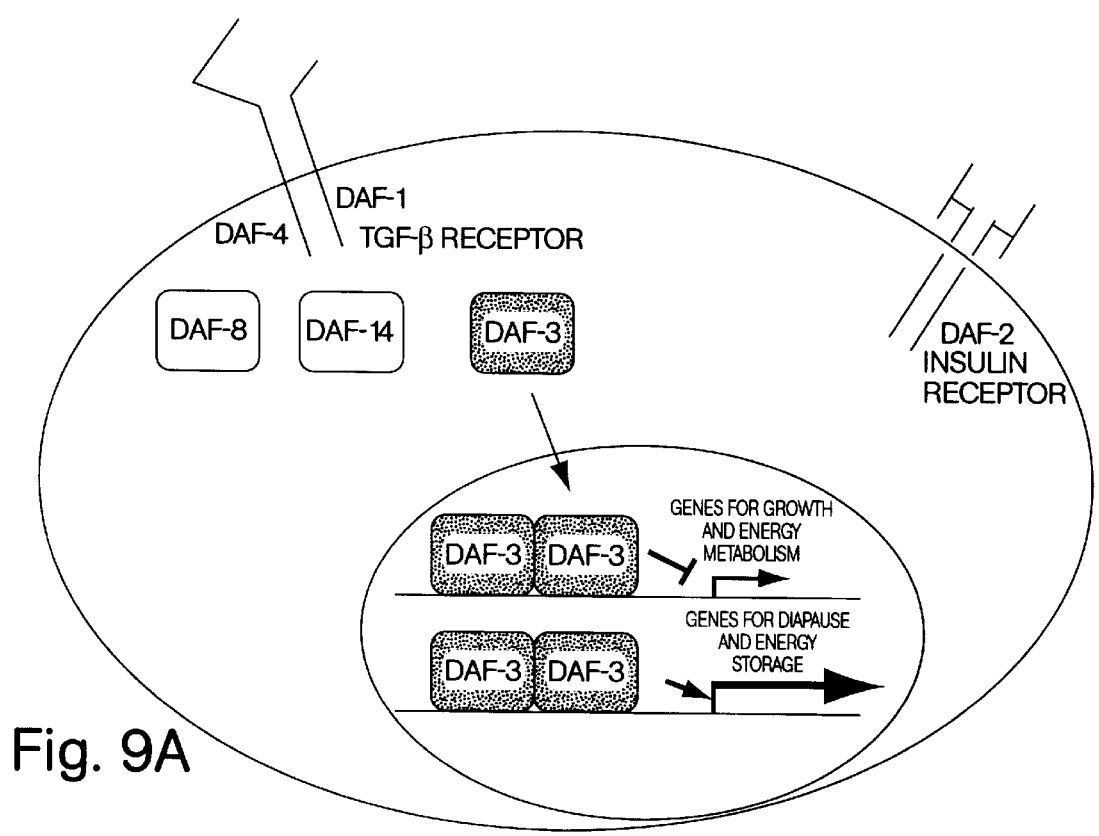
Figure 9B:
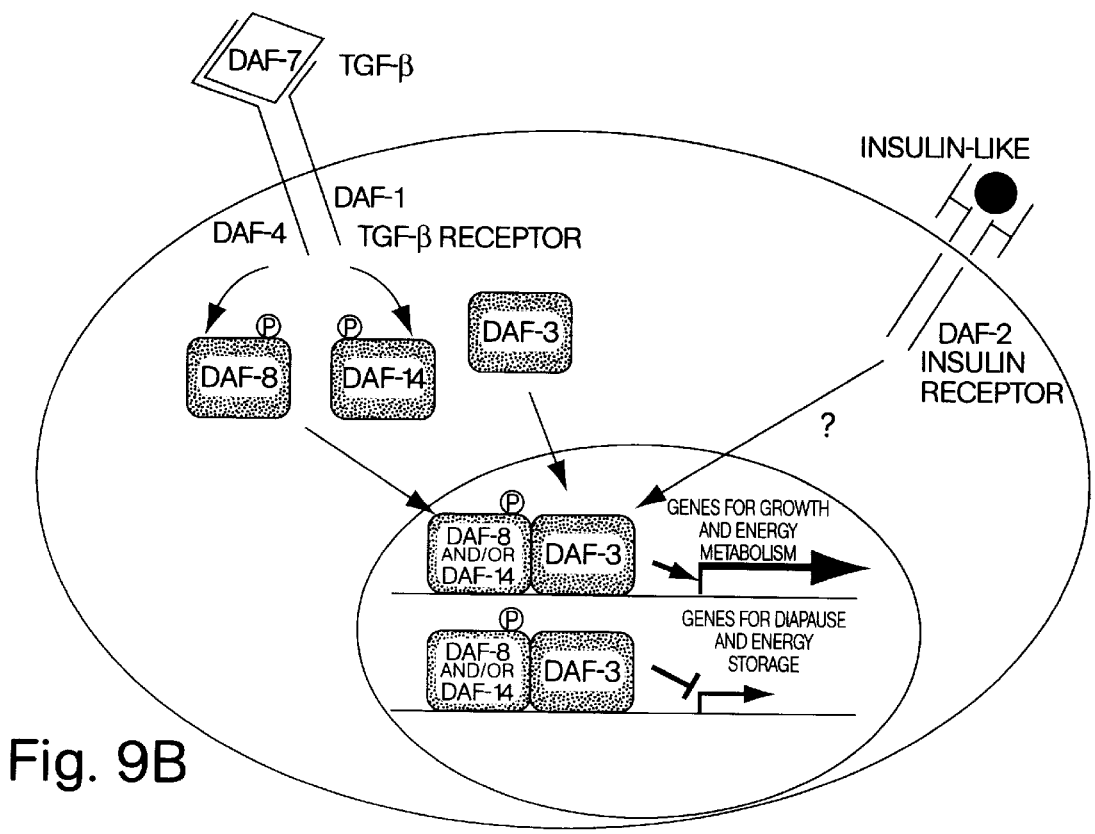
Figure 10:
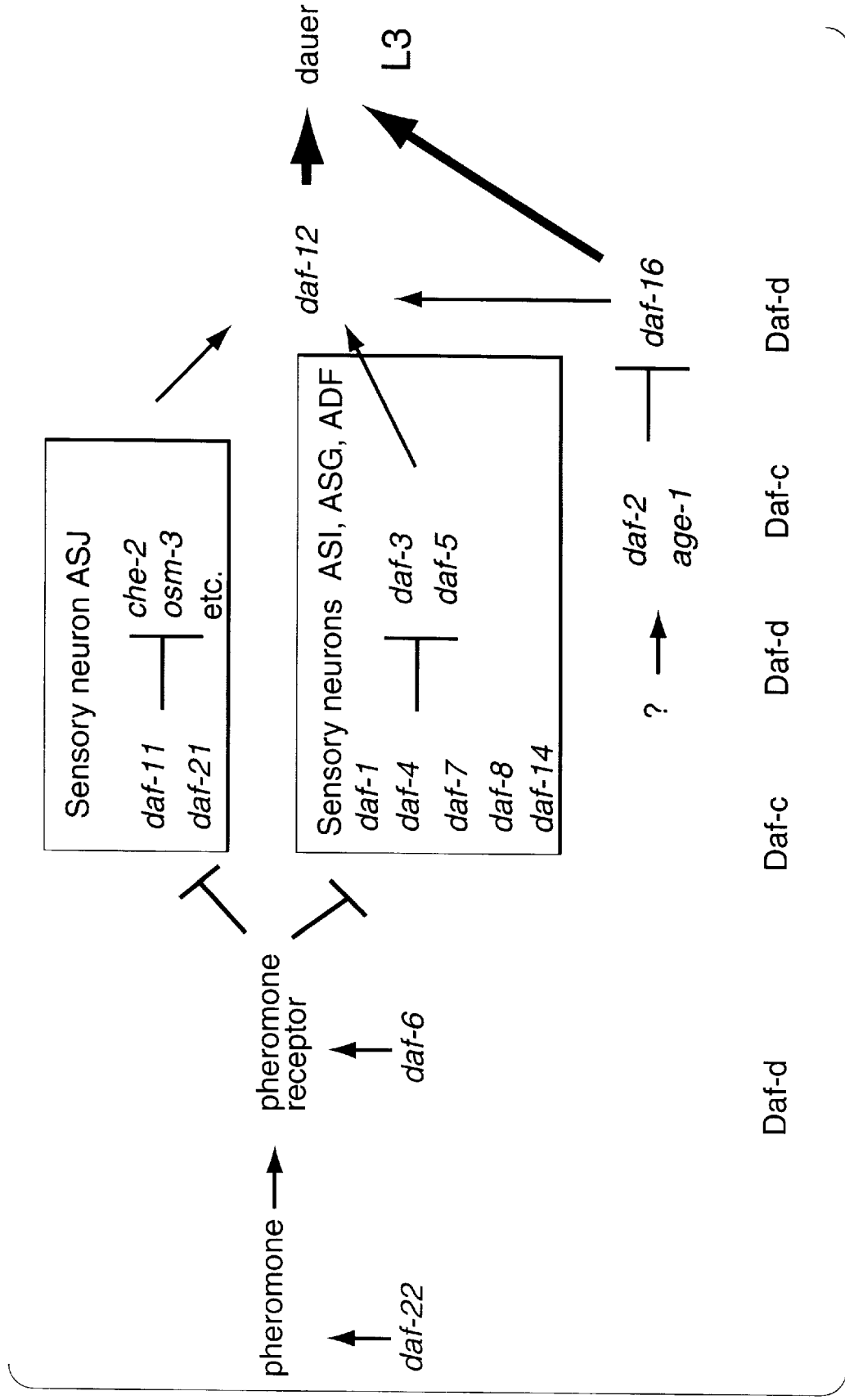
FIG. 10 is a schematic illustration showing the genetic pathway that regulates C. elegans dauer formation.

The constitutive nuclear localization of truncated DAF-3/GFP fusion gene missing part of domain II suggests that control of Smad localization is complex. A Smad2 construct containing only the conserved domain II of the protein is constitutively nuclear, leading to the suggestion that the C-terminus is an effector domain, and the N-terminus tethers the protein in the cytoplasm (Baker and Harland, *Genes and Development* 10:1880, 1996; Hoodless et al., *Cell* 85:489, 1996; Liu et al., *Nature* 381:620, 1996; and Macias-Silva et al., *Cell* 87:1215, 1996). Our construct, in which the N-terminus is intact, is nuclear. Perhaps both domains provide tethering in the cytoplasm, and any disruption leads to nuclear entry. Alternatively, entry may be differently regulated for DAF-3 and Smad2. Significantly, Smad2, like Smad1 and Smad3 has an SSXS motif at the C terminus (Zhang et al., *Nature* 383:168, 1996; Lagna et al., *Nature* 383:832, 1996; Savage et al., *PNAS* 93:790; Baker and Harland, *Genes and Development* 10:1880, 1996; Hoodless et al., *Cell* 85:489, 1996; Liu et al., *Nature* 381:620, 1996; Macias-Silva et al., *Cell* 87:1215, 1996; and Graf et al., *Cell* 85:479, 1996); this motif is a substrate for phosphorylation and required for nuclear localization of Smad2 (Baker and Harland, *Genes and Development* 10:1880, 1996; Hoodless et al., *Cell* 85:489, 1996; Liu et al., *Nature* 381:620, 1996; and Macias-Silva et al., *Cell* 87:1215, 1996). DAF-3 has a single serine in the C terminal region, and DPC4 has no serines at this location. We propose a model for the TGF-β pathway in dauer formation (FIGS. 9A–B). The DAF-7 TGF-β ligand, which is produced by the ASI sensory neuron in conditions that induce reproductive organ (Ren et al., Science 274:1389, 1996; Schakwitz et al., Neuron 17:719, 1996), binds to the DAF-1/DAF-4 receptor kinases on target tissues. These receptor kinases then phosphorylate the Smads DAF-8 and/or DAF-14, analogous to the phosphorylation and activation of Smad1, Smad2, and Smad3 (Zhang et al., Nature 383:168, 1996; Lagna et al., Nature 383:832, 1996; Savage et al., PNAS 93:790, 1996). We propose that DAF-3 functions like its closest homolog, DPC4, which dimerizes with phosphorylated Smad1 and Smad2, even under conditions that do not lead to detectable DPC4 phosphorylation (Zhang et al., Nature 383:168, 1996; Lagna et al., Nature 383:832, 1996; and Savage et al., PNAS 93:790). We suggest that DAF-3 forms dauer-inducing homodimers in the absence of DAF-7 signaling (FIGS. 9A–B) that are disrupted when DAF-3 heterodimerizes with a phosphorylated DAF-8 and/or DAF-14 (FIG. 9B). Because daf-8 and daf-14 are only partially redundant (Riddle et al., Nature 290:668, 1981; Vowels and Thomas, Genetics 130:105, 1992; and Thomas et al., Genetics 134:1105, 1993), each is likely to perform a unique function in dauer formation. Thus, DAF-3/DAF-8 dimers are proposed to have different activity from DAF-3/DAF-14. Perhaps each activates a subset of genes required for dauer formation. The formation of DAF-8/DAF-3 and/or DAF-14/DAF-3 heterodimers antagonizes dauer induction by the DAF-3/DAF-3 homodimer. A daf-8(sa233); daf-14(m77); daf-3 (mgDf90) triple mutant can form some dauers in dauer-inducing conditions (data not shown); we suggest that activity of the Daf-2 pathway may induce dauer in this mutant background.

The dauer genetic pathway represents a neuroendocrine pathway for control of a diapause arrest and its associated shifts in metabolism and rates of senescence (Ren et al., Science 274:1389, 1996; Schackwitz et al., Neuron 17:719, 1996; and Georgi et al., Cell 61:635, 1990). Similarly, activins, members of the TGF-β family, were originally identified based on their neuroendocrine regulatory activity, for example, in regulation of gonadotropin signaling (Vale et al., in Peptide Growth Factors and Their Receptors, Sporn and Roberts, Eds., Springer-Verlag, Heidelberg, 1990). The DAF-7 signal is not the only signal that is necessary for reproductive development. Because mutations in the DAF-7 TGF-β pathway and in the DAF-2 insulin-like signaling pathway cause the same dauer arrest phenotypes, we propose that both the DAF-7 TGF-β signals and the DAF-2 insulin-like signals are necessary for reproductive development. The involvement of an insulin-like signaling pathway in diapause with its associated metabolic shifts is consistent with metabolic regulation by insulin in vertebrates. Genetic experiments indicate that these pathways act in parallel (Riddle et al., Nature 290:668, 1981; Vowels and Thomas, Genetics 130:105, 1992; and Thomas et al., Genetics 134:1105, 1993). In particular, daf-3 mutants efficiently suppress daf-7 mutants, but not daf-2 mutants, and daf-16 mutants efficiently suppress daf-2 mutants, but poorly suppress daf-7 mutants. It is not yet clear whether these two signaling pathways coverage on target tissues or in other regulatory (e.g., hormone secreting) cells. However, the expression of the DAF-7 receptor pathway genes and the DAF-16 gene in essentially all target tissues suggests that the TGF-β and insulin pathways act there, and therefore that integration must occur there. Thus, we suggest in FIGS. 9A and 9B that the DAF-2 pathway converges on DAF-3/DAF-8DAF-1 Smad signaling to regulate metabolic gene expression in target tissues.

The integration of insulin-like and TGF-β signals in metabolic control has important implications for the molecular basis of diabetes. For example, these converging pathways for dauer control suggest that in human metabolic control both a DAF-7-like signal and insulin may be necessary for full metabolic control. Thus, declines in signaling from the human homolog of DAF-7 could underlie the insulin resistance associated with Type II diabetes. In fact the dauer pheromone has been reported to be a fatty acid and to cause down-regulation of DAF-7 expression (Ren et al., supra). Thus pheromone regulation of metabolism may be related to mammalian obesity induced diabetes, and a human mutation in DAF-7 or its receptors is expected to contribute to a diabetic condition, just like mutations in the insulin receptor. In addition if obesity or age or both cause human DAF-7 to decline, e.g., under high leptin conditions, such a result would explain late onset/obesity related diabetes.

Cloning Mammalian DAF Sequences

Based on our isolation of novel nematode DAF cDNAs, the isolation of mammalian DAF nucleic acid sequences, including human DAF sequences, is made possible using the sequences described herein and standard techniques. In particular, using all or a portion of a nematode DAF sequence, one may readily design oligonucleotide probes, including degenerate oligonucleotide probes (i.e., a mixture of all possible coding sequences for a given amino acid sequence). These oligonucleotides may be based upon the sequence of either strand of the DNA.

Exemplary probes or primers for isolating mammalian DAF sequences preferably correspond to conserved blocks of amino acids, for example, conserved DAF motifs. Exemplary motifs are as follows:

DAF-2 (tyrosine kinase domain) (SEQ ID NO: 33)
1242 KFHEWAAQICDGMAYLESLKFCHRD-LAARNCMINRDETVKIGDFGM ARDLFYHDYYKPS-GKRMMPRWMSPESLKDGKFDSKSDVWSFGVVLYE MVTLGAQPYIGLSNDEVLNYIGMARKVIKKPEC 1368

DAF-2 (ligand binding domain) (SEQ ID NO: 34)
242 NTTCQKSCAYDRLLPTKEIGPGCDAN-GDRCHDQCVGGCERVNDATA CHACKN-VYGKCIEKCDAHLYLLLQRRCVTREQ-CLQLNPVLSNKTVPIK ATAGLCSDKCPDGYQINPDDHRECRKCVGKCEIVC 372

DAF-2 (67 amino acid motif) (SEQ ID NO: 79)
1158 AIKINVDDPASTENLNYLMEANIMKNFK-TNFIVQLYGVISTVQPAMV VMEMMDLGNLRDYLR-SKRED 1224

DAF-2 (54 amino acid motif) (SEQ ID NO: 80)
1362 VIKKPECCENYWYKVMKM-CWRYSPRDRPTFLQLVHLLAAEASPEFR DLSFVLTD 1415

DAF-2 (69 amino acid motif) (SEQ ID NO: 81)
404 KQDSGMASELKDIFANIHTIT-GYLLVRQSSPFISLNMFRNLRRIEAKSL FRN-LYAITVFENPNLKKLFD 472

DAF-2 (52 amino acid motif) (SEQ ID NO: 82)
98 FPHILREITGTLLVFETEGLVDLRKIFP-NLRVIGGRSLIQHYALIIYRN PDLE 149

DAF-2 (46 amino acid motif) (SEQ ID NO: 83)
149 EIGLDKLSVIRNGGVRIIDNRKLCYTK-TIDWKHLITSSINDWVDN 194

DAF-2 (36 amino acid motif) (SEQ ID NO: 84)
1112 YNADDWELRQDDVVLGQQCGEGSF-
GKVYLGTGNNVV 1147

DAF-3 (Smad Domain I) (SEQ ID NO: 35)
240 FDQKACESLVKKLKDKKNDLQNLIDVVL-
SKGTKYTGCITIPRTLDGR LQVHGRKGFPHV-
VYGKLWRFNEMTKNETRHVDHCKHAFEMKSDMVC
VNPYHYEIVI 342

DAF-3 (Smad Domain II) (SEQ ID NO: 36)
690 NRYSLGLEPNPIREPVAFKVRKAIVD-
GIRFSYKKDGSVWLQNRMKYPV FVTSGYLDEQSG-
GLKKDKVHKVYGCASIKTF 768

DAF-3 (79 amino acid motif) (SEQ ID NO: 85)
819 DSLAKYCCVRVSFCKGFGEAYPER 842

DAF-16 (forkhead DNA binding domain) (SEQ ID NO: 37)
727 KKTTTRRNAWGNMSYAELITTAIMASPE-
KRLTLAQVYEWMVQNVPY FRDKGDSNSSAGWKN-
SIRHNLSLHSRFMRIQNEGAGKSSWWVINPDAKPG
MNPRRTRERS 1044

DAF-16 (103 amino acid motif) (SEQ ID NO: 54)
242 KKTTTRRNAWGNMSYAELITTAIMASPE-
KRLTLAQVYEWMVQNVPY FRDKGDSNSSAGWKN-
SIRHNLSLHSRFMRIQNEGAGKSSWWVIPDAKPG
MNPRRTR 344

DAF-16 (41 amino acid motif) (SEQ ID NO: 55)
137 TFMNTPDDVMMNDDMEPIPRDRCNTWPM-
RRPQLEPPLNSSP 177

DAF-16 (109 amino acid motif) (SEQ ID NO: 56)
236 DDTVSGKKTTTRRNAWGNMSYAELIT-
TAIMASPEKRLTLAQVYEWM VQNVPYFRDKGD-
SNSSAGWKNSIRHNLSLHSRFMRIQNE-
GAGKSSWWVI NPDAKPGMNPRRTR 344

DAF-16 (98 amino acid motif) (SEQ ID NO: 58)
372 KPNPWGEESYSDIIAKALESAPDGRLKL-
NEIYQWFSDNIPYFGERSSPE EAAGWKN-
SIRHNLSLHSRFMRIQNEGAGKSSW-
WVINPDAKPGMNP RRTR 469

Using such motifs, mammalian DAF-2, DAF-3, and DAF-16 genes may be isolated from sequence databases (for example, by the use of standard programs such as Pileup). Alternatively, such sequences may be used to design degenerate oligonucleotide probes to probe large genomic or cDNA libraries directly. General methods for designing and preparing such probes are provided, for example, in Ausubel et al., *Current Protocols in Molecular Biology,* 1996, Wiley & Sons, New York, N.Y.; and *Guide to Molecular Cloning Techniques,* 1987, S. L. Berger and A. R. Kimmel, eds., Academic Press, New York. These oligonucleotides are useful for DAF gene isolation, either through their use as probes for hybridizing to DAF complementary sequences or as primers for various polymerase chain reaction (PCR) cloning strategies. If a PCR approach is utilized, the primers are optionally designed to allow cloning of the amplified product into a suitable vector. PCR is particularly useful for screening cDNA libraries from rare tissue types.

Hybridization techniques and procedures are well known to those skilled in the art and are described, for example, in Ausubel et al., supra, and *Guide to Molecular Cloning Techniques,* supra. If desired, a combination of different oligonucleotide probes may be used for the screening of the recombinant DNA library. The oligonucleotides are, for example, labelled with $^{32}P$ using methods known in the art, and the detectably-labelled oligonucleotides are used to probe filter replicas from a recombinant DNA library. Recombinant DNA libraries (for example, human cDNA libraries, such as hypothalamus- or pancreas-derived cDNA libraries, particularly for DAF-2 and DAF-7 cDNAs) may be prepared according to methods well known in the art, for example, as described in Ausubel et al., supra, or may be obtained from commercial sources.

For detection or isolation of closely related DAF sequences, high stringency hybridization conditions may be employed; such conditions include hybridization at about 42° C. and about 50% formamide; a first wash at about 65° C., about 2X SSC, and 1% SDS; followed by a second wash at about 65° C. and about 0.1% SDS, 1X SSC. Lower stringency conditions for detecting DAF genes having less sequence identity to the nematode DAF genes described herein include, for example, hybridization at about 42° C. in the absence of formamide; a first wash at about 42° C., about 6X SSC, and about 1% SDS; and a second wash at about 50° C., about 6X SSC, and about 1% SDS.

As discussed above, DAF-specific oligonucleotides may also be used as primers in PCR cloning strategies. Such PCR methods are well known in the art and are described, for example, in *PCR Technology,* H. A. Erlich, ed., Stockton Press, London, 1989; *PCR Protocols: A Guide to Methods and Applications,* M. A. Innis, D. H. Gelfand, J. J. Sninsky, and T. J. White, eds., Academic Press, Inc., New York, 1990; and Ausubel et al., supra. Again, sequences corresponding to conserved regions in a DAF sequence (for example, those regions described above) are preferred for use in isolating mammalian DAF sequences. Such probes may be used to screen cDNA as well as genomic DNA libraries.

Sequences obtained are then examined (for example, using the Pileup program) to identify those sequences having the highest amino acid sequence identity to the *C. elegans* sequence, particularly in or between conserved DAF domains (for example, those domains described above). In one particular example, the human FKHR and AFX genes are $10^{33}$ more closely related to the DAF-16 forkhead domain than the next most closely related forkhead domain protein, making FKHR and AFX candidates for mammalian DAF-16 genes.

Following isolation of such candidate genes by sequence homology, the genes are then tested for their ability to functionally complement a daf mutation. This is most readily assayed by transformation of the sequence into a *C. elegans* strain having an appropriate mutant background. Exemplary *C. elegans* transformation techniques are described, for example, in Mello et al., *EMBO J.* 10: 3959–3970, 1991, and assays for DAF-2, DAF-3, and DAF-16 polypeptide function are described herein. To be considered useful in the invention, a mammalian sequence need not fully complement a *C. elegans* defect, but must provide a detectable level of functional complementation.

The DAF, AGE, or AKT gene homologue identified as above, may also complement or alter the metabolic phenotypes of a mammalian cell line.

For example, addition of DAF-7, TGF-β-like growth factor to an insulin responsive cell line (e.g., the 3T3-L1 cell line) may accentuate insulin responsiveness. Similarly genetic transformation of such a cell line with wild type or dominantly activated versions of a DAF, AGE, or AKT gene may alter metabolism. Such perturbations of metabolic control are stringent tests of candidate genes as DAF, AGE, or AKT homologues.

In addition, if that mammalian candidate homologue acts in a metabolic control pathway, and is expressed in similar metabolic control tissues (liver, adipose), it is likely to function homologously to DAF proteins from *C. elegans*. Addition of a wild type or activated DAF, AKT, or AGE protein (for example by VP16 activation of the DAF-3 or DAF-16 transcription factors) can confer on cell lines altered metabolic phenotypes. Thus supplying daf, age, or akt gene activity to such a cell line can alter its metabolism. This is one explemplary test of homologous DAF function in metabolic control.

DAF Polypeptide Expression

In general, DAF polypeptides according to the invention may be produced by transformation of a suitable host cell with all or part of DAF-encoding cDNA fragment (e.g., one of the cDNAs described herein or isolated as described above) in a suitable expression vehicle.

Those skilled in the field of molecular biology will understand that any of a wide variety of expression systems may be used to provide the recombinant protein. The precise host cell used is not critical to the invention. The DAF polypeptide may be produced in a prokaryotic host (e.g., *E. coli*) or in a eukaryotic host (e.g., *Saccharomyces cerevisiae*, insect cells, e.g., Sf9 or Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., supra). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, Sf9 cells and the method of Ausubel et al., supra). Another baculovirus system makes use of the vector pBacPAK9 and is available from Clontech (Palo Alto, Calif.).

Alternatively, an DAF polypeptide is produced in a mammalian system, for example, by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the DAF protein is cloned into an expression vector which includes the dihydrofolate reductase (DHFR) gene. Integration of the plasmid and, therefore, the DAF protein-encoding gene into the host cell chromosome is selected for by inclusion of 0.01–300 μM methotrexate in the cell culture medium (as described in Ausubel et al., supra). This dominant selection may be accomplished in most cell types. Recombinant protein expression may be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR⁻ cells, ATCC Accession No. CRL 9096) are among the host cells preferred for DHFR selection of a stably-transfected cell line or DHFR-mediated gene amplification.

In yet other alternative approaches, the DAF polypeptide is produced in vivo or, preferably, in vitro using a T7 system (see, for example, Ausubel et al., supra, or other standard techniques).

Once the recombinant DAF protein is expressed, it is isolated, e.g., using affinity chromatography. In one example, an anti-DAF protein antibody (e.g., produced as described herein) may be attached to a column and used to isolate the DAF protein. Lysis and fractionation of DAF protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short DAF polypeptide fragments, may also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification may also be used to produce and isolate useful DAF fragments or analogs (described herein).

Anti-DAF Antibodies

Using any of the DAF polypeptides described herein or isolated as described above, anti-DAF antibodies may be produced by any standard technique. In one particular example, a DAF cDNA or cDNA fragment encoding a conserved DAF domain is fused to GST, and the fusion protein produced in *E. coli* by standard techniques. The fusion protein is then purified on a glutathione column, also by standard techniques, and is used to immunize rabbits. The antisera obtained is then itself purified on a GST-DAF affinity column, for example, by the method of Finney and Ruvkun (*Cell* 63:895–905, 1990), and is shown to specifically identify GST-DAF, for example, by Western blotting.

Polypeptides for antibody production may be produced by recombinant or peptide synthetic techniques (see, e.g., *Solid Phase Peptide Synthesis*, supra; Ausubel et al., supra).

For polyclonal antisera, the peptides may, if desired, be coupled to a carrier protein, such as KLH as described in Ausubel et al, supra. The KLH-peptide is mixed with Freund's adjuvant and injected into guinea pigs, rats, or preferably rabbits. Antibodies may be purified by any method of peptide antigen affinity chromatography.

Alternatively, monoclonal antibodies may be prepared using a DAF polypeptide (or immunogenic fragment or analog) and standard hybridoma technology (see, e.g., Kohler et al., *Nature* 256:495, 1975; Kohler et al., *Eur. J. Immunol.* 6:511, 1976; Kohler et al.,*Eur. J. Immunol.* 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific DAF recognition by Western blot or immunoprecipitation analysis (by the methods described in Ausubel et al., supra). Antibodies which specifically recognize a DAF polypeptide described herein are considered to be useful in the invention. Anti-DAF antibodies, as isolated above, may be used, e.g., in an immunoassay to measure or monitor the level of DAF polypeptide produced by a mammal or to screen for compounds which modulate DAF polypeptide production (for example, in the screens described herein). In one particular example, antibodies to human DAF-7 polypeptide are useful for screening blood samples from patients to determine whether they possess decreased DAF-7 polypeptide levels. Such antibodies may be used in any immunological assay, for example, an ELISA assay, and a decrease in DAF-7 is taken as an indication of a diabetic condition, for example, obesity onset Type II diabetes. In another particular example, anti-DAF antibodies are useful for carrying out pedigree analysis. For example, blood samples from individuals may be screened with anti-DAF-7 antibodies to detect those members of a family with a predisposition to a diabetic condition. Anti-DAF antibodies may also be used to identify cells that express a DAF gene.

DAF-7 Therapy for Obesity-Onset Type II Diabetes

Our data indicates that DAF-7 represents an endocrine hormone for metabolic control that acts synergistically with insulin. Declines in DAF-7 may be induced by obesity, just as the dauer pheromone, a fatty acid, causes declines in *C. elegans* DAF-7 production.

Figure 23:
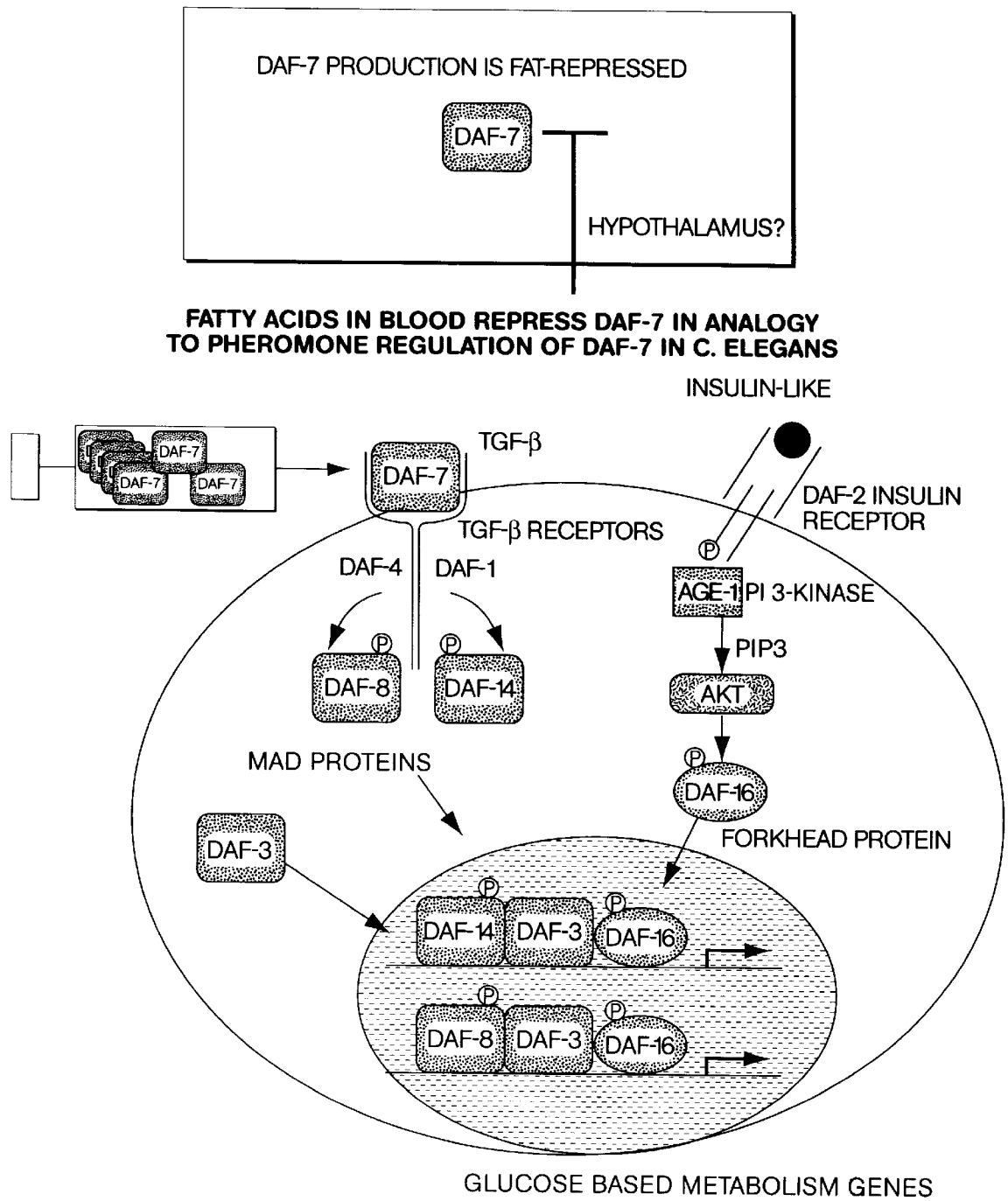
FIG. 23 is an illustration showing a model for treatment of obesity-induced diabetes with DAF-7 protein.

Accordingly, obesity onset Type II diabetes, glucose intolerance, and the associated atherosclerosis may be treated if DAF-7 hormone is injected intramuscularly or intravenously (FIG. 23).

In addition, antibodies to human DAF-7 should detect declines in DAF-7 in pre-diabetic, glucose-intolerant, or obesity induced diabetes. Such antibodies will detect DAF-7 levels in blood, just as insulin levels are detected in metabolic disease.

DAF-7 therapeutic potential and dosage can be developed in mouse models of obesity onset diabetes—the db and ob mouse.

DAF-7 will in injected either intravenously or intramuscularly, in analogy to insulin therapy.

The decision of which classes of diabetics to treat with DAF-7 will come from a combination of blood tests for DAF-7 levels and genetic testing for which daf, age, or akt mutations a particular diabetic, pre-diabetic patient carries.

Screening Systems for Identifying Therapeutics

Based on our experimental results, we have developed a number of screening procedures for identifying therapeutic compounds (e.g., anti-diabetic and anti-obesity pharmaceuticals or both) which can be used in human patients. In particular examples, compounds that down regulate daf-3 or daf-16 or their human homologs are considered useful in the invention. Similarly, compounds that up regulate or activate daf-1, daf-2, daf-4, daf-7, daf-8, daf-11 daf-14, age-1, and akt (or each of their corresponding human homologs) are also considered useful as drugs for the treatment of impaired glucose tolerance conditions, such as diabetes and obesity. In general, the screening methods of the invention involve screening any number of compounds for therapeutically active agents by employing any number of in vitro or in vivo experimental systems. Exemplary methods useful for the identification of such compounds are detailed below.

The methods of the invention simplify the evaluation, identification, and development of active agents for the treatment and prevention of impaired glucose tolerance conditions, such as diabetes and obesity. In general, the screening methods provide a facile means for selecting natural product extracts or compounds of interest from a large population which are further evaluated and condensed to a few active and selective materials. Constituents of this pool are then purified and evaluated in the methods of the invention to determine their anti-diabetic or anti-obesity activities or both.

Below we describe screening methods for evaluating the efficacy of a compound as anti-diabetic or anti-obesity agents or both. These examples are intended to illustrate, not limit, the scope of the claimed invention.

Test Extracts and Compounds

In general, novel drugs for the treatment of impaired glucose tolerance conditions are identified from large libraries of both natural product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-diabetic and anti-obesity activities should be employed whenever possible.

When a crude extract is found to have anti-diabetic or anti-obesity activities or both, further fractionation of the positive lead extract is necessary to isolate chemical constituents responsible for the observed effect. Thus, the goal of the extraction, fractionation, and purification process is the careful characterization and identification of a chemical entity within the crude extract having anti-diabetic or anti-obesity activities. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of diabetes or obesity known in the art.

There now follow examples of high-throughput systems useful for evaluating the efficacy of a molecule or compound in treating (or preventing) an impaired glucose tolerance condition.

Nematode Release of Dauer Arrest Bioasssy

To enable mass screening of large quantities of natural products, extracts, or test compounds in an efficient and systematic fashion, C. elegans mutant dauer larvae (e.g., C. elegans containing mutations described herein, such as C. elegans daf-2 mutant dauer larvae) are cultured in wells of a microtiter plate, facilitating the semiautomation of manipulations and full automation of data collection. As discussed above, compounds that down regulate DAF-3 or DAF-16 activities or up regulate DAF-1, DAF-2, DAF-4, DAF-7, DAF-8, DAF-11, DAF-14, AGE-1, or AKT activities are considered useful in the invention. Such compounds are identified by their effect on dauer formation in C. elegans strains carrying mutations in these genes (as described above).

In particular examples, nematodes bearing mutations in the DAF-2 polypeptide arrest as dauer larvae, never producing progeny. All of the metabolic and growth arrest phenotypes caused by lack of daf-2 are suppressed by mutations in daf-16. Mutations in the PI 3-kinase, AGE-1, have the same phenotype as lack of daf-2, and such mutations are also suppressed by daf-16 mutations. Biochemical analysis of insulin signaling in mammals supports the view that AGE-1 transduces signals from the DAF-2 receptor by generating a PIP3 signal. Because daf-16 mutations suppress lack of daf-2, or age-1 gene activity, it is believed that PIP3 down regulates or modifies daf-16 gene activity. The biochemical overlap between DAF-2/AGE-1 and insulin receptors/PI 3-kinase indicates that the human homolog of the C. elegans daf-16 gene acts in the insulin pathway as well. Thus, the C. elegans insulin signaling pathway yields the surprising result that the animals can live without insulin signaling, provided they are mutant in daf-16. This analysis therefore indicates that a compound that inhibits DAF-16 activity would reverse the effects of diabetic lesions, e.g., in the production or secretion of insulin or in the reception of insulin signals by target tissues. Such drugs would be expected to be efficacious in the treatment of insulin deficiencies due to pancreatic β cell destruction in Type I diabetes, as well as some Type II diabetes due to defects in insulin signaling.

Figure 19:
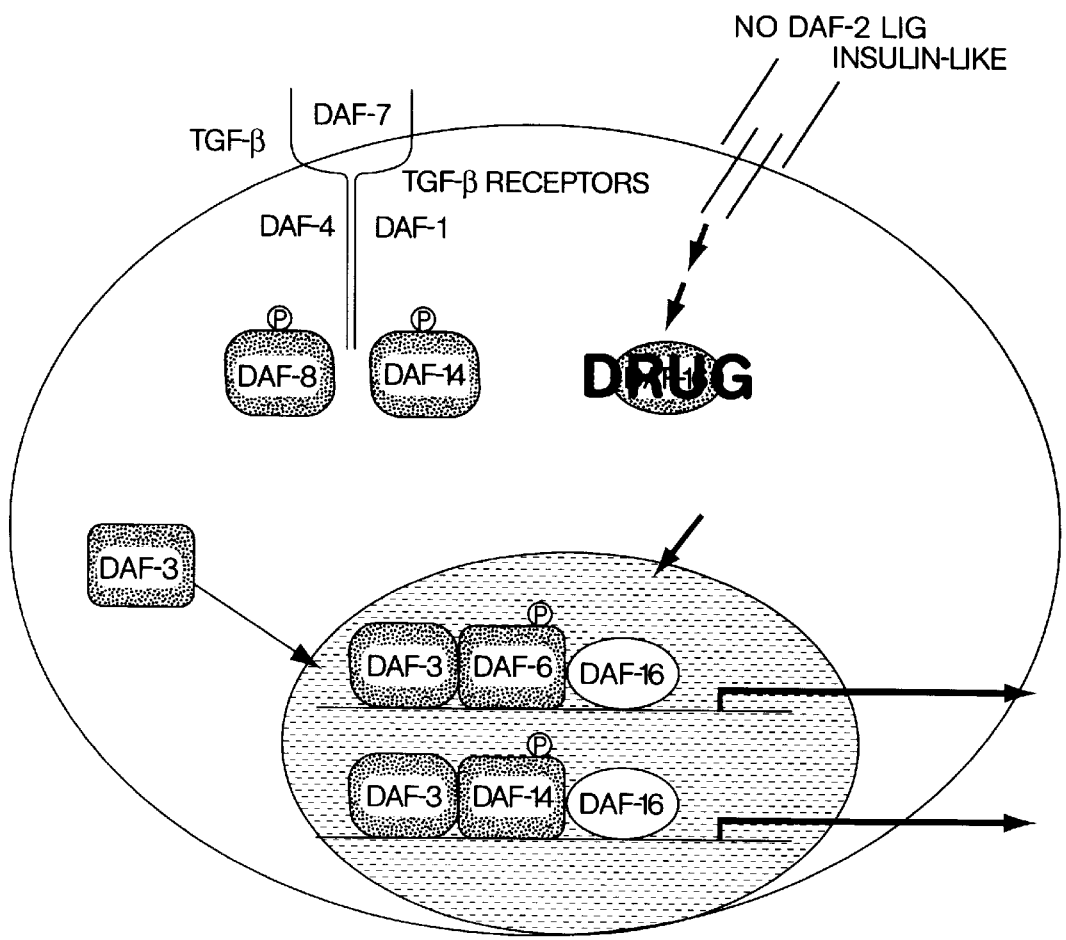
FIG. 19 is a schematic diagram illustrating inhibition of the DAF-16 pathway by drugs to ameliorate lack of insulin signaling.

To evaluate the ability of a test compound or an extract to decrease daf-16 gene activity, mutant daf-2 (e1370); daf-16 (mgDf50) animals carrying an integrated human DAF-16 gene are incubated in microtiter dishes in the presence of a test compound. This human DAF-16 gene supplies all of the DAF-16 activity in the C. elegans strain and thus allows daf-2-induced dauer arrest unless its activity is decreased by the candidate test compound. If desired, various concentrations of the test compound or extract can be inoculated to assess the dosage effect. Control wells are incubated in the absence of a test compound or extract. Plates are then incubated at 25° C. After an appropriate period of time, e.g., 2 to 5 days, wells are examined for progeny. The presence of progeny is taken as an indication that the test compound or extract is effective at inhibiting daf-3 or daf-16 activity, and therefore is considered useful in the invention. Any compound that inhibits DAF-16 gene activity (or activates upstream signaling in the absence of receptor function) will allow reproduction. This is shown schematically in FIG. 19.

Figure 20:
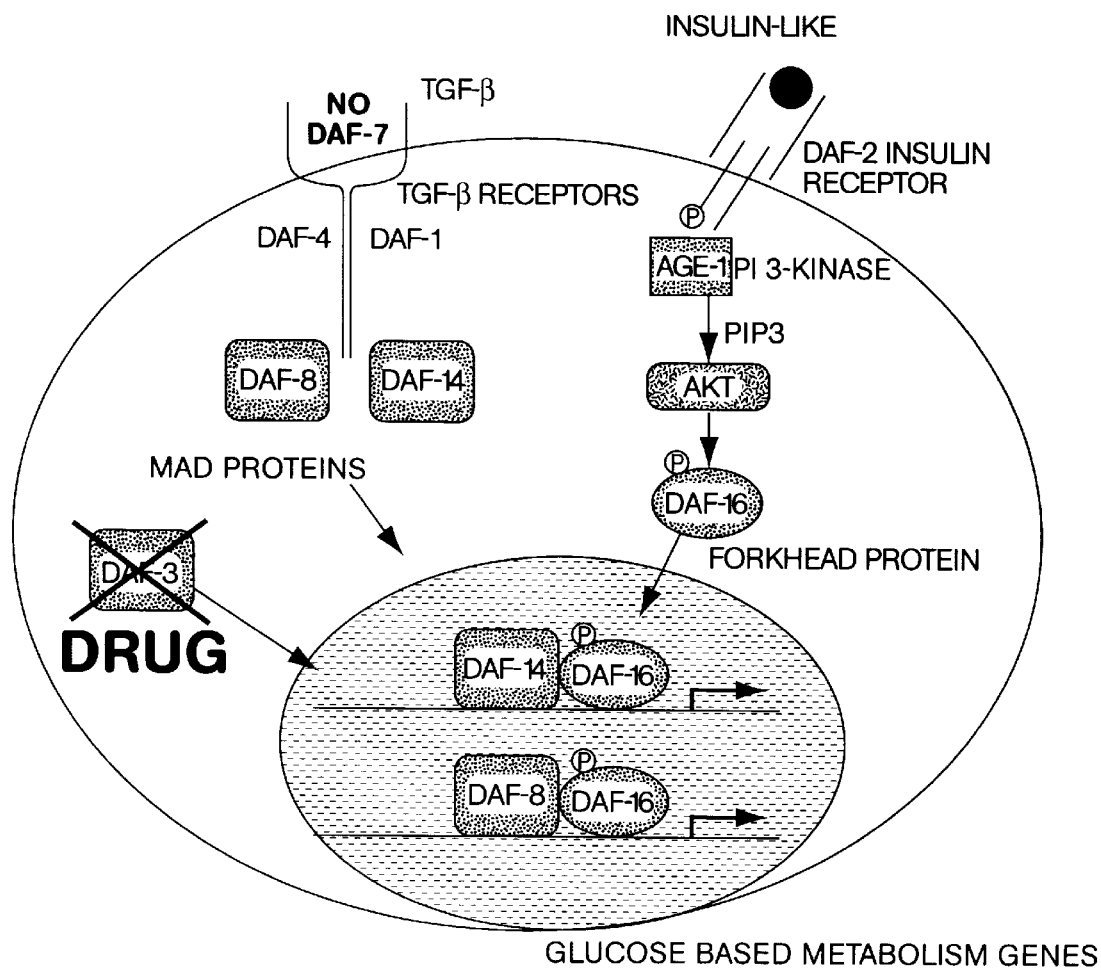
FIG. 20 is a schematic diagram illustrating inhibition of DAF-3 by drugs to ameliorate a lack of DAF-7 signaling (for example in obesity-induced diabetes).

Alternatively, a diabetic condition may arise from defects in the DAF-7 TGF-β signaling pathway. Since a decrease in DAF-3 activity bypasses the need for DAF-7 activity in C. elegans metabolic control, drugs that down regulate DAF-3 activity are useful for ameliorating the metabolic defects associated with diabetes. To screen for such drugs, daf-7 (e1372); daf-3 (mg90) nematodes expressing human DAF-3 are exposed to chemicals as described above. In this strain, human DAF-3 supplies all DAF-3 activity, causing daf-7 induced dauer arrest unless its activity is inhibited (FIG. 20). Compounds capable of inhibiting this activity are considered useful therapeutics in the invention.

Finally, in a less complex screen for drugs that inhibit C. elegans daf-3 or daf-16, daf-7 or daf-2 mutants are directly screened for compounds that decrease C. elegans daf-3 or daf-16 gene activity.

In addition, C. elegans worms carrying other daf mutations may be utilized in an assay to obtain additional information on the mode of action of the test compound in the insulin or TGF-β signaling pathways. For example, a drug having PIP3 agonist activity would be expected to allow age-1 and daf-2 mutants (but not akt or daf-7 mutants) to not arrest at the dauer stage. Similarly, drugs that inhibit daf-3 are expected to suppress daf-7 mutants but not daf-2 or age-1 mutants.

Other Screening Assay

Other drug screening assays may also be performed using either C. elegans worms or mammalian cell cultures. If desired, such assays may include the use of reporter gene constructs.

For example, evaluation of the effects of test compounds on dauer formation or reporter gene expression in mutant C. elegans strains expressing particular human homologs of the daf, age, or akt genes (i.e., humanized C. elegans) represent useful screening methods. Expression of the human homologs in C. elegans is accomplished according to standard methods and, if desired, such genes may be operatively linked to a gene promoter obtained from C. elegans. Such promoters include, without limitation, the C. elegans daf-16, age-1, daf-3, daf-4, and akt gene promoters. For example, the 2.5 kb age-1 promoter can be generated and isolated by employing standard PCR methods using the following primers: 5'GGAAATATTTTAGGCCAGATGCG3' (SEQ IS NO: 49) and 5'CGGACAGTCCTGAATACACC3' (SEQ ID NO: 50).

Additionally, mammalian tissue culture cells expressing C. elegans daf, age-1, or akt homologs may be used to evaluate the ability of a test compound or extract to modulate the insulin or TGF-β signaling pathways. Because the signaling pathways from the ligands, receptors, kinase cascades, and downstream transcription factors are conserved from man to worm, test compounds or extracts that inhibit or activate the worm signaling proteins should also inhibit or activate their respective human homolog. For example, our identification that DAF-16 is a transcription factor that acts downstream of insulin-like signaling in C. elegans indicates that human DAF-16 transcription reporter genes also can be used to identify drugs that inhibit any of the kinases in the signaling pathway downstream of insulin signaling. For example, the use of DAF-16 and DAF-3 protein binding sites in reporter gene constructs may be used to monitor insulin signaling. Candidate compounds mimicking insulin signaling (e.g., PIP3 agonists) are expected to increase reporter gene expression and are considered useful in the invention.

Reporter Gene Construct

In one particular example, the invention involves the use of a reporter gene that is expressed under the control of a *C. elegans* gene promoter, e.g., a promoter that includes the TCTCGTTGTTTGCCGTCGGATGTCTGCC (SEQ ID NO: 51) enhancer element, such as the *C. elegans* pharyngeal myosin promoter (Okkema and Fire, *Development* 120: 2175–2186, 1994). This enhancer element is known to respond to DAF-3 regulation (i.e., in daf-7 mutants, where daf-3 is active, the element confers high level expression to reporter genes; whereas in a daf-7; daf-3 mutant (for example, daf-7 (e1372); daf-3), the element confers low level expression to reporter genes). Other equivalent enhancer elements may also be used in the invention, e.g., the enhancer element which is bound by the Xenopus Smad1 and Fast1 forkhead proteins (*Nature* 383 600–608, 1996). The enhancer element is cloned upstream of any standard reporter gene, e.g., the luciferase or green fluorescent protein (GFP) reporter genes. In preferred embodiments, the GFP reporter gene is used in *C. elegans*. In other preferred embodiments, either the GFP or the luciferase reporter genes may used in a mammalian cell based assay. The reporter gene construct is subsequently introduced into an appropriate host (e.g., *C. elegans* or a mammalian cell) according to any standard method known in the art. Analysis of reporter gene activity in the host organism or cell is determined according to any standard method, e.g., those methods described herein. Such reporter gene (and host cell systems) are useful for screening for drugs that modulate insulin or DAF-7 metabolic control signaling.

*C. elegans*

In one working example, the above-described reporter gene construct is introduced into wild-type *C. elegans* according to standard methods known in the art. If the enhancer element is operational, then it is expected that reporter gene expression is turned on. Alternatively, in daf mutants (e.g., daf-7 or daf-2 mutants, where insulin signaling is defective) carrying the above-described reporter gene construct, reporter gene activity is turned off.

Using this on/off distinction, test compounds or extracts are evaluated for the ability to disrupt the signaling pathways described herein. In one working example, daf-2 mutant worms carrying the reporter gene construct are used to assay the expression of the reporter gene. The majority of worms expressing the reporter gene will arrest at the dauer stage because of the daf-2 phenotype. If however the test compound or extract inhibits DAF-16 activity, then the worms will exhibit a daf-2; daf-16 phenotype (i.e., do not arrest), developing to produce eggs. Such eggs are selected using a bleach treatment and reporter gene expression in the test compound or extract is assayed according to standard methods, e.g., worms are examined with an automated fluorometer to reveal the presence of reporter gene expression, e.g., GFP. Candidate compounds that suppress the daf-2 phenotype or turn on reporter gene expression, i.e., activate signals in the absence of DAF-2 receptor (e.g., PIP3 mimetics) or inactivate DAF-16, are considered useful in the invention.

Analogous screens may also be performed using daf-7 mutants as a means to identify drugs that inactivate other daf-genes, such as DAF-3, or compounds that activate the DAF-1/DAF-4 receptors. Such screens may be coupled to reporter screens, for example, using GFP reporter genes whose expression is under DAF-3 transcriptional control (e.g., the myoII element). Drugs identified in such screens are useful as DAF-7 mimetics. Because DAF-7 expression may be down regulated in obesity, such drugs are useful in the treatment of obesity induced Type II diabetes.

In yet another working example, *C. elegans* DAF-3 and DAF-16 genes can be replaced with a human homolog, (e.g., FKHR for DAF-16), and screens similar to those described above performed in the nematode system. Because drugs may act upstream of the transcription factors, it is useful to replace DAF-1, DAF-4, DAF-8,DAF-14, DAF-2, DAF-3, DAF-16, or AGE-1 with the appropriate human homolog, and to screen the humanized *C. elegans* animals. Such screens are useful for identifying compounds having activities in humans.

Mammalian Cells

Mammalian insulin-responsive cell lines are also useful in the screening methods of the invention. Here reporter gene constructs (for example, those described above) are introduced into the cell line to evaluate the ability of a test compound or extract to modulate insulin and TGF-$\beta$ signaling pathways using a second construct expressing a *C. elegans* daf, age, or akt gene or their corresponding human homologs. Exemplary cell lines include, but are not limited to, mouse 3T3, L6 ,and L1 cells (MacDougald et al., *Ann. Rev. Biochem.* 64: 345–373, 1995) Introduction of the constructs into such cell lines is carried out according to standard methods well known in the art.

To test a compound or extract, it is added to the cell line, and reporter gene expression is monitored. Compounds that induce reporter gene expression in the absense of insulin or DAF-7 signaling are considered useful in the invention. Such compounds may also turn the cells into adipocytes, as insulin does.

Compounds identified in mammalian cells may be tested in other screening assays described herein, and, in general, test compounds may be assayed in multiple screens to confirm involvement in insulin or DAF-7 signaling.

Metabolic control by DAF-7 protein may be tested using any known cell line, e.g., those described herein.

In Vitro Screening Methods

A variety of methods are also available for identifying useful compounds in in vitro assays. In one particular example, test compounds are screened for the ability to activate the phosphorylation of Smad proteins, DAF-8, DAF-14, or DAF-3, by DAF-1 or DAF-4 in vitro. In these assays, DAF-8, DAF-14, or DAF-3 is preferably tagged with a heterologous protein domain, for example, the myc epitope tag domain(s) by the method of Ausubel et al., and are incubated with the C-terminal kinase domain of DAF-1 or DAF-4. Phosphorylation of the Smad proteins is preferably detected by immunoprecipation using antibodies specific to the tag, followed by scintillation counting. Test compounds may be screened in high throughout microtiter plate assays. A test compound that effectively stimulates the phosphorylation of DAF-8, DAF-14, or DAF-3 is considered useful in the invention. Using these same general assays, compounds that activate the phosphorylation of DAF-16 by AKT or GSK-3 may also be identified.

In another working example, test compounds are screened for the ability to inhibit the in vitro association of DAF-16 and the Smad proteins DAF-3, or preferentially activates the association of DAF-16 with DAF-8 and DAF-14, DAF-8, or DAF-14, or to inhibit the association of DAF-3 and DAF-16 with DNA in vitro. These assays are carried out by any standard biochemical methods that test protein-protein binding or protein-DNA binding. In one particular example, to test for interactions between proteins, each protein is tagged with a different heterologous protein domain (as described above). Immunoprecipitations are carried out using an antibody to one tag, and an ELISA assay is carried out on the immunoprecipitation complex to test for the presence of the second tag. In addition, if interaction capability is enhanced by a DAF or AKT kinase, this protein is also preferably included in the reaction mixture. Similarly, to test for interactions of these proteins with DNA, antibodies to the tag are utilized in immunoprecipitations, and the presence of the DNA detected by the presence of the DNA label in the immunoprecipitation complex. A test compound that effectively inhibits the association between these proteins or between DAF-3 and DAF-16 with DNA or both is considered useful in the invention.

In still another working example, test derivatives of PIP3 are screened for the ability to increase in vitro AKT activity. This is accomplished, in general, by combining a labeled PIP3 and an AKT polypeptide in the presence and absence of the test compound under conditions that allow PIP3:AKT to bind in vitro. Compounds are then identified that interfere with the formation of the PIP3:AKT complex. Test compounds that pass this first screen may then be tested for increased AKT activation in vitro using GSK3 targets, or may be tested in nematodes or mammalian cells (as described above). An increase in AKT kinase activity is taken as an indication of a compound useful for ameliorating or delaying an impaired glucose tolerance condition.

In yet another working example, DAF-3 or DAF-16 may be expressed in a yeast one-hybrid assay for transcriptional activation. Methods for such assays are described in Brent and Ptashne (*Cell* 43:729–736, 1985). A test compound that blocks the ability of DAF-3 or DAF-16 or both to activate (or repress) transcription in this system is considered useful in the invention.

In a final working example, compounds may be screened for their ability to inhibit an interaction between any of DAF-3, DAF-8, and DAF-14, or between DAF-3 and DAF-16. These in vivo assays may be carried out by any "two-hybrid" or "interaction trap" method (for example, by using the methods described by Vijaychander et al (Biotechniques 20: 564–568)).

Modulatory Compounds

Our experimental results facilitate the isolation of compounds useful in the treatment of impaired glucose tolerance diseases that are antagonists or agonists of the insulin or TGF-β signaling pathways identified in *C. elegans* and described above. Exemplary methods for the isolation of such compounds now follow.

Antagonists

As discussed above, useful therapeutic compounds include those which down regulate the expression or activity of DAF-3 or DAF-16. To isolate such compounds, DAF-3 or DAF-16 expression is measured following the addition of candidate antagonist molecules to a culture medium of DAF-3 or DAF-16-expressing cells. Alternatively, the candidate antagonists may be directly administered to animals (for example, nematodes or mice) and used to screen for their effects on DAF-3 or DAF-16 expression.

DAF-3 or DAF-16 expression is measured, for example, by standard Northern blot analysis (Ausubel et al., supra) using a DAF-3 or DAF-16 nucleic acid sequence (or fragment thereof) as a hybridization probe. The level of DAF-3 or DAF-16 expression in the presence of the candidate molecule is compared to the level measured for the same cells, in the same culture medium, or in a parallel set of test animals, but in the absence of the candidate molecule. Preferred modulators for anti-diabetic or anti-obesity purposes are those which cause a decrease in DAF-3 or DAF-16 expression.

Alternatively, the effect of candidate modulators on expression or activity may be measured at the level of DAF-3 or DAF-16 protein production using the same general approach in combination with standard immunological detection techniques, such as Western blotting or immunoprecipitation with a DAF-3 or DAF-16-specific antibody (for example, the DAF-3 or DAF-16 antibodies described herein). Again, useful anti-diabetic or anti-obesity therapeutic modulators are identified as those which produce a decrease in DAF-3 or DAF-16 polypeptide production. Antagonists may also affect DAF-3 or DAF-16 activity without any effect on expression level. For example, the identification of kinase cascades upstream of DAF-3 and DAF-16 (as described herein) suggest that the phosphorylation state of these polypeptides is correlated with activity. Phosphorylation state may be monitored by standard Western blotting using antibodies specific for phosphorylated amino acids. In addition, because DAF-3 and DAF-16 are transcription factors, reporter genes bearing operably linked DAF-3 or DAF-16 binding sites (for example, the myoII enhancer element) may be used to directly monitor the effects of antagonists on DAF-3 or DAF-16 gene activity.

Candidate modulators may be purified (or substantially purified) molecules or may be one component of a mixture of compounds (e.g., an extract or supernatant obtained from cells). In a mixed compound assay, DAF-3 or DAF-16 expression is tested against progressively smaller subsets of the candidate compound pool (e.g., produced by standard purification techniques, e.g., HPLC or FPLC; Ausubel et al., supra) until a single compound or minimal compound mixture is demonstrated to modulate DAF-3 or DAF-16 expression.

Candidate DAF-3 or DAF-16 antagonists include peptide as well as non-peptide molecules (e.g., peptide or non-peptide molecules found, e.g., in a cell extract, mammalian serum, or growth medium on which mammalian cells have been cultured).

Antagonists found to be effective at the level of cellular DAF-3 or DAF-16 expression or activity may be confirmed as useful in animal models (for example, nematodes or mice). For example, the compound may ameliorate the glucose intolerance and diabetic symptoms of mouse models for Type II diabetes (e.g., a db mouse model), mouse models for Type I diabetes, or models of streptozocin-induced β cell destruction.

A molecule which promotes a decrease in DAF-3 or DAF-16 expression or DAF-3 or DAF-16 activity is considered particularly useful in the invention; such a molecule may be used, for example, as a therapeutic to decrease the level or activity of native, cellular DAF-3 or DAF-16 and thereby treat a glucose intolerance condition in an animal (for example, a human).

If desired, treatment with an antagonist of the invention may be combined with any other anti-diabetic or anti-obesity therapies.

Agonists

Also as discussed above, useful therapeutic compounds are those which up regulate the expression or activity of DAF-1, DAF-2, DAF-4, DAF-7, DAF-8, DAF-11, DAF-14, AGE-1, or AKT. To isolate such compounds, expression of these genes is measured following the addition of candidate agonist molecules to a culture medium of DAF-1, DAF-2, DAF-4, DAF-7, DAF-8, DAF-11, DAF-14, AGE-1, or AKT-expressing cells. Alternatively, the candidate agonists may be directly administered to animals (for example, nematodes or mice) and used to screen for effects on DAF-1, DAF-2, DAF-4, DAF-7, DAF-8, DAF-11, DAF-14, AGE-1, or AKT expression.

DAF-1, DAF-2, DAF-4, DAF-7, DAF-8, DAF-11, DAF-14, AGE-1, or AKT-expression is measured, for example, by standard Northern blot analysis (Ausubel et al., supra) using all or a portion of one of these genes as a hybridization probe. The level of DAF-1, DAF-2, DAF-4, DAF-7, DAF-8, DAF-11, DAF-14, AGE-1, or AKT expression in the presence of the candidate molecule is compared to the level measured for the same cells, in the same culture medium, or in a parallel set of test animals, but in the absence of the candidate molecule. Preferred modulators for anti-diabetic or anti-obesity purposes are those which cause an increase in DAF-1, DAF-2, DAF-4, DAF-7, DAF-8, DAF-11, DAF-14, AGE-1, or AKT expression.

Alternatively, the effect of candidate modulators on expression may be measured at the level of DAF-1, DAF-2, DAF-4, DAF-7, DAF-8, DAF-11, DAF-14, AGE-1, or AKT protein production using the same general approach in combination with standard immunological detection techniques, such as Western blotting or immunoprecipitation with an appropriate antibody. Again, the phosphorylation state of these polypeptides is indicative of DAF activity and may be measured on Western blots. Useful anti-diabetic or anti-obesity modulators are identified as those which produce an increase in DAF-1, DAF-2, DAF-4, DAF-7, DAF-8, DAF-11, DAF-14, AGE-1, or AKT polypeptide production.

Candidate modulators may be purified (or substantially purified) molecules or may be one component of a mixture of compounds (e.g., an extract or supernatant obtained from cells). In a mixed compound assay, DAF-1, DAF-2, DAF-4, DAF-7, DAF-8, DAF-11, DAF-14, AGE-1, or AKT expression is tested against progressively smaller subsets of the candidate compound pool (e.g., produced by standard purification techniques, e.g., HPLC or FPLC; Ausubel et al., supra) until a single compound or minimal compound mixture is demonstrated to modulate DAF-1, DAF-2, DAF-4, DAF-7, DAF-8, DAF-11, DAF-14, AGE-1, or AKT expression.

Alternatively, or in addition, candidate compounds may be screened for those which agonize native or recombinant DAF-1, DAF-2, DAF-4, DAF-7, DAF-8, DAF-11, DAF-14, AGE-1, or AKT activities. In one particular example, DAF-1 and DAF-4 phosphorylation of DAF-8 and DAF-14, or AKT phosphorylation of DAF-16, may be activated by agonists.

Candidate DAF-1, DAF-2, DAF-4, DAF-7, DAF-8, DAF-11, DAF-14, AGE-1, or AKT agonists include peptide as well as non-peptide molecules (e.g., peptide or non-peptide molecules found, e.g., in a cell extract, mammalian serum, or growth medium on which mammalian cells have been cultured).

Agonists found to be effective at the level of cellular DAF-1, DAF-2, DAF-4, DAF-7, DAF-8, DAF-11, DAF-14, AGE-1, or AKT expression or activity may be confirmed as useful in animal models (for example, nematodes or mice).

A molecule which promotes an increase in DAF-1, DAF-2, DAF-4, DAF-7, DAF-8, DAF-11, DAF-14, AGE-1, or AKT expression or DAF-1, DAF-2, DAF-4, DAF-7, DAF-8, DAF-11, DAF-14, AGE-1, or AKT activities is considered particularly useful in the invention; such a molecule may be used, for example, as a therapeutic to increase the level or activity of these native, cellular genes and thereby treat a glucose intolerance condition.

If desired, treatment with an DAF-1, DAF-2, DAF-4, DAF-7, DAF-8, DAF-11, DAF-14, AGE-1, or AKT agonist may be combined with any other anti-diabetic or anti-obesity therapies.

Animal Model Systems

Compounds identified as having activity in any of the above-described assays are subsequently screened in any number of available diabetic or obesity animal model systems, including, but not limited to ob (Coleman, *Dibetologia* 14: 141–148, 1978; Chua et al., *Science* 271: 994–996, 1996; Vaisse et al., *Nature Genet.* 14:95–100, 1996), db (Chen et al., Cell 84: 491–495, 1996), agouti mice, or fatty rats (Takaga et al. *Biochem. Biophys. Res. Comm.* 225: 75–83, 1996). Test compounds are administered to these animals according to standard methods. Additionally, test compounds may be tested in mice bearing knockout mutations in the insulin receptor, IGF-1 receptor (e.g., Liu et al., Cell 75:59–72, 1993), IR-related receptor, DAF-7 homolog, or any of the daf (FKHR, AFX) genes described herein. Compounds can also be tested using any standard mouse or rat model of Type I diabetes, e.g., a streptozin ablated pancreas model.

In one particular example, the invention involves the administration of DAF-7 or its homolog as a method for treating diabetes or obesity. Evaluation of the effectiveness of such a compound is accomplished using any standard animal model, for example, the animal diabetic model systems described above. Because these mouse diabetic models are also associated with obesity, they provide preferred models for human obesity associated Type II diabetes as well. Such diabetic or obese mice are administered *C. elegans* or human DAF-7 according to standard methods well known in the art. Treated and untreated controls are then monitored for the ability of the compound to ameliorate the symptoms of the disease, e.g., by monitoring blood glucose, ketoacidosis, and atherosclerosis. Normalization of blood glucose and insulin levels is taken as an indication that the compound is effective at treating a glucose intolerance condition.

Therapy

Compounds of the invention, including but not limited to, DAF-7 and its homologs, and any antagonist or agonist therapeutic agent identified using any of the methods disclosed herein, may be administered with a pharmaceutically-acceptable diluent, carrier, or excipient, in unit dosage form. Conventional pharmaceutical practice may be employed to provide suitable formulations or compositions to administer such compositions to patients. Although intravenous administration is preferred, any appropriate route of administration may be employed, for example, parenteral, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for antagonists or agonists of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

DAF polypeptides are administered at any appropriate concentration, for example, for DAF-7, at a concentration of around 10 nM.

Pedigree Analysis and Genetic Testing

The discovery described herein that DAF polypeptides are involved in glucose metabolism enables assays for genetic testing to identify those individuals with predispositions toward the development of glucose intolerance conditions, such as diabetes or obesity, by determining the presence of a mutation found in a human gene having identity to any of the C. elegans daf-1, daf-2, daf-3, daf-4, daf-7, daf-8, daft-11, daf-14, daf-16, age-1, or akt genes. In one embodiment, the development of this testing method requires that the individual be a member of a family that has multiple affected and unaffected members carrying one mutation from the list of above-listed genes. Those skilled in the art will understand that a diabetic or obesity phenotype may be produced by daf, age, or akt mutations found on different chromosomes, and that low resolution genetic mapping of the diabetic condition in single family pedigrees will be sufficient to favor some daf, age, or akt genes over others as causing the glucose intolerance condition in a particular pedigree. In one particular example, mutations associated with glucose intolerance may be found in different genes in, for example, the DAF-7 signaling pathway in each pedigree. In addition, because mutations in a common pathway can show complex genetic interactions, multiple DAF mutations may segregate in single pedigress. These mutations can behave recessively in some genetic backgrounds and dominantly in others.

Those skilled in the art further understand that, to determine disease linkage with a chromosomal marker, it may be necessary to evaluate the association of inheritance patterns of several different chromosomal markers (for example, from the collection of highly polymorphic mapped DNA allelic variants) in the genomic DNAs of family members and of the clinically affected individuals. Methods commonly used in determining segregation patterns of human genetic diseases are well known in the art. In addition, methods are known in the art for determining whether individuals in a family are useful for providing information to determine co-segregation of an allele with a glucose intolerance trait.

Here, fragments of genomic DNA (e.g., RFLP fragments) are prepared from each of the available members of the family, and each distinctive DNA allelic variant of the polymorphic chromosome marker within the family is evaluated to determine which polymorphisms (i.e., chromosomal region) is linked with the glucose intolerance phenotype within a particular family. It is preferred that the parents of the marker individual be heterozyous for a DNA allelic variant so that the segregation pattern of the DNA allelic variant linked with the diabetic or obese phenotype in the marker can be recognized. The inheritance of the diabetic phenotype can be judged to be dominant or recessive, depending on the pattern of inheritance. Most diabetes is dominantly inherited, and therefore inbred pedigrees are generally not necessary in the etiology of the diabetic condition.

With respect to Type II diabetes, the highest rate of this kind of diabetes in the world is found in American Indians of the Pima tribe. Such families are useful for mapping one particular cause of diabetes, but, in general, diabetes is caused by mutations in a variety of genes, including daf genes. Thus, by testing for low resolution linkage to a candidate daf, age, or akt mutation, and then by sequencing the particular linked daf gene in affected and unaffected individuals, a particular daf mutation can be associated with a particular diabetic pedigree.

Human DAF homologues are mapped to chromosome regions using standard methods. For example, the probable DAF-16 homologue FKHR is located on chromosome 13, and AFX is located on the X chromosome. Any daf, akt, or age genes mapping to the approximate chromosomal regions associated with diabetes or glucose intolerance are sequenced from affected and unaffected individuals. Preferably, at least two genes per pedigree of 5–20 affected (and unaffected controls) are sequenced. The daf genomic regions are PCR amplified and compared between affected and unaffected DNA samples. Mutations detected in affected individuals are expected to (but need not) map to conserved domains of the DAF genes. Because it is known that not all carriers of known diabetes-inducing mutations show metabolic defects, we expect that some non-diabetic non-glucose intolerant family members will carry the same daf mutation as affected family members. For this reason, a correlation of affected family members with a daf mutation is more important than a correlation of nonaffected with no mutation. Those skilled in the art will know that phenotypic classification of affected and unaffected individuals can greatly enhance the power of this genetic analysis (Nature Genet. 11: 241–247, 1995). In addition, other mutations in the same daf gene are expected in some but not all diabetic pedigrees. For dominant diabetic inheritance, the affected individuals carry a daf, age, or akt mutation as well as a normal allele. For recessive diabetic inheritance, individuals carry two daf mutations that may be identical or two independent mutations in the same gene. In addition, some diabetic individuals may carry mutations in more than one daf, age, or akt gene (so called non-allelic non-complementation).

It is routine in the art of genetic counseling to determine risk factors given the presence of a closely linked molecular genetic marker in the genomic DNA of the individual and when combined with the additional understanding provided by the pedigree of the individual in the family. For example, a risk factor may be calculated for an individual in an age, akt, or daf chromosome family in a manner similar to those described for assessing the risk of other commonly known genetic diseases that are known to run in families, e.g., Huntington's disease and cystic fibrosis.

Once mutations in daf, akt, or age genes are associated with diabetes in a pedigree analysis, diagnostic PCR sequencing of these daf genes can be used to diagnose glucose intolerant, prediabetic, diabetic, obesity, and atherosclerotic conditions. Preferably, the daf, akt, or age gene regions are PCR amplified from patients and mutations detected in the daf genes using standard DNA sequencing or oligonucleotide hybridization techniques. The use of such gene sequences or specific antibody probes to the products of these sequences provide valuable diagnostics, particularly in view of the likelihood there exist two classes of type II diabetics: those with defects in the TGF-β signaling genes, and those with defects in insulin signaling genes. Such genetic tests will influence whether drugs that affect DAF-7 TGF-β or DAF-2 insulin like signals are prescribed.

To carry out the above analysis (as well as the other screening, diagnostic, and therapeutic methods described herein), mammalian homologs corresponding to the *C. elegans* daf-1, age-1, daf-4, daf-8, and daf-7 genes are isolated as described above for daf-2, daf-3, and daf-16. Again, standard hybridization or PCR cloning strategies are employed, preferably utilizing conserved DAF, AGE, or AKT motifs for probe design followed by comparison of less conserved flanking sequences between these motifs. Exemplary motifs for these genes are as follows:

DAF-1 (139 amino acid motif) (SEQ ID NO: 13)
274 TSGSGMGPTTLHKLTIGGQIRLTGRVGS-GRFGNVSRGDYRGEAVAVK VFNALDEPAFHKETEIF-ETRMLRHPNVLRYIGSDRVDTGFVTELWLVTEYH PSGSLHDFLLENTVNIETYYNLMRSTAS-GLAFLHNQIGGSK 412

DAF-1 (62 amino acid motif) (SEQ ID NO: 14)
450 EDAASDIIANENYKCGTVRYLAPEILN-STMQFTVFESYQCADVYSFSL VMWETLCRCEDGDV 511

DAF-1 (31 amino acid motif) (SEQ ID NO: 15)
416 KPAMAHRDIKSKNIMVKNDLTCAIGDLGLSL 466

DAF-1 (72 amino acid motif) (SEQ ID NO: 16)
520 IPYIEWTDRDPQDAQMFDVVCTRRL-RPTENPLWKDHPEMKHIMEIIKT CWNGNPSARFTS YICRKRMDERQQ 591

AGE-1 (150 amino acid motif) (SEQ ID NO: 17)
991 YFESVDRFLYSCVGYSVATY-IMGIKDRHSDNLMLTEDGKYVHIDFGHI LGHGKT-KLGIQRDRQPFILTEHFMTVIRSGKS-VDGNSHELQKFKTLCVEAY EVMWNNRDLFVSLFTLMLGMELPELST-KADLDHLKKTLFCNGESKEEAR KF 1140

AGE-1 (113 ammo acid motif) (SEQ ID NO: 18)
826 SPLDPVYKLGEMIIDKALGSAKRPLMLH-WKNKNPKSDLHLPFCAMI FKNGDDLRQDMLVLQV-LEVMDNIWKAACCLNPYAVLPMGEMIGIIE VVP-NCKTIFEIQVGTG 938

AGE-1 (106 amino acid motif) (SEQ ID NO: 19)
642 LAFVWTDRENFSELYVMLEKWKPPS-VAAALTLLGKRCTDRVIRKFAV EKLNEQLSPVTFHL-FILPLIQALKYEPRAQSEVGMMLLTRAL-CDYRIGHRLF WLLRAEI 747

AGE-1 (60 amino acid motif) (SEQ ID NO: 38)
91 EIKLSDFKHQLFELIAPMKWGTYSVK-PQDYVFRQLNNFGEIEVIFND DQPLSKLELHGTF 150

AKT (121 amino acid motif) (SEQ ID NO: 60)
33685 QVLDDHDYGRCVDWWGVGVVMYEMMCGR-LPFYSKDHNKLF ELIMAGDLRFPSKLSQEARTLLT-GLLVKDPTQRLGGGPEDALEICRADFFR TVD-WEATYRKEIEPPYKPNVQSETDTSYFD 34047

AKT (66 amino acid motif) (SEQ ID NO: 61)
32314 TMEDFDFLKVLGKGTFGKVILCK-EKRTQKLYAKILKKDVIIARE EVAHTLTENRV-LQRCKHPFLT 32511

AKT (45 amino acid motif) (SEQ ID NO: 62)
33509 KLENLLLDKDGHIIAIFGLCKEEISFGD-KTSTFCGTPEYL APEV 33643

AKT (57 amino acid motif) (SEQ ID NO: 63)
32667 YFQELKYSFQEQHYLCFVMQFANGGEL-FTHVRKCGTFSEPRARFY GAEIVLALGYLH 32837

AKT (59 amino acid motif) (SEQ ID NO: 64)
31846 STFAIFYFQTMLFEKPRPNMFMVR-CLQWTTVIERTFYAESAEVRQ RWIHAIESISKKYK 32022

AKT (33 amino acid motif) (SEQ ID NO: 65)
33156 LQELKYSFQTNDRLCFVMEFAIGGD-LYYHLNRE 33254

AKT (21 amino acid motif) (SEQ ID NO: 66)
30836 VVIEGWLHKKGEHIRNWRPRF 30898

AKT (26 amino acid motif) (SEQ ID NO: 67)
33276 FSEPRARFYGSEIVLALGYLHANSIV 33353

DAF-4 (139 amino acid motif) (SEQ ID NO: 20)
380 EYWIVTEFHERLSLYELLKNNVISIT-SANRIIMSMIDGLQFLHDDRPYFF GHPKKPIIHRDIK-SKNILVKSDMTTCIADFGLARIYSY-DIEQSDLLGQVGTK RYMSPEMLEGATEFTPTAFKAMD-VYSMGLVMWEVISR 518

DAF-4 (61 amino acid motif) (SEQ ID NO: 21)
537 IGFDPTIGRMRNYVVSKKERPQWRDEI-IKHEYMSLLKKVTEEMWDPE ACARITAGCAFARV 597

DAF-4 (20 amino acid motif) (SEQ ID NO: 22)
305 PITDFQLISKGRFGKVFKAQ 324

DAF-8 (163 amino acid motif) (SEQ ID NO: 23)
382 TDSETRSRFSLGWYNNPNRSPQTAEVR-GLIGKGVRFYLLAGEVYVENL CNIPVFVQSIGAN-MKNGFQLNTVSKLPPTGTMKVFDMRLF-SKQLRTAAEK TYQDVYCLSRMCTVRVSFCKGWGE-HYRRSTVLRSPVWFQAHLNNPMHW VDSVLTCM-GAPPRICSS 544

DAF-8 (44 amino acid motif) (SEQ ID NO: 24)
91 RAFRFPVIRYESQVKSILTCRHAFNSH-SRNVCLNPYHYRWVELP 134

DAF-8 (38 amino acid motif) (SEQ ID NO: 25)
341 VEYEESPSWLKLIYYEEGTMIGEKAD-VEGHHCLIDGFT 378

DAF-14 (39 amino acid motif) (SEQ ID NO: 68)
9709 IRVSFCKGFGETYSRLKVVNLPCWIEI-ILHEPADEYDTV 9825

DAF-14 (45 amino acid motif) (SEQ ID NO: 69)
9409 SRNSKSSQIRNTVGAGIQLAYENGEL-WLTVLTDQIVFVQCPFLNQ 9543

DAF-14 (29 amino acid motif) (SEQ ID NO: 70)
9160 NEMLDPEPKYPKEEKPWCTIFYYELTVRV 9246

DAF-14 (29 amino acid motif) (SEQ ID NO: 71)
9307 QLGKAFEAKVPTITIDGATGASDECRMSL 9393

DAF-12 (105 amino acid motif) (SEQ ID NO: 72)
103 SPDDGLLDSSEESRRRQKT-CRVCGDHATGYNFNVITCESCKAFFRR NALRP-KEFKCPYSEDCEINSVSRRFCQKCRL-RKCFTVGMKKEWILNEEQLR RRKNSRLN 207

DAF-12 (89 amino acid motif) (SEQ ID NO: 73)
109 LDSSEESRRRQKTCRVCGDHATGYNFN-VITCESCKAFFRRNALRPKE FKCPYSEDCEINSVSR-RFCQKCRLRKCFTVGMKKEWILNEEQ 197

DAF-12 (73 amino acid motif) (SEQ ID NO: 74)
551 DIMNIMDVTMRRFVKVAKGV-PAFREVSQEGKFSLLKGGMIEMLTV RGVTRYDAST-NSFKTPTIKGQNVSVNVD 623

DAF-11 (112 amino acid motif) (SEQ ID NO: 75)
708 SGSLVDLMIKNLTAYTQGLNETVKNR-TAELEKEQEKGDQLLMELL PKSVANDLKNGIAVDP-KVYENATILYSDIVGFTSLCSQSQPMEWTLLSGM YQRFDLIISQQGGYKV 819

DAF-11 (107 amino acid motif) (SEQ ID NO: 76)
825 METIGDAYCVAAGLPVVMEKDHVKSIC-MIALLQRDCLHHFEIPHR PGTFLNCRWGFNSGPVF-AGVIGQKAPRYACFGEAVILASKMESSGVEDRIQ MTLASQQLLEE 931

DAF-11 (43 amino acid motif) (SEQ ID NO: 77)
520 DILKGLEYIHASAIDFHGNLTLHNCMLD-SHWIVKLSGFGVNRL 562

DAF-11 (15 amino acid motif) (SEQ ID NO: 78)
618 DMYSFGVILHEIILK 632

DAF-7 (60 amino acid motif) (SEQ ID NO: 26)
290 NLAETGHSKIMRAAHKVSNPEIGYC-CHPTEYDYIKLIYVNRDGRVSIA NVNGMIAKKCGC 349

DAF-7 (20 amino acid motif) (SEQ ID NO: 27)
265 DWIVAPPRYNAYMCRGDCHY 284

DAF-7 (43 amino acid motif) (SEQ ID NO: 28)
240 VCNAEAQSKGCCLYDLEIEFEKIGWD-WIVAPPRYNAYMCRGDC 282

DAF-7 (70 amino acid motif) (SEQ ID NO: 29)
281 DCHYNAHHFNLAETGHSKIMRAAHKVSN-PEIGYCCHPTEYDYIKLIYV NRDGRVSIANVN GMI-AKKCGCS 350

DAF-7 (35 amino acid motif) (SEQ ID NO: 30)
250 CCLYDLEIEFEKIGWDWIVAPPRYNAYM-CRGDCHY 284

DAF-7 (13 amino acid motif)(SEQ ID NO: 51)
GWDWIVAPPRYNA

In one particular example, mammalian DAF-7 may be identified using the sub-domain amino acids 314–323. Exemplary degenerate oligonucleotides designed to PCR amplify this domain or hybridize (for example, as described in Burglin et al., (*Nature* 341:239–243, 1989) are as follows:

aa 263 oligo: GGNTGGGAYTRNRTNRTNGCNCC (23-mer, 16,000-fold degeneracy) (SEQ ID NO: 31)

aa 314 oligo: TGYTGYNNNCCNACNGAR (18-mer, 8000-fold degeneracy) (SEQ ID NO: 32).

The DNA sequence between the oligonucleotide probes is determined, and those sequences having the highest degree of homology are selected. Once isolated, these sequences are then tested in a *C. elegans* daf-7 mutant or mouse model as described above for the ability to functionally complement the mutation or ameliorate the glucose intolerance phenotype.

Other Embodiments

In other embodiments, the invention includes any protein which possesses the requisite level of amino acid sequence identity (as defined herein) to DAF-2, DAF-3, or a DAF-16 sequence; such homologs include other substantially pure naturally-occurring mammalian DAF polypeptides (for example, human DAF polypeptides) as well as allelic variants; natural mutants; induced mutants; proteins encoded by DNA that hybridizes to the DAF DNA sequence or degenerate conserved domains of DAF proteins (e.g., those described herein) under high stringency conditions; and proteins specifically bound by antisera directed to a DAF-2, DAF-3, or DAF-16 polypeptide.

The invention further includes analogs of any naturally-occurring DAF-2, DAF-3, or DAF-16 polypeptides. Analogs can differ from the naturally-occurring protein by amino acid sequence differences which do not destroy function, by post-translational modifications, or by both. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring DAF polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes DAF-2, DAF-3, and DAF-16 polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of such DAF polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

For certain purposes, all or a portion of the DAF-2, DAF-3, or DAF-16 polypeptide sequence may be fused to another protein (for example, by recombinant means). In one example, the DAF polypeptide may be fused to the green fluorescent protein, GFP (Chalfie et al., *Science* 263:802–805, 1994). Such a fusion protein is useful, for example, for monitoring the expression level of the DAF polypeptide in vivo (for example, by fluorescence microscopy) following treatment with candidate or known DAF agonists or antagonists.

The methods of the invention may be used to diagnose or treat any condition related to glucose intolerance or obesity in any mammal, for example, humans, domestic pets, or livestock. Where a non-human mammal is diagnosed or treated, the DAF polypeptide, nucleic acid, or antibody employed is preferably specific for that species.

All publications and patent applications mentioned in this specification are herein incorporated by reference to the same extent as if each independent publication or patent application was specifically and individually indicated to be incorporated by reference.

Other embodiments are within the following claims.

We claim:

1. A method for the identification of a modulatory compound that is capable of increasing the expression or activity of a daf-2 gene, said method comprising:
   (a) providing a nematode, isolated nematode cell, or isolated mammalian cell expressing the *C. elegans* daf-2 gene; and
   (b) contacting said nematode, said isolated cell, or said isolated mammalian cell with a candidate compound, an increase in daf-2 expression or activity following contact of said nematode, said isolated nematode cell, or said isolated mammalian cell with said candidate compound identifying a modulatory compound.

2. The method of claim 1, wherein said compound is a candidate compound for treating an impaired glucose tolerance condition, atherosclerosis, or obesity.

3. A method for the identification of a compound that is a candidate compound for ameliorating or delaying an impaired glucose tolerance condition, said method comprising the steps of:
   (a) providing a dauer larva comprising a mutation in the *C. elegans* daf-2 gene; and
   (b) contacting said dauer larva with a compound, wherein release from the dauer larval state is an indication that said compound is a candidate compound for ameliorating or delaying an impaired glucose tolerance condition.

4. The method of claim 3 or 1, wherein said dauer larva is from *C. elegans*.

5. The method of claim 3 or 1, wherein said compound is a candidate compound for ameliorating or delaying an impaired glucose tolerance condition that involves obesity or atherosclerosis.

6. A method for evaluating whether a compound is a candidate compound for modulating insulin signaling, said method comprising the steps of:
   (a) providing a dauer larva comprising a mutation in the *C. elegans* daf-2 gene; and
   (b) contacting said dauer larva with a compound, wherein release from the dauer larval state is an indication that said compound is a candidate compound for modulating insulin signaling.

* * * * *

UNITED STATES PATENT AND TRADEMARK OFFICE
CERTIFICATE OF CORRECTION

PATENT NO. : 6,225,120 B1
DATED : May 1, 2001
INVENTOR(S) : Gary Ruvkun et al.

It is certified that error appears in the above-identified patent and that said Letters Patent is hereby corrected as shown below:

<u>Title page,</u>
Item [56], References Cited, OTHER PUBLICATIONS, within the Larsan et al. author's name, replace "Larsan" with -- Larsen --;

<u>Column 13,</u>
Line 5, replace "C elegans" with -- *C. elegans* --;

<u>Column 14,</u>
Line 46, replace "Wis." with -- WI --;

<u>Column 15,</u>
Line 13, replace "Wis." with -- WI --;

<u>Column 16,</u>
Line 29, replace "71 kb" with -- 7 kb --;

<u>Column 24,</u>
Lines 10 and 11, replace "daf-2 (mg43)" with -- *daf-2(mg43)* --;

<u>Column 25,</u>
Lines 2 and 3, replace "daf-2 (e1391)/+," with -- *daf-2(e1391)*/+, --;

<u>Column 28,</u>
Line 67, replace "14A-14C" with -- 14A-14B --;

<u>Column 29,</u>
Lines 17 and 18, replace "DAF-2/ AGE-1" with -- DAF-2/AGE-1 --;
Lines 66 and 67, replace "TGF- β-like" with -- TGF-β-like --;

<u>Column 30,</u>
Lines 44 and 45, replace "daf-2 (e1370);" with -- daf-2(e1370); --;

<u>Column 31,</u>
Line 11, replace "Sup(mg142)" with -- sup(mg142) --;
Lines 13 and 14, replace "(age-1 (mg44)," with -- *(age-1(mg44)*, --;

UNITED STATES PATENT AND TRADEMARK OFFICE
CERTIFICATE OF CORRECTION

PATENT NO. : 6,225,120 B1
DATED : May 1, 2001
INVENTOR(S) : Gary Ruvkun et al.

It is certified that error appears in the above-identified patent and that said Letters Patent is hereby corrected as shown below:

Column 34,
Line 52, replace "mgDf9O" with -- *mgDf 90* --;
Lines 58 and 59, replace "daf-3 (mg132)" with -- *daf-3(mg132)* --;

Column 35,
Lines 64 and 65, replace "daf-4 m72)" with -- *daf-4(m72)* --;

Column 36,
Lines 19 and 20, replace "DAF-4/ GFP" with -- DAF-4/GFP --;
Line 26, replace "DAF-3" with -- DAF-*3* --;
Line 48, replace "DAF-3" with --DAF-*3* --;

Column 37,
Lines 16 and 17, replace "daf- 8(sa233)," with -- *daf-8(sa233)*, --;
Lines 19 and 20, replace "daf-4 (m72)" with -- *daf-4(m72)* --;
Line 50, replace "daft-1" with -- *daf-1* --;

Column 38,
Lines 31 and 32, replace "DAF-3/ GFP" with -- DAF-3/GFP --;
Lines 38 and 39, replace "DAF- 3/GFP" with -- DAF-3/GFP --;
Line 64, start a new paragraph before the word "We";

Column 39,
Lines 25 and 26, replace "DAF-3/ DAF-3" with -- DAF-3/DAF-3 --;

Column 44,
Line 25, replace "Ill.)." with -- IL). --;

Column 46,
Line 32, replace "N.H.)" with -- NH). --;
Line 33, replace "Wis.)." with -- WI). --;
Line 38, replace "Fla.)," with -- FL), --;
Line 39, replace "Mass.)." with -- MA). --;

UNITED STATES PATENT AND TRADEMARK OFFICE
CERTIFICATE OF CORRECTION

PATENT NO.    : 6,225,120 B1
DATED         : May 1, 2001
INVENTOR(S)   : Gary Ruvkun et al.

It is certified that error appears in the above-identified patent and that said Letters Patent is hereby corrected as shown below:

Column 48,
Line 29, replace "Assay" with -- Assays --;

Column 49,
Line 19 , replace "383 600-608," with -- 383:600-608, --;

Column 50,
Line 13, replace "DAF-8,DAF-14," with -- DAF-8, DAF-14, --.

Signed and Sealed this

Eighteenth Day of November, 2003

JAMES E. ROGAN
*Director of the United States Patent and Trademark Office*

SEQUENCE LISTING

<160> NUMBER OF SEQ ID NOS: 114

<210> SEQ ID NO 1
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 1
cgctacggca aaaaagtgaa                                          20

<210> SEQ ID NO 2
<211> LENGTH: 18
<212> TYPE: DNA
<213> ORGANISM: Artificial Sequence
<220> FEATURE:
<223> OTHER INFORMATION: Primer/probe derived from C. elegans

<400> SEQUENCE: 2
cgatgatgaa gatacccc                                            18

<210> SEQ ID NO 3
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 3
tgatgcgaac ggcgatcgat                                          20

<210> SEQ ID NO 4
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 4
acgctggatc atctacatta                                          20

<210> SEQ ID NO 5
<211> LENGTH: 22
<212> TYPE: DNA
<213> ORGANISM: Artificial Sequence
<220> FEATURE:
<223> OTHER INFORMATION: Primer/probe derived from C. elegans

<400> SEQUENCE: 5
ggtttaatta cccaagtttg ag                                       22

<210> SEQ ID NO 6
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 6
gctcacgggt cacacaacga                                            20

<210> SEQ ID NO 7
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 7
tgatgcgaac ggcgatcgat                                            20

<210> SEQ ID NO 8
<211> LENGTH: 21
<212> TYPE: DNA
<213> ORGANISM: Artificial Sequence
<220> FEATURE:
<223> OTHER INFORMATION: Primer/probe derived from C. elegans

<400> SEQUENCE: 8
tgagggccaa ctaaagaaga c                                          21

<210> SEQ ID NO 9
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 9
cgctacggca aaaaagtgaa                                            20

<210> SEQ ID NO 10
<211> LENGTH: 20
<212> TYPE: DNA
<213> ORGANISM: Artificial Sequence
<220> FEATURE:
<223> OTHER INFORMATION: Primer/probe derived from C. elegans

<400> SEQUENCE: 10
gacgatcccg aggtgagtat                                            20

<210> SEQ ID NO 11
<211> LENGTH: 5816
<212> TYPE: DNA
<213> ORGANISM: Caenorhabditis elegans
<220> FEATURE:
<221> NAME/KEY: misc_feature
<222> LOCATION: (1)...(5816)
<223> OTHER INFORMATION: n = A,T,C or G

<400> SEQUENCE: 11
ggtttaatta cccaagtttg agctccaaga gcacacatct gatcgtcgga ttctactgta    60 ctcccccgaaa aaccaacaaa aaacacaagt ttttgaacac ttgtaaatgc agacagaacg   120
atgacgagaa tgaatattgt cagatgtcgg agacgacaca aaattttgga aaatttggaa   180

```
gaagagaatc tcggcccgag ctgctcgtcg acgacttcaa caaccgctgc caccgaagct    240
ctcggaacaa ccactgagga tatgaggctt aagcagcagc gaagctcgtc gcgtgccacg    300
gagcacgata ttgtcgacgg caatcaccac gacgacgagc acatcacaat gagacggctt    360
cgacttgtca aaaattcgcg gacgcggcgt agaacgacgc ccgattcaag tatggactgc    420
tatgaggaaa acccgccatc acaaaaactt caataaatta ttcttggatt tctaaaaagt    480
catcaatgac gtcattaatg cttttactgc tattcgcttt tgtacagccg tgtgcctcaa    540
tagtcgaaaa acgatgcggc ccaatcgata ttcgaaatag gccgtgggat attaagccgc    600
aatggtcgaa acttggtgat ccgaacgaaa aagatttggc tggtcagaga atggtcaact    660
gcacagtggt ggaaggttcg ctgacaatct catttgtact gaaacacaag acaaaagcac    720
aagaagaaat gcatcgaagt ctacagccaa gatattccca agacgaattt atcacttttc    780
cgcatctacg tgaaattact ggaactctgc tcgttttga gactgaagga ttagtggatt     840
tgcgtaaaat tttcccaaat cttcgtgtaa ttggaggccg ttcgctgatt caacactatg    900
cgctgataat ttatcgaaat ccggatttgg agatcggtct tgacaagctt ccgtaattc     960 gaaatggtgg tgtacggata atcgataatc gaaaactgtg ctacacgaaa acgattgatt   1020
ggaaacattt gatcacttct tccatcaacg atgttgtcgt tgataatgct gccgagtacg   1080
ctgtcactga gactggattg atgtgcccac gtggagcttg cgaagaggat aaaggcgaat   1140
caaagtgtca ttatttggag gaaaagaatc aggaacaagg tgtcgaaaga gttcagagtt   1200
gttggtcgaa caccacttgc caaaagtctt gtgcttatga tcgtcttctt ccaacgaaag   1260
aaatcggacc gggatgtgat gcgaacggcg atcgatgtca cgatcaatgc gtgggcggtt   1320
gtgagcgtgt gaatgatgcc acagcatgcc acgcgtgcaa gaatgtctat cacaagggaa   1380
agtgtatcga aaagtgtgat gctcacctgt accttctcct tcaacgtcgt tgtgtgaccc   1440
gtgagcagtg tctgcagctg aatccggtgc tctcgaacaa acagtgcct atcaaggcga    1500 cggcaggcct ttgctcggat aaatgtcccg atggttatca aatcaacccg gatgatcatc   1560
gagaatgccg aaaatgcgtt ggcaagtgtg agattgtgtg cgagatcaat cacgtcattg   1620
atacgtttcc gaaggcacag gcgatcaggc tatgcaatat tattgacgga aatctgacga   1680
tcgagattcg cggaaaacag gattcgggaa tggcgtccga gttgaaggat atatttgcga   1740
acattcacac gatcaccggc tacctgttgg tacgtcaatc gtcaccgttt atctcgttga   1800
acatgttccg gaatttacga cgtattgagg caaagtcact gttcagaaat ctatatgcta   1860
tcacagtttt tgaaaatccg aatttaaaaa agctattcga ttcaacgacg gatttgacgc   1920
ttgatcgtgg aactgtgtca attgccaata acaagatgtt atgcttcaag tatatcaagc   1980
agctaatgtc aaagttaaat ataccactcg atccgataga tcaatcagaa gggacaaatg   2040
gtgagaaggn aatctgtgag gatatggcaa tcaacgtgag catcacagcg gtcaacgcgg   2100
actcggtctt ctttagttgg ccctcattca acattaccga tatagatcag cgaaagtttc   2160
tcggctacga gctcttcttc aaagaagtcc cacgaatcga tgagaacatg acgatcgaag   2220
aggatcgaag tgcgtgtgtc gattcgtggc agagtgtctt caaacagtac tacgagacgt   2280
cgaacggtga accgaccccg gacatttta tggatattgg accgcgcgag cgaattcggc    2340
cgaatacgct ctacgcgtac tatgtggcga cgcagatggt gttgcatgcc ggtgcgaaga   2400
acggtgtatc gaagattggt tttgtgagga cgagctacta tacgcctgat cctccgacgt   2460
tggcactagc gcaagtcgat tcggacgcta ttcatattac gtgggaagcg ccgctccaac   2520
cgaacggaga cctcacgcat tacacaatta tgtggcgtga gaatgaagtg agcccgtacg   2580
```

```
aggaagccga aaagttttgt acagatgcaa gcaccccgc  aaatcgacaa cgcacgaaag  2640
atccgaaaga gacgattgta gccgataagc cagtcgatat tccgtcatca cgtaccgtag  2700
ctccgacact tttgactatg atgggtcacg aagatcagca gaaaacgtgc gctgcaacgc  2760
ccggttgttg ttcgtgttcg gctatcgaag aatcatcgga acagaacaag aagaagcgac  2820
cggatccgat gtcggcgatc gaatcatctg catttgagaa taagctgttg gatgaggttt  2880
taatgccgag agacacgatg cgagtgagac gatcaattga agacgcgaat cgagtcagtg  2940
aagagttgga aaaagctgaa aatttgggaa aagctccaaa aactctcggt ggaaagaagc  3000
cgctgatcca tatttcgaag aagaagccgt cgagcagcag caccacatcc acaccggctc  3060
caacgatcgc atcaatgtat gccttaacaa ggaaaccgac tacggtgccg ggaacaagga  3120
ttcggctcta cgagatctac gaacctttac ccggaagctg gcgattaat  gtatcagctc  3180 tggcattgga ataagttat  gtgatacgaa atttgaagca ttacacactt tatgcgattt  3240
ctctatccgc gtgccaaaac atgacagtac ccggagcatc ttgctcaata tcccatcgtg  3300
cgggagcatt gaaacgaaca aaacacatca cagacattga taaagtgttg aatgaaacaa  3360
ttgaatggag atttatgaat aatagtcaac aagtcaacgt gacgtgggat ccaccgactg  3420
aagtgaatgg tggaatattc ggttatgttg taaagcttaa gtcaaaagtc gatggatcaa  3480
ttgttatgac gagatgtgtc ggtgcgaaga gaggatattc aacacggaat cagggtgtcc  3540
tattccagaa tttggccgat ggacgttatt ttgtctcagt aacggcgacc tctgtacacg  3600
gcgctggacc ggaagccgaa tcctccgacc caatcgtcgt catgacgcca ggcttcttca  3660
ctgtggaaat cattctcggc atgcttctcg tcttttgat tttaatgtca attgccggtt  3720
gtataatcta ctactacatt caagtacgct acggcaaaaa agtgaaagct ctatctgact  3780
ttatgcaatt gaatcccgaa tattgtgtgg acaataagta caatgcagac gattgggagc  3840
tacggcagga tgatgttgtg ctcggacaac agtgtggaga gggatcattc ggaaaagtgt  3900
acctaggaac tggaaataat gttgtttctc tgatgggtga tcgtttcgga ccgtgtgcta  3960
ttaagattaa tgtagatgat ccagcgtcga ctgagaatct caactatctc atggaagcta  4020
atattatgaa gaactttaag actaaccttta tcgtccaact gtacggagtt atctctactg  4080
tacaaccagc gatggttgtg atggaaatga tggatcttgg aaatctccgt gactatctcc  4140
gatcgaaacg cgaagacgaa gtgttcaatg agacggactg caacttttttc gacataatcc  4200 cgagggataa attccatgag tgggccgcac agatttgtga tggtatggcg tacctggagt  4260
cgctcaagtt ttgccatcga gatctcgccg cacgtaattg catgataaat cgggatgaga  4320
ctgtcaagat tggagatttc ggaatggctc gtgatctatt ctatcatgac tattataagc  4380
catcgggcaa gcgtatgatg cctgttcgat ggatgtcacc cgagtcgttg aaagacggaa  4440
agtttgactc gaaatctgat gttttggagct tcggagttgt tctctatgaa atggttacac  4500
tcggtgctca gccatatatt ggtttgagta atgatgaggt gttgaattat attggaatgg  4560
cccggaaggt tatcaagaag cccgaatgtt gtgaaaacta ttggtataag gtgatgaaaa  4620
tgtgctggag atactcacct cgggatcgtc cgacgttcct ccagctcgtt catcttctag  4680
cagctgaagc ttcaccagaa ttccgagatt tatcatttgt cctaaccgat aatcaaatga  4740
tccttgacga ttcagaagca ctggatcttg atgatattga tgatactgat atgaatgatc  4800
aggttgtcga ggtggcaccg gatgttgaga acgtcgaggt tcagagtgat tcggaacgtc  4860
ggaatacgga ttcaataccg ttgaaacagt ttaagacgat ccctccgatc aatgcgacga  4920
```

-continued

```
cgagtcattc gacaatatcg attgatgaga caccgatgaa agcgaagcag cgagaaggat    4980
cgctggatga ggagtacgca ttgatgaatc atagtggagg tccgagtgat gcggaagttc    5040
ggacgtatgc tggtgatgga gattatgtgg agagagatgt tcgagagaat gatgtgccaa    5100
cgcgacgaaa tactggtgca tcaacatcaa gttacacagg tggtggtcca tattgcctaa    5160
caaatcgtgg tggttcaaat gaacgaggag ccggtttcgg tgaagcagta cgattaactg    5220
atggtgttgg aagtggacat ttaaatgatg atgattatgt tgaaaagag atatcatcca    5280 tggatacgcg ccggagcacg ggcgcctcga gctcttccta cggtgttcca cagacgaatt    5340
ggagtggaaa tcgtggtgcc acgtattata cgagtaaagc tcaacaggca gcaactgcag    5400
cagcagcagc agcagcagct ctccaacagc aacaaaatgg tggtcgaggc gatcgattaa    5460
ctcaactacc cggaactgga catttacaat cgacacgtgg tggacaagat ggagattata    5520
ttgaaactga accgaaaaat tatagaaata atggatctcc atcgcgaaac ggcaacagcc    5580
gtgacatttt caacggacgt tcggctttcg gtgaaaatga gcatctaatc gaggataatg    5640
agcatcatcc acttgtctga aaccccaaa aaatcccgcc tcttaaatta taaattatct    5700
cccacattat catatctcta cacgaatatc ggattttttt tcagatttt tctgaaaaat    5760 tctgaataat tttaccccat ttttcaaatc tctgtatttt tttttgttat tacccc        5816
```

<210> SEQ ID NO 12
<211> LENGTH: 1724
<212> TYPE: PRT
<213> ORGANISM: Caenorhabditis elegans

<400> SEQUENCE: 12

```
Met Thr Ser Leu Met Leu Leu Leu Phe Ala Phe Val Gln Pro Cys
 1               5                  10                  15

Ala Ser Ile Val Glu Lys Arg Cys Gly Pro Ile Asp Ile Arg Asn Arg
            20                  25                  30

Pro Trp Asp Ile Lys Pro Gln Trp Ser Lys Leu Gly Asp Pro Asn Glu
        35                  40                  45

Lys Asp Leu Ala Gly Gln Arg Met Val Asn Cys Thr Val Val Glu Gly
    50                  55                  60

Ser Leu Thr Ile Ser Phe Val Leu Lys His Lys Thr Lys Ala Gln Glu
65                  70                  75                  80

Glu Met His Arg Ser Leu Gln Pro Arg Tyr Ser Gln Asp Glu Phe Ile
                85                  90                  95

Thr Phe Pro His Leu Arg Glu Ile Thr Gly Thr Leu Leu Val Phe Glu
            100                 105                 110

Thr Glu Gly Leu Val Asp Leu Arg Lys Ile Phe Pro Asn Leu Arg Val
        115                 120                 125

Ile Gly Gly Arg Ser Leu Ile Gln His Tyr Ala Leu Ile Ile Tyr Arg
    130                 135                 140

Asn Pro Asp Leu Glu Ile Gly Leu Asp Lys Leu Ser Val Ile Arg Asn
145                 150                 155                 160

Gly Gly Val Arg Ile Ile Asp Asn Arg Lys Leu Cys Tyr Thr Lys Thr
                165                 170                 175

Ile Asp Trp Lys His Leu Ile Thr Ser Ser Ile Asn Asp Val Val Val
            180                 185                 190

Asp Asn Ala Ala Glu Tyr Ala Val Thr Glu Thr Gly Leu Met Cys Pro
        195                 200                 205

Arg Gly Ala Cys Glu Glu Asp Lys Gly Glu Ser Lys Cys His Tyr Leu
    210                 215                 220
```

-continued

```
Glu Glu Lys Asn Gln Glu Gln Gly Val Glu Arg Val Gln Ser Cys Trp
225                 230                 235                 240

Ser Asn Thr Thr Cys Gln Lys Ser Cys Ala Tyr Asp Arg Leu Leu Pro
            245                 250                 255

Thr Lys Glu Ile Gly Pro Gly Cys Asp Ala Asn Gly Asp Arg Cys His
                260                 265                 270

Asp Gln Cys Val Gly Gly Cys Glu Arg Val Asn Asp Ala Thr Ala Cys
        275                 280                 285

His Ala Cys Lys Asn Val Tyr His Lys Gly Lys Cys Ile Glu Lys Cys
    290                 295                 300

Asp Ala His Leu Tyr Leu Leu Leu Gln Arg Arg Cys Val Thr Arg Glu
305                 310                 315                 320

Gln Cys Leu Gln Leu Asn Pro Val Leu Ser Asn Lys Thr Val Pro Ile
            325                 330                 335

Lys Ala Thr Ala Gly Leu Cys Ser Asp Lys Cys Pro Asp Gly Tyr Gln
                340                 345                 350

Ile Asn Pro Asp Asp His Arg Glu Cys Arg Lys Cys Val Gly Lys Cys
        355                 360                 365

Glu Ile Val Cys Glu Ile Asn His Val Ile Asp Thr Phe Pro Lys Ala
370                 375                 380

Gln Ala Ile Arg Leu Cys Asn Ile Ile Asp Gly Asn Leu Thr Ile Glu
385                 390                 395                 400

Ile Arg Gly Lys Gln Asp Ser Gly Met Ala Ser Glu Leu Lys Asp Ile
            405                 410                 415

Phe Ala Asn Ile His Thr Ile Thr Gly Tyr Leu Leu Val Arg Gln Ser
                420                 425                 430

Ser Pro Phe Ile Ser Leu Asn Met Phe Arg Asn Leu Arg Arg Ile Glu
        435                 440                 445

Ala Lys Ser Leu Phe Arg Asn Leu Tyr Ala Ile Thr Val Phe Glu Asn
    450                 455                 460

Pro Asn Leu Lys Lys Leu Phe Asp Ser Thr Thr Asp Leu Thr Leu Asp
465                 470                 475                 480

Arg Gly Thr Val Ser Ile Ala Asn Asn Lys Met Leu Cys Phe Lys Tyr
            485                 490                 495

Ile Lys Gln Leu Met Ser Lys Leu Asn Ile Pro Leu Asp Pro Ile Asp
                500                 505                 510

Gln Ser Glu Gly Thr Asn Gly Glu Lys Ala Ile Cys Glu Asp Met Ala
        515                 520                 525

Ile Asn Val Ser Ile Thr Ala Val Asn Ala Asp Ser Val Phe Phe Ser
    530                 535                 540

Trp Pro Ser Phe Asn Ile Thr Asp Ile Asp Gln Arg Lys Phe Leu Gly
545                 550                 555                 560

Tyr Glu Leu Phe Phe Lys Glu Val Pro Arg Ile Asp Glu Asn Met Thr
            565                 570                 575

Ile Glu Glu Asp Arg Ser Ala Cys Val Asp Ser Trp Gln Ser Val Phe
                580                 585                 590

Lys Gln Tyr Tyr Glu Thr Ser Asn Gly Glu Pro Thr Pro Asp Ile Phe
        595                 600                 605

Met Asp Ile Gly Pro Arg Glu Arg Ile Arg Pro Asn Thr Leu Tyr Ala
    610                 615                 620

Tyr Tyr Val Ala Thr Gln Met Val Leu His Ala Gly Ala Lys Asn Gly
625                 630                 635                 640
```

-continued

```
Val Ser Lys Ile Gly Phe Val Arg Thr Ser Tyr Tyr Thr Pro Asp Pro
            645                 650                 655

Pro Thr Leu Ala Leu Ala Gln Val Asp Ser Asp Ala Ile His Ile Thr
            660                 665                 670

Trp Glu Ala Pro Leu Gln Pro Asn Gly Asp Leu Thr His Tyr Thr Ile
            675                 680                 685

Met Trp Arg Glu Asn Glu Val Ser Pro Tyr Glu Ala Glu Lys Phe
            690                 695                 700

Cys Thr Asp Ala Ser Thr Pro Ala Asn Arg Gln Arg Thr Lys Asp Pro
705                 710                 715                 720

Lys Glu Thr Ile Val Ala Asp Lys Pro Val Asp Ile Pro Ser Ser Arg
            725                 730                 735

Thr Val Ala Pro Thr Leu Leu Thr Met Met Gly His Glu Asp Gln Gln
            740                 745                 750

Lys Thr Cys Ala Ala Thr Pro Gly Cys Cys Ser Cys Ser Ala Ile Glu
            755                 760                 765

Glu Ser Ser Glu Gln Asn Lys Lys Lys Arg Pro Asp Pro Met Ser Ala
            770                 775                 780

Ile Glu Ser Ser Ala Phe Glu Asn Lys Leu Leu Asp Glu Val Leu Met
785                 790                 795                 800

Pro Arg Asp Thr Met Arg Val Arg Arg Ser Ile Glu Asp Ala Asn Arg
            805                 810                 815

Val Ser Glu Glu Leu Glu Lys Ala Glu Asn Leu Gly Lys Ala Pro Lys
            820                 825                 830

Thr Leu Gly Gly Lys Lys Pro Leu Ile His Ile Ser Lys Lys Lys Pro
            835                 840                 845

Ser Ser Ser Thr Thr Ser Thr Pro Ala Pro Thr Ile Ala Ser Met
850                 855                 860

Tyr Ala Leu Thr Arg Lys Pro Thr Thr Val Pro Gly Thr Arg Ile Arg
865                 870                 875                 880

Leu Tyr Glu Ile Tyr Glu Pro Leu Pro Gly Ser Trp Ala Ile Asn Val
            885                 890                 895

Ser Ala Leu Ala Leu Asp Asn Ser Tyr Val Ile Arg Asn Leu Lys His
            900                 905                 910

Tyr Thr Leu Tyr Ala Ile Ser Leu Ser Ala Cys Gln Asn Met Thr Val
            915                 920                 925

Pro Gly Ala Ser Cys Ser Ile Ser His Arg Ala Gly Ala Leu Lys Arg
            930                 935                 940

Thr Lys His Ile Thr Asp Ile Asp Lys Val Leu Asn Glu Thr Ile Glu
945                 950                 955                 960

Trp Arg Phe Met Asn Asn Ser Gln Gln Val Asn Val Thr Trp Asp Pro
            965                 970                 975

Pro Thr Glu Val Asn Gly Gly Ile Phe Gly Tyr Val Val Lys Leu Lys
            980                 985                 990

Ser Lys Val Asp Gly Ser Ile Val Met Thr Arg Cys Val Gly Ala Lys
            995                 1000                1005

Arg Gly Tyr Ser Thr Arg Asn Gln Gly Val Leu Phe Gln Asn Leu Ala
            1010                1015                1020

Asp Gly Arg Tyr Phe Val Ser Val Thr Ala Thr Ser Val His Gly Ala
1025                1030                1035                1040

Gly Pro Glu Ala Glu Ser Ser Asp Pro Ile Val Val Met Thr Pro Gly
            1045                1050                1055

Phe Phe Thr Val Glu Ile Ile Leu Gly Met Leu Leu Val Phe Leu Ile
```

-continued

```
                1060                1065                1070
Leu Met Ser Ile Ala Gly Cys Ile Ile Tyr Tyr Ile Gln Val Arg
            1075                1080                1085
Tyr Gly Lys Lys Val Lys Ala Leu Ser Asp Phe Met Gln Leu Asn Pro
    1090                1095                1100
Glu Tyr Cys Val Asp Asn Lys Tyr Asn Ala Asp Asp Trp Glu Leu Arg
1105                1110                1115                1120
Gln Asp Asp Val Val Leu Gly Gln Gln Cys Gly Glu Gly Ser Phe Gly
            1125                1130                1135
Lys Val Tyr Leu Gly Thr Gly Asn Asn Val Val Ser Leu Met Gly Asp
        1140                1145                1150
Arg Phe Gly Pro Cys Ala Ile Lys Ile Asn Val Asp Asp Pro Ala Ser
        1155                1160                1165
Thr Glu Asn Leu Asn Tyr Leu Met Glu Ala Asn Ile Met Lys Asn Phe
    1170                1175                1180
Lys Thr Asn Phe Ile Val Gln Leu Tyr Gly Val Ile Ser Thr Val Gln
1185                1190                1195                1200
Pro Ala Met Val Val Met Glu Met Met Asp Leu Gly Asn Leu Arg Asp
            1205                1210                1215
Tyr Leu Arg Ser Lys Arg Glu Asp Glu Val Phe Asn Glu Thr Asp Cys
        1220                1225                1230
Asn Phe Phe Asp Ile Ile Pro Arg Asp Lys Phe His Glu Trp Ala Ala
        1235                1240                1245
Gln Ile Cys Asp Gly Met Ala Tyr Leu Glu Ser Leu Lys Phe Cys His
        1250                1255                1260
Arg Asp Leu Ala Ala Arg Asn Cys Met Ile Asn Arg Asp Glu Thr Val
1265                1270                1275                1280
Lys Ile Gly Asp Phe Gly Met Ala Arg Asp Leu Phe Tyr His Asp Tyr
            1285                1290                1295
Tyr Lys Pro Ser Gly Lys Arg Met Met Pro Val Arg Trp Met Ser Pro
        1300                1305                1310
Glu Ser Leu Lys Asp Gly Lys Phe Asp Ser Lys Ser Asp Val Trp Ser
        1315                1320                1325
Phe Gly Val Val Leu Tyr Glu Met Val Thr Leu Gly Ala Gln Pro Tyr
        1330                1335                1340
Ile Gly Leu Ser Asn Asp Glu Val Leu Asn Tyr Ile Gly Met Ala Arg
1345                1350                1355                1360
Lys Val Ile Lys Lys Pro Glu Cys Cys Glu Asn Tyr Trp Tyr Lys Val
            1365                1370                1375
Met Lys Met Cys Trp Arg Tyr Ser Pro Arg Asp Arg Pro Thr Phe Leu
        1380                1385                1390
Gln Leu Val His Leu Leu Ala Ala Glu Ala Ser Pro Glu Phe Arg Asp
        1395                1400                1405
Leu Ser Phe Val Leu Thr Asp Asn Gln Met Ile Leu Asp Asp Ser Glu
    1410                1415                1420
Ala Leu Asp Leu Asp Asp Ile Asp Thr Asp Met Asn Asp Gln Val
1425                1430                1435                1440
Val Glu Val Ala Pro Asp Val Glu Asn Val Glu Val Gln Ser Asp Ser
            1445                1450                1455
Glu Arg Arg Asn Thr Asp Ser Ile Pro Leu Lys Gln Phe Lys Thr Ile
        1460                1465                1470
Pro Pro Ile Asn Ala Thr Thr Ser His Ser Thr Ile Ser Ile Asp Glu
        1475                1480                1485
```

-continued

```
Thr Pro Met Lys Ala Lys Gln Arg Glu Gly Ser Leu Asp Glu Glu Tyr
        1490                1495                1500
Ala Leu Met Asn His Ser Gly Gly Pro Ser Asp Ala Glu Val Arg Thr
1505                1510                1515                1520
Tyr Ala Gly Asp Gly Asp Tyr Val Glu Arg Asp Val Arg Glu Asn Asp
            1525                1530                1535
Val Pro Thr Arg Arg Asn Thr Gly Ala Ser Thr Ser Tyr Thr Gly
        1540                1545                1550
Gly Gly Pro Tyr Cys Leu Thr Asn Arg Gly Ser Asn Glu Arg Gly
        1555                1560                1565
Ala Gly Phe Gly Glu Ala Val Arg Leu Thr Asp Gly Val Gly Ser Gly
1570                1575                1580
His Leu Asn Asp Asp Tyr Val Glu Lys Glu Ile Ser Ser Met Asp
1585                1590                1595                1600
Thr Arg Arg Ser Thr Gly Ala Ser Ser Ser Tyr Gly Val Pro Gln
            1605                1610                1615
Thr Asn Trp Ser Gly Asn Arg Gly Ala Thr Tyr Tyr Thr Ser Lys Ala
            1620                1625                1630
Gln Gln Ala Ala Thr Ala Ala Ala Ala Ala Ala Leu Gln Gln
        1635                1640                1645
Gln Gln Asn Gly Gly Arg Gly Asp Arg Leu Thr Gln Leu Pro Gly Thr
        1650                1655                1660
Gly His Leu Gln Ser Thr Arg Gly Gly Gln Asp Gly Asp Tyr Ile Glu
1665                1670                1675                1680
Thr Glu Pro Lys Asn Tyr Arg Asn Asn Gly Ser Pro Ser Arg Asn Gly
            1685                1690                1695
Asn Ser Arg Asp Ile Phe Asn Gly Arg Ser Ala Phe Gly Glu Asn Glu
            1700                1705                1710
His Leu Ile Glu Asp Asn Glu His His Pro Leu Val
            1715                1720

<210> SEQ ID NO 13
<211> LENGTH: 139
<212> TYPE: PRT
<213> ORGANISM: Caenorhabditis elegans

<400> SEQUENCE: 13

Thr Ser Gly Ser Gly Met Gly Pro Thr Thr Leu His Lys Leu Thr Ile
1               5                   10                  15
Gly Gly Gln Ile Arg Leu Thr Gly Arg Val Gly Ser Gly Arg Phe Gly
            20                  25                  30
Asn Val Ser Arg Gly Asp Tyr Arg Gly Glu Ala Val Ala Val Lys Val
        35                  40                  45
Phe Asn Ala Leu Asp Glu Pro Ala Phe His Lys Glu Thr Glu Ile Phe
    50                  55                  60
Glu Thr Arg Met Leu Arg His Pro Asn Val Leu Arg Tyr Ile Gly Ser
65                  70                  75                  80
Asp Arg Val Asp Thr Gly Phe Val Thr Glu Leu Trp Leu Val Thr Glu
                85                  90                  95
Tyr His Pro Ser Gly Ser Leu His Asp Phe Leu Leu Glu Asn Thr Val
            100                 105                 110
Asn Ile Glu Thr Tyr Tyr Asn Leu Met Arg Ser Thr Ala Ser Gly Leu
        115                 120                 125
Ala Phe Leu His Asn Gln Ile Gly Gly Ser Lys
```

-continued

```
          130               135

<210> SEQ ID NO 14
<211> LENGTH: 62
<212> TYPE: PRT
<213> ORGANISM: Caenorhabditis elegans

<400> SEQUENCE: 14

Glu Asp Ala Ala Ser Asp Ile Ile Ala Asn Glu Asn Tyr Lys Cys Gly
1               5                   10                  15

Thr Val Arg Tyr Leu Ala Pro Glu Ile Leu Asn Ser Thr Met Gln Phe
            20                  25                  30

Thr Val Phe Glu Ser Tyr Gln Cys Ala Asp Val Tyr Ser Phe Ser Leu
        35                  40                  45

Val Met Trp Glu Thr Leu Cys Arg Cys Glu Asp Gly Asp Val
    50                  55                  60

<210> SEQ ID NO 15
<211> LENGTH: 31
<212> TYPE: PRT
<213> ORGANISM: Caenorhabditis elegans

<400> SEQUENCE: 15

Lys Pro Ala Met Ala His Arg Asp Ile Lys Ser Lys Asn Ile Met Val
1               5                   10                  15

Lys Asn Asp Leu Thr Cys Ala Ile Gly Asp Leu Gly Leu Ser Leu
            20                  25                  30

<210> SEQ ID NO 16
<211> LENGTH: 72
<212> TYPE: PRT
<213> ORGANISM: Caenorhabditis elegans

<400> SEQUENCE: 16

Ile Pro Tyr Ile Glu Trp Thr Asp Arg Asp Pro Gln Asp Ala Gln Met
1               5                   10                  15

Phe Asp Val Val Cys Thr Arg Arg Leu Arg Pro Thr Glu Asn Pro Leu
            20                  25                  30

Trp Lys Asp His Pro Glu Met Lys His Ile Met Glu Ile Ile Lys Thr
        35                  40                  45

Cys Trp Asn Gly Asn Pro Ser Ala Arg Phe Thr Ser Tyr Ile Cys Arg
    50                  55                  60

Lys Arg Met Asp Glu Arg Gln Gln
65                  70

<210> SEQ ID NO 17
<211> LENGTH: 150
<212> TYPE: PRT
<213> ORGANISM: Caenorhabditis elegans

<400> SEQUENCE: 17

Tyr Phe Glu Ser Val Asp Arg Phe Leu Tyr Ser Cys Val Gly Tyr Ser
1               5                   10                  15

Val Ala Thr Tyr Ile Met Gly Ile Lys Asp Arg His Ser Asp Asn Leu
            20                  25                  30

Met Leu Thr Glu Asp Gly Lys Tyr Val His Ile Asp Phe Gly His Ile
        35                  40                  45

Leu Gly His Gly Lys Thr Lys Leu Gly Ile Gln Arg Asp Arg Gln Pro
    50                  55                  60
```

```
Phe Ile Leu Thr Glu His Phe Met Thr Val Ile Arg Ser Gly Lys Ser
65                  70                  75                  80

Val Asp Gly Asn Ser His Glu Leu Gln Lys Phe Lys Thr Leu Cys Val
                85                  90                  95

Glu Ala Tyr Glu Val Met Trp Asn Asn Arg Asp Leu Phe Val Ser Leu
            100                 105                 110

Phe Thr Leu Met Leu Gly Met Glu Leu Pro Gly Leu Ser Thr Lys Ala
            115                 120                 125

Asp Leu Asp His Leu Lys Lys Thr Leu Phe Cys Asn Gly Glu Ser Lys
130                 135                 140

Glu Glu Ala Arg Lys Phe
145             150

<210> SEQ ID NO 18
<211> LENGTH: 113
<212> TYPE: PRT
<213> ORGANISM: Caenorhabditis elegans

<400> SEQUENCE: 18

Ser Pro Leu Asp Pro Val Tyr Lys Leu Gly Glu Met Ile Ile Asp Lys
1               5                   10                  15

Ala Ile Val Leu Gly Ser Ala Lys Arg Pro Leu Met Leu His Trp Lys
            20                  25                  30

Asn Lys Asn Pro Lys Ser Asp Leu His Leu Pro Phe Cys Ala Met Ile
            35                  40                  45

Phe Lys Asn Gly Asp Asp Leu Arg Gln Asp Met Leu Val Leu Gln Val
    50                  55                  60

Leu Glu Val Met Asp Asn Ile Trp Lys Ala Ala Asn Ile Asp Cys Cys
65                  70                  75                  80

Leu Asn Pro Tyr Ala Val Leu Pro Met Gly Glu Met Ile Gly Ile Ile
                85                  90                  95

Glu Val Val Pro Asn Cys Lys Thr Ile Phe Glu Ile Gln Val Gly Thr
            100                 105                 110

Gly

<210> SEQ ID NO 19
<211> LENGTH: 106
<212> TYPE: PRT
<213> ORGANISM: Caenorhabditis elegans

<400> SEQUENCE: 19

Leu Ala Phe Val Trp Thr Asp Arg Glu Asn Phe Ser Glu Leu Tyr Val
1               5                   10                  15

Met Leu Glu Lys Trp Lys Pro Pro Ser Val Ala Ala Leu Thr Leu
            20                  25                  30

Leu Gly Lys Arg Cys Thr Asp Arg Val Ile Arg Lys Phe Ala Val Glu
            35                  40                  45

Lys Leu Asn Glu Gln Leu Ser Pro Val Thr Phe His Leu Phe Ile Leu
    50                  55                  60

Pro Leu Ile Gln Ala Leu Lys Tyr Glu Pro Arg Ala Gln Ser Glu Val
65                  70                  75                  80

Gly Met Met Leu Leu Thr Arg Ala Leu Cys Asp Tyr Arg Ile Gly His
                85                  90                  95

Arg Leu Phe Trp Leu Leu Arg Ala Glu Ile
            100                 105
```

```
<210> SEQ ID NO 20
<211> LENGTH: 139
<212> TYPE: PRT
<213> ORGANISM: Caenorhabditis elegans

<400> SEQUENCE: 20

Glu Tyr Trp Ile Val Thr Glu Phe His Glu Arg Leu Ser Leu Tyr Glu
1               5                   10                  15

Leu Leu Lys Asn Asn Val Ile Ser Ile Thr Ser Ala Asn Arg Ile Ile
            20                  25                  30

Met Ser Met Ile Asp Gly Leu Gln Phe Leu His Asp Asp Arg Pro Tyr
        35                  40                  45

Phe Phe Gly His Pro Lys Lys Pro Ile Ile His Arg Asp Ile Lys Ser
    50                  55                  60

Lys Asn Ile Leu Val Lys Ser Asp Met Thr Thr Cys Ile Ala Asp Phe
65                  70                  75                  80

Gly Leu Ala Arg Ile Tyr Ser Tyr Asp Ile Glu Gln Ser Asp Leu Leu
                85                  90                  95

Gly Gln Val Gly Thr Lys Arg Tyr Met Ser Pro Glu Met Leu Glu Gly
            100                 105                 110

Ala Thr Glu Phe Thr Pro Thr Ala Phe Lys Ala Met Asp Val Tyr Ser
        115                 120                 125

Met Gly Leu Val Met Trp Glu Val Ile Ser Arg
    130                 135

<210> SEQ ID NO 21
<211> LENGTH: 61
<212> TYPE: PRT
<213> ORGANISM: Caenorhabditis elegans

<400> SEQUENCE: 21

Ile Gly Phe Asp Pro Thr Ile Gly Arg Met Arg Asn Tyr Val Val Ser
1               5                   10                  15

Lys Lys Glu Arg Pro Gln Trp Arg Asp Glu Ile Ile Lys His Glu Tyr
            20                  25                  30

Met Ser Leu Leu Lys Lys Val Thr Glu Glu Met Trp Asp Pro Glu Ala
        35                  40                  45

Cys Ala Arg Ile Thr Ala Gly Cys Ala Phe Ala Arg Val
    50                  55                  60

<210> SEQ ID NO 22
<211> LENGTH: 20
<212> TYPE: PRT
<213> ORGANISM: Caenorhabditis elegans

<400> SEQUENCE: 22

Pro Ile Thr Asp Phe Gln Leu Ile Ser Lys Gly Arg Phe Gly Lys Val
1               5                   10                  15

Phe Lys Ala Gln
            20

<210> SEQ ID NO 23
<211> LENGTH: 163
<212> TYPE: PRT
<213> ORGANISM: Caenorhabditis elegans

<400> SEQUENCE: 23

Thr Asp Ser Glu Thr Arg Ser Arg Phe Ser Leu Gly Trp Tyr Asn Asn
1               5                   10                  15
```

```
Pro Asn Arg Ser Pro Gln Thr Ala Glu Val Arg Gly Leu Ile Gly Lys
            20                  25                  30

Gly Val Arg Phe Tyr Leu Leu Ala Gly Glu Val Tyr Val Glu Asn Leu
        35                  40                  45

Cys Asn Ile Pro Val Phe Val Gln Ser Ile Gly Ala Asn Met Lys Asn
    50                  55                  60

Gly Phe Gln Leu Asn Thr Val Ser Lys Leu Pro Pro Thr Gly Thr Met
65                  70                  75                  80

Lys Val Phe Asp Met Arg Leu Phe Ser Lys Gln Leu Arg Thr Ala Ala
                85                  90                  95

Glu Lys Thr Tyr Gln Asp Val Tyr Cys Leu Ser Arg Met Cys Thr Val
            100                 105                 110

Arg Val Ser Phe Cys Lys Gly Trp Gly Glu His Tyr Arg Arg Ser Thr
        115                 120                 125

Val Leu Arg Ser Pro Val Trp Phe Gln Ala His Leu Asn Asn Pro Met
    130                 135                 140

His Trp Val Asp Ser Val Leu Thr Cys Met Gly Ala Pro Pro Arg Ile
145                 150                 155                 160

Cys Ser Ser

<210> SEQ ID NO 24
<211> LENGTH: 44
<212> TYPE: PRT
<213> ORGANISM: Caenorhabditis elegans

<400> SEQUENCE: 24

Arg Ala Phe Arg Phe Pro Val Ile Arg Tyr Glu Ser Gln Val Lys Ser
1               5                   10                  15

Ile Leu Thr Cys Arg His Ala Phe Asn Ser His Ser Arg Asn Val Cys
            20                  25                  30

Leu Asn Pro Tyr His Tyr Arg Trp Val Glu Leu Pro
        35                  40

<210> SEQ ID NO 25
<211> LENGTH: 38
<212> TYPE: PRT
<213> ORGANISM: Caenorhabditis elegans

<400> SEQUENCE: 25

Val Glu Tyr Glu Glu Ser Pro Ser Trp Leu Lys Leu Ile Tyr Tyr Glu
1               5                   10                  15

Glu Gly Thr Met Ile Gly Glu Lys Ala Asp Val Glu Gly His His Cys
            20                  25                  30

Leu Ile Asp Gly Phe Thr
        35

<210> SEQ ID NO 26
<211> LENGTH: 60
<212> TYPE: PRT
<213> ORGANISM: Caenorhabditis elegans

<400> SEQUENCE: 26

Asn Leu Ala Glu Thr Gly His Ser Lys Ile Met Arg Ala Ala His Lys
1               5                   10                  15

Val Ser Asn Pro Glu Ile Gly Tyr Cys Cys His Pro Thr Glu Tyr Asp
            20                  25                  30

Tyr Ile Lys Leu Ile Tyr Val Asn Arg Asp Gly Arg Val Ser Ile Ala
        35                  40                  45
```

```
Asn Val Asn Gly Met Ile Ala Lys Lys Cys Gly Cys
        50                  55                  60

<210> SEQ ID NO 27
<211> LENGTH: 20
<212> TYPE: PRT
<213> ORGANISM: Caenorhabditis elegans

<400> SEQUENCE: 27

Asp Trp Ile Val Ala Pro Pro Arg Tyr Asn Ala Tyr Met Cys Arg Gly
  1               5                  10                  15

Asp Cys His Tyr
            20

<210> SEQ ID NO 28
<211> LENGTH: 43
<212> TYPE: PRT
<213> ORGANISM: Caenorhabditis elegans

<400> SEQUENCE: 28

Val Cys Asn Ala Glu Ala Gln Ser Lys Gly Cys Cys Leu Tyr Asp Leu
  1               5                  10                  15

Glu Ile Glu Phe Glu Lys Ile Gly Trp Asp Trp Ile Val Ala Pro Pro
            20                  25                  30

Arg Tyr Asn Ala Tyr Met Cys Arg Gly Asp Cys
        35                  40

<210> SEQ ID NO 29
<211> LENGTH: 70
<212> TYPE: PRT
<213> ORGANISM: Caenorhabditis elegans

<400> SEQUENCE: 29

Asp Cys His Tyr Asn Ala His His Phe Asn Leu Ala Glu Thr Gly His
  1               5                  10                  15

Ser Lys Ile Met Arg Ala Ala His Lys Val Ser Asn Pro Glu Ile Gly
            20                  25                  30

Tyr Cys Cys His Pro Thr Glu Tyr Asp Tyr Ile Lys Leu Ile Tyr Val
        35                  40                  45

Asn Arg Asp Gly Arg Val Ser Ile Ala Asn Val Asn Gly Met Ile Ala
    50                  55                  60

Lys Lys Cys Gly Cys Ser
 65                  70

<210> SEQ ID NO 30
<211> LENGTH: 35
<212> TYPE: PRT
<213> ORGANISM: Caenorhabditis elegans

<400> SEQUENCE: 30

Cys Cys Leu Tyr Asp Leu Glu Ile Glu Phe Glu Lys Ile Gly Trp Asp
  1               5                  10                  15

Trp Ile Val Ala Pro Pro Arg Tyr Asn Ala Tyr Met Cys Arg Gly Asp
            20                  25                  30

Cys His Tyr
        35

<210> SEQ ID NO 31
<211> LENGTH: 23
<212> TYPE: DNA
```

```
<213> ORGANISM: Artificial Sequence
<220> FEATURE:
<223> OTHER INFORMATION: Degenerate probe
<220> FEATURE:
<221> NAME/KEY: misc_feature
<222> LOCATION: (1)...(23)
<223> OTHER INFORMATION: n = A,T,C or G

<400> SEQUENCE: 31
ggntgggayt rnrtnrtngc ncc                                               23

<210> SEQ ID NO 32
<211> LENGTH: 18
<212> TYPE: DNA
<213> ORGANISM: Artificial Sequence
<220> FEATURE:
<223> OTHER INFORMATION: Degenerate probe
<220> FEATURE:
<221> NAME/KEY: misc_feature
<222> LOCATION: (1)...(18)
<223> OTHER INFORMATION: n = A,T,C or G

<400> SEQUENCE: 32
tgytgynnnc cnacngar                                                     18

<210> SEQ ID NO 33
<211> LENGTH: 127
<212> TYPE: PRT
<213> ORGANISM: Caenorhabditis elegans

<400> SEQUENCE: 33
```

Lys Phe His Glu Trp Ala Ala Gln Ile Cys Asp Gly Met Ala Tyr Leu
 1               5                  10                  15

Glu Ser Leu Lys Phe Cys His Arg Asp Leu Ala Ala Arg Asn Cys Met
            20                  25                  30

Ile Asn Arg Asp Glu Thr Val Lys Ile Gly Asp Phe Gly Met Ala Arg
        35                  40                  45

Asp Leu Phe Tyr His Asp Tyr Tyr Lys Pro Ser Gly Lys Arg Met Met
    50                  55                  60

Pro Val Arg Trp Met Ser Pro Glu Ser Leu Lys Asp Gly Lys Phe Asp
65                  70                  75                  80

Ser Lys Ser Asp Val Trp Ser Phe Gly Val Val Leu Tyr Glu Met Val
                85                  90                  95

Thr Leu Gly Ala Gln Pro Tyr Ile Gly Leu Ser Asn Asp Glu Val Leu
            100                 105                 110

Asn Tyr Ile Gly Met Ala Arg Lys Val Ile Lys Pro Glu Cys
        115                 120                 125

```
<210> SEQ ID NO 34
<211> LENGTH: 131
<212> TYPE: PRT
<213> ORGANISM: Caenorhabditis elegans

<400> SEQUENCE: 34
```

Asn Thr Thr Cys Gln Lys Ser Cys Ala Tyr Asp Arg Leu Leu Pro Thr
 1               5                  10                  15

Lys Glu Ile Gly Pro Gly Cys Asp Ala Asn Gly Asp Arg Cys His Asp
            20                  25                  30

Gln Cys Val Gly Gly Cys Glu Arg Val Asn Asp Ala Thr Ala Cys His
        35                  40                  45

Ala Cys Lys Asn Val Tyr His Lys Gly Lys Cys Ile Glu Lys Cys Asp
    50                  55                  60

Ala His Leu Tyr Leu Leu Leu Gln Arg Arg Cys Val Thr Arg Glu Gln
65                  70                  75                  80

Cys Leu Gln Leu Asn Pro Val Leu Ser Asn Lys Thr Val Pro Ile Lys
                85                  90                  95

Ala Thr Ala Gly Leu Cys Ser Asp Lys Cys Pro Asp Gly Tyr Gln Ile
            100                 105                 110

Asn Pro Asp Asp His Arg Glu Cys Arg Lys Cys Val Gly Lys Cys Glu
        115                 120                 125

Ile Val Cys
    130

<210> SEQ ID NO 35
<211> LENGTH: 103
<212> TYPE: PRT
<213> ORGANISM: Caenorhabditis elegans

<400> SEQUENCE: 35

Phe Asp Gln Lys Ala Cys Glu Ser Leu Val Lys Lys Leu Lys Asp Lys
1               5                   10                  15

Lys Asn Asp Leu Gln Asn Leu Ile Asp Val Leu Ser Lys Gly Thr
                20                  25                  30

Lys Tyr Thr Gly Cys Ile Thr Ile Pro Arg Thr Leu Asp Gly Arg Leu
            35                  40                  45

Gln Val His Gly Arg Lys Gly Phe Pro His Val Tyr Gly Lys Leu
    50                  55                  60

Trp Arg Phe Asn Glu Met Thr Lys Asn Glu Thr Arg His Val Asp His
65                  70                  75                  80

Cys Lys His Ala Phe Glu Met Lys Ser Asp Met Val Cys Val Asn Pro
                85                  90                  95

Tyr His Tyr Glu Ile Val Ile
            100

<210> SEQ ID NO 36
<211> LENGTH: 79
<212> TYPE: PRT
<213> ORGANISM: Caenorhabditis elegans

<400> SEQUENCE: 36

Asn Arg Tyr Ser Leu Gly Leu Glu Pro Asn Pro Ile Arg Glu Pro Val
1               5                   10                  15

Ala Phe Lys Val Arg Lys Ala Ile Val Asp Gly Ile Arg Phe Ser Tyr
                20                  25                  30

Lys Lys Asp Gly Ser Val Trp Leu Gln Asn Arg Met Lys Tyr Pro Val
            35                  40                  45

Phe Val Thr Ser Gly Tyr Leu Asp Glu Gln Ser Gly Gly Leu Lys Lys
        50                  55                  60

Asp Lys Val His Lys Val Tyr Gly Cys Ala Ser Ile Lys Thr Phe
65                  70                  75

<210> SEQ ID NO 37
<211> LENGTH: 106
<212> TYPE: PRT
<213> ORGANISM: Caenorhabditis elegans

<400> SEQUENCE: 37

Lys Lys Thr Thr Thr Arg Arg Asn Ala Trp Gly Asn Met Ser Tyr Ala
1               5                   10                  15

-continued

```
Glu Leu Ile Thr Thr Ala Ile Met Ala Ser Pro Glu Lys Arg Leu Thr
                20                  25                  30

Leu Ala Gln Val Tyr Glu Trp Met Val Gln Asn Val Pro Tyr Phe Arg
            35                  40                  45

Asp Lys Gly Asp Ser Asn Ser Ser Ala Gly Trp Lys Asn Ser Ile Arg
        50                  55                  60

His Asn Leu Ser Leu His Ser Arg Phe Met Arg Ile Gln Asn Glu Gly
65                  70                  75                  80

Ala Gly Lys Ser Ser Trp Trp Val Ile Asn Pro Asp Ala Lys Pro Gly
                85                  90                  95

Met Asn Pro Arg Arg Thr Arg Glu Arg Ser
                100                 105
```

<210> SEQ ID NO 38
<211> LENGTH: 60
<212> TYPE: PRT
<213> ORGANISM: Caenorhabditis elegans

<400> SEQUENCE: 38

```
Glu Ile Lys Leu Ser Asp Phe Lys His Gln Leu Phe Glu Leu Ile Ala
1               5                   10                  15

Pro Met Lys Trp Gly Thr Tyr Ser Val Lys Pro Gln Asp Tyr Val Phe
                20                  25                  30

Arg Gln Leu Asn Asn Phe Gly Glu Ile Glu Val Ile Phe Asn Asp Asp
            35                  40                  45

Gln Pro Leu Ser Lys Leu Glu Leu His Gly Thr Phe
        50                  55                  60
```

<210> SEQ ID NO 39
<211> LENGTH: 2784
<212> TYPE: DNA
<213> ORGANISM: Caenorhabditis elegans

<400> SEQUENCE: 39

| | | |
|---|---|---|
| atgaagctaa tagcaacttc tcttctagtt cccgacgagc acacaccgat gatgtcacca | 60 |
| gtgaatacaa ctacaaagat tctacaacgg agtggtatta aaatggaaat cccgccatat | 120 |
| ttggatccag acagtcagga tgatgacccg gaagatggtg tcaactaccc ggatccagat | 180 |
| ttatttgaca caaaaaacac aaatatgacc gagtacgatt tggatgtgtt gaagcttgga | 240 |
| aaaccagcag tagatgaagc acggaaaaag atcgaagttc ccgacgctag tgcgccgcca | 300 |
| aacaaaattg tagaatattt gatgtattat agaacgttaa agaaagtgaa actcatacaa | 360 |
| ctgaatgcgt atcggacaaa acgaaatcga ttatcgttga acttggtcaa aaacaatatt | 420 |
| gatcgagagt tcgaccaaaa agcttgcgag tccctggtga aaaaattgaa ggataagaag | 480 |
| aatgatctcc agaacctgat tgatgtggtt ctttcaaaag gtacaaaata taccggttgc | 540 |
| attacaattc caaggacact tgatggccgg ttacaggtcc acggaagaaa aggtttccct | 600 |
| cacgtagtct atggcaaact gtggaggttt aatgaaatga caaaaaacga aacgcgtcat | 660 |
| gtggaccact gcaagcacgc atttgaaatg aaaagtgaca tggtatgcgt gaatccctat | 720 |
| cactacgaaa ttgtcattgg aactatgatt gttgggcaga gggatcatga caatcgagat | 780 |
| atgccgccgc cacatcaacg ctaccacact ccaggtcggc aggatccagt tgacgatatg | 840 |
| agtagattta taccaccagc ttccattcgt ccgcctccga tgaacatgca cacaaggcct | 900 |
| cagcctatgc ctcaacaatt gccttcagtt ggcgcaacgt ttgcccatcc tctcccacat | 960 |
| caggcgccac ataacccagg ggtttcacat ccgtactcca ttgctccaca gacccattac | 1020 |

```
ccgttgaaca tgaacccaat tccgcaaatg ccgcaaatgc cacaaatgcc accacctctc   1080
catcagggat atggaatgaa tgggccgagt tgctcttcag aaaacaacaa tccattccac   1140
caaaatcacc attataatga tattagccat ccaaatcact attcctacga ctgtggtccg   1200
aacttgtacg ggtttccaac tccttatccg gattttcacc atcctttcaa tcagcaacca   1260
caccagccgc cacaactatc acaaaaccat acgtcccaac aaggcagtca tcaaccaggg   1320
caccaaggtc aggtaccgaa tgatccacca atttcaagac cagtgttaca accatcaaca   1380
gtcaccttgg acgtgttccg tcggtactgt agacagacat ttggaaatcg atttttttgaa   1440 ggagaaagtg aacaatccgg cgcaataatt cggtctagta acaaattcat gaagaattt   1500 gattcgccga tttgtggtgt gacagttgtt cgaccgcgga tgacgacgg tgaggtttg   1560 gagaacatca tgccggaaga tgcaccatat catgacattt gcaagttcat tttgaggctc   1620
acatcagaaa gtgtaacttt ctcaggagag gggccagaag ttagtgattt gaacgaaaaa   1680
tggggaacaa ttgtgtacta tgagaaaaat ttgcaaattg gcgagaaaaa atgttcgaga   1740
ggaaatttcc acgtggatgg cggattcatt tgctctgaga tcgttacag tctcggactt   1800 gagccaaatc caattagaga accagtggcg tttaaagttc gtaaagcaat agtggatgga   1860
attcgctttt cctacaaaaa agacgggagt gttttggcttc aaaaccgcat gaagtacccg   1920
gtatttgtca cttctgggta tctcgacgag caatcaggag gcctaaagaa ggataaagtg   1980
cacaaagttt acggatgtgc gtctatcaaa acgtttggct tcaacgtttc caaacaaatc   2040
atcagagacg cgcttctttc caagcaaatg gcaacaatgt acttgcaagg aaaattgact   2100
ccgatgaatt atatctacga gaagaagact caggaagagc tgcgaaggga agcaacacgc   2160
accactgatt cattggccaa gtactgttgt gtccgtgtct cgttctgcaa aggatttgga   2220
gaagcatacc cagaacgccc gtcaattcat gattgtccag tttggattga gttgaaaatc   2280
aacattgcct acgatttcat ggattcaatc tgccagtaca taaccaactg cttcgagccg   2340
ctaggaatgg aagatttttgc aaaattggga atcaacgtca gtgatgacta atgataact   2400 tttttcactc accctactag atactgattt agtcttattc caaatcatcc aacgatatca   2460
aactttttcc tttgaacttt gcatactatg ttatcacaag ttccaagcag tttcaataca   2520
aacataggat atgttaacaa ctttttgataa gaatcaagtt accaactgtt cattgtgagc   2580
tttgagctgt atagaaggac aatgtatccc atacctcaat cttttaatagt catcagtcac   2640 tggtcccgca ccaatttttt cgattcgcat atgtcatata ttgcaccgtg gccctttta   2700 ttgtaacttt taatatattt tcttcccaac ttgtgaatat gattgatgaa ccaccatttt   2760
gagtaataaa tgtattttt gtgg                                          2784
```

<210> SEQ ID NO 40
<211> LENGTH: 796
<212> TYPE: PRT
<213> ORGANISM: Caenorhabditis elegans

<400> SEQUENCE: 40

```
Met Lys Leu Ile Ala Thr Ser Leu Leu Val Pro Asp Glu His Thr Pro
  1               5                  10                  15

Met Met Ser Pro Val Asn Thr Thr Lys Ile Leu Gln Arg Ser Gly
             20                  25                  30

Ile Lys Met Glu Ile Pro Pro Tyr Leu Asp Pro Asp Ser Gln Asp Asp
         35                  40                  45

Asp Pro Glu Asp Gly Val Asn Tyr Pro Asp Pro Asp Leu Phe Asp Thr
```

-continued

```
            50                  55                  60
Lys Asn Thr Asn Met Thr Glu Tyr Asp Leu Asp Val Leu Lys Leu Gly
 65                  70                  75                  80
Lys Pro Ala Val Asp Glu Ala Arg Lys Lys Ile Glu Val Pro Asp Ala
                     85                  90                  95
Ser Ala Pro Pro Asn Lys Ile Val Glu Tyr Leu Met Tyr Tyr Arg Thr
                    100                 105                 110
Leu Lys Glu Ser Glu Leu Ile Gln Leu Asn Ala Tyr Arg Thr Lys Arg
                    115                 120                 125
Asn Arg Leu Ser Leu Asn Leu Val Lys Asn Asn Ile Asp Arg Glu Phe
        130                 135                 140
Asp Gln Lys Ala Cys Glu Ser Leu Val Lys Lys Leu Lys Asp Lys Lys
145                 150                 155                 160
Asn Asp Leu Gln Asn Leu Ile Asp Val Val Leu Ser Lys Gly Thr Lys
                    165                 170                 175
Tyr Thr Gly Cys Ile Thr Ile Pro Arg Thr Leu Asp Gly Arg Leu Gln
                    180                 185                 190
Val His Gly Arg Lys Gly Phe Pro His Val Val Tyr Gly Lys Leu Trp
        195                 200                 205
Arg Phe Asn Glu Met Thr Lys Asn Glu Thr Arg His Val Asp His Cys
210                 215                 220
Lys His Ala Phe Glu Met Lys Ser Asp Met Val Cys Val Asn Pro Tyr
225                 230                 235                 240
His Tyr Glu Ile Val Ile Gly Thr Met Ile Val Gly Gln Arg Asp His
                    245                 250                 255
Asp Asn Arg Asp Met Pro Pro His Gln Arg Tyr His Thr Pro Gly
        260                 265                 270
Arg Gln Asp Pro Val Asp Asp Met Ser Arg Phe Ile Pro Pro Ala Ser
        275                 280                 285
Ile Arg Pro Pro Pro Met Asn Met His Thr Arg Pro Gln Pro Met Pro
        290                 295                 300
Gln Gln Leu Pro Ser Val Gly Ala Thr Phe Ala His Pro Leu Pro His
305                 310                 315                 320
Gln Ala Pro His Asn Pro Gly Val Ser His Pro Tyr Ser Ile Ala Pro
                    325                 330                 335
Gln Thr His Tyr Pro Leu Asn Met Asn Pro Ile Pro Gln Met Pro Gln
                    340                 345                 350
Met Pro Gln Met Pro Pro Leu His Gln Gly Tyr Gly Met Asn Gly
        355                 360                 365
Pro Ser Cys Ser Ser Glu Asn Asn Asn Pro Phe His Gln Asn His His
        370                 375                 380
Tyr Asn Asp Ile Ser His Pro Asn His Tyr Ser Tyr Asp Cys Gly Pro
385                 390                 395                 400
Asn Leu Tyr Gly Phe Pro Thr Pro Tyr Pro Asp Phe His His Pro Phe
                    405                 410                 415
Asn Gln Gln Pro His Gln Pro Pro Gln Leu Ser Gln Asn His Thr Ser
                    420                 425                 430
Gln Gln Gly Ser His Gln Pro Gly His Gln Gly Gln Val Pro Asn Asp
        435                 440                 445
Pro Pro Ile Ser Arg Pro Val Leu Gln Pro Ser Thr Val Thr Leu Asp
        450                 455                 460
Val Phe Arg Arg Tyr Cys Arg Gln Thr Phe Gly Asn Arg Phe Phe Glu
465                 470                 475                 480
```

```
Gly Glu Ser Glu Gln Ser Gly Ala Ile Ile Arg Ser Ser Asn Lys Phe
                485                 490                 495
Ile Glu Glu Phe Asp Ser Pro Ile Cys Gly Val Thr Val Val Arg Pro
            500                 505                 510
Arg Met Thr Asp Gly Glu Val Leu Glu Asn Ile Met Pro Glu Asp Ala
        515                 520                 525
Pro Tyr His Asp Ile Cys Lys Phe Ile Leu Arg Leu Thr Ser Glu Ser
    530                 535                 540
Val Thr Phe Ser Gly Glu Gly Pro Glu Val Ser Asp Leu Asn Glu Lys
545                 550                 555                 560
Trp Gly Thr Ile Val Tyr Tyr Glu Lys Asn Leu Gln Ile Gly Glu Lys
                565                 570                 575
Lys Cys Ser Arg Gly Asn Phe His Val Asp Gly Gly Phe Ile Cys Ser
            580                 585                 590
Glu Asn Arg Tyr Ser Leu Gly Leu Glu Pro Asn Pro Ile Arg Glu Pro
        595                 600                 605
Val Ala Phe Lys Val Arg Lys Ala Ile Val Asp Gly Ile Arg Phe Ser
    610                 615                 620
Tyr Lys Lys Asp Gly Ser Val Trp Leu Gln Asn Arg Met Lys Tyr Pro
625                 630                 635                 640
Val Phe Val Thr Ser Gly Tyr Leu Asp Glu Gln Ser Gly Gly Leu Lys
                645                 650                 655
Lys Asp Lys Val His Lys Val Tyr Gly Cys Ala Ser Ile Lys Thr Phe
            660                 665                 670
Gly Phe Asn Val Ser Lys Gln Ile Ile Arg Asp Ala Leu Leu Ser Lys
        675                 680                 685
Gln Met Ala Thr Met Tyr Leu Gln Gly Lys Leu Thr Pro Met Asn Tyr
    690                 695                 700
Ile Tyr Glu Lys Lys Thr Gln Glu Glu Leu Arg Arg Glu Ala Thr Arg
705                 710                 715                 720
Thr Thr Asp Ser Leu Ala Lys Tyr Cys Cys Val Arg Val Ser Phe Cys
                725                 730                 735
Lys Gly Phe Gly Glu Ala Tyr Pro Glu Arg Pro Ser Ile His Asp Cys
            740                 745                 750
Pro Val Trp Ile Glu Leu Lys Ile Asn Ile Ala Tyr Asp Phe Met Asp
        755                 760                 765
Ser Ile Cys Gln Tyr Ile Thr Asn Cys Phe Glu Pro Leu Gly Met Glu
    770                 775                 780
Asp Phe Ala Lys Leu Gly Ile Asn Val Ser Asp Asp
785                 790                 795

<210> SEQ ID NO 41
<211> LENGTH: 858
<212> TYPE: PRT
<213> ORGANISM: Caenorhabditis elegans

<400> SEQUENCE: 41

Met Gly Asp His His Asn Leu Thr Gly Leu Pro Gly Thr Ser Ile Pro
1               5                   10                  15
Pro Gln Phe Asn Tyr Ser Gln Pro Gly Thr Ser Thr Gly Gly Pro Leu
            20                  25                  30
Tyr Gly Gly Lys Pro Ser His Gly Leu Glu Asp Ile Pro Asp Val Glu
        35                  40                  45
Glu Tyr Glu Arg Asn Leu Leu Gly Ala Gly Ala Gly Phe Asn Leu Leu
```

```
                        50                     55                     60
Asn Val Gly Asn Met Ala Asn Val Pro Asp Glu His Thr Pro Met Met
 65                      70                     75                     80

Ser Pro Val Asn Thr Thr Thr Lys Ile Leu Gln Arg Ser Gly Ile Lys
                         85                     90                     95

Met Glu Ile Pro Pro Tyr Leu Asp Pro Asp Ser Gln Asp Asp Asp Pro
                        100                    105                    110

Glu Asp Gly Val Asn Tyr Pro Asp Pro Asp Leu Phe Asp Thr Lys Asn
                115                    120                    125

Thr Asn Met Thr Glu Tyr Asp Leu Asp Val Leu Lys Leu Gly Lys Pro
                130                    135                    140

Ala Val Asp Glu Ala Arg Lys Lys Ile Glu Val Pro Asp Ala Ser Ala
145                     150                    155                    160

Pro Pro Asn Lys Ile Val Glu Tyr Leu Met Tyr Tyr Arg Thr Leu Lys
                        165                    170                    175

Glu Ser Glu Leu Ile Gln Leu Asn Ala Tyr Arg Thr Lys Arg Asn Arg
                        180                    185                    190

Leu Ser Leu Asn Leu Val Lys Asn Asn Ile Asp Arg Glu Phe Asp Gln
                        195                    200                    205

Lys Ala Cys Glu Ser Leu Val Lys Lys Leu Lys Asp Lys Lys Asn Asp
                210                    215                    220

Leu Gln Asn Leu Ile Asp Val Val Leu Ser Lys Gly Thr Lys Tyr Thr
225                     230                    235                    240

Gly Cys Ile Thr Ile Pro Arg Thr Leu Asp Gly Arg Leu Gln Val His
                        245                    250                    255

Gly Arg Lys Gly Phe Pro His Val Val Tyr Gly Lys Leu Trp Arg Phe
                260                    265                    270

Asn Glu Met Thr Lys Asn Glu Thr Arg His Val Asp His Cys Lys His
                        275                    280                    285

Ala Phe Glu Met Lys Ser Asp Met Val Cys Val Asn Pro Tyr His Tyr
                290                    295                    300

Glu Ile Val Ile Gly Thr Met Ile Val Gly Gln Arg Asp His Asp Asn
305                     310                    315                    320

Arg Asp Met Pro Pro Pro His Gln Arg Tyr His Thr Pro Gly Arg Gln
                        325                    330                    335

Asp Pro Val Asp Asp Met Ser Arg Phe Ile Pro Pro Ala Ser Ile Arg
                        340                    345                    350

Pro Pro Pro Met Asn Met His Thr Arg Pro Gln Pro Met Pro Gln Gln
                355                    360                    365

Leu Pro Ser Val Gly Ala Thr Phe Ala His Pro Leu Pro His Gln Ala
                370                    375                    380

Pro His Asn Pro Gly Val Ser His Pro Tyr Ser Ile Ala Pro Gln Thr
385                     390                    395                    400

His Tyr Pro Leu Asn Met Asn Pro Ile Pro Gln Met Pro Gln Met Pro
                        405                    410                    415

Gln Met Pro Pro Pro Leu His Gln Gly Tyr Gly Met Asn Gly Pro Ser
                420                    425                    430

Cys Ser Ser Glu Asn Asn Asn Pro Phe His Gln Asn His His Tyr Asn
                435                    440                    445

Asp Ile Ser His Pro Asn His Tyr Ser Tyr Asp Cys Gly Pro Asn Leu
                450                    455                    460

Tyr Gly Phe Pro Thr Pro Tyr Pro Asp Phe His His Pro Phe Asn Gln
465                     470                    475                    480
```

```
Gln Pro His Gln Pro Pro Gln Leu Ser Gln Asn His Thr Ser Gln Gln
                485                 490                 495
Gly Ser His Gln Pro Gly His Gln Gly Gln Val Pro Asn Asp Pro Pro
            500                 505                 510
Ile Ser Arg Pro Val Leu Gln Pro Ser Thr Val Thr Leu Asp Val Phe
            515                 520                 525
Arg Arg Tyr Cys Arg Gln Thr Phe Gly Asn Arg Phe Phe Glu Gly Glu
        530                 535                 540
Ser Glu Gln Ser Gly Ala Ile Ile Arg Ser Ser Asn Lys Phe Ile Glu
545                 550                 555                 560
Glu Phe Asp Ser Pro Ile Cys Gly Val Thr Val Val Arg Pro Arg Met
                565                 570                 575
Thr Asp Gly Glu Val Leu Glu Asn Ile Met Pro Glu Asp Ala Pro Tyr
            580                 585                 590
His Asp Ile Cys Lys Phe Ile Leu Arg Leu Thr Ser Glu Ser Val Thr
            595                 600                 605
Phe Ser Gly Glu Gly Pro Glu Val Ser Asp Leu Asn Glu Lys Trp Gly
        610                 615                 620
Thr Ile Val Tyr Tyr Glu Lys Asn Leu Gln Ile Gly Glu Lys Lys Cys
625                 630                 635                 640
Ser Arg Gly Asn Phe His Val Asp Gly Gly Phe Ile Cys Ser Glu Asn
                645                 650                 655
Arg Tyr Ser Leu Gly Leu Glu Pro Asn Pro Ile Arg Glu Pro Val Ala
            660                 665                 670
Phe Lys Val Arg Lys Ala Ile Val Asp Gly Ile Arg Phe Ser Tyr Lys
            675                 680                 685
Lys Asp Gly Ser Val Trp Leu Gln Asn Arg Met Lys Tyr Pro Val Phe
        690                 695                 700
Val Thr Ser Gly Tyr Leu Asp Glu Gln Ser Gly Gly Leu Lys Lys Asp
705                 710                 715                 720
Lys Val His Lys Val Tyr Gly Cys Ala Ser Ile Lys Thr Phe Gly Phe
                725                 730                 735
Asn Val Ser Lys Gln Ile Ile Arg Asp Ala Leu Leu Ser Lys Gln Met
            740                 745                 750
Ala Thr Met Tyr Leu Gln Gly Lys Leu Thr Pro Met Asn Tyr Ile Tyr
            755                 760                 765
Glu Lys Lys Thr Gln Glu Glu Leu Arg Arg Glu Ala Thr Arg Thr Thr
        770                 775                 780
Asp Ser Leu Ala Lys Tyr Cys Cys Val Arg Val Ser Phe Cys Lys Gly
785                 790                 795                 800
Phe Gly Glu Ala Tyr Pro Glu Arg Pro Ser Ile His Asp Cys Pro Val
                805                 810                 815
Trp Ile Glu Leu Lys Ile Asn Ile Ala Tyr Asp Phe Met Asp Ser Ile
            820                 825                 830
Cys Gln Tyr Ile Thr Asn Cys Phe Glu Pro Leu Gly Met Glu Asp Phe
            835                 840                 845
Ala Lys Leu Gly Ile Asn Val Ser Asp Asp
    850                 855

<210> SEQ ID NO 42
<211> LENGTH: 892
<212> TYPE: PRT
<213> ORGANISM: Caenorhabditis elegans
```

-continued

```
<400> SEQUENCE: 42

Met Gly Asp His His Asn Leu Thr Gly Leu Pro Gly Thr Ser Ile Pro
1               5                   10                  15

Pro Gln Phe Asn Tyr Ser Gln Pro Gly Thr Ser Thr Gly Gly Pro Leu
            20                  25                  30

Tyr Gly Gly Lys Pro Ser His Gly Leu Glu Asp Ile Pro Asp Val Glu
        35                  40                  45

Glu Tyr Glu Arg Asn Leu Leu Gly Ala Gly Ala Gly Phe Asn Leu Leu
    50                  55                  60

Asn Val Gly Asn Met Ala Asn Glu Phe Lys Pro Ile Ile Thr Leu Asp
65                  70                  75                  80

Thr Lys Pro Pro Arg Asp Ala Asn Lys Ser Leu Ala Phe Asn Gly Gly
                85                  90                  95

Leu Lys Leu Ile Thr Pro Lys Thr Glu Val Pro Asp Glu His Thr Pro
            100                 105                 110

Met Met Ser Pro Val Asn Thr Thr Thr Lys Ile Leu Gln Arg Ser Gly
            115                 120                 125

Ile Lys Met Glu Ile Pro Pro Tyr Leu Asp Pro Asp Ser Gln Asp Asp
    130                 135                 140

Asp Pro Glu Asp Gly Val Asn Tyr Pro Asp Pro Asp Leu Phe Asp Thr
145                 150                 155                 160

Lys Asn Thr Asn Met Thr Glu Tyr Asp Leu Asp Val Leu Lys Leu Gly
                165                 170                 175

Lys Pro Ala Val Asp Glu Ala Arg Lys Lys Ile Glu Val Pro Asp Ala
            180                 185                 190

Ser Ala Pro Pro Asn Lys Ile Val Glu Tyr Leu Met Tyr Tyr Arg Thr
            195                 200                 205

Leu Lys Glu Ser Glu Leu Ile Gln Leu Asn Ala Tyr Arg Thr Lys Arg
    210                 215                 220

Asn Arg Leu Ser Leu Asn Leu Val Lys Asn Asn Ile Asp Arg Glu Phe
225                 230                 235                 240

Asp Gln Lys Ala Cys Glu Ser Leu Val Lys Lys Leu Lys Asp Lys Lys
                245                 250                 255

Asn Asp Leu Gln Asn Leu Ile Asp Val Val Leu Ser Lys Gly Thr Lys
            260                 265                 270

Tyr Thr Gly Cys Ile Thr Ile Pro Arg Thr Leu Asp Gly Arg Leu Gln
        275                 280                 285

Val His Gly Arg Lys Gly Phe Pro His Val Val Tyr Gly Lys Leu Trp
    290                 295                 300

Arg Phe Asn Glu Met Thr Lys Asn Glu Thr Arg His Val Asp His Cys
305                 310                 315                 320

Lys His Ala Phe Glu Met Lys Ser Asp Met Val Cys Val Asn Pro Tyr
                325                 330                 335

His Tyr Glu Ile Val Ile Gly Thr Met Ile Val Gly Gln Arg Asp His
            340                 345                 350

Asp Asn Arg Asp Met Pro Pro His Gln Arg Tyr His Thr Pro Gly
    355                 360                 365

Arg Gln Asp Pro Val Asp Asp Met Ser Arg Phe Ile Pro Pro Ala Ser
        370                 375                 380

Ile Arg Pro Pro Met Asn Met His Thr Arg Pro Gln Pro Met Pro
385                 390                 395                 400

Gln Gln Leu Pro Ser Val Gly Ala Thr Phe Ala His Pro Leu Pro His
            405                 410                 415
```

-continued

```
Gln Ala Pro His Asn Pro Gly Val Ser His Pro Tyr Ser Ile Ala Pro
            420                 425                 430
Gln Thr His Tyr Pro Leu Asn Met Asn Pro Ile Pro Gln Met Pro Gln
        435                 440                 445
Met Pro Gln Met Pro Pro Leu His Gln Gly Tyr Gly Met Asn Gly
    450                 455                 460
Pro Ser Cys Ser Ser Glu Asn Asn Pro Phe His Gln Asn His His
465                 470                 475                 480
Tyr Asn Asp Ile Ser His Pro Asn His Tyr Ser Tyr Asp Cys Gly Pro
                485                 490                 495
Asn Leu Tyr Gly Phe Pro Thr Pro Tyr Pro Asp Phe His His Pro Phe
            500                 505                 510
Asn Gln Gln Pro His Gln Pro Pro Gln Leu Ser Gln Asn His Thr Ser
        515                 520                 525
Gln Gln Gly Ser His Gln Pro Gly His Gln Gly Val Pro Asn Asp
    530                 535                 540
Pro Pro Ile Ser Arg Pro Val Leu Gln Pro Ser Thr Val Thr Leu Asp
545                 550                 555                 560
Val Phe Arg Arg Tyr Cys Arg Gln Thr Phe Gly Asn Arg Phe Phe Glu
                565                 570                 575
Gly Glu Ser Glu Gln Ser Gly Ala Ile Ile Arg Ser Ser Asn Lys Phe
            580                 585                 590
Ile Glu Glu Phe Asp Ser Pro Ile Cys Gly Val Thr Val Arg Pro
        595                 600                 605
Arg Met Thr Asp Gly Glu Val Leu Glu Asn Ile Met Pro Glu Asp Ala
    610                 615                 620
Pro Tyr His Asp Ile Cys Lys Phe Ile Leu Arg Leu Thr Ser Glu Ser
625                 630                 635                 640
Val Thr Phe Ser Gly Glu Gly Pro Glu Val Ser Asp Leu Asn Glu Lys
                645                 650                 655
Trp Gly Thr Ile Val Tyr Tyr Glu Lys Asn Leu Gln Ile Gly Glu Lys
            660                 665                 670
Lys Cys Ser Arg Gly Asn Phe His Val Asp Gly Gly Phe Ile Cys Ser
        675                 680                 685
Glu Asn Arg Tyr Ser Leu Gly Leu Glu Pro Asn Pro Ile Arg Glu Pro
    690                 695                 700
Val Ala Phe Lys Val Arg Lys Ala Ile Val Asp Gly Ile Arg Phe Ser
705                 710                 715                 720
Tyr Lys Lys Asp Gly Ser Val Trp Leu Gln Asn Arg Met Lys Tyr Pro
                725                 730                 735
Val Phe Val Thr Ser Gly Tyr Leu Asp Glu Gln Ser Gly Gly Leu Lys
            740                 745                 750
Lys Asp Lys Val His Lys Val Tyr Gly Cys Ala Ser Ile Lys Thr Phe
        755                 760                 765
Gly Phe Asn Val Ser Lys Gln Ile Ile Arg Asp Ala Leu Leu Ser Lys
    770                 775                 780
Gln Met Ala Thr Met Tyr Leu Gln Gly Lys Leu Thr Pro Met Asn Tyr
785                 790                 795                 800
Ile Tyr Glu Lys Lys Thr Gln Glu Glu Leu Arg Arg Glu Ala Thr Arg
                805                 810                 815
Thr Thr Asp Ser Leu Ala Lys Tyr Cys Cys Val Arg Val Ser Phe Cys
            820                 825                 830
```

Lys Gly Phe Gly Glu Ala Tyr Pro Glu Arg Pro Ser Ile His Asp Cys
    835                 840                 845

Pro Val Trp Ile Glu Leu Lys Ile Asn Ile Ala Tyr Asp Phe Met Asp
        850                 855                 860

Ser Ile Cys Gln Tyr Ile Thr Asn Cys Phe Glu Pro Leu Gly Met Glu
865                 870                 875                 880

Asp Phe Ala Lys Leu Gly Ile Asn Val Ser Asp Asp
                885                 890

<210> SEQ ID NO 43
<211> LENGTH: 3499
<212> TYPE: DNA
<213> ORGANISM: Caenorhabditis elegans

<400> SEQUENCE: 43

| | | | | | |
|---|---|---|---|---|---|
| tgatctttca | agccgaagca | atcaagacct | caaagccaat | caactctact | cacttttctt | 60 |
| cagaaccttact | acttttgtg | tcactttccc | caaaaaccgt | tcaagctgct | gccttcactc | 120 |
| tcatcccctc | ctcttactcc | ttctttctcg | tccgctacta | ctgtatcttc | tggacatcta | 180 |
| cctgtataca | caccagtggc | cagtcatctg | ccattacaat | ttcatcaatt | gacacttctt | 240 |
| caacaacaac | cgccgtcctc | attcactccc | gattcttcct | catcctcaac | atcgtcgtct | 300 |
| ttggctgaaa | ttcccgaaga | cgttatgatg | gagatgctgg | tagatcaggg | aactgatgca | 360 |
| tcgtcatccg | cctccacgtc | cacctcatct | gtttcgagat | tcggagcgga | cacgttcatg | 420 |
| aatacaccgg | atgatgtgat | gatgaatgat | gatatgtgaac | cgattcctcg | tgatcggtgc | 480 |
| aatacgtggc | caatgcgtag | gccgcaactc | gaaccaccac | tcaactcgag | tcccattatt | 540 |
| catgaacaaa | ttcctgaaga | agatgctgac | ctatacggga | gcaatgagca | atgtggacag | 600 |
| ctcggcggag | catcttcaaa | cgggtcgaca | gcaatgcttc | atactccaga | tggaagcaat | 660 |
| tctcatcaga | atcgtttct | tcggagtttc | agaatgtccg | aatcgccaga | cgataccgta | 720 |
| tcgggaaaaa | agacaacgac | cagacggaac | gcttgggaa | atatgtcata | tgctgaactt | 780 |
| atcactacag | ccattatggc | tagtccagag | aaacggttaa | ctcttgcaca | agtttacgaa | 840 |
| tggatggtcc | agaatgttcc | atacttcagg | gataagggag | attcgaacag | ttcagctgga | 900 |
| tggaagaact | cgatccgtca | caatctgtct | cttcattctc | gtttcatgcg | aattcagaat | 960 |
| gaaggagccg | gaaagagctc | gtggtgggtt | attaatccag | atgcaaagcc | aggaatgaat | 1020 |
| ccacggcgta | cacgtgaacg | atccaatact | attgagacga | ctacaaaggc | tcaactcgaa | 1080 |
| aaatctcgcc | gcggagccaa | gaagaggata | aaggagagag | cattgatggg | ctcccttcac | 1140 |
| tcgacactta | atggaaattc | gattgccgga | tcgattcaaa | cgatttctca | cgatttgtat | 1200 |
| gatgatgatc | aatgcaagga | gcatttgata | acgttccatc | atctttccgt | ccccgaactc | 1260 |
| aatcgaacct | ctcgattcct | ggatcgtcgt | ctcgtgtttc | tccagctatt | ggaagtgata | 1320 |
| tctatgatga | tctagaattc | ccatcatggg | ttggcgaatc | ggttccagca | attccaagtg | 1380 |
| atattgttga | tagaactgat | caaatgcgta | tcgatgcaac | tactcatagt | tggtggagtt | 1440 |
| cagattaagc | aggagtcgaa | gccgattaag | acggaaccaa | ttgctccacc | accatcatac | 1500 |
| cacgagttga | acagtgtccg | tggatcgtgt | gctcagaatc | cacttcttcg | aaatccaatt | 1560 |
| gtgccaagca | ctaacttcaa | gccaatgcca | ctaccgggtg | cctatggaaa | ctatcaaaat | 1620 |
| ggtggaataa | ctccaatcaa | ttggctatca | acatccaact | catctccact | gcctggaatt | 1680 |
| caatcgtgtg | gaattgtagc | tgcacagcat | actgtcgctt | cttcatcggc | tcttccaatt | 1740 |
| gatttggaaa | atctgacact | tcccgatcag | ccactgatgg | atactatgga | tgttgatgca | 1800 |

```
ttgatcagac atgagctgag tcaagctgga gggcagcata ttcattttga tttgtaaatt    1860
ctcttcattt tgtttccct ggtgttgttc gaaagagaga tagcaaagca gcgaggagtg     1920
aggtaagcag caataaaaat tttggatttt tttttggttt ttccagaaat aatcgatttt    1980
ctggaaaatt tcaaaaaaaa atcgaattt ttagttaatt atttgatgag aaaaaaaat     2040 tagaaaacat aaggaaaaat gaaaagcgtt tttttttttc gaaattttta gaattctcct   2100
acatttccaa taagggcctt agaactgcaa acaaacaaaa attggaattt tcgaatcaaa   2160
aagttcccga ataaaagtag ttcgaatatt aaaaagcatt taatttcctc tttaaaaaaa   2220
ttgaataata gccgaaattt gcagatttt tttctgaaaa tcgaaaaacc aaaattttt    2280 gatttttta atttttttt tactttccag atagtaaaat cattagcact gaaaattatt    2340
tgaaaaaaaa cttcaaatac aaattttgtt ttcgaaaaaa aaaatttaaa tatatatttt   2400
cagaaatctt ccgtcttcat cttttcaaat ccctacctac acacactcaa cgatcatcac   2460
agccagacca tcaatattct tccaaatttt gacgtcgtta attttttttc agttttttca   2520
aaaactctat tttctatttt ctgtcgtttg ttcccctttc tctcgtctaa ttccaacaca   2580
ttcatcccag tgacgtcgtg taataataat ataaatacc tcttctctct ttcttccct    2640 aatgcgaaat atcgaaaaac cgttgattat tacctctttt ttcttgtttt tttttctct   2700 ctctctctcc cgtcatccag gttcttcact ctttaaatgc tacctctatc ccatcttttt   2760
cgctgtaaat ttgtttcgca atcaaaactg ctaaaacaca ttccccaatc tgtcttttt   2820 aattgaattt ttcaaaaaat ttgatttctt gatttctctt gtaattcttt aatttcctc   2880 tttttttcc ccctggtagc aaatgtctag cgattctctt tcttttttg tttaactttc    2940 acatctggcc gattcgaatc ctccgtatac acacacacat agtaatctac ctccaaaatt   3000
ttactgaaag atgtgatccc ctctctgtct ccctctacaa aacattattt gtctgtttgt   3060
gtatattgcc accacgtcga ttttaaatta aaaccatcgt ttttcttct tttctactt    3120 tttctcgaaa aatttaacaa cacacaaaaa aatccttcaa aaatctcag ttttaaatgg    3180 tgtggcaata tatcggatcc ccctctacac cagaacagtc ttgcaatttc agagaatgat   3240
tttcagattt tcatatcac aggcccccctt ttttgcttg ttttttttctc tacctctctt   3300 tcttttcatt ctatttctct ctcttgtttt ctctctgtta tcctgtacat tttccttcca   3360
attctttctg gctatttctg attttcgagt tcatattctc tacgtctcac tttctctcgc   3420
gccacgcccc cttttcgtc tccctccgcc cccaaatata tttgcgactg tatgatgatg    3480
atgatgattt aataaaaat                                                 3499

<210> SEQ ID NO 44
<211> LENGTH: 2704
<212> TYPE: DNA
<213> ORGANISM: Caenorhabditis elegans

<400> SEQUENCE: 44
ttacacgtgg ccaatgcaac aatacatcta tcaggaatcg tcagcaacca ttccccatca     60
ccatttaaat caacacaaca atccgtatca tccaatgcat cctcatcatc aattacctca    120
tatgcaacaa cttcctcaac ctctattgaa tcttaacatg acgacgttaa catcttctgg    180
cagttccgtg gccagttcca ttggaggcgg agctcaatgc tctccgtgcg cgtcgggctc    240
ctcgaccgct gcaacaaatt cctctcaaca gcagcagacc gttggtcaaa tgcttgctgc    300
atcggtgcct tgttcttcat ctggcatgac acttggaatg tcacttaatc tgtcacaagg    360
```

-continued

```
cggtggtcca atgccggcaa aaagaagcg ttgtcgtaag aagccaaccg atcaattggc    420
acagaagaaa ccgaatccat ggggtgagga atcctattcg atatcattg ccaaagcatt    480 ggaatcggcg ccagacggaa ggcttaaact caatgagatt tatcaatggt tctctgataa    540
tattccctac tttggagaac gatctagtcc cgaggaggcc gccggatgga agaactcgat    600
ccgtcacaat ctgtctcttc attctcgttt catgcgaatt cagaatgaag gagccggaaa    660
gagctcgtgg tgggttatta atccagatgc aaagccagga atgaatccac ggcgtacacg    720
tgaacgatcc aatactattg agacgactac aaaggctcaa ctcgaaaaat ctcgccgcgg    780
agccaagaag aggataaagg agagagcatt gatgggctcc cttcactcga cacttaatgg    840
aaattcgatt gccggatcga ttcaaacgat ttctcacgat ttgtatgatg atgattcaat    900
gcaaggagca tttgataacg ttccatcatc tttccgtccc cgaactcaat cgaacctctc    960
gattcctgga tcgtcgtctc gtgtttctcc agctattgga agtgatatct atgatgatct   1020
agaattccca tcatgggttg gcgaatcggt tccagcaatt ccaagtgata ttgttgatag   1080
aactgatcaa atgcgtatcg atgcaactac tcatattggt ggagttcaga ttaagcagga   1140
gtcgaagccg attaagacgg aaccaattgc tccaccacca tcataccacg agttgaacag   1200
tgtccgtgga tcgtgtgctc agaatccact tcttcgaaat ccaattgtgc caagcactaa   1260
cttcaagcca atgccactac cgggtgccta tggaaactat caaaatggtg gaataactcc   1320
aatcaattgg ctatcaacat ccaactcatc tccactgcct ggaattcaat cgtgtggaat   1380
tgtagctgca cagcatactg tcgcttcttc atcggctctt ccaattgatt tggaaaatct   1440
gacacttccc gatcagccac tgatggatac tatggatgtt gatgcattga tcagacatga   1500
gctgagtcaa gctggagggc agcatattca ttttgatttg taaattctct tcattttgtt   1560 tccctggtg ttgttcgaaa gagagatagc aaagcagcga ggagtgagaa atcttccgtc   1620
ttcatctttt caaatcccta cctacacaca ctcaacgatc atcacagcca gaccatcaat   1680
attcttccaa attttgacgt cgttaatttt ttttcagttt tttcaaaaac tctatttttct   1740 attttctgtc gtttgttccc ctttctctcg tctaattcca acacattcat cccagtgacg   1800
tcgtgtaata ataatataaa atacctcttc tctcttttctt cccctaatgc gaaatatcga   1860 aaaccgttg attattacct ctttttttctt gttttttttt tctctctctc tctcccgtca   1920
tccaggttct tcactcttta aatgctacct ctatcccatc ttttttcgctg taaatttgtt   1980 tcgcaatcaa aactgctaaa acacattccc caatctgtct tttttaattg aattttttcaa   2040 aaaatttgat tcttgatttt ctcttgtaat tctttaattt tcctcttttt tttcccctg    2100 gtagcaaatg tctagcgatt ctctttcttt ttttgtttaa ctttcacatc tggccgattc   2160
gaatcctccg tatacacaca cacatagtaa tctacctcca aaattttact gaaagatgtg   2220 atccctctc tgtctccctc tacaaaacat tatttgtctg tttgtgtata ttgccaccac   2280
gtcgatttta aattaaaacc atcgtttttt cttcttttct acttttttct cgaaaaattt   2340
aacaacacac aaaaaaatcc ttcaaaaaat ctcagtttta aatggtgtgg caatatatcg   2400 gatcccctc tacaccagaa cagtcttgca atttcagaga atgatttttca gattttttcat   2460 atcacaggcc ccctttttt gcttgttttt ttctctacct ctctttcttt tcattctatt   2520
tctctctctt gttttctctc tgttatcctg tacattttcc ttccaattct ttctggctat   2580
ttctgatttt cgagttcata ttctctacgt ctcacttttct ctcgcgccac gcccccttttt   2640 tcgtctccct ccgcccccaa atatatttgc gactgtatga tgatgatgat gattaataa   2700 aaat                                                                2704
```

<210> SEQ ID NO 45
<211> LENGTH: 510
<212> TYPE: PRT
<213> ORGANISM: Caenorhabditis elegans

<400> SEQUENCE: 45

| Met | Met | Glu | Met | Leu | Val | Asp | Gln | Gly | Thr | Asp | Ala | Ser | Ser | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Thr | Ser | Thr | Ser | Ser | Val | Ser | Arg | Phe | Gly | Ala | Asp | Thr | Phe | Met |
|     |     |     | 20  |     |     |     |     | 25  |     |     |     |     | 30  |     |     |
| Asn | Thr | Pro | Asp | Asp | Val | Met | Met | Asn | Asp | Asp | Met | Glu | Pro | Ile | Pro |
|     |     | 35  |     |     |     |     | 40  |     |     |     |     | 45  |     |     |     |
| Arg | Asp | Arg | Cys | Asn | Thr | Trp | Pro | Met | Arg | Arg | Pro | Gln | Leu | Glu | Pro |
|     | 50  |     |     |     |     | 55  |     |     |     |     | 60  |     |     |     |     |
| Pro | Leu | Asn | Ser | Ser | Pro | Ile | Ile | His | Glu | Gln | Ile | Pro | Glu | Glu | Asp |
| 65  |     |     |     |     | 70  |     |     |     |     | 75  |     |     |     |     | 80  |
| Ala | Asp | Leu | Tyr | Gly | Ser | Asn | Glu | Gln | Cys | Gly | Gln | Leu | Gly | Gly | Ala |
|     |     |     |     | 85  |     |     |     |     | 90  |     |     |     |     | 95  |     |
| Ser | Ser | Asn | Gly | Ser | Thr | Ala | Met | Leu | His | Thr | Pro | Asp | Gly | Ser | Asn |
|     |     |     | 100 |     |     |     |     | 105 |     |     |     |     | 110 |     |     |
| Ser | His | Gln | Thr | Ser | Phe | Pro | Ser | Asp | Phe | Arg | Met | Ser | Glu | Ser | Pro |
|     |     |     | 115 |     |     |     |     | 120 |     |     |     |     | 125 |     |     |
| Asp | Asp | Thr | Val | Ser | Gly | Lys | Lys | Thr | Thr | Thr | Arg | Arg | Asn | Ala | Trp |
|     | 130 |     |     |     |     | 135 |     |     |     |     | 140 |     |     |     |     |
| Gly | Asn | Met | Ser | Tyr | Ala | Glu | Leu | Ile | Thr | Thr | Ala | Ile | Met | Ala | Ser |
| 145 |     |     |     |     | 150 |     |     |     |     | 155 |     |     |     |     | 160 |
| Pro | Glu | Lys | Arg | Leu | Thr | Leu | Ala | Gln | Val | Tyr | Glu | Trp | Met | Val | Gln |
|     |     |     |     | 165 |     |     |     |     | 170 |     |     |     |     | 175 |     |
| Asn | Val | Pro | Tyr | Phe | Arg | Asp | Lys | Gly | Asp | Ser | Asn | Ser | Ser | Ala | Gly |
|     |     |     | 180 |     |     |     |     | 185 |     |     |     |     | 190 |     |     |
| Trp | Lys | Asn | Ser | Ile | Arg | His | Asn | Leu | Ser | Leu | His | Ser | Arg | Phe | Met |
|     |     |     | 195 |     |     |     |     | 200 |     |     |     |     | 205 |     |     |
| Arg | Ile | Gln | Asn | Glu | Gly | Ala | Gly | Lys | Ser | Ser | Trp | Trp | Val | Ile | Asn |
|     | 210 |     |     |     |     | 215 |     |     |     |     | 220 |     |     |     |     |
| Pro | Asp | Ala | Lys | Pro | Gly | Met | Asn | Pro | Arg | Arg | Thr | Arg | Glu | Arg | Ser |
| 225 |     |     |     |     | 230 |     |     |     |     | 235 |     |     |     |     | 240 |
| Asn | Thr | Ile | Glu | Thr | Thr | Thr | Lys | Ala | Gln | Leu | Glu | Lys | Ser | Arg | Arg |
|     |     |     |     | 245 |     |     |     |     | 250 |     |     |     |     | 255 |     |
| Gly | Ala | Lys | Lys | Arg | Ile | Lys | Glu | Arg | Ala | Leu | Met | Gly | Ser | Leu | His |
|     |     |     | 260 |     |     |     |     | 265 |     |     |     |     | 270 |     |     |
| Ser | Thr | Leu | Asn | Gly | Asn | Ser | Ile | Ala | Gly | Ser | Ile | Gln | Thr | Ile | Ser |
|     |     |     | 275 |     |     |     |     | 280 |     |     |     |     | 285 |     |     |
| His | Asp | Leu | Tyr | Asp | Asp | Ser | Met | Gln | Gly | Ala | Phe | Asp | Asn | Val |     |
|     | 290 |     |     |     |     | 295 |     |     |     |     | 300 |     |     |     |     |
| Pro | Ser | Ser | Phe | Arg | Pro | Arg | Thr | Gln | Ser | Asn | Leu | Ser | Ile | Pro | Gly |
| 305 |     |     |     |     | 310 |     |     |     |     | 315 |     |     |     |     | 320 |
| Ser | Ser | Ser | Arg | Val | Ser | Pro | Ala | Ile | Gly | Ser | Asp | Ile | Tyr | Asp | Asp |
|     |     |     |     | 325 |     |     |     |     | 330 |     |     |     |     | 335 |     |
| Leu | Glu | Phe | Pro | Ser | Trp | Val | Gly | Glu | Ser | Val | Pro | Ala | Ile | Pro | Ser |
|     |     |     | 340 |     |     |     |     | 345 |     |     |     |     | 350 |     |     |
| Asp | Ile | Val | Asp | Arg | Thr | Asp | Gln | Met | Arg | Ile | Asp | Ala | Thr | Thr | His |
|     |     |     | 355 |     |     |     |     | 360 |     |     |     |     | 365 |     |     |
| Ile | Gly | Gly | Val | Gln | Ile | Lys | Gln | Glu | Ser | Lys | Pro | Ile | Lys | Thr | Glu |

-continued

```
                370                 375                 380
        Pro Ile Ala Pro Pro Ser Tyr His Glu Leu Asn Ser Val Arg Gly
        385                 390                 395                 400

Ser Cys Ala Gln Asn Pro Leu Leu Arg Asn Pro Ile Val Pro Ser Thr
                        405                 410                 415

Asn Phe Lys Pro Met Pro Leu Pro Gly Ala Tyr Gly Asn Tyr Gln Asn
                    420                 425                 430

Gly Gly Ile Thr Pro Ile Asn Trp Leu Ser Thr Ser Asn Ser Ser Pro
                435                 440                 445

Leu Pro Gly Ile Gln Ser Cys Gly Ile Val Ala Ala Gln His Thr Val
            450                 455                 460

Ala Ser Ser Ala Leu Pro Ile Asp Leu Glu Asn Leu Thr Leu Pro
        465                 470                 475                 480

Asp Gln Pro Leu Met Asp Thr Met Asp Val Asp Ala Leu Ile Arg His
                        485                 490                 495

Glu Leu Ser Gln Ala Gly Gly Gln His Ile His Phe Asp Leu
                    500                 505                 510

<210> SEQ ID NO 46
<211> LENGTH: 509
<212> TYPE: PRT
<213> ORGANISM: Caenorhabditis elegans

<400> SEQUENCE: 46

Met Gln Gln Tyr Ile Tyr Gln Glu Ser Ser Ala Thr Ile Pro His His
        1               5                   10                  15

His Leu Asn Gln His Asn Asn Pro Tyr His Pro Met His Pro His His
                        20                  25                  30

Gln Leu Pro His Met Gln Gln Leu Pro Gln Pro Leu Leu Asn Leu Asn
                    35                  40                  45

Met Thr Thr Leu Thr Ser Ser Gly Ser Ser Val Ala Ser Ser Ile Gly
                50                  55                  60

Gly Gly Ala Gln Cys Ser Pro Cys Ala Ser Gly Ser Ser Thr Ala Ala
        65                  70                  75                  80

Thr Asn Ser Ser Gln Gln Gln Thr Val Gly Gln Met Leu Ala Ala
                        85                  90                  95

Ser Val Pro Cys Ser Ser Ser Gly Met Thr Leu Gly Met Ser Leu Asn
                    100                 105                 110

Leu Ser Gln Gly Gly Pro Met Pro Ala Lys Lys Arg Cys Arg
                115                 120                 125

Lys Lys Pro Thr Asp Gln Leu Ala Gln Lys Lys Pro Asn Pro Trp Gly
        130                 135                 140

Glu Ser Tyr Ser Asp Ile Ile Ala Lys Ala Leu Glu Ser Ala Pro
        145                 150                 155                 160

Asp Gly Arg Leu Lys Leu Asn Glu Ile Tyr Gln Trp Phe Ser Asp Asn
                        165                 170                 175

Ile Pro Tyr Phe Gly Glu Arg Ser Ser Pro Glu Glu Ala Ala Gly Trp
                    180                 185                 190

Lys Asn Ser Ile Arg His Asn Leu Ser Leu His Ser Arg Phe Met Arg
                195                 200                 205

Ile Gln Asn Glu Gly Ala Gly Lys Ser Ser Trp Trp Val Ile Asn Pro
        210                 215                 220

Asp Ala Lys Pro Gly Met Asn Pro Arg Arg Thr Arg Glu Arg Ser Asn
        225                 230                 235                 240
```

```
Thr Ile Glu Thr Thr Thr Lys Ala Gln Leu Glu Lys Ser Arg Arg Gly
                245                 250                 255

Ala Lys Lys Arg Ile Lys Glu Arg Ala Leu Met Gly Ser Leu His Ser
            260                 265                 270

Thr Leu Asn Gly Asn Ser Ile Ala Gly Ser Ile Gln Thr Ile Ser His
        275                 280                 285

Asp Leu Tyr Asp Asp Ser Met Gln Gly Ala Phe Asp Asn Val Pro
    290                 295                 300

Ser Ser Phe Arg Pro Arg Thr Gln Ser Asn Leu Ser Ile Pro Gly Ser
305                 310                 315                 320

Ser Ser Arg Val Ser Pro Ala Ile Gly Ser Asp Ile Tyr Asp Asp Leu
            325                 330                 335

Glu Phe Pro Ser Trp Val Gly Glu Ser Val Pro Ala Ile Pro Ser Asp
            340                 345                 350

Ile Val Asp Arg Thr Asp Gln Met Arg Ile Asp Ala Thr Thr His Ile
            355                 360                 365

Gly Gly Val Gln Ile Lys Gln Glu Ser Lys Pro Ile Lys Thr Glu Pro
    370                 375                 380

Ile Ala Pro Pro Pro Ser Tyr His Glu Leu Asn Ser Val Arg Gly Ser
385                 390                 395                 400

Cys Ala Gln Asn Pro Leu Leu Arg Asn Pro Ile Val Pro Ser Thr Asn
                405                 410                 415

Phe Lys Pro Met Pro Leu Pro Gly Ala Tyr Gly Asn Tyr Gln Asn Gly
            420                 425                 430

Gly Ile Thr Pro Ile Asn Trp Leu Ser Thr Ser Asn Ser Ser Pro Leu
        435                 440                 445

Pro Gly Ile Gln Ser Cys Gly Ile Val Ala Ala Gln His Thr Val Ala
    450                 455                 460

Ser Ser Ser Ala Leu Pro Ile Asp Leu Glu Asn Leu Thr Leu Pro Asp
465                 470                 475                 480

Gln Pro Leu Met Asp Thr Met Asp Val Asp Ala Leu Ile Arg His Glu
                485                 490                 495

Leu Ser Gln Ala Gly Gly Gln His Ile His Phe Asp Leu
            500                 505
```

<210> SEQ ID NO 47
<211> LENGTH: 3504
<212> TYPE: DNA
<213> ORGANISM: Caenorhabditis elegans

<400> SEQUENCE: 47
cggaagccat ggagctcgag atctgattgc tggacacgga cggaactccg acgtatctcg    60
cagatgcatg ttaacatttt acatccacaa ctgcaaacga tggtcgagca gtggcaaatg   120
cgagaacgcc catcgctgga gaccgagaat ggcaaaggat cgctgctcct ggaaaatgaa   180
ggtgtcgcag atatcatcac tatgtgtcca ttcgagaag ttattagtgt agtatttccg   240
tggtttcttg caaatgtgcg aacatcgcta gaaatcaagc tatcagattt caaacatcaa   300
cttttcgaat tgattgctcc gatgaagtgg ggaacatatt ccgtaaagcc acaggattat   360
gtgttcagac agttgaataa tttcggcgaa attgaagtta tatttaacga cgatcaaccc   420
ctgtcgaaat tagagctcca cggcactttc ccaatgcttt ttctctacca acctgatgga   480
ataaacaggg ataaagaatt aatgagtgat ataagtcatt gtctaggata ctcactggat   540
aaactggaag agagcctcga tgaggaactc cgtcaatttc gtgcttctct ctgggctcgt   600

```
acgaagaaaa cgtgcttgac acgtggactt gagggtacca gtcactacgc gttccccgaa      660
gaacagtact tgtgtgttgg tgaatcgtgc ccgaaagatt tggaatcaaa agtcaaggct      720
gccaagctga gttatcagat gttttggaga aacgtaaag cggaaatcaa tggagtttgc       780
gagaaaatga tgaagattca aattgaattc aatccgaacg aaactccgaa atctctgctt      840
cacacgtttc tctacgaaat gcgaaaattg gatgtatacg ataccgatga tcctgcagat      900
gaaggatggt ttcttcaatt ggctggacgt accacgtttg ttacaaatcc agatgtcaaa      960
cttacgtctt atgatggtgt ccgttcggaa ctggaaagct atcgatgccc tggattcgtt     1020
gttcgccgac aatcactagt cctcaaagac tattgtcgcc caaaaccact ctacgaacca     1080
cattatgtga gagcacacga acgaaaactt gctctagacg tgctcagcgt gtctatagat     1140
agcacaccaa acagagcaa gaacagtgac atggttatga ctgattttcg tccgacagct      1200
tcactcaaac aagtttcact ttgggacctt gacgcgaatc ttatgatacg gcctgtgaat     1260
atttctggat tcgatttccc ggccgacgtg gatatgtacg ttcgaatcga attcagtgta     1320
tatgtgggga cactgacgct ggcatcaaaa tctacaacaa agtgaatgc tcaatttgca      1380 aaatggaata aggaaatgta cacttttgat ctatacatga aggatatgcc accatctgca     1440
gtactcagca ttcgtgtttt gtacggaaaa gtgaaattaa aaagtgaaga attcgaagtt     1500
ggttgggtaa atatgtccct aaccgattgg agagatgaac tacgacaagg acaattttta     1560
ttccatctgt gggctcctga accgactgcc aatcgtagta ggatcggaga aaatggagca     1620
aggataggca ccaacgcagc ggttacaatt gaaatctcaa gttatggtgg tagagttcga     1680
atgccgagtc aaggacaata cacatatctc gtcaagcacc gaagtacttg gacggaaact     1740
ttgaatatta tgggtgatga ctatgagtcg tgtatcagag atccaggata taagaagctt     1800
cagatgcttg tcaagaagca tgaatctgga attgtattag aggaagatga acaacgtcat     1860
gtctggatgt ggaggagata cattcaaaag caggagcctg atttgctcat tgtgctctcc     1920
gaactcgcat ttgtgtggac tgatcgtgag aacttttccg agctctatgt gatgcttgaa     1980
aaatggaaac cgccgagtgt ggcagccgcg ttgactttgc ttggaaaacg ttgcacggat     2040
cgtgtgattc gaaagtttgc agtggagaag ttgaatgagc agctgagccc ggtcacattc     2100
catcttttca tattgcctct catacaggcg ttgaagtacg aaccgcgtgc tcaatcggaa     2160
gttggaatga tgctcttgac tagagctctc tgcgattatc gaattggaca tcgactttc     2220 tggctgctcc gtgcagagat tgctcgtttg agagattgtg atctgaaaag tgaagaatat     2280
cgccgtatct cacttctgat ggaagcttac ctccgtggaa atgaagagca catcaagatc     2340
atcacccgac aagttgacat ggttgatgag ctcacacgaa tcagcactct tgtcaaagga     2400
atgccaaaag atgttgctac gatgaaactg cgtgacgagc ttcgatcgat tagtcataaa     2460
atggaaaata tggattctcc actggatcct gtgtacaaac tgggtgaaat gataatcgac     2520
aaagccatcg tcctaggaag tgcaaaacgt ccgttaatgc ttcactggaa gaacaaaaat     2580
ccaaagagtg acctgcacct tccgttctgt gcaatgatct tcaagaatgg agacgatctt     2640
cgccaggaca tgcttgttct tcaagttctc gaagttatgg ataacatctg gaaggctgca     2700
aacattgatt gctgtttgaa cccgtacgca gttcttccaa tggagaaat gattggaatt      2760 attgaagttg tgcctaattg taaaacaata ttcgagattc aagttggaac aggattcatg     2820
aatacagcag ttcggagtat tgatccttcg tttatgaata gtggattcg gaaacaatgc      2880 ggaattgaag atgaaaagaa gaaaagcaaa aaggactcta cgaaaaatcc catcgaaaag     2940
aagattgata atactcaagc catgaagaaa tattttgaaa gtgtcgatcg attcctatac     3000
```

-continued

```
tcgtgtgttg gatattcagt tgccacgtac ataatgggaa tcaaggatcg tcacagtgat    3060
aatctgatgc tcactgaaga tggaaaatat gtccacattg atttcggtca cattttggga    3120
cacggaaaga ccaaacttgg gatccagcga gatcgtcaac cgtttattct aaccgaacac    3180
tttatgacag tgattcgatc gggtaaatct gtggatggaa attcgcatga gctacaaaaa    3240
ttcaaaacgt tatgcgtcga agcctacgaa gtaatgtgga ataatcgaga tttgttcgtt    3300
tccttgttca ccttgatgct cggaatggag ttgcctgagc tgtcgacgaa agcggatttg    3360
gatcatttga agaaaaccct cttctgcaat ggagaaagca aagaagaagc gagaaagttt    3420
ttcgctggaa tctacgaaga agccttcaat ggatcatggt ctaccaaaac gaattggctc    3480
ttccacgcag tcaaacacta ctga                                           3504
```

<210> SEQ ID NO 48
<211> LENGTH: 1167
<212> TYPE: PRT
<213> ORGANISM: Caenorhabditis elegans

<400> SEQUENCE: 48

```
Arg Lys Pro Trp Ser Arg Ser Asp Cys Trp Thr Arg Thr Glu Leu
 1               5                  10                  15

Arg Arg Ile Ser Gln Met His Val Asn Ile Leu His Pro Gln Leu Gln
            20                  25                  30

Thr Met Val Glu Gln Trp Gln Met Arg Glu Arg Pro Ser Leu Glu Thr
        35                  40                  45

Glu Asn Gly Lys Gly Ser Leu Leu Glu Asn Glu Gly Val Ala Asp
    50                  55                  60

Ile Ile Thr Met Cys Pro Phe Gly Glu Val Ile Ser Val Val Phe Pro
65                  70                  75                  80

Trp Phe Leu Ala Asn Val Arg Thr Ser Leu Glu Ile Lys Leu Ser Asp
                85                  90                  95

Phe Lys His Gln Leu Phe Glu Leu Ile Ala Pro Met Lys Trp Gly Thr
            100                 105                 110

Tyr Ser Val Lys Pro Gln Asp Tyr Val Phe Arg Gln Leu Asn Asn Phe
        115                 120                 125

Gly Glu Ile Glu Val Ile Phe Asn Asp Asp Gln Pro Leu Ser Lys Leu
    130                 135                 140

Glu Leu His Gly Thr Phe Pro Met Leu Phe Leu Tyr Gln Pro Asp Gly
145                 150                 155                 160

Ile Asn Arg Asp Lys Glu Leu Met Ser Asp Ile Ser His Cys Leu Gly
                165                 170                 175

Tyr Ser Leu Asp Lys Leu Glu Glu Ser Leu Asp Glu Glu Leu Arg Gln
            180                 185                 190

Phe Arg Ala Ser Leu Trp Ala Arg Thr Lys Lys Thr Cys Leu Thr Arg
        195                 200                 205

Gly Leu Glu Gly Thr Ser His Tyr Ala Phe Pro Glu Glu Gln Tyr Leu
    210                 215                 220

Cys Val Gly Glu Ser Cys Pro Lys Asp Leu Glu Ser Lys Val Lys Ala
225                 230                 235                 240

Ala Lys Leu Ser Tyr Gln Met Phe Trp Arg Lys Arg Lys Ala Glu Ile
                245                 250                 255

Asn Gly Val Cys Glu Lys Met Met Lys Ile Gln Ile Glu Phe Asn Pro
            260                 265                 270

Asn Glu Thr Pro Lys Ser Leu Leu His Thr Phe Leu Tyr Glu Met Arg
```

-continued

```
                275                 280                 285
Lys Leu Asp Val Tyr Asp Thr Asp Pro Ala Asp Glu Gly Trp Phe
    290                 295                 300
Leu Gln Leu Ala Gly Arg Thr Thr Phe Val Thr Asn Pro Asp Val Lys
305                 310                 315                 320
Leu Thr Ser Tyr Asp Gly Val Arg Ser Glu Leu Glu Ser Tyr Arg Cys
                325                 330                 335
Pro Gly Phe Val Val Arg Arg Gln Ser Leu Val Leu Lys Asp Tyr Cys
                340                 345                 350
Arg Pro Lys Pro Leu Tyr Glu Pro His Tyr Val Arg Ala His Glu Arg
                355                 360                 365
Lys Leu Ala Leu Asp Val Leu Ser Val Ser Ile Asp Ser Thr Pro Lys
    370                 375                 380
Gln Ser Lys Asn Ser Asp Met Val Met Thr Asp Phe Arg Pro Thr Ala
385                 390                 395                 400
Ser Leu Lys Gln Val Ser Leu Trp Asp Leu Asp Ala Asn Leu Met Ile
                405                 410                 415
Arg Pro Val Asn Ile Ser Gly Phe Asp Phe Pro Ala Asp Val Asp Met
                420                 425                 430
Tyr Val Arg Ile Glu Phe Ser Val Tyr Val Gly Thr Leu Thr Leu Ala
                435                 440                 445
Ser Lys Ser Thr Thr Lys Val Asn Ala Gln Phe Ala Lys Trp Asn Lys
    450                 455                 460
Glu Met Tyr Thr Phe Asp Leu Tyr Met Lys Asp Met Pro Pro Ser Ala
465                 470                 475                 480
Val Leu Ser Ile Arg Val Leu Tyr Gly Lys Val Lys Leu Lys Ser Glu
                485                 490                 495
Glu Phe Glu Val Gly Trp Val Asn Met Ser Leu Thr Asp Trp Arg Asp
                500                 505                 510
Glu Leu Arg Gln Gly Gln Phe Leu Phe His Leu Trp Ala Pro Glu Pro
                515                 520                 525
Thr Ala Asn Arg Ser Arg Ile Gly Glu Asn Gly Ala Arg Ile Gly Thr
    530                 535                 540
Asn Ala Ala Val Thr Ile Glu Ile Ser Ser Tyr Gly Gly Arg Val Arg
545                 550                 555                 560
Met Pro Ser Gln Gly Gln Tyr Thr Tyr Leu Val Lys His Arg Ser Thr
                565                 570                 575
Trp Thr Glu Thr Leu Asn Ile Met Gly Asp Asp Tyr Glu Ser Cys Ile
                580                 585                 590
Arg Asp Pro Gly Tyr Lys Lys Leu Gln Met Leu Val Lys Lys His Glu
                595                 600                 605
Ser Gly Ile Val Leu Glu Glu Asp Glu Gln Arg His Val Trp Met Trp
    610                 615                 620
Arg Arg Tyr Ile Gln Lys Gln Glu Pro Asp Leu Leu Ile Val Leu Ser
625                 630                 635                 640
Glu Leu Ala Phe Val Trp Thr Asp Arg Glu Asn Phe Ser Glu Leu Tyr
                645                 650                 655
Val Met Leu Glu Lys Trp Lys Pro Pro Ser Val Ala Ala Ala Leu Thr
                660                 665                 670
Leu Leu Gly Lys Arg Cys Thr Asp Arg Val Ile Arg Lys Phe Ala Val
                675                 680                 685
Glu Lys Leu Asn Glu Gln Leu Ser Pro Val Thr Phe His Leu Phe Ile
    690                 695                 700
```

-continued

```
Leu Pro Leu Ile Gln Ala Leu Lys Tyr Glu Pro Arg Ala Gln Ser Glu
705                 710                 715                 720

Val Gly Met Met Leu Leu Thr Arg Ala Leu Cys Asp Tyr Arg Ile Gly
                725                 730                 735

His Arg Leu Phe Trp Leu Leu Arg Ala Glu Ile Ala Arg Leu Arg Asp
            740                 745                 750

Cys Asp Leu Lys Ser Glu Glu Tyr Arg Arg Ile Ser Leu Leu Met Glu
            755                 760                 765

Ala Tyr Leu Arg Gly Asn Glu Glu His Ile Lys Ile Thr Arg Gln
770                 775                 780

Val Asp Met Val Asp Glu Leu Thr Arg Ile Ser Thr Leu Val Lys Gly
785                 790                 795                 800

Met Pro Lys Asp Val Ala Thr Met Lys Leu Arg Asp Glu Leu Arg Ser
                805                 810                 815

Ile Ser His Lys Met Glu Asn Met Asp Ser Pro Leu Asp Pro Val Tyr
                820                 825                 830

Lys Leu Gly Glu Met Ile Ile Asp Lys Ala Ile Val Leu Gly Ser Ala
            835                 840                 845

Lys Arg Pro Leu Met Leu His Trp Lys Asn Lys Asn Pro Lys Ser Asp
850                 855                 860

Leu His Leu Pro Phe Cys Ala Met Ile Phe Lys Asn Gly Asp Asp Leu
865                 870                 875                 880

Arg Gln Asp Met Leu Val Leu Gln Val Leu Glu Val Met Asp Asn Ile
                885                 890                 895

Trp Lys Ala Ala Asn Ile Asp Cys Cys Leu Asn Pro Tyr Ala Val Leu
                900                 905                 910

Pro Met Gly Glu Met Ile Gly Ile Ile Glu Val Val Pro Asn Cys Lys
            915                 920                 925

Thr Ile Phe Glu Ile Gln Val Gly Thr Gly Phe Met Asn Thr Ala Val
            930                 935                 940

Arg Ser Ile Asp Pro Ser Phe Met Asn Lys Trp Ile Arg Lys Gln Cys
945                 950                 955                 960

Gly Ile Glu Asp Glu Lys Lys Lys Ser Lys Lys Asp Ser Thr Lys Asn
                965                 970                 975

Pro Ile Glu Lys Lys Ile Asp Asn Thr Gln Ala Met Lys Lys Tyr Phe
                980                 985                 990

Glu Ser Val Asp Arg Phe Leu Tyr Ser Cys Val Gly Tyr Ser Val Ala
            995                 1000                1005

Thr Tyr Ile Met Gly Ile Lys Asp Arg His Ser Asp Asn Leu Met Leu
1010                1015                1020

Thr Glu Asp Gly Lys Tyr Val His Ile Asp Phe Gly His Ile Leu Gly
1025                1030                1035                1040

His Gly Lys Thr Lys Leu Gly Ile Gln Arg Asp Arg Gln Pro Phe Ile
                1045                1050                1055

Leu Thr Glu His Phe Met Thr Val Ile Arg Ser Gly Lys Ser Val Asp
                1060                1065                1070

Gly Asn Ser His Glu Leu Gln Lys Phe Lys Thr Leu Cys Val Glu Ala
            1075                1080                1085

Tyr Glu Val Met Trp Asn Asn Arg Asp Leu Phe Val Ser Leu Phe Thr
            1090                1095                1100

Leu Met Leu Gly Met Glu Leu Pro Glu Leu Ser Thr Lys Ala Asp Leu
1105                1110                1115                1120
```

```
Asp His Leu Lys Lys Thr Leu Phe Cys Asn Gly Glu Ser Lys Glu Glu
            1125                1130                1135

Ala Arg Lys Phe Phe Ala Gly Ile Tyr Glu Glu Ala Phe Asn Gly Ser
            1140                1145                1150

Trp Ser Thr Lys Thr Asn Trp Leu Phe His Ala Val Lys His Tyr
            1155                1160                1165

<210> SEQ ID NO 49
<211> LENGTH: 23
<212> TYPE: DNA
<213> ORGANISM: Artificial Sequence
<220> FEATURE:
<223> OTHER INFORMATION: Probe/primer derived from C. elegans

<400> SEQUENCE: 49
ggaaatattt taggccagat gcg                                           23

<210> SEQ ID NO 50
<211> LENGTH: 20
<212> TYPE: DNA
<213> ORGANISM: Artificial Sequence
<220> FEATURE:
<223> OTHER INFORMATION: Probe/primer derived from C. elegans

<400> SEQUENCE: 50
cggacagtcc tgaatacacc                                               20

<210> SEQ ID NO 51
<211> LENGTH: 28
<212> TYPE: DNA
<213> ORGANISM: Artificial Sequence
<220> FEATURE:
<223> OTHER INFORMATION: Probe/primer derived from C. elegans

<400> SEQUENCE: 51
tctcgttgtt tgccgtcgga tgtctgcc                                      28

<210> SEQ ID NO 52
<211> LENGTH: 3017
<212> TYPE: DNA
<213> ORGANISM: Caenorhabditis elegans

<400> SEQUENCE: 52
gtaatcaaat tgtaaaggaa aatattaat agtcagagta cacataaatg ggtgatcatc     60
ataatttaac gggccttccc ggtacctcca tcccgccaca gttcaactat tctcagcccg   120
gtaccagcac cggaggcccg ctttatggtg gaaaaccttc tcatggattg gaagatattc   180
ctgatgtaga ggaatatgag aggaacctgc tcggggctgg agcaggtttt aatctgctca   240
atgtaggaaa tatggctaat gttcccgacg agcacacacc gatgatgtca ccagtgaata   300
caactacaaa gattctacaa cggagtggta ttaaaatgga atcccgcca tatttggatc    360 cagacagtca ggatgatgac ccggaagatg tgtcaactaa cccggatcca gatttatttg   420
acacaaaaaa cacaaatatg accgagtacg atttggatgt gttgaagctt ggaaaaccag   480
cagtagatga agcacggaaa aagatcgaag ttcccgacgc tagtgcgccg ccaaacaaaa   540
ttgtagaata tttgatgtat tatagaacgt taaagaaag tgaactcata caactgaatg   600
cgtatcggac aaaacgaaat cgattatcgt tgaacttggt caaaaacaat attgatcgag   660
agttcgacca aaaagcttgc gagtccctgg tgaaaaaatt gaaggataag aagaatgatc   720
tccagaacct gattgatgtg gttctttcaa aaggtacaaa atataccggt tgcattacaa   780
```

```
ttccaaggac acttgatggc cggttacagg tccacggaag aaaaggtttc cctcacgtag    840
tctatggcaa actgtggagg tttaatgaaa tgacaaaaaa cgaaacgcgt catgtggacc    900
actgcaagca cgcatttgaa atgaaaagtg acatggtatg cgtgaatccc tatcactacg    960
aaattgtcat tggaactatg attgttgggc agagggatca tgacaatcga gatatgccgc   1020
cgccacatca acgctaccac actccaggtc ggcaggatcc agttgacgat atgagtagat   1080
ttataccacc agcttccatt cgtccgcctc cgatgaacat gcacacaagg cctcagccta   1140
tgcctcaaca attgccttca gttggcgcaa cgtttgccca tcctctccca catcaggcgc   1200
cacataaccc aggggtttca catccgtact ccattgctcc acagacccat tacccgttga   1260
acatgaaccc aattccgcaa atgccgcaaa tgccacaaat gccaccacct ctccatcagg   1320
gatatggaat gaatgggccg agttgctctt cagaaaacaa caatccattc caccaaaatc   1380
accattataa tgatattagc catccaaatc actattccta cgactgtggt ccgaacttgt   1440
acgggttttcc aactccttat ccggattttc accatccttt caatcagcaa ccacaccagc   1500
cgccacaact atcacaaaac catacgtccc aacaaggcag tcatcaacca gggcaccaag   1560
gtcaggtacc gaatgatcca ccaatttcaa gaccagtgtt acaaccatca acagtcacct   1620
tggacgtgtt ccgtcggtac tgtagacaga catttggaaa tcgattttttt gaaggagaaa   1680
gtgaacaatc cggcgcaata attcggtcta gtaacaaatt cattgaagaa tttgattcgc   1740
cgatttgtgg tgtgacagtt gttcgaccgc ggatgacaga cggtgaggtt ttggagaaca   1800
tcatgccgga agatgcacca tatcatgaca tttgcaagtt cattttgagg ctcacatcag   1860
aaagtgtaac tttctcagga gaggggccag aagttagtga tttgaacgaa aaatggggaa   1920
caattgtgta ctatgagaaa aatttgcaaa ttggcgagaa aaaatgttcg agaggaaatt   1980
tccacgtgga tggcggattc atttgctctg agaatcgtta cagtctcgga cttgagccaa   2040
atccaattag agaaccagtg gcgtttaaag ttcgtaaagc aatagtggat ggaattcgct   2100
tttcctacaa aaaagacggg agtgtttggc ttcaaaaccg catgaagtac ccggtatttg   2160
tcacttctgg gtatctcgac gagcaatcag gaggcctaaa gaaggataaa gtgcacaaag   2220
tttacggatg tgcgtctatc aaaacgtttg gcttcaacgt tccaaacaa atcatcagag   2280
acgcgcttct ttccaagcaa atggcaacaa tgtacttgca aggaaaattg actccgatga   2340
attatatcta cgagaagaag actcaggaag agctgcgaag ggaagcaaca cgcaccactg   2400
attcattggc caagtactgt tgtgtccgtg tctcgttctg caaaggattt ggagaagcat   2460
acccagaacg cccgtcaatt catgattgtc cagtttggat tgagttgaaa atcaacattg   2520
cctacgattt catggattca atctgccagt acataaccaa ctgcttcgag ccgctaggaa   2580
tggaagattt tgcaaaattg ggaatcaacg tcagtgatga ctaaatgata actttttttca   2640
ctcaccctac tagatactga tttagtctta ttccaaatca tccaacgata tcaaactttt   2700
tcctttgaac tttgcatact atgttatcac aagttccaag cagtttcaat acaaacatag   2760
gatatgttaa caacttttga taagaatcaa gttaccaact gttcattgtg agctttgagc   2820
tgtatagaag gacaatgtat cccataaacctc aatctttaat agtcatcagt cactggtccc   2880
gcaccaattt tttcgattcg catatgtcat atattgcacc gtggcccttt ttattgtaac   2940
ttttaatata ttttcttccc aacttgtgaa tatgattgat gaaccaccat tttgagtaat   3000
aaatgtattt tttgtgg                                                 3017
```

<210> SEQ ID NO 53
<211> LENGTH: 3119

```
<212> TYPE: DNA
<213> ORGANISM: Caenorhabditis elegans

<400> SEQUENCE: 53
gtaatcaaat tgtaaaggaa aaatattaat agtcagagta cacataaatg ggtgatcatc      60
ataatttaac gggccttccc ggtacctcca tcccgccaca gttcaactat tctcagcccg     120
gtaccagcac cggaggcccg ctttatggtg aaaaccttc tcatggattg gaagatattc     180
ctgatgtaga ggaatatgag aggaacctgc tcggggctgg agcaggtttt aatctgctca     240
atgtaggaaa tatggctaat gaatttaaac caataatcac attggacacg aaaccacctc     300
gtgatgccaa caagtcattg gcattcaatg gcgggttgaa gctaatcact ccgaaaactg     360
aagttcccga cgagcacaca ccgatgatgt caccagtgaa tacaactaca aagattctac     420
aacggagtgg tattaaaatg gaaatcccgc catatttgga tccagacagt caggatgatg     480
acccggaaga tggtgtcaac tacccggatc cagatttatt tgacacaaaa acacaaata      540
tgaccgagta cgatttggat gtgttgaagc ttggaaaacc agcagtagat gaagcacgga     600
aaagatcga agttcccgac gctagtgcgc cgccaaacaa aattgtagaa tatttgatgt       660
attatagaac gttaaaagaa agtgaactca tacaactgaa tgcgtatcgg acaaaacgaa     720
atcgattatc gttgaacttg gtcaaaaaca atattgatcg agagttcgac caaaaagctt     780
gcgagtccct ggtgaaaaaa ttgaaggata agaagaatga tctccagaac ctgattgatg     840
tggttctttc aaaaggtaca aaatataccg gttgcattac aattccaagg acacttgatg     900
gccggttaca ggtccacgga agaaaaggtt ccctcacgt agtctatggc aaactgtgga      960
ggtttaatga atgacaaaaa acgaaacgc gtcatgtgga ccactgcaag cacgcatttg    1020
aaatgaaaag tgacatggta tgcgtgaatc cctatcacta cgaaattgtc attggaacta    1080
tgattgttgg gcagagggat catgacaatc gagatatgcc ccgccacat caacgctacc      1140
acactccagg tcggcaggat ccagttgacg atatgagtag atttatacca ccagcttcca    1200
ttcgtccgcc tccgatgaac atgcacacaa ggcctcagcc tatgcctcaa caattgcctt    1260
cagttggcgc aacgtttgcc catcctctcc cacatcaggc gccacataac ccaggggttt    1320
cacatccgta ctccattgct ccacagaccc attacccgtt gaacatgaac ccaattccgc    1380
aaatgccgca aatgccacaa atgccaccac ctctccatca gggatatgga atgaatgggc    1440
cgagttgctc ttcagaaaac aacaatccat tccaccaaaa tcaccattat aatgatatta    1500
gccatccaaa tcactattcc tacgactgtg gtccgaactt gtacgggttt ccaactcctt    1560
atccggattt tcaccatcct ttcaatcagc aaccacacac gccgccacaa ctatcacaaa    1620
accatacgtc ccaacaaggc agtcatcaac cagggcacca aggtcaggta ccgaatgatc    1680
caccaatttc aagaccagtg ttacaaccat caacagtcac cttggacgtg ttccgtcggt    1740
actgtagaca gacatttgga aatcgatttt ttgaaggaga agtgaacaa tccggcgcaa    1800
taattcggtc tagtaacaaa ttcattgaag aatttgattc gccgatttgt ggtgtgacag    1860
ttgttcgacc gcggatgaca gacggtgagg ttttggagaa catcatgccg gaagatgcac    1920
catatcatga catttgcaag ttcattttga ggctcacatc agaaagtgta actttctcag    1980
gagaggggcc agaagttagt gatttgaacg aaaaatgggg aacaattgtg tactatgaga    2040
aaaatttgca aattggcgag aaaaaatgtt cgagaggaaa tttccacgtg gatggcggat    2100
tcatttgctc tgagaatcgt tacagtctcg gacttgagcc aaatccaatt agagaaccag    2160
tggcgtttaa agttcgtaaa gcaatagtgg atggaattcg cttttcctac aaaaaagacg    2220
```

-continued

```
ggagtgtttg gcttcaaaac cgcatgaagt acccggtatt tgtcacttct gggtatctcg    2280
acgagcaatc aggaggccta agaaggata aagtgcacaa agtttacgga tgtgcgtcta     2340
tcaaaacgtt tggcttcaac gtttccaaac aaatcatcag agacgcgctt ctttccaagc    2400
aaatggcaac aatgtacttg caaggaaaat tgactccgat gaattatatc tacgagaaga    2460
agactcagga agagctgcga agggaagcaa cacgcaccac tgattcattg gccaagtact    2520
gttgtgtccg tgtctcgttc tgcaaaggat ttggagaagc atacccagaa cgcccgtcaa    2580
ttcatgattg tccagtttgg attgagttga aaatcaacat tgcctacgat tcatggattt    2640
caatctgcca gtacataacc aactgcttcg agccgctagg aatggaagat tttgcaaaat    2700
tgggaatcaa cgtcagtgat gactaaatga taacttttttt cactcaccct actagatact    2760
gatttagtct tattccaaat catccaacga tatcaaactt tttcctttga actttgcata    2820
ctatgttatc acaagttcca agcagtttca atacaaacat aggatatgtt aacaactttt    2880
gataagaatc aagttaccaa ctgttcattg tgagctttga gctgtataga aggacaatgt    2940
atcccatacc tcaatcttta atagtcatca gtcactggtc ccgcaccaat tttttcgatt    3000
cgcatatgtc atatattgca ccgtggccct ttttattgta acttttaata tattttcttc    3060
ccaacttgtg aatatgattg atgaaccacc attttgagta ataaatgtat tttttgtgg    3119
```

<210> SEQ ID NO 54
<211> LENGTH: 103
<212> TYPE: PRT
<213> ORGANISM: Caenorhabditis elegans

<400> SEQUENCE: 54

Lys Lys Thr Thr Thr Arg Arg Asn Ala Trp Gly Asn Met Ser Tyr Ala
1               5                   10                  15

Glu Leu Ile Thr Thr Ala Ile Met Ala Ser Pro Glu Lys Arg Leu Thr
            20                  25                  30

Leu Ala Gln Val Tyr Glu Trp Met Val Gln Asn Val Pro Tyr Phe Arg
        35                  40                  45

Asp Lys Gly Asp Ser Asn Ser Ser Ala Gly Trp Lys Asn Ser Ile Arg
    50                  55                  60

His Asn Leu Ser Leu His Ser Arg Phe Met Arg Ile Gln Asn Glu Gly
65                  70                  75                  80

Ala Gly Lys Ser Ser Trp Trp Val Ile Asn Pro Asp Ala Lys Pro Gly
                85                  90                  95

Met Asn Pro Arg Arg Thr Arg
            100

<210> SEQ ID NO 55
<211> LENGTH: 41
<212> TYPE: PRT
<213> ORGANISM: Caenorhabditis elegans

<400> SEQUENCE: 55

Thr Phe Met Asn Thr Pro Asp Asp Val Met Met Asn Asp Asp Met Glu
1               5                   10                  15

Pro Ile Pro Arg Asp Arg Cys Asn Thr Trp Pro Met Arg Arg Pro Gln
            20                  25                  30

Leu Glu Pro Pro Leu Asn Ser Ser Pro
        35                  40

<210> SEQ ID NO 56
<211> LENGTH: 109

```
<212> TYPE: PRT
<213> ORGANISM: Caenorhabditis elegans

<400> SEQUENCE: 56

Asp Asp Thr Val Ser Gly Lys Lys Thr Thr Arg Arg Asn Ala Trp
1               5                   10                  15

Gly Asn Met Ser Tyr Ala Glu Leu Ile Thr Thr Ala Ile Met Ala Ser
            20                  25                  30

Pro Glu Lys Arg Leu Thr Leu Ala Gln Val Tyr Glu Trp Met Val Gln
            35                  40                  45

Asn Val Pro Tyr Phe Arg Asp Lys Gly Asp Ser Asn Ser Ser Ala Gly
50                  55                  60

Trp Lys Asn Ser Ile Arg His Asn Leu Ser Leu His Ser Arg Phe Met
65                  70                  75                  80

Arg Ile Gln Asn Glu Gly Ala Gly Lys Ser Ser Trp Trp Val Ile Asn
                85                  90                  95

Pro Asp Ala Lys Pro Gly Met Asn Pro Arg Arg Thr Arg
                100                 105

<210> SEQ ID NO 57
<211> LENGTH: 655
<212> TYPE: PRT
<213> ORGANISM: Homo sapiens

<400> SEQUENCE: 57

Met Ala Glu Ala Pro Gln Val Val Glu Ile Asp Pro Asp Phe Glu Pro
1               5                   10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
            35                  40                  45

Ala Ala Asn Pro Asp Ala Ala Ala Gly Leu Pro Ser Ala Ser Ala Ala
50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Val Ala Ala
                85                  90                  95

Ala Ala Ala Ala Ala Thr Gly Gly Leu Cys Gly Asp Phe Gln Gly
            100                 105                 110

Pro Glu Ala Gly Cys Leu His Pro Ala Pro Pro Gln Pro Pro Pro Pro
            115                 120                 125

Gly Pro Val Ser Gln His Pro Pro Val Pro Pro Ala Ala Ala Gly Pro
130                 135                 140

Leu Ala Gly Gln Pro Arg Lys Ser Ser Ser Ser Arg Arg Asn Ala Trp
145                 150                 155                 160

Gly Asn Leu Ser Tyr Ala Asp Leu Ile Thr Lys Ala Ile Glu Ser Ser
                165                 170                 175

Ala Glu Lys Arg Leu Thr Leu Ser Gln Ile Tyr Glu Trp Met Val Lys
                180                 185                 190

Ser Val Pro Tyr Phe Lys Asp Lys Gly Asp Ser Asn Ser Ser Ala Gly
                195                 200                 205

Trp Lys Asn Ser Ile Arg His Asn Leu Ser Leu His Ser Lys Phe Ile
210                 215                 220

Arg Val Gln Asn Glu Gly Thr Gly Lys Ser Ser Trp Trp Met Leu Asn
225                 230                 235                 240
```

```
Pro Glu Gly Gly Lys Ser Gly Lys Ser Pro Arg Arg Ala Ala Ser
            245                 250                 255

Met Asp Asn Asn Ser Lys Phe Ala Lys Ser Arg Ser Arg Ala Ala Lys
            260                 265                 270

Lys Lys Ala Ser Leu Gln Ser Gly Gln Glu Gly Ala Gly Asp Ser Pro
            275                 280                 285

Gly Ser Gln Phe Ser Lys Trp Pro Ala Ser Pro Gly Ser His Ser Asn
            290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
            325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
            355                 360                 365

Glu Asn Met Glu Asn Leu Leu Asp Asn Leu Asn Leu Leu Ser Ser Pro
            370                 375                 380

Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
            405                 410                 415

Pro Ser Pro Asn Tyr Gln Lys Tyr Thr Tyr Gly Gln Ser Ser Met Ser
            420                 425                 430

Pro Leu Pro Gln Met Pro Ile Gln Thr Leu Gln Asp Asn Lys Ser Ser
            435                 440                 445

Tyr Gly Gly Met Ser Gln Tyr Asn Cys Ala Pro Gly Leu Leu Lys Glu
            450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
            485                 490                 495

Met Met Gly Pro Asn Ser Val Met Ser Thr Tyr Gly Ser Gln Ala Ser
            500                 505                 510

His Asn Lys Met Met Asn Pro Ser Ser His Thr His Pro Gly His Ala
            515                 520                 525

Gln Gln Thr Ser Ala Val Asn Gly Arg Pro Leu Pro His Thr Val Ser
            530                 535                 540

Thr Met Pro His Thr Ser Gly Met Asn Arg Leu Thr Gln Val Lys Thr
545                 550                 555                 560

Pro Val Gln Val Pro Leu Pro His Pro Met Gln Met Ser Ala Leu Gly
            565                 570                 575

Gly Tyr Ser Ser Val Ser Ser Cys Asn Gly Tyr Gly Arg Met Gly Leu
            580                 585                 590

Leu His Gln Glu Lys Leu Pro Ser Asp Leu Asp Gly Met Phe Ile Glu
            595                 600                 605

Arg Leu Asp Cys Asp Met Glu Ser Ile Ile Arg Asn Asp Leu Met Asp
            610                 615                 620

Gly Asp Thr Leu Asp Phe Asn Phe Asp Asn Val Leu Pro Asn Gln Ser
625                 630                 635                 640

Phe Pro His Ser Val Lys Thr Thr Thr His Ser Trp Val Ser Gly
            645                 650                 655
```

```
<210> SEQ ID NO 58
<211> LENGTH: 98
<212> TYPE: PRT
<213> ORGANISM: Caenorhabditis elegans

<400> SEQUENCE: 58

Lys Pro Asn Pro Trp Gly Glu Ser Tyr Ser Asp Ile Ile Ala Lys
 1               5                  10                  15

Ala Leu Glu Ser Ala Pro Asp Gly Arg Leu Lys Leu Asn Glu Ile Tyr
            20                  25                  30

Gln Trp Phe Ser Asp Asn Ile Pro Tyr Phe Gly Glu Arg Ser Ser Pro
            35                  40                  45

Glu Glu Ala Ala Gly Trp Lys Asn Ser Ile Arg His Asn Leu Ser Leu
        50                  55                  60

His Ser Arg Phe Met Arg Ile Gln Asn Glu Gly Ala Gly Lys Ser Ser
65                  70                  75                  80

Trp Trp Val Ile Asn Pro Asp Ala Lys Pro Gly Met Asn Pro Arg Arg
                85                  90                  95

Thr Arg

<210> SEQ ID NO 59
<211> LENGTH: 7
<212> TYPE: PRT
<213> ORGANISM: Caenorhabditis elegans

<400> SEQUENCE: 59

Trp Lys Asn Ser Ile Arg His
 1               5

<210> SEQ ID NO 60
<211> LENGTH: 121
<212> TYPE: PRT
<213> ORGANISM: Caenorhabditis elegans

<400> SEQUENCE: 60

Gln Val Leu Asp Asp His Asp Tyr Gly Arg Cys Val Asp Trp Trp Gly
 1               5                  10                  15

Val Gly Val Val Met Tyr Glu Met Met Cys Gly Arg Leu Pro Phe Tyr
            20                  25                  30

Ser Lys Asp His Asn Lys Leu Phe Glu Leu Ile Met Ala Gly Asp Leu
            35                  40                  45

Arg Phe Pro Ser Lys Leu Ser Gln Glu Ala Arg Thr Leu Leu Thr Gly
        50                  55                  60

Leu Leu Val Lys Asp Pro Thr Gln Arg Leu Gly Gly Gly Pro Glu Asp
65                  70                  75                  80

Ala Leu Glu Ile Cys Arg Ala Asp Phe Phe Arg Thr Val Asp Trp Glu
                85                  90                  95

Ala Thr Tyr Arg Lys Glu Ile Glu Pro Pro Tyr Lys Pro Asn Val Gln
            100                 105                 110

Ser Glu Thr Asp Thr Ser Tyr Phe Asp
            115                 120

<210> SEQ ID NO 61
<211> LENGTH: 66
<212> TYPE: PRT
<213> ORGANISM: Caenorhabditis elegans

<400> SEQUENCE: 61

Thr Met Glu Asp Phe Asp Phe Leu Lys Val Leu Gly Lys Gly Thr Phe
```

```
            1               5                  10                 15
Gly Lys Val Ile Leu Cys Lys Glu Lys Arg Thr Gln Lys Leu Tyr Ala
                    20              25                  30

Ile Lys Ile Leu Lys Lys Asp Val Ile Ile Ala Arg Glu Glu Val Ala
            35                  40                  45

His Thr Leu Thr Glu Asn Arg Val Leu Gln Arg Cys Lys His Pro Phe
        50                  55                  60

Leu Thr
65
```

<210> SEQ ID NO 62
<211> LENGTH: 45
<212> TYPE: PRT
<213> ORGANISM: Caenorhabditis elegans

<400> SEQUENCE: 62

```
Lys Leu Glu Asn Leu Leu Leu Asp Lys Asp Gly His Ile Lys Ile Ala
1               5                   10                  15

Asp Phe Gly Leu Cys Lys Glu Glu Ile Ser Phe Gly Asp Lys Thr Ser
                20                  25                  30

Thr Phe Cys Gly Thr Pro Glu Tyr Leu Ala Pro Glu Val
            35                  40                  45
```

<210> SEQ ID NO 63
<211> LENGTH: 57
<212> TYPE: PRT
<213> ORGANISM: Caenorhabditis elegans

<400> SEQUENCE: 63

```
Tyr Phe Gln Glu Leu Lys Tyr Ser Phe Gln Glu His Tyr Leu Cys
1               5                   10                  15

Phe Val Met Gln Phe Ala Asn Gly Gly Glu Leu Phe Thr His Val Arg
                20                  25                  30

Lys Cys Gly Thr Phe Ser Glu Pro Arg Ala Arg Phe Tyr Gly Ala Glu
            35                  40                  45

Ile Val Leu Ala Leu Gly Tyr Leu His
        50                  55
```

<210> SEQ ID NO 64
<211> LENGTH: 59
<212> TYPE: PRT
<213> ORGANISM: Caenorhabditis elegans

<400> SEQUENCE: 64

```
Ser Thr Phe Ala Ile Phe Tyr Phe Gln Thr Met Leu Phe Glu Lys Pro
1               5                   10                  15

Arg Pro Asn Met Phe Met Val Arg Cys Leu Gln Trp Thr Thr Val Ile
                20                  25                  30

Glu Arg Thr Phe Tyr Ala Glu Ser Ala Glu Val Arg Gln Arg Trp Ile
            35                  40                  45

His Ala Ile Glu Ser Ile Ser Lys Lys Tyr Lys
        50                  55
```

<210> SEQ ID NO 65
<211> LENGTH: 33
<212> TYPE: PRT
<213> ORGANISM: Caenorhabditis elegans

<400> SEQUENCE: 65

Leu Gln Glu Leu Lys Tyr Ser Phe Gln Thr Asn Asp Arg Leu Cys Phe
1               5                   10                  15

Val Met Glu Phe Ala Ile Gly Gly Asp Leu Tyr Tyr His Leu Asn Arg
            20                  25                  30

Glu

<210> SEQ ID NO 66
<211> LENGTH: 21
<212> TYPE: PRT
<213> ORGANISM: Caenorhabditis elegans

<400> SEQUENCE: 66

Val Val Ile Glu Gly Trp Leu His Lys Lys Gly Glu His Ile Arg Asn
1               5                   10                  15

Trp Arg Pro Arg Phe
            20

<210> SEQ ID NO 67
<211> LENGTH: 26
<212> TYPE: PRT
<213> ORGANISM: Caenorhabditis elegans

<400> SEQUENCE: 67

Phe Ser Glu Pro Arg Ala Arg Phe Tyr Gly Ser Glu Ile Val Leu Ala
1               5                   10                  15

Leu Gly Tyr Leu His Ala Asn Ser Ile Val
            20                  25

<210> SEQ ID NO 68
<211> LENGTH: 39
<212> TYPE: PRT
<213> ORGANISM: Caenorhabditis elegans

<400> SEQUENCE: 68

Ile Arg Val Ser Phe Cys Lys Gly Phe Gly Glu Thr Tyr Ser Arg Leu
1               5                   10                  15

Lys Val Val Asn Leu Pro Cys Trp Ile Glu Ile Leu His Glu Pro
            20                  25                  30

Ala Asp Glu Tyr Asp Thr Val
        35

<210> SEQ ID NO 69
<211> LENGTH: 45
<212> TYPE: PRT
<213> ORGANISM: Caenorhabditis elegans

<400> SEQUENCE: 69

Ser Arg Asn Ser Lys Ser Ser Gln Ile Arg Asn Thr Val Gly Ala Gly
1               5                   10                  15

Ile Gln Leu Ala Tyr Glu Asn Gly Glu Leu Trp Leu Thr Val Leu Thr
            20                  25                  30

Asp Gln Ile Val Phe Val Gln Cys Pro Phe Leu Asn Gln
        35                  40                  45

<210> SEQ ID NO 70
<211> LENGTH: 29
<212> TYPE: PRT
<213> ORGANISM: Caenorhabditis elegans

<400> SEQUENCE: 70

Asn Glu Met Leu Asp Pro Glu Pro Lys Tyr Pro Lys Glu Glu Lys Pro

-continued

```
                 1               5                  10                 15
Trp Cys Thr Ile Phe Tyr Tyr Glu Leu Thr Arg Val
                20              25
```

<210> SEQ ID NO 71
<211> LENGTH: 29
<212> TYPE: PRT
<213> ORGANISM: Caenorhabditis elegans

<400> SEQUENCE: 71

```
Gln Leu Gly Lys Ala Phe Glu Ala Lys Val Pro Thr Ile Thr Ile Asp
  1               5                  10                 15
Gly Ala Thr Gly Ala Ser Asp Glu Cys Arg Met Ser Leu
                20                  25
```

<210> SEQ ID NO 72
<211> LENGTH: 105
<212> TYPE: PRT
<213> ORGANISM: Caenorhabditis elegans

<400> SEQUENCE: 72

```
Ser Pro Asp Asp Gly Leu Leu Asp Ser Ser Glu Glu Ser Arg Arg Arg
  1               5                  10                 15
Gln Lys Thr Cys Arg Val Cys Gly Asp His Ala Thr Gly Tyr Asn Phe
                20                  25                 30
Asn Val Ile Thr Cys Glu Ser Cys Lys Ala Phe Phe Arg Arg Asn Ala
                35                  40                 45
Leu Arg Pro Lys Glu Phe Lys Cys Pro Tyr Ser Glu Asp Cys Glu Ile
 50                  55                 60
Asn Ser Val Ser Arg Arg Phe Cys Gln Lys Cys Arg Leu Arg Lys Cys
 65                  70                 75                 80
Phe Thr Val Gly Met Lys Lys Glu Trp Ile Leu Asn Glu Glu Gln Leu
                85                  90                 95
Arg Arg Arg Lys Asn Ser Arg Leu Asn
                100                 105
```

<210> SEQ ID NO 73
<211> LENGTH: 89
<212> TYPE: PRT
<213> ORGANISM: Caenorhabditis elegans

<400> SEQUENCE: 73

```
Leu Asp Ser Ser Glu Glu Ser Arg Arg Arg Gln Lys Thr Cys Arg Val
  1               5                  10                 15
Cys Gly Asp His Ala Thr Gly Tyr Asn Phe Asn Val Ile Thr Cys Glu
                20                  25                 30
Ser Cys Lys Ala Phe Phe Arg Arg Asn Ala Leu Arg Pro Lys Glu Phe
                35                  40                 45
Lys Cys Pro Tyr Ser Glu Asp Cys Glu Ile Asn Ser Val Ser Arg Arg
 50                  55                 60
Phe Cys Gln Lys Cys Arg Leu Arg Lys Cys Phe Thr Val Gly Met Lys
 65                  70                 75                 80
Lys Glu Trp Ile Leu Asn Glu Glu Gln
                85
```

<210> SEQ ID NO 74
<211> LENGTH: 73
<212> TYPE: PRT
<213> ORGANISM: Caenorhabditis elegans

<400> SEQUENCE: 74

Asp Ile Met Asn Ile Met Asp Val Thr Met Arg Arg Phe Val Lys Val
1               5                   10                  15

Ala Lys Gly Val Pro Ala Phe Arg Glu Val Ser Gln Glu Gly Lys Phe
            20                  25                  30

Ser Leu Leu Lys Gly Gly Met Ile Glu Met Leu Thr Val Arg Gly Val
        35                  40                  45

Thr Arg Tyr Asp Ala Ser Thr Asn Ser Phe Lys Thr Pro Thr Ile Lys
    50                  55                  60

Gly Gln Asn Val Ser Val Asn Val Asp
65              70

<210> SEQ ID NO 75
<211> LENGTH: 112
<212> TYPE: PRT
<213> ORGANISM: Caenorhabditis elegans

<400> SEQUENCE: 75

Ser Gly Ser Leu Val Asp Leu Met Ile Lys Asn Leu Thr Ala Tyr Thr
1               5                   10                  15

Gln Gly Leu Asn Glu Thr Val Lys Asn Arg Thr Ala Glu Leu Glu Lys
            20                  25                  30

Glu Gln Glu Lys Gly Asp Gln Leu Leu Met Glu Leu Leu Pro Lys Ser
        35                  40                  45

Val Ala Asn Asp Leu Lys Asn Gly Ile Ala Val Asp Pro Lys Val Tyr
    50                  55                  60

Glu Asn Ala Thr Ile Leu Tyr Ser Asp Ile Val Gly Phe Thr Ser Leu
65                  70                  75                  80

Cys Ser Gln Ser Gln Pro Met Glu Val Val Thr Leu Leu Ser Gly Met
                85                  90                  95

Tyr Gln Arg Phe Asp Leu Ile Ile Ser Gln Gln Gly Gly Tyr Lys Val
                100                 105                 110

<210> SEQ ID NO 76
<211> LENGTH: 107
<212> TYPE: PRT
<213> ORGANISM: Caenorhabditis elegans

<400> SEQUENCE: 76

Met Glu Thr Ile Gly Asp Ala Tyr Cys Val Ala Ala Gly Leu Pro Val
1               5                   10                  15

Val Met Glu Lys Asp His Val Lys Ser Ile Cys Met Ile Ala Leu Leu
            20                  25                  30

Gln Arg Asp Cys Leu His His Phe Glu Ile Pro His Arg Pro Gly Thr
        35                  40                  45

Phe Leu Asn Cys Arg Trp Gly Phe Asn Ser Gly Pro Val Phe Ala Gly
    50                  55                  60

Val Ile Gly Gln Lys Ala Pro Arg Tyr Ala Cys Phe Gly Glu Ala Val
65                  70                  75                  80

Ile Leu Ala Ser Lys Met Glu Ser Ser Gly Val Glu Asp Arg Ile Gln
                85                  90                  95

Met Thr Leu Ala Ser Gln Gln Leu Leu Glu Glu
                100                 105

<210> SEQ ID NO 77
<211> LENGTH: 43

```
<212> TYPE: PRT
<213> ORGANISM: Caenorhabditis elegans

<400> SEQUENCE: 77

Asp Ile Leu Lys Gly Leu Glu Tyr Ile His Ala Ser Ala Ile Asp Phe
1               5                   10                  15

His Gly Asn Leu Thr Leu His Asn Cys Met Leu Asp Ser His Trp Ile
            20                  25                  30

Val Lys Leu Ser Gly Phe Gly Val Asn Arg Leu
        35                  40

<210> SEQ ID NO 78
<211> LENGTH: 15
<212> TYPE: PRT
<213> ORGANISM: Caenorhabditis elegans

<400> SEQUENCE: 78

Asp Met Tyr Ser Phe Gly Val Ile Leu His Glu Ile Ile Leu Lys
1               5                   10                  15

<210> SEQ ID NO 79
<211> LENGTH: 67
<212> TYPE: PRT
<213> ORGANISM: Caenorhabditis elegans

<400> SEQUENCE: 79

Ala Ile Lys Ile Asn Val Asp Asp Pro Ala Ser Thr Glu Asn Leu Asn
1               5                   10                  15

Tyr Leu Met Glu Ala Asn Ile Met Lys Asn Phe Lys Thr Asn Phe Ile
            20                  25                  30

Val Gln Leu Tyr Gly Val Ile Ser Thr Val Gln Pro Ala Met Val Val
        35                  40                  45

Met Glu Met Met Asp Leu Gly Asn Leu Arg Asp Tyr Leu Arg Ser Lys
    50                  55                  60

Arg Glu Asp
65

<210> SEQ ID NO 80
<211> LENGTH: 54
<212> TYPE: PRT
<213> ORGANISM: Caenorhabditis elegans

<400> SEQUENCE: 80

Val Ile Lys Lys Pro Glu Cys Cys Glu Asn Tyr Trp Tyr Lys Val Met
1               5                   10                  15

Lys Met Cys Trp Arg Tyr Ser Pro Arg Asp Arg Pro Thr Phe Leu Gln
            20                  25                  30

Leu Val His Leu Leu Ala Ala Glu Ala Ser Pro Glu Phe Arg Asp Leu
        35                  40                  45

Ser Phe Val Leu Thr Asp
    50

<210> SEQ ID NO 81
<211> LENGTH: 69
<212> TYPE: PRT
<213> ORGANISM: Caenorhabditis elegans

<400> SEQUENCE: 81

Lys Gln Asp Ser Gly Met Ala Ser Glu Leu Lys Asp Ile Phe Ala Asn
1               5                   10                  15
```

-continued

```
Ile His Thr Ile Thr Gly Tyr Leu Leu Val Arg Gln Ser Ser Pro Phe
             20                  25                  30

Ile Ser Leu Asn Met Phe Arg Asn Leu Arg Arg Ile Glu Ala Lys Ser
         35                  40                  45

Leu Phe Arg Asn Leu Tyr Ala Ile Thr Val Phe Glu Asn Pro Asn Leu
     50                  55                  60

Lys Lys Leu Phe Asp
 65
```

<210> SEQ ID NO 82
<211> LENGTH: 52
<212> TYPE: PRT
<213> ORGANISM: Caenorhabditis elegans

<400> SEQUENCE: 82

```
Phe Pro His Leu Arg Glu Ile Thr Gly Thr Leu Leu Val Phe Glu Thr
 1               5                  10                  15

Glu Gly Leu Val Asp Leu Arg Lys Ile Phe Pro Asn Leu Arg Val Ile
             20                  25                  30

Gly Gly Arg Ser Leu Ile Gln His Tyr Ala Leu Ile Ile Tyr Arg Asn
         35                  40                  45

Pro Asp Leu Glu
     50
```

<210> SEQ ID NO 83
<211> LENGTH: 46
<212> TYPE: PRT
<213> ORGANISM: Caenorhabditis elegans

<400> SEQUENCE: 83

```
Glu Ile Gly Leu Asp Lys Leu Ser Val Ile Arg Asn Gly Gly Val Arg
 1               5                  10                  15

Ile Ile Asp Asn Arg Lys Leu Cys Tyr Thr Lys Thr Ile Asp Trp Lys
             20                  25                  30

His Leu Ile Thr Ser Ser Ile Asn Asp Val Val Asp Asn
         35                  40                  45
```

<210> SEQ ID NO 84
<211> LENGTH: 36
<212> TYPE: PRT
<213> ORGANISM: Caenorhabditis elegans

<400> SEQUENCE: 84

```
Tyr Asn Ala Asp Asp Trp Glu Leu Arg Gln Asp Asp Val Val Leu Gly
 1               5                  10                  15

Gln Gln Cys Gly Glu Gly Ser Phe Gly Lys Val Tyr Leu Gly Thr Gly
             20                  25                  30

Asn Asn Val Val
         35
```

<210> SEQ ID NO 85
<211> LENGTH: 24
<212> TYPE: PRT
<213> ORGANISM: Caenorhabditis elegans

<400> SEQUENCE: 85

```
Asp Ser Leu Ala Lys Tyr Cys Cys Val Arg Val Ser Phe Cys Lys Gly
 1               5                  10                  15

Phe Gly Glu Ala Tyr Pro Glu Arg
             20
```

```
<210> SEQ ID NO 86
<211> LENGTH: 13
<212> TYPE: PRT
<213> ORGANISM: Caenorhabditis elegans

<400> SEQUENCE: 86

Gly Trp Asp Trp Ile Val Ala Pro Pro Arg Tyr Asn Ala
 1               5                  10

<210> SEQ ID NO 87
<211> LENGTH: 121
<212> TYPE: PRT
<213> ORGANISM: Homo sapiens

<400> SEQUENCE: 87

Glu Val Leu Glu Asp Asn Asp Tyr Gly Arg Ala Val Asp Trp Trp Gly
 1               5                  10                  15

Leu Gly Val Val Met Tyr Glu Met Met Cys Gly Arg Leu Pro Phe Tyr
                20                  25                  30

Asn Gln Asp His Glu Lys Leu Phe Glu Leu Ile Leu Met Glu Glu Ile
            35                  40                  45

Arg Phe Pro Arg Thr Leu Gly Pro Glu Ala Lys Ser Leu Leu Ser Gly
        50                  55                  60

Leu Leu Lys Lys Asp Pro Thr Gln Arg Leu Gly Gly Gly Ser Glu Asp
 65                 70                  75                  80

Ala Lys Glu Ile Met Gln His Arg Phe Phe Ala Asn Ile Val Trp Gln
                85                  90                  95

Asp Val Tyr Glu Lys Lys Leu Ser Pro Pro Phe Lys Pro Gln Val Thr
            100                 105                 110

Ser Glu Thr Asp Thr Arg Tyr Phe Asp
        115                 120

<210> SEQ ID NO 88
<211> LENGTH: 121
<212> TYPE: PRT
<213> ORGANISM: Caenorhabditis elegans

<400> SEQUENCE: 88

Gln Val Leu Asp Asp His Asp Tyr Gly Arg Cys Val Asp Trp Trp Gly
 1               5                  10                  15

Val Gly Val Val Met Tyr Glu Met Met Cys Gly Arg Leu Pro Phe Tyr
                20                  25                  30

Ser Lys Asp His Asn Lys Leu Phe Glu Leu Ile Met Ala Gly Asp Leu
            35                  40                  45

Arg Phe Pro Ser Lys Leu Ser Gln Glu Ala Arg Thr Leu Leu Thr Gly
        50                  55                  60

Leu Leu Val Lys Asp Pro Thr Gln Arg Leu Gly Gly Pro Glu Asp
 65                 70                  75                  80

Ala Leu Glu Ile Cys Arg Ala Asp Phe Phe Arg Thr Val Asp Trp Glu
                85                  90                  95

Ala Thr Tyr Arg Lys Glu Ile Glu Pro Pro Tyr Lys Pro Asn Val Gln
            100                 105                 110

Ser Glu Thr Asp Thr Ser Tyr Phe Asp
        115                 120

<210> SEQ ID NO 89
<211> LENGTH: 66
```

-continued

```
<212> TYPE: PRT
<213> ORGANISM: Homo sapiens

<400> SEQUENCE: 89

Thr Met Asn Glu Phe Glu Tyr Leu Lys Leu Leu Gly Lys Gly Thr Phe
 1               5                  10                  15

Gly Lys Val Ile Leu Val Lys Glu Lys Ala Thr Gly Arg Tyr Tyr Ala
            20                  25                  30

Met Lys Ile Leu Lys Lys Glu Val Ile Val Ala Lys Asp Glu Val Ala
        35                  40                  45

His Thr Leu Thr Glu Asn Arg Val Leu Gln Asn Ser Arg His Pro Phe
    50                  55                  60

Leu Thr
65

<210> SEQ ID NO 90
<211> LENGTH: 66
<212> TYPE: PRT
<213> ORGANISM: Caenorhabditis elegans

<400> SEQUENCE: 90

Thr Met Glu Asp Phe Asp Phe Leu Lys Val Leu Gly Lys Gly Thr Phe
 1               5                  10                  15

Gly Lys Val Ile Leu Cys Lys Glu Lys Arg Thr Gln Lys Leu Tyr Ala
            20                  25                  30

Ile Lys Ile Leu Lys Lys Asp Val Ile Ile Ala Arg Glu Glu Val Ala
        35                  40                  45

His Thr Leu Thr Glu Asn Arg Val Leu Gln Arg Cys Lys His Pro Phe
    50                  55                  60

Leu Thr
65

<210> SEQ ID NO 91
<211> LENGTH: 45
<212> TYPE: PRT
<213> ORGANISM: Homo sapiens

<400> SEQUENCE: 91

Lys Leu Glu Asn Leu Met Leu Asp Lys Asp Gly His Ile Lys Ile Thr
 1               5                  10                  15

Asp Phe Gly Leu Cys Lys Glu Gly Ile Lys Asp Gly Ala Thr Met Lys
            20                  25                  30

Thr Phe Cys Gly Thr Pro Glu Tyr Leu Ala Pro Glu Val
        35                  40                  45

<210> SEQ ID NO 92
<211> LENGTH: 45
<212> TYPE: PRT
<213> ORGANISM: Caenorhabditis elegans

<400> SEQUENCE: 92

Lys Leu Glu Asn Leu Leu Leu Asp Lys Asp Gly His Ile Lys Ile Ala
 1               5                  10                  15

Asp Phe Gly Leu Cys Lys Glu Glu Ile Ser Phe Gly Asp Lys Thr Ser
            20                  25                  30

Thr Phe Cys Gly Thr Pro Glu Tyr Leu Ala Pro Glu Val
        35                  40                  45

<210> SEQ ID NO 93
```

```
<211> LENGTH: 57
<212> TYPE: PRT
<213> ORGANISM: Homo sapiens

<400> SEQUENCE: 93

Phe Leu Thr Ala Leu Lys Tyr Ser Phe Gln Thr His Asp Arg Leu Cys
1               5                   10                  15

Phe Val Met Glu Tyr Ala Asn Gly Gly Glu Leu Phe Phe His Leu Ser
            20                  25                  30

Arg Glu Arg Val Phe Ser Glu Asp Arg Ala Arg Phe Tyr Gly Ala Glu
        35                  40                  45

Ile Val Ser Ala Leu Asp Tyr Leu His
50                  55

<210> SEQ ID NO 94
<211> LENGTH: 57
<212> TYPE: PRT
<213> ORGANISM: Caenorhabditis elegans

<400> SEQUENCE: 94

Tyr Phe Gln Glu Leu Lys Tyr Ser Phe Gln Glu Gln His Tyr Leu Cys
1               5                   10                  15

Phe Val Met Gln Phe Ala Asn Gly Gly Glu Leu Phe Thr His Val Arg
            20                  25                  30

Lys Cys Gly Thr Phe Ser Glu Pro Arg Ala Arg Phe Tyr Gly Ala Glu
        35                  40                  45

Ile Val Leu Ala Leu Gly Tyr Leu His
50                  55

<210> SEQ ID NO 95
<211> LENGTH: 59
<212> TYPE: PRT
<213> ORGANISM: Homo sapiens

<400> SEQUENCE: 95

Asn Asn Phe Ser Val Ala Gln Cys Gln Leu Met Lys Thr Glu Arg Pro
1               5                   10                  15

Arg Pro Asn Thr Phe Ile Ile Arg Cys Leu Gln Trp Thr Thr Val Ile
            20                  25                  30

Glu Arg Thr Phe His Val Glu Thr Pro Glu Glu Arg Glu Glu Trp Ala
        35                  40                  45

Thr Ala Ile Gln Thr Val Ala Asp Gly Leu Lys
50                  55

<210> SEQ ID NO 96
<211> LENGTH: 59
<212> TYPE: PRT
<213> ORGANISM: Caenorhabditis elegans

<400> SEQUENCE: 96

Ser Thr Phe Ala Ile Phe Tyr Phe Gln Thr Met Leu Phe Glu Lys Pro
1               5                   10                  15

Arg Pro Asn Met Phe Met Val Arg Cys Leu Gln Trp Thr Thr Val Ile
            20                  25                  30

Glu Arg Thr Phe Tyr Ala Glu Ser Ala Glu Val Arg Gln Arg Trp Ile
        35                  40                  45

His Ala Ile Glu Ser Ile Ser Lys Lys Tyr Lys
50                  55
```

```
<210> SEQ ID NO 97
<211> LENGTH: 33
<212> TYPE: PRT
<213> ORGANISM: Homo sapiens

<400> SEQUENCE: 97
```

Leu Thr Ala Leu Lys Tyr Ser Phe Gln Thr His Asp Arg Leu Cys Phe
 1               5                  10                  15

Val Met Glu Tyr Ala Asn Gly Gly Glu Leu Phe Phe His Leu Ser Arg
            20                  25                  30

Glu

```
<210> SEQ ID NO 98
<211> LENGTH: 33
<212> TYPE: PRT
<213> ORGANISM: Caenorhabditis elegans

<400> SEQUENCE: 98
```

Leu Gln Glu Leu Lys Tyr Ser Phe Gln Thr Asn Asp Arg Leu Cys Phe
 1               5                  10                  15

Val Met Glu Phe Ala Ile Gly Gly Asp Leu Tyr Tyr His Leu Asn Arg
            20                  25                  30

Glu

```
<210> SEQ ID NO 99
<211> LENGTH: 473
<212> TYPE: PRT
<213> ORGANISM: Homo sapiens

<400> SEQUENCE: 99
```

Met Leu Gly Thr Val Lys Met Glu Gly His Glu Thr Ser Asp Trp Asn
 1               5                  10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Pro Ala Leu Gly Ala Gly Leu Ser Pro Gly
65                  70                  75                  80

Ala Val Ala Gly Met Pro Gly Gly Ser Ala Gly Ala Met Asn Ser Met
                85                  90                  95

Thr Ala Ala Gly Val Thr Ala Met Gly Thr Ala Leu Ser Pro Ser Gly
            100                 105                 110

Met Gly Ala Met Gly Ala Gln Gln Ala Ala Ser Met Met Asn Gly Leu
        115                 120                 125

Gly Pro Tyr Ala Ala Ala Met Asn Pro Cys Met Ser Pro Met Ala Tyr
    130                 135                 140

Ala Pro Ser Asn Leu Gly Arg Ser Arg Ala Gly Gly Gly Asp Ala
145                 150                 155                 160

Lys Thr Phe Lys Arg Ser Tyr Pro His Ala Lys Pro Pro Tyr Ser Tyr
                165                 170                 175

Ile Ser Leu Ile Thr Met Ala Ile Gln Arg Ala Pro Ser Lys Met Leu
            180                 185                 190

Thr Leu Ser Glu Ile Tyr Gln Trp Ile Met Asp Leu Phe Pro Tyr Tyr
        195                 200                 205

Arg Gln Asn Gln Gln Arg Trp Gln Asn Ser Ile Arg His Ser Leu Ser

-continued

```
            210                 215                 220
Phe Asn Asp Cys Phe Val Lys Val Ala Arg Ser Pro Asp Lys Pro Gly
225                 230                 235                 240

Lys Gly Ser Tyr Trp Thr Leu His Pro Asp Ser Gly Asn Met Phe Glu
                245                 250                 255

Asn Gly Cys Tyr Leu Arg Arg Gln Lys Arg Phe Lys Cys Glu Lys Gln
                260                 265                 270

Pro Gly Ala Gly Gly Gly Gly Ser Gly Ser Gly Gly Ser Gly Ala
                275                 280                 285

Lys Gly Gly Pro Glu Ser Arg Lys Asp Pro Ser Gly Ala Ser Asn Pro
                290                 295                 300

Ser Ala Asp Ser Pro Leu His Arg Gly Val His Gly Lys Thr Gly Gln
305                 310                 315                 320

Leu Glu Gly Ala Pro Ala Pro Gly Pro Ala Ala Ser Pro Gln Thr Leu
                325                 330                 335

Asp His Ser Gly Ala Thr Ala Thr Gly Gly Ala Ser Glu Leu Lys Thr
                340                 345                 350

Pro Ala Ser Ser Thr Ala Pro Pro Ile Ser Ser Gly Pro Gly Ala Leu
                355                 360                 365

Ala Ser Val Pro Ala Ser His Pro Ala His Gly Leu Ala Pro His Glu
370                 375                 380

Ser Gln Leu His Leu Lys Gly Asp Pro His Tyr Ser Phe Asn His Pro
385                 390                 395                 400

Phe Ser Ile Asn Asn Leu Met Ser Ser Glu Gln Gln His Lys Leu
                405                 410                 415

Asp Phe Lys Ala Tyr Glu Gln Ala Leu Gln Tyr Ser Pro Tyr Gly Ser
                420                 425                 430

Thr Leu Pro Ala Ser Leu Pro Leu Gly Ser Ala Ser Val Thr Thr Arg
                435                 440                 445

Ser Pro Ile Glu Pro Ser Ala Leu Glu Pro Ala Tyr Tyr Gln Gly Val
                450                 455                 460

Tyr Ser Arg Pro Val Leu Asn Thr Ser
465                 470

<210> SEQ ID NO 100
<211> LENGTH: 347
<212> TYPE: PRT
<213> ORGANISM: Homo sapiens

<400> SEQUENCE: 100

Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
                20                  25                  30

Thr Met Ala Pro Leu Asn Ser Tyr Met Thr Leu Asn Pro Leu Ser Ser
                35                  40                  45

Pro Tyr Pro Gly Gly Leu Pro Ala Ser Pro Leu Pro Ser Gly Pro Leu
                50                  55                  60

Ala Pro Pro Ala Pro Ala Ala Pro Leu Gly Pro Thr Phe Pro Gly Leu
65                  70                  75                  80

Gly Leu Ser Gly Gly Ser Ser Ser Gly Tyr Gly Ala Pro Gly Pro
                85                  90                  95

Gly Leu Val His Gly Lys Glu Met Pro Lys Gly Tyr Arg Ala Pro Ala
                100                 105                 110
```

-continued

```
His Ala Lys Pro Pro Tyr Ser Tyr Ile Ser Leu Ile Thr Met Ala Ile
            115                 120                 125
Gln Gln Ala Pro Gly Lys Val Leu Thr Leu Ser Glu Ile Tyr Gln Trp
        130                 135                 140
Ile Met Asp Leu Phe Pro Tyr Tyr Arg Asp Asn Gln Gln Arg Trp Gln
145                 150                 155                 160
Asn Ser Ile Arg His Ser Leu Ser Phe Asn Asp Cys Phe Val Lys Val
                165                 170                 175
Ala Arg Ser Pro Asp Lys Pro Gly Lys Gly Ser Tyr Trp Ala Leu His
            180                 185                 190
Pro Ser Ser Gly Asn Met Phe Glu Asn Gly Cys Tyr Leu Arg Arg Gln
        195                 200                 205
Lys Arg Phe Lys Leu Glu Glu Lys Val Lys Lys Gly Gly Ser Gly Ala
    210                 215                 220
Ser Thr Thr Arg Asn Gly Thr Gly Ser Ala Ala Ser Thr Thr Thr Pro
225                 230                 235                 240
Ala Ala Thr Val Thr Ser Pro Pro Gln Pro Pro Pro Ala Pro Glu
                245                 250                 255
Pro Glu Ala Gln Gly Gly Glu Asp Val Gly Ala Leu Asp Cys Gly Ser
            260                 265                 270
Pro Ala Ser Ser Thr Pro Tyr Phe Thr Gly Leu Glu Leu Pro Gly Asp
        275                 280                 285
Leu Lys Leu Asp Ala Pro Tyr Asn Phe Asn His Pro Phe Ser Ile Asn
    290                 295                 300
Asn Leu Met Ser Glu Gln Thr Pro Ala Pro Pro Lys Leu Asp Val Gly
305                 310                 315                 320
Phe Gly Gly Tyr Gly Ala Glu Gly Gly Glu Pro Gly Val Tyr Tyr Gln
                325                 330                 335
Gly Leu Tyr Ser Arg Ser Leu Leu Asn Ala Ser
            340                 345

<210> SEQ ID NO 101
<211> LENGTH: 635
<212> TYPE: PRT
<213> ORGANISM: Caenorhabditis elegans

<400> SEQUENCE: 101

Met Met Glu Met Leu Val Asp Gln Gly Thr Asp Ala Ser Ser Ser Ala
 1               5                  10                  15
Ser Thr Ser Thr Ser Ser Val Ser Arg Phe Gly Ala Asp Thr Phe Met
                20                  25                  30
Asn Thr Pro Asp Asp Val Met Met Asn Asp Asp Met Glu Pro Ile Pro
            35                  40                  45
Arg Asp Arg Cys Asn Thr Trp Pro Met Arg Arg Pro Gln Leu Glu Pro
        50                  55                  60
Pro Leu Asn Ser Ser Pro Ile Ile His Glu Gln Ile Pro Glu Glu Asp
65                  70                  75                  80
Ala Asp Leu Tyr Gly Ser Asn Glu Gln Cys Gly Gln Leu Gly Gly Ala
                85                  90                  95
Ser Ser Asn Gly Ser Thr Ala Met Leu His Thr Pro Asp Gly Ser Asn
            100                 105                 110
Ser His Gln Thr Ser Phe Pro Ser Glu Cys Tyr Thr Trp Pro Met Gln
        115                 120                 125
Gln Tyr Ile Tyr Gln Glu Ser Ser Ala Thr Ile Pro His His His Leu
    130                 135                 140
```

-continued

```
Asn Gln His Asn Asn Pro Tyr His Pro Met His Pro His His Gln Leu
145                 150                 155                 160

Pro His Met Gln Gln Leu Pro Gln Pro Leu Leu Asn Leu Asn Met Thr
                165                 170                 175

Thr Leu Thr Ser Ser Gly Ser Ser Val Ala Ser Ser Ile Gly Gly Gly
            180                 185                 190

Ala Gln Cys Ser Pro Cys Ala Ser Gly Ser Ser Thr Ala Ala Thr Asn
        195                 200                 205

Ser Ser Gln Gln Gln Gln Thr Val Gly Gln Met Leu Ala Ala Ser Val
    210                 215                 220

Pro Cys Ser Ser Ser Gly Met Thr Leu Gly Met Ser Leu Asn Leu Ser
225                 230                 235                 240

Gln Gly Gly Gly Pro Met Pro Ala Lys Lys Lys Arg Cys Arg Lys Lys
                245                 250                 255

Pro Thr Asp Gln Leu Ala Gln Lys Lys Pro Asn Pro Trp Gly Glu Glu
                260                 265                 270

Ser Tyr Ser Asp Ile Ile Ala Lys Ala Leu Glu Ser Ala Pro Asp Gly
    275                 280                 285

Arg Leu Lys Leu Asn Glu Ile Tyr Gln Trp Phe Ser Asp Asn Ile Pro
290                 295                 300

Tyr Phe Gly Glu Arg Ser Ser Pro Glu Glu Ala Ala Gly Trp Lys Asn
305                 310                 315                 320

Ser Ile Arg His Asn Leu Ser Leu His Ser Arg Phe Met Arg Ile Gln
                325                 330                 335

Asn Glu Gly Ala Gly Lys Ser Ser Trp Trp Val Ile Asn Pro Asp Ala
                340                 345                 350

Lys Pro Gly Met Asn Pro Arg Arg Thr Arg Glu Arg Ser Asn Thr Ile
                355                 360                 365

Glu Thr Thr Thr Lys Ala Gln Leu Glu Lys Ser Arg Arg Gly Ala Lys
        370                 375                 380

Lys Arg Ile Lys Glu Arg Ala Leu Met Gly Ser Leu His Ser Thr Leu
385                 390                 395                 400

Asn Gly Asn Ser Ile Ala Gly Ser Ile Gln Thr Ile Ser His Asp Leu
                405                 410                 415

Tyr Asp Asp Asp Ser Met Gln Gly Ala Phe Asp Asn Val Pro Ser Ser
            420                 425                 430

Phe Arg Pro Arg Thr Gln Ser Asn Leu Ser Ile Pro Gly Ser Ser Ser
        435                 440                 445

Arg Val Ser Pro Ala Ile Gly Ser Asp Ile Tyr Asp Asp Leu Glu Phe
    450                 455                 460

Pro Ser Trp Val Gly Glu Ser Val Pro Ala Ile Pro Ser Asp Ile Val
465                 470                 475                 480

Asp Arg Thr Asp Gln Met Arg Ile Asp Ala Thr Thr His Ile Gly Gly
                485                 490                 495

Val Gln Ile Lys Gln Glu Ser Lys Pro Ile Lys Thr Glu Pro Ile Ala
            500                 505                 510

Pro Pro Pro Ser Tyr His Glu Leu Asn Ser Val Arg Gly Ser Cys Ala
        515                 520                 525

Gln Asn Pro Leu Leu Arg Asn Pro Ile Val Pro Ser Thr Asn Phe Lys
    530                 535                 540

Pro Met Pro Leu Pro Gly Ala Tyr Gly Asn Tyr Gln Asn Gly Gly Ile
545                 550                 555                 560
```

```
Thr Pro Ile Asn Trp Leu Ser Thr Ser Asn Ser Ser Pro Leu Pro Gly
            565                 570                 575

Ile Gln Ser Cys Gly Ile Val Ala Ala Gln His Thr Val Ala Ser Ser
            580                 585                 590

Ser Ala Leu Pro Ile Asp Leu Glu Asn Leu Thr Leu Pro Asp Gln Pro
            595                 600                 605

Leu Met Asp Thr Met Asp Val Asp Ala Leu Ile Arg His Glu Leu Ser
            610                 615                 620

Gln Ala Gly Gly Gln His Ile His Phe Asp Leu
625                 630                 635

<210> SEQ ID NO 102
<211> LENGTH: 501
<212> TYPE: PRT
<213> ORGANISM: Homo sapiens

<400> SEQUENCE: 102

Met Arg Ile Gln Pro Gln Lys Ala Ala Ile Ile Asp Leu Asp Pro
1               5                   10                  15

Asp Phe Glu Pro Gln Ser Arg Pro Arg Ser Cys Thr Trp Pro Leu Pro
            20                  25                  30

Arg Pro Glu Ile Ala Asn Gln Pro Ser Glu Pro Pro Glu Val Glu Pro
            35                  40                  45

Asp Leu Gly Glu Lys Val His Thr Glu Gly Arg Ser Glu Pro Ile Leu
50                  55                  60

Leu Pro Ser Arg Leu Ser Glu Pro Ala Gly Gly Pro Gln Pro Gly Ile
65                  70                  75                  80

Leu Gly Ala Val Thr Gly Pro Arg Lys Gly Gly Ser Arg Arg Asn Ala
                85                  90                  95

Trp Gly Asn Gln Ser Tyr Ala Glu Phe Ile Ser Gln Ala Ile Glu Ser
            100                 105                 110

Ala Pro Glu Lys Arg Leu Thr Leu Ala Gln Ile Tyr Glu Trp Met Val
            115                 120                 125

Arg Thr Val Pro Tyr Phe Lys Asp Lys Gly Asp Ser Asn Ser Ser Ala
            130                 135                 140

Gly Trp Lys Asn Ser Ile Arg His Asn Leu Ser Leu His Ser Lys Phe
145                 150                 155                 160

Ile Lys Val His Asn Glu Ala Thr Gly Lys Ser Ser Trp Trp Met Leu
                165                 170                 175

Asn Pro Glu Gly Gly Lys Ser Gly Lys Ala Pro Arg Arg Ala Ala
            180                 185                 190

Ser Met Asp Ser Ser Ser Lys Leu Leu Arg Gly Arg Ser Lys Ala Pro
            195                 200                 205

Lys Lys Lys Pro Ser Val Leu Pro Ala Pro Glu Gly Ala Thr Pro
210                 215                 220

Thr Ser Pro Val Gly His Phe Ala Lys Trp Ser Gly Ser Pro Cys Ser
225                 230                 235                 240

Arg Asn Arg Glu Glu Ala Asp Met Trp Thr Thr Phe Arg Pro Arg Ser
                245                 250                 255

Ser Ser Asn Ala Ser Ser Val Ser Thr Arg Leu Ser Pro Leu Arg Pro
            260                 265                 270

Glu Ser Glu Val Leu Ala Glu Ile Pro Ala Ser Val Ser Ser Tyr
            275                 280                 285

Ala Gly Gly Val Pro Pro Thr Leu Asn Glu Gly Leu Glu Leu Leu Asp
290                 295                 300
```

-continued

```
Gly Leu Asn Leu Thr Ser Ser His Ser Leu Leu Ser Arg Ser Gly Leu
305                 310                 315                 320

Ser Gly Phe Ser Leu Gln His Pro Gly Val Thr Gly Pro Leu His Thr
            325                 330                 335

Tyr Ser Ser Ser Leu Phe Ser Pro Ala Glu Gly Pro Leu Ser Ala Gly
            340                 345                 350

Glu Gly Cys Phe Ser Ser Gln Ala Leu Glu Ala Leu Leu Thr Ser
        355                 360                 365

Asp Thr Pro Pro Pro Ala Asp Val Leu Met Thr Gln Val Asp Pro
    370                 375                 380

Ile Leu Ser Gln Ala Pro Thr Leu Leu Leu Gly Leu Pro Ser
385             390                 395                 400

Ser Ser Lys Leu Ala Thr Gly Val Gly Leu Cys Pro Lys Pro Leu Glu
            405                 410                 415

Ala Arg Gly Pro Ser Ser Leu Val Pro Thr Leu Ser Met Ile Ala Pro
            420                 425                 430

Pro Pro Val Met Ala Ser Ala Pro Ile Pro Lys Ala Leu Gly Thr Pro
            435                 440                 445

Val Leu Thr Pro Pro Thr Glu Ala Ala Ser Gln Asp Arg Met Pro Gln
    450                 455                 460

Asp Leu Asp Leu Asp Met Tyr Met Glu Asn Leu Glu Cys Asp Met Asp
465                 470                 475                 480

Asn Ile Ile Ser Asp Leu Met Asp Glu Gly Glu Gly Leu Asp Phe Asn
                485                 490                 495

Phe Glu Pro Asp Pro
            500

<210> SEQ ID NO 103
<211> LENGTH: 366
<212> TYPE: PRT
<213> ORGANISM: Homo sapiens

<400> SEQUENCE: 103

Arg Gly Ala Ile Arg Ile Glu Lys Asn Ala Asp Leu Cys Tyr Leu Ser
1               5                   10                  15

Thr Val Asp Trp Ser Leu Ile Leu Asp Ala Val Ser Asn Asn Tyr Ile
            20                  25                  30

Val Gly Asn Lys Pro Pro Lys Glu Cys Gly Asp Leu Cys Pro Gly Thr
        35                  40                  45

Met Glu Glu Lys Pro Met Cys Glu Lys Thr Thr Ile Asn Asn Glu Tyr
    50                  55                  60

Asn Tyr Arg Cys Trp Thr Thr Asn Arg Cys Gln Lys Met Cys Pro Ser
65                  70                  75                  80

Thr Cys Gly Lys Arg Ala Cys Thr Glu Asn Asn Glu Cys Cys His Pro
                85                  90                  95

Glu Cys Leu Gly Ser Cys Ser Ala Pro Asp Asn Asp Thr Ala Cys Val
            100                 105                 110

Ala Cys Arg His Tyr Tyr Tyr Ala Gly Val Cys Val Pro Ala Cys Pro
        115                 120                 125

Pro Asn Thr Tyr Arg Phe Glu Gly Trp Arg Cys Val Asp Arg Asp Phe
    130                 135                 140

Cys Ala Asn Ile Leu Ser Ala Glu Ser Ser Asp Ser Glu Gly Phe Val
145                 150                 155                 160

Ile His Asp Gly Glu Cys Met Gln Glu Cys Pro Ser Gly Phe Ile Arg
```

```
                        165                 170                 175
Asn Gly Ser Gln Ser Met Tyr Cys Ile Pro Cys Glu Gly Pro Cys Pro
                180                 185                 190

Lys Val Cys Glu Glu Lys Lys Thr Lys Thr Ile Asp Ser Val Thr
            195                 200                 205

Ser Ala Gln Met Leu Gln Gly Cys Thr Ile Phe Lys Gly Asn Leu Leu
            210                 215                 220

Ile Asn Ile Arg Arg Gly Asn Asn Ile Ala Ser Glu Leu Glu Asn Phe
225                 230                 235                 240

Met Gly Leu Ile Glu Val Val Thr Gly Tyr Val Lys Ile Arg His Ser
                245                 250                 255

His Ala Leu Val Ser Leu Ser Phe Leu Lys Asn Leu Arg Leu Ile Leu
                260                 265                 270

Gly Glu Glu Gln Leu Glu Gly Asn Tyr Ser Phe Tyr Val Leu Asp Asn
                275                 280                 285

Gln Asn Leu Gln Gln Leu Trp Asp Trp Asp His Arg Asn Leu Thr Ile
            290                 295                 300

Lys Ala Gly Lys Met Tyr Phe Ala Phe Asn Pro Lys Leu Cys Val Ser
305                 310                 315                 320

Glu Ile Tyr Arg Met Glu Glu Val Thr Gly Thr Lys Gly Arg Gln Ser
                325                 330                 335

Lys Gly Asp Ile Asn Thr Arg Asn Asn Gly Glu Arg Ala Ser Cys Glu
                340                 345                 350

Ser Asp Val Leu His Phe Thr Ser Thr Thr Thr Ser Lys Asn
                355                 360                 365

<210> SEQ ID NO 104
<211> LENGTH: 370
<212> TYPE: PRT
<213> ORGANISM: Homo sapiens

<400> SEQUENCE: 104

Arg Gly Ser Val Arg Ile Glu Lys Asn Asn Glu Leu Cys Tyr Leu Ala
1               5                   10                  15

Thr Ile Asp Trp Ser Arg Ile Leu Asp Ser Val Glu Asp Asn Tyr Ile
            20                  25                  30

Val Leu Asn Lys Asp Asp Asn Glu Glu Cys Gly Asp Ile Cys Pro Gly
        35                  40                  45

Thr Ala Lys Gly Lys Thr Asn Cys Pro Ala Thr Val Ile Asn Gly Gln
    50                  55                  60

Phe Val Glu Arg Cys Trp Thr His Ser His Cys Gln Lys Val Cys Pro
65                  70                  75                  80

Thr Ile Cys Lys Ser His Gly Cys Thr Ala Glu Gly Leu Cys Cys His
                85                  90                  95

Ser Glu Cys Leu Gly Asn Cys Ser Gln Pro Asp Asp Pro Thr Lys Cys
                100                 105                 110

Val Ala Cys Arg Asn Phe Tyr Leu Asp Gly Arg Cys Val Glu Thr Cys
            115                 120                 125

Pro Pro Pro Tyr Tyr His Phe Gln Asp Trp Arg Cys Val Asn Phe Ser
        130                 135                 140

Phe Cys Gln Asp Leu His His Lys Cys Lys Asn Ser Arg Arg Gln Gly
145                 150                 155                 160

Cys His Gln Tyr Val Ile His Asn Asn Lys Cys Ile Pro Glu Cys Pro
                165                 170                 175
```

```
Ser Gly Tyr Thr Met Asn Ser Ser Asn Leu Leu Cys Thr Pro Cys Leu
            180                 185                 190

Gly Pro Cys Pro Lys Val Cys His Leu Leu Glu Gly Glu Lys Thr Ile
            195                 200                 205

Asp Ser Val Thr Ser Ala Gln Glu Leu Arg Gly Cys Thr Val Ile Asn
            210                 215                 220

Gly Ser Leu Ile Ile Asn Ile Arg Gly Gly Asn Asn Leu Ala Ala Glu
225                 230                 235                 240

Leu Glu Ala Asn Leu Gly Leu Ile Glu Ile Ser Gly Tyr Leu Lys
                245                 250                 255

Ile Arg Arg Ser Tyr Ala Leu Val Ser Leu Ser Phe Phe Arg Lys Leu
            260                 265                 270

Arg Leu Ile Arg Gly Glu Thr Leu Glu Ile Gly Asn Tyr Ser Phe Tyr
            275                 280                 285

Ala Leu Asp Asn Gln Asn Leu Arg Gln Leu Trp Asp Trp Ser Lys His
            290                 295                 300

Asn Leu Thr Ile Thr Gln Gly Lys Leu Phe Phe His Tyr Asn Pro Lys
305                 310                 315                 320

Leu Cys Leu Ser Glu Ile His Lys Met Glu Glu Val Ser Gly Thr Lys
                325                 330                 335

Gly Arg Gln Glu Arg Asn Asp Ile Ala Leu Lys Thr Asn Gly Asp Gln
            340                 345                 350

Ala Ser Cys Glu Asn Glu Leu Leu Lys Phe Ser Tyr Ile Arg Thr Ser
            355                 360                 365

Phe Asp
    370

<210> SEQ ID NO 105
<211> LENGTH: 383
<212> TYPE: PRT
<213> ORGANISM: Drosophila melanogaster

<400> SEQUENCE: 105

Arg Gly Gly Val Arg Ile Glu Lys Asn His Lys Leu Cys Tyr Asp Arg
1               5                   10                  15

Thr Ile Asp Trp Leu Glu Ile Leu Ala Glu Asn Glu Ser Gln Leu Val
            20                  25                  30

Val Leu Thr Glu Asn Gly Lys Glu Lys Glu Cys Ser Leu Ser Lys Cys
            35                  40                  45

Pro Gly Glu Ile Arg Ile Glu Glu Gly His Asp Asn Thr Ala Ile Glu
    50                  55                  60

Gly Glu Leu Asn Ala Ser Cys Gln Leu His Asn Asn Arg Arg Leu Cys
65                  70                  75                  80

Trp Asn Ser Lys Leu Cys Gln Thr Lys Cys Pro Glu Lys Cys Arg Asn
                85                  90                  95

Asn Cys Ile Asp Glu His Thr Cys Cys Ser Gln Asp Cys Leu Gly Gly
            100                 105                 110

Cys Val Ile Asp Lys Asn Gly Asn Glu Ser Cys Ile Ser Cys Arg Asn
            115                 120                 125

Val Ser Phe Asn Asn Ile Cys Met Asp Ser Cys Pro Lys Gly Tyr Tyr
            130                 135                 140

Gln Phe Asp Ser Arg Cys Val Thr Ala Asn Glu Cys Ile Thr Leu Thr
145                 150                 155                 160

Lys Phe Glu Thr Asn Ser Val Tyr Ser Gly Ile Pro Tyr Asn Gly Gln
                165                 170                 175
```

```
Cys Ile Thr His Cys Pro Thr Gly Tyr Gln Lys Ser Glu Asn Lys Arg
            180                 185                 190

Met Cys Glu Pro Cys Pro Gly Gly Lys Cys Asp Lys Glu Cys Ser Ser
        195                 200                 205

Gly Leu Ile Asp Ser Leu Glu Arg Ala Arg Glu Phe His Gly Cys Thr
        210                 215                 220

Ile Ile Thr Gly Thr Glu Pro Leu Thr Ile Ser Ile Lys Arg Glu Ser
225                 230                 235                 240

Gly Ala His Val Met Asp Glu Leu Lys Tyr Gly Leu Ala Ala Val His
                245                 250                 255

Lys Ile Gln Ser Ser Leu Met Val His Leu Thr Tyr Gly Leu Lys Ser
            260                 265                 270

Leu Lys Phe Phe Gln Ser Leu Thr Glu Ile Ser Gly Asp Pro Pro Met
            275                 280                 285

Asp Ala Asp Lys Tyr Ala Leu Tyr Val Leu Asp Asn Arg Asp Leu Asp
        290                 295                 300

Glu Leu Trp Gly Pro Asn Gln Thr Val Phe Ile Arg Lys Gly Gly Val
305                 310                 315                 320

Phe Phe His Phe Asn Pro Lys Leu Cys Val Ser Thr Ile Asn Gln Leu
                325                 330                 335

Leu Pro Met Leu Ala Ser Lys Pro Lys Phe Phe Glu Lys Ser Asp Glu
            340                 345                 350

Gly Ala Asp Ser Asn Gly Asn Arg Gly Ser Cys Gly Thr Ala Val Leu
            355                 360                 365

Asn Val Thr Leu Gln Ser Val Gly Ala Asn Ser Ala Ser Leu Asn
        370                 375                 380

<210> SEQ ID NO 106
<211> LENGTH: 381
<212> TYPE: PRT
<213> ORGANISM: Caenorhabditis elegans

<400> SEQUENCE: 106

Asn Gly Gly Val Arg Ile Ile Asp Asn Arg Lys Leu Cys Tyr Thr Lys
  1               5                  10                  15

Thr Ile Asp Trp Lys His Leu Ile Thr Ser Ser Ile Asn Asp Val Val
            20                  25                  30

Val Asp Asn Ala Ala Glu Tyr Ala Val Thr Glu Thr Gly Leu Met Cys
        35                  40                  45

Pro Arg Gly Ala Cys Glu Glu Asp Lys Gly Glu Ser Lys Cys His Tyr
    50                  55                  60

Leu Glu Glu Lys Asn Gln Glu Gln Gly Val Glu Arg Val Gln Ser Cys
65                  70                  75                  80

Trp Ser Asn Thr Thr Cys Gln Lys Ser Cys Ala Tyr Asp Arg Leu Leu
                85                  90                  95

Pro Thr Lys Glu Ile Gly Pro Cys Asp Ala Asn Gly Asp Arg Cys
            100                 105                 110

His Asp Gln Cys Val Gly Gly Cys Glu Arg Val Asn Asp Ala Thr Ala
        115                 120                 125

Cys His Ala Cys Lys Asn Val Tyr His Lys Gly Lys Cys Ile Glu Lys
    130                 135                 140

Cys Asp Ala His Leu Tyr Leu Leu Gln Arg Arg Cys Val Thr Arg
145                 150                 155                 160

Glu Gln Cys Leu Gln Leu Asn Pro Val Leu Ser Asn Lys Thr Val Pro
```

-continued

```
                165                 170                 175
Ile Lys Ala Thr Ala Gly Leu Cys Ser Asp Lys Cys Pro Asp Gly Tyr
            180                 185                 190

Gln Ile Asn Pro Asp Asp His Arg Glu Cys Arg Lys Cys Val Gly Lys
        195                 200                 205

Cys Glu Ile Val Cys Glu Ile Asn His Val Ile Asp Thr Phe Pro Lys
    210                 215                 220

Ala Gln Ala Ile Arg Leu Cys Asn Ile Ile Asp Gly Asn Leu Thr Ile
225                 230                 235                 240

Glu Ile Arg Gly Lys Gln Asp Ser Gly Met Ala Ser Glu Leu Lys Asp
                245                 250                 255

Ile Phe Ala Asn Ile His Thr Ile Thr Gly Tyr Leu Leu Val Arg Gln
            260                 265                 270

Ser Ser Pro Phe Ile Ser Leu Asn Met Phe Arg Asn Leu Arg Arg Ile
        275                 280                 285

Glu Ala Lys Ser Leu Phe Arg Asn Leu Tyr Ala Ile Thr Val Phe Glu
    290                 295                 300

Asn Pro Asn Leu Lys Lys Leu Phe Asp Ser Thr Thr Asp Leu Thr Leu
305                 310                 315                 320

Asp Arg Gly Thr Val Ser Ile Ala Asn Asn Lys Met Leu Cys Phe Lys
                325                 330                 335

Tyr Ile Lys Gln Leu Met Ser Lys Leu Asn Ile Pro Leu Asp Pro Ile
            340                 345                 350

Asp Gln Ser Glu Gly Thr Asn Gly Glu Lys Ala Ile Cys Glu Asp Met
        355                 360                 365

Ala Ile Asn Val Ser Ile Thr Ala Val Asn Ala Asp Ser
370                 375                 380

<210> SEQ ID NO 107
<211> LENGTH: 370
<212> TYPE: PRT
<213> ORGANISM: Homo sapiens

<400> SEQUENCE: 107

Ala Leu Pro Val Ala Val Leu Leu Ile Val Gly Gly Leu Val Ile Met
1               5                   10                  15

Leu Tyr Val Phe His Arg Lys Arg Asn Asn Ser Arg Leu Gly Asn Gly
                20                  25                  30

Val Leu Tyr Ala Ser Val Asn Pro Glu Tyr Phe Ser Ala Ala Asp Val
            35                  40                  45

Tyr Val Pro Asp Glu Trp Glu Val Ala Arg Glu Lys Ile Thr Met Ser
        50                  55                  60

Arg Glu Leu Gly Gln Gly Ser Phe Gly Met Val Tyr Glu Gly Val Ala
65                  70                  75                  80

Lys Gly Val Val Lys Asp Glu Pro Glu Thr Arg Val Ala Ile Lys Thr
                85                  90                  95

Val Asn Glu Ala Ala Ser Met Arg Glu Arg Ile Glu Phe Leu Asn Glu
            100                 105                 110

Ala Ser Val Met Lys Glu Phe Asn Cys His His Val Val Arg Leu Leu
        115                 120                 125

Gly Val Val Ser Gln Gly Gln Pro Thr Leu Val Ile Met Glu Leu Met
    130                 135                 140

Thr Arg Gly Asp Leu Lys Ser Tyr Leu Arg Ser Leu Arg Pro Glu Met
145                 150                 155                 160
```

-continued

```
Glu Asn Asn Pro Val Leu Ala Pro Pro Ser Leu Ser Lys Met Ile Gln
            165                 170                 175

Met Ala Gly Glu Ile Ala Asp Gly Met Ala Tyr Leu Asn Ala Asn Lys
            180                 185                 190

Phe Val His Arg Asp Leu Ala Ala Arg Asn Cys Met Val Ala Glu Asp
            195                 200                 205

Phe Thr Val Lys Ile Gly Asp Phe Gly Met Thr Arg Asp Ile Tyr Glu
            210                 215                 220

Thr Asp Tyr Tyr Arg Lys Gly Lys Gly Leu Leu Pro Val Arg Trp
225                 230                 235                 240

Met Ser Pro Glu Ser Leu Lys Asp Gly Val Phe Thr Thr Tyr Ser Asp
            245                 250                 255

Val Trp Ser Phe Gly Val Val Leu Trp Glu Ile Ala Thr Leu Ala Glu
            260                 265                 270

Gln Pro Tyr Gln Gly Leu Ser Asn Glu Gln Val Leu Arg Phe Val Met
            275                 280                 285

Glu Gly Gly Leu Leu Asp Lys Pro Asp Asn Cys Pro Asp Met Leu Phe
            290                 295                 300

Glu Leu Met Arg Met Cys Trp Gln Tyr Asn Pro Lys Met Arg Pro Ser
305                 310                 315                 320

Phe Leu Glu Ile Ile Ser Ser Ile Lys Glu Glu Met Glu Pro Gly Phe
            325                 330                 335

Arg Glu Val Ser Phe Tyr Tyr Ser Glu Glu Asn Lys Leu Pro Glu Pro
            340                 345                 350

Glu Glu Leu Asp Leu Glu Pro Glu Asn Met Glu Ser Val Pro Leu Asp
            355                 360                 365

Pro Ser
    370

<210> SEQ ID NO 108
<211> LENGTH: 374
<212> TYPE: PRT
<213> ORGANISM: Homo sapiens

<400> SEQUENCE: 108

Ile Gly Pro Leu Ile Phe Val Phe Leu Phe Ser Val Val Ile Gly Ser
1               5                   10                  15

Ile Tyr Leu Phe Leu Arg Lys Arg Gln Pro Asp Gly Pro Leu Gly Pro
            20                  25                  30

Leu Tyr Ala Ser Ser Asn Pro Glu Tyr Leu Ser Ala Ser Asp Val Phe
            35                  40                  45

Pro Cys Ser Val Tyr Val Pro Asp Glu Trp Glu Val Ser Arg Glu Lys
        50                  55                  60

Ile Thr Leu Leu Arg Glu Leu Gly Gln Gly Ser Phe Gly Met Val Tyr
65              70                  75                  80

Glu Gly Asn Ala Arg Asp Ile Ile Lys Gly Glu Ala Glu Thr Arg Val
            85                  90                  95

Ala Val Lys Thr Val Asn Glu Ser Ala Ser Leu Arg Glu Arg Ile Glu
            100                 105                 110

Phe Leu Asn Glu Ala Ser Val Met Lys Gly Phe Thr Cys His His Val
            115                 120                 125

Val Arg Leu Leu Gly Val Ser Lys Gly Gln Pro Thr Leu Val Val
            130                 135                 140

Met Glu Leu Met Ala His Gly Asp Leu Lys Ser Tyr Leu Arg Ser Leu
145                 150                 155                 160
```

```
Arg Pro Glu Ala Glu Asn Asn Pro Gly Arg Pro Pro Thr Leu Gln
            165                 170                 175

Glu Met Ile Gln Met Ala Ala Glu Ile Ala Asp Gly Met Ala Tyr Leu
            180                 185                 190

Asn Ala Lys Lys Phe Val His Arg Asp Leu Ala Ala Arg Asn Cys Met
            195                 200                 205

Val Ala His Asp Phe Thr Val Lys Ile Gly Asp Phe Gly Met Thr Arg
            210                 215                 220

Asp Ile Tyr Glu Thr Asp Tyr Tyr Arg Lys Gly Gly Lys Gly Leu Leu
225                 230                 235                 240

Pro Val Arg Trp Met Ala Pro Glu Ser Leu Lys Asp Gly Val Phe Thr
            245                 250                 255

Thr Ser Ser Asp Met Trp Ser Phe Gly Val Val Leu Trp Glu Ile Thr
            260                 265                 270

Ser Leu Ala Glu Gln Pro Tyr Gln Gly Leu Ser Asn Glu Gln Val Leu
            275                 280                 285

Lys Phe Val Met Asp Gly Gly Tyr Leu Asp Gln Pro Asp Asn Cys Pro
            290                 295                 300

Glu Arg Val Thr Asp Leu Met Arg Met Cys Trp Gln Phe Asn Pro Lys
305                 310                 315                 320

Met Arg Pro Thr Phe Leu Glu Ile Val Asn Leu Leu Lys Asp Asp Leu
            325                 330                 335

His Pro Ser Phe Pro Glu Val Ser Phe Phe His Ser Glu Glu Asn Lys
            340                 345                 350

Ala Pro Glu Ser Glu Glu Leu Glu Met Glu Phe Glu Asp Met Glu Asn
            355                 360                 365

Val Pro Leu Asp Arg Ser
            370

<210> SEQ ID NO 109
<211> LENGTH: 384
<212> TYPE: PRT
<213> ORGANISM: Drosophila melanogaster

<400> SEQUENCE: 109

Gly Ile Gly Leu Ala Phe Leu Ile Val Ser Leu Phe Gly Tyr Val Cys
1               5                   10                  15

Tyr Leu His Lys Arg Lys Val Pro Ser Asn Asp Leu His Met Asn Thr
            20                  25                  30

Glu Val Asn Pro Phe Tyr Ala Ser Met Gln Tyr Ile Pro Asp Asp Trp
            35                  40                  45

Glu Val Leu Arg Glu Asn Ile Ile Gln Leu Ala Pro Leu Gly Gln Gly
        50                  55                  60

Ser Phe Gly Met Val Tyr Glu Gly Ile Leu Lys Ser Phe Pro Pro Asn
65                  70                  75                  80

Gly Val Asp Arg Glu Cys Ala Ile Lys Thr Val Asn Glu Asn Ala Thr
            85                  90                  95

Asp Arg Glu Arg Thr Asn Phe Leu Ser Glu Ala Ser Val Met Lys Glu
            100                 105                 110

Phe Asp Thr Tyr His Val Val Arg Leu Leu Gly Val Cys Ser Arg Gly
            115                 120                 125

Gln Pro Ala Leu Val Val Met Glu Leu Met Lys Lys Gly Asp Leu Lys
            130                 135                 140

Ser Tyr Leu Arg Ala His Arg Pro Glu Glu Arg Asp Glu Ala Met Met
```

```
                145                 150                 155                 160
Thr Tyr Leu Asn Arg Ile Gly Val Thr Gly Asn Val Gln Pro Pro Thr
                165                 170                 175
Tyr Gly Arg Ile Tyr Gln Met Ala Ile Glu Ile Ala Asp Gly Met Ala
                180                 185                 190
Tyr Leu Ala Ala Lys Lys Phe Val His Arg Asp Leu Ala Ala Arg Asn
                195                 200                 205
Cys Met Val Ala Asp Asp Leu Thr Val Lys Ile Gly Asp Phe Gly Met
                210                 215                 220
Thr Arg Asp Ile Tyr Glu Thr Asp Tyr Tyr Arg Lys Gly Thr Lys Gly
225                 230                 235                 240
Leu Leu Pro Val Arg Trp Met Pro Glu Ser Leu Arg Asp Gly Val
                245                 250                 255
Tyr Ser Ser Ala Ser Asp Val Phe Ser Phe Gly Val Val Leu Trp Glu
                260                 265                 270
Met Ala Thr Leu Ala Ala Gln Pro Tyr Gln Gly Leu Ser Asn Glu Gln
                275                 280                 285
Val Leu Arg Tyr Val Ile Asp Gly Gly Val Met Glu Arg Pro Glu Asn
                290                 295                 300
Cys Pro Asp Phe Leu His Lys Leu Met Gln Arg Cys Trp His His Arg
305                 310                 315                 320
Ser Ser Ala Arg Pro Ser Phe Leu Asp Ile Ile Ala Tyr Leu Glu Pro
                325                 330                 335
Gln Cys Pro Asn Ser Gln Phe Lys Glu Val Ser Phe Tyr His Ser Glu
                340                 345                 350
Ala Gly Leu Gln His Arg Glu Lys Glu Arg Lys Glu Arg Asn Gln Leu
                355                 360                 365
Asp Ala Phe Ala Ala Val Pro Leu Asp Gln Asp Leu Gln Asp Arg Glu
                370                 375                 380

<210> SEQ ID NO 110
<211> LENGTH: 380
<212> TYPE: PRT
<213> ORGANISM: Caenorhabditis elegans

<400> SEQUENCE: 110

Gly Met Leu Leu Val Phe Leu Ile Leu Met Ser Ile Ala Gly Cys Ile
1               5                   10                  15
Ile Tyr Tyr Tyr Ile Gln Val Arg Tyr Gly Lys Lys Val Lys Ala Leu
                20                  25                  30
Ser Asp Phe Met Gln Leu Asn Pro Glu Tyr Cys Val Asp Asn Lys Tyr
                35                  40                  45
Asn Ala Asp Asp Trp Glu Leu Arg Gln Asp Asp Val Val Leu Gly Gln
            50                  55                  60
Gln Cys Gly Glu Gly Ser Phe Gly Lys Val Tyr Leu Gly Thr Gly Asn
65                  70                  75                  80
Asn Val Val Ser Leu Met Gly Asp Arg Phe Gly Pro Cys Ala Ile Lys
                85                  90                  95
Ile Asn Val Asp Asp Pro Ala Ser Thr Glu Asn Leu Asn Tyr Leu Met
                100                 105                 110
Glu Ala Asn Ile Met Lys Asn Phe Lys Thr Asn Phe Ile Val Gln Leu
                115                 120                 125
Tyr Gly Val Ile Ser Thr Val Gln Pro Ala Met Val Val Met Glu Met
                130                 135                 140
```

-continued

Met Asp Leu Gly Asn Leu Arg Asp Tyr Leu Arg Ser Lys Arg Glu Asp
145                 150                 155                 160

Glu Val Phe Asn Glu Thr Asp Cys Asn Phe Phe Asp Ile Ile Pro Arg
                165                 170                 175

Asp Lys Phe His Glu Trp Ala Ala Gln Ile Cys Asp Gly Met Ala Tyr
            180                 185                 190

Leu Glu Ser Leu Lys Phe Cys His Arg Asp Leu Ala Ala Arg Asn Cys
        195                 200                 205

Met Ile Asn Arg Asp Glu Thr Val Lys Ile Gly Asp Phe Gly Met Ala
    210                 215                 220

Arg Asp Leu Phe Tyr His Asp Tyr Tyr Lys Pro Ser Gly Lys Arg Met
225                 230                 235                 240

Met Pro Val Arg Trp Met Ser Pro Glu Ser Leu Lys Asp Gly Lys Phe
                245                 250                 255

Asp Ser Lys Ser Asp Val Trp Ser Phe Gly Val Val Leu Tyr Glu Met
            260                 265                 270

Val Thr Leu Gly Ala Gln Pro Tyr Ile Gly Leu Ser Asn Asp Glu Val
        275                 280                 285

Leu Asn Tyr Ile Gly Met Ala Arg Lys Val Ile Lys Lys Pro Glu Cys
    290                 295                 300

Cys Glu Asn Tyr Trp Tyr Lys Val Met Lys Met Cys Trp Arg Tyr Ser
305                 310                 315                 320

Pro Arg Asp Arg Pro Thr Phe Leu Gln Leu Val His Leu Leu Ala Ala
                325                 330                 335

Glu Ala Ser Pro Glu Phe Arg Asp Leu Ser Phe Val Leu Thr Asp Asn
            340                 345                 350

Gln Met Ile Leu Asp Asp Ser Glu Ala Leu Asp Leu Asp Asp Ile Asp
        355                 360                 365

Asp Thr Asp Met Asn Asp Gln Val Val Glu Val Ala
    370                 375                 380

<210> SEQ ID NO 111
<211> LENGTH: 103
<212> TYPE: PRT
<213> ORGANISM: Caenorhabditis elegans

<400> SEQUENCE: 111

Asn Ile Asp Arg Glu Phe Asp Gln Lys Ala Cys Glu Ser Leu Val Lys
1               5                   10                  15

Lys Leu Lys Asp Lys Asn Asp Leu Gln Asn Leu Ile Asp Val Val
            20                  25                  30

Leu Ser Lys Gly Thr Lys Tyr Thr Gly Cys Ile Thr Ile Pro Arg Thr
        35                  40                  45

Leu Asp Gly Arg Leu Gln Val His Gly Arg Lys Gly Phe Pro His Val
    50                  55                  60

Val Tyr Gly Lys Leu Trp Arg Phe Asn Glu Met Thr Lys Asn Glu Thr
65                  70                  75                  80

Arg His Val Asp His Cys Lys His Ala Phe Glu Met Lys Ser Asp Met
                85                  90                  95

Val Cys Val Asn Pro Tyr His
            100

<210> SEQ ID NO 112
<211> LENGTH: 104
<212> TYPE: PRT
<213> ORGANISM: Homo sapiens

<400> SEQUENCE: 112

| Gly | Gly | Glu | Ser | Glu | Thr | Phe | Ala | Lys | Arg | Ala | Ile | Glu | Ser | Leu | Val |
|---|---|---|---|---|---|---|---|---|---|---|---|---|---|---|---|
| 1 | | | | 5 | | | | | 10 | | | | | 15 | |

| Lys | Lys | Leu | Lys | Glu | Lys | Lys | Asp | Glu | Leu | Asp | Ser | Leu | Ile | Thr | Ala |
|---|---|---|---|---|---|---|---|---|---|---|---|---|---|---|---|
| | | | 20 | | | | | 25 | | | | | 30 | | |

| Ile | Thr | Thr | Asn | Gly | Ala | His | Pro | Ser | Lys | Cys | Val | Thr | Ile | Gln | Arg |
|---|---|---|---|---|---|---|---|---|---|---|---|---|---|---|---|
| | | 35 | | | | | 40 | | | | | 45 | | | |

| Thr | Leu | Asp | Gly | Arg | Leu | Gln | Val | Ala | Gly | Arg | Lys | Gly | Phe | Pro | His |
|---|---|---|---|---|---|---|---|---|---|---|---|---|---|---|---|
| | 50 | | | | | 55 | | | | | 60 | | | | |

| Val | Ile | Tyr | Ala | Arg | Leu | Trp | Arg | Trp | Pro | Asp | Leu | His | Lys | Asn | Glu |
|---|---|---|---|---|---|---|---|---|---|---|---|---|---|---|---|
| 65 | | | | | 70 | | | | | 75 | | | | | 80 |

| Leu | Lys | His | Val | Lys | Tyr | Cys | Gln | Tyr | Ala | Phe | Asp | Leu | Lys | Cys | Asp |
|---|---|---|---|---|---|---|---|---|---|---|---|---|---|---|---|
| | | | | 85 | | | | | 90 | | | | | 95 | |

| Ser | Val | Cys | Val | Asn | Pro | Tyr | His |
|---|---|---|---|---|---|---|---|
| | | | 100 | | | | |

<210> SEQ ID NO 113
<211> LENGTH: 205
<212> TYPE: PRT
<213> ORGANISM: Caenorhabditis elegans

<400> SEQUENCE: 113

| Ile | Val | Tyr | Tyr | Glu | Lys | Asn | Leu | Gln | Ile | Gly | Glu | Lys | Lys | Cys | Ser |
|---|---|---|---|---|---|---|---|---|---|---|---|---|---|---|---|
| 1 | | | | 5 | | | | | 10 | | | | | 15 | |

| Arg | Gly | Asn | Phe | His | Val | Asp | Gly | Gly | Phe | Ile | Cys | Ser | Glu | Asn | Arg |
|---|---|---|---|---|---|---|---|---|---|---|---|---|---|---|---|
| | | | 20 | | | | | 25 | | | | | 30 | | |

| Tyr | Ser | Leu | Gly | Leu | Glu | Pro | Asn | Pro | Ile | Arg | Glu | Pro | Val | Ala | Phe |
|---|---|---|---|---|---|---|---|---|---|---|---|---|---|---|---|
| | | 35 | | | | | 40 | | | | | 45 | | | |

| Lys | Val | Arg | Lys | Ala | Ile | Val | Asp | Gly | Ile | Arg | Phe | Ser | Tyr | Lys | Lys |
|---|---|---|---|---|---|---|---|---|---|---|---|---|---|---|---|
| | 50 | | | | | 55 | | | | | 60 | | | | |

| Asp | Gly | Ser | Val | Trp | Leu | Gln | Asn | Arg | Met | Lys | Tyr | Pro | Val | Phe | Val |
|---|---|---|---|---|---|---|---|---|---|---|---|---|---|---|---|
| 65 | | | | | 70 | | | | | 75 | | | | | 80 |

| Thr | Ser | Gly | Tyr | Leu | Asp | Glu | Gln | Ser | Gly | Gly | Leu | Lys | Lys | Asp | Lys |
|---|---|---|---|---|---|---|---|---|---|---|---|---|---|---|---|
| | | | | 85 | | | | | 90 | | | | | 95 | |

| Val | His | Lys | Val | Tyr | Gly | Cys | Ala | Ser | Ile | Lys | Thr | Phe | Gly | Phe | Asn |
|---|---|---|---|---|---|---|---|---|---|---|---|---|---|---|---|
| | | | 100 | | | | | 105 | | | | | 110 | | |

| Val | Ser | Lys | Gln | Ile | Ile | Arg | Asp | Ala | Leu | Leu | Ser | Lys | Gln | Met | Ala |
|---|---|---|---|---|---|---|---|---|---|---|---|---|---|---|---|
| | | 115 | | | | | 120 | | | | | 125 | | | |

| Thr | Met | Tyr | Leu | Gln | Gly | Lys | Leu | Thr | Pro | Met | Asn | Tyr | Ile | Tyr | Glu |
|---|---|---|---|---|---|---|---|---|---|---|---|---|---|---|---|
| | 130 | | | | | 135 | | | | | 140 | | | | |

| Lys | Lys | Thr | Gln | Glu | Glu | Leu | Arg | Arg | Glu | Ala | Thr | Arg | Thr | Thr | Asp |
|---|---|---|---|---|---|---|---|---|---|---|---|---|---|---|---|
| 145 | | | | | 150 | | | | | 155 | | | | | 160 |

| Ser | Leu | Ala | Lys | Tyr | Cys | Cys | Val | Arg | Val | Ser | Phe | Cys | Lys | Gly | Phe |
|---|---|---|---|---|---|---|---|---|---|---|---|---|---|---|---|
| | | | | 165 | | | | | 170 | | | | | 175 | |

| Gly | Glu | Ala | Tyr | Pro | Glu | Arg | Pro | Ser | Ile | His | Asp | Cys | Pro | Val | Trp |
|---|---|---|---|---|---|---|---|---|---|---|---|---|---|---|---|
| | | | 180 | | | | | 185 | | | | | 190 | | |

| Ile | Glu | Leu | Lys | Ile | Asn | Ile | Ala | Tyr | Asp | Phe | Met | Asp |
|---|---|---|---|---|---|---|---|---|---|---|---|---|
| | | 195 | | | | | 200 | | | | | 205 |

<210> SEQ ID NO 114
<211> LENGTH: 212
<212> TYPE: PRT
<213> ORGANISM: Homo sapiens

<400> SEQUENCE: 114

-continued

```
Ile Ala Tyr Phe Glu Met Asp Val Gln Val Gly Glu Thr Phe Lys Val
 1               5                  10                  15

Pro Ser Ser Cys Pro Ile Val Thr Val Asp Gly Tyr Val Asp Pro Ser
            20                  25                  30

Gly Gly Asp Arg Phe Cys Leu Gly Gln Leu Ser Asn Val His Arg Thr
            35                  40                  45

Glu Ala Ile Glu Arg Ala Arg Leu His Ile Gly Lys Gly Val Gln Leu
        50                  55                  60

Glu Cys Lys Gly Glu Gly Asp Val Trp Val Arg Cys Leu Ser Asp His
65                      70                  75                  80

Ala Val Phe Val Gln Ser Tyr Tyr Leu Asp Arg Glu Ala Gly Arg Ala
                85                  90                  95

Pro Gly Asp Ala Val His Lys Ile Tyr Pro Ser Ala Tyr Ile Lys Val
                100                 105                 110

Phe Asp Leu Arg Gln Cys His Arg Gln Met Gln Gln Gln Ala Ala Thr
            115                 120                 125

Ala Gln Ala Ala Ala Ala Ala Gln Ala Ala Val Ala Gly Asn Ile
            130                 135                 140

Pro Gly Pro Gly Ser Val Gly Gly Ile Ala Pro Ala Ile Ser Leu Ser
145                 150                 155                 160

Ala Ala Ala Gly Ile Gly Val Asp Asp Leu Arg Arg Leu Cys Ile Leu
                165                 170                 175

Arg Met Ser Phe Val Lys Gly Trp Gly Pro Asp Tyr Pro Arg Gln Ser
                180                 185                 190

Ile Lys Glu Thr Pro Cys Trp Ile Glu Ile His Leu His Arg Ala Leu
        195                 200                 205

Gln Leu Leu Asp
210
```